United States Patent
Wacker et al.

(10) Patent No.: US 12,030,835 B2
(45) Date of Patent: Jul. 9, 2024

(54) SUBSTITUTED AMIDE COMPOUNDS USEFUL AS FARNESOID X RECEPTOR MODULATORS

(71) Applicant: BRISTOL-MYERS SQUIBB COMPANY, Princeton, NJ (US)

(72) Inventors: Dean A. Wacker, Yardley, PA (US); Susheel Jethanand Nara, Mumbai (IN); Srinivas Cheruku, Bangalore (IN); Kandhasamy Sarkunam, Hosur (IN); Firoz Ali Jaipuri, Bengaluru (IN); Soodamani Thangavel, Krishnagiri (IN); Rishikesh Narayan, Mumbai (IN); Subba Reddy Bandreddy, Bangalore (IN); Srinivas Jogi, Bangalore (IN); Pavan Kalyan Kathi, Bangalore (IN)

(73) Assignee: Bristol-Myers Squibb Company, Princeton, NJ (US)

( * ) Notice: Subject to any disclaimer, the term of this patent is extended or adjusted under 35 U.S.C. 154(b) by 505 days.

(21) Appl. No.: 17/431,091

(22) PCT Filed: Feb. 14, 2020

(86) PCT No.: PCT/US2020/018217
§ 371 (c)(1),
(2) Date: Aug. 13, 2021

(87) PCT Pub. No.: WO2020/168152
PCT Pub. Date: Aug. 20, 2020

(65) Prior Publication Data
US 2022/0213026 A1    Jul. 7, 2022

Related U.S. Application Data

(60) Provisional application No. 62/806,047, filed on Feb. 15, 2019.

(51) Int. Cl.
| | | |
|---|---|---|
| C07C 233/61 | (2006.01) |
| C07D 205/04 | (2006.01) |
| C07D 207/06 | (2006.01) |
| C07D 271/06 | (2006.01) |
| C07D 277/64 | (2006.01) |
| C07D 295/04 | (2006.01) |
| C07D 309/04 | (2006.01) |
| C07D 405/04 | (2006.01) |

(Continued)

(52) U.S. Cl.
CPC .......... *C07C 233/61* (2013.01); *C07D 205/04* (2013.01); *C07D 207/06* (2013.01); *C07D 271/06* (2013.01); *C07D 277/64* (2013.01); *C07D 295/04* (2013.01); *C07D 309/04* (2013.01); *C07D 405/04* (2013.01); *C07D 405/14* (2013.01); *C07D 413/04* (2013.01)

(58) Field of Classification Search
None
See application file for complete search history.

(56) References Cited

U.S. PATENT DOCUMENTS

| 8,158,665 B2 | 4/2012 | Caldwell et al. |
| 8,907,095 B2 | 12/2014 | Xia et al. |

(Continued)

FOREIGN PATENT DOCUMENTS

| CN | 106146483 A | 11/2016 |
| CN | 106632294 A | 5/2017 |

(Continued)

OTHER PUBLICATIONS

Claudel, Thierry et al., "The Farnesoid X Receptor: A Novel Drug Target?", Expert Opin. Investig. Drugs, vol. 13(9), pp. 1135-1148, (2004).
Crawley, Matthew Lantz, "Farnesoid X receptor modulators: a patent review," Expert Opinion on Therapeutic Patents, (2010) 20:8, pp. 1047-1057.
International Preliminary Report on Patentability Application No. PCT/US2020/018217, dated Aug. 10, 2021.

(Continued)

*Primary Examiner* — Samantha L Shterengarts
(74) *Attorney, Agent, or Firm* — Gary Greenblatt

(57) ABSTRACT

Disclosed are compounds of Formula (I) or a stereoisomer, a tautomer, or a pharmaceutically acceptable salt or solvate thereof, wherein Q is a 5-membered heterocyclyl or 5-membered heteroaryl having 1 to 4 heteroatoms independently selected from N, O, and S, substituted with zero to 4 $R^1$; and A, $X^1$, $X^2$, $X^3$, $X^4$, $Z^1$, $Z^2$, $R^1$, $R^2$, $R^{3a}$, $R^{3b}$, a, b, and d are defined herein. Also disclosed are methods of using these compounds to modulate the activity of farnesoid X receptor (FXR); pharmaceutical compositions comprising these compounds; and methods of treating a disease, disorder, or condition associated with FXR dysregulation, such as pathological fibrosis, transplant rejection, cancer, osteoporosis, and inflammatory disorders, by using the compounds and pharmaceutical compositions.

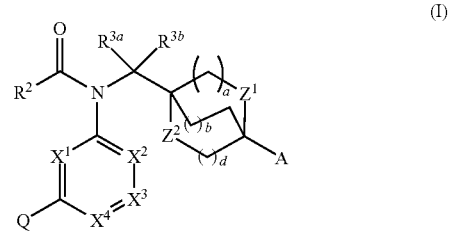

(I)

15 Claims, No Drawings

(51) Int. Cl.
  *C07D 405/14* (2006.01)
  *C07D 413/04* (2006.01)

(56) References Cited

U.S. PATENT DOCUMENTS

| | | | |
|---|---|---|---|
| 9,539,244 | B2 | 1/2017 | Kinzel et al. |
| 9,751,874 | B2 | 9/2017 | Gege et al. |
| 2010/0152166 | A1 | 6/2010 | Genin et al. |
| 2011/0034507 | A1 | 2/2011 | Akwabi-ameyaw et al. |
| 2015/0366856 | A1 | 12/2015 | Tully et al. |
| 2016/0176861 | A1 | 6/2016 | Gege et al. |
| 2017/0298068 | A1 | 10/2017 | Gege et al. |
| 2017/0304270 | A1 | 10/2017 | Or et al. |
| 2017/0304271 | A1 | 10/2017 | Or et al. |
| 2017/0304272 | A1 | 10/2017 | Or et al. |
| 2017/0333399 | A1 | 11/2017 | Or et al. |
| 2017/0355693 | A1 | 12/2017 | Blomgren et al. |
| 2017/0355694 | A1 | 12/2017 | Gege |
| 2017/0368038 | A1 | 12/2017 | Badman et al. |
| 2019/0002452 | A1 | 1/2019 | Zhang et al. |
| 2019/0127358 | A1 | 5/2019 | Yoon et al. |

FOREIGN PATENT DOCUMENTS

| | | | |
|---|---|---|---|
| CN | 107021958 | A | 8/2017 |
| EP | 3034499 | A1 | 6/2016 |
| EP | 3034501 | A1 | 6/2016 |
| EP | 3401315 | A1 | 11/2018 |
| WO | 9313101 | A1 | 7/1993 |
| WO | 9817276 | A1 | 4/1998 |
| WO | 03099821 | A1 | 12/2003 |
| WO | 2004046162 | A2 | 6/2004 |
| WO | 2006006490 | A1 | 1/2006 |
| WO | 2007076260 | A2 | 7/2007 |
| WO | 2008051942 | A2 | 5/2008 |
| WO | 2008094556 | A2 | 8/2008 |
| WO | 2008109177 | A2 | 9/2008 |
| WO | 2008109179 | A1 | 9/2008 |
| WO | 2008109180 | A2 | 9/2008 |
| WO | 2009009059 | A1 | 1/2009 |
| WO | 2009149795 | A2 | 12/2009 |
| WO | 2010058318 | A1 | 5/2010 |
| WO | 2011006935 | A2 | 1/2011 |
| WO | 2011045292 | A1 | 4/2011 |
| WO | 2012087520 | A1 | 6/2012 |
| WO | 2013007387 | A1 | 1/2013 |
| WO | 2013186159 | A1 | 12/2013 |
| WO | 2014054053 | A1 | 4/2014 |
| WO | 2015138969 | A1 | 9/2015 |
| WO | 2015172747 | A1 | 11/2015 |
| WO | 2016096115 | A1 | 6/2016 |
| WO | 2017049173 | A1 | 3/2017 |
| WO | 2017049176 | A1 | 3/2017 |
| WO | 20170078927 | A1 | 5/2017 |
| WO | 2017133521 | A1 | 8/2017 |
| WO | 2017145040 | A1 | 8/2017 |
| WO | 2017145041 | A1 | 8/2017 |
| WO | 2017161002 | A1 | 9/2017 |
| WO | 2018059314 | A1 | 4/2018 |
| WO | 2018170165 | A1 | 9/2018 |
| WO | 2018170166 | A1 | 9/2018 |
| WO | 2018170167 | A1 | 9/2018 |
| WO | 2018170173 | A1 | 9/2018 |
| WO | 2018170182 | A1 | 9/2018 |
| WO | 2020061114 | A1 | 3/2020 |

OTHER PUBLICATIONS

International Search Report Application No. PCT/US2020/018217, dated Aug. 13, 2020.

Sepe, Valentina et al., "Farnesoid X Receptor Modulators 2014-present: A Patent Review", Expert Opinion on Therapeutic Patents, vol. 28, No. 5, pp. 351-364 (2018).

Tully, David C. et al., "Discovery of Tropifexor (LJN452), a Highly Potent Non-bile Acid FXR Agonist for the Treatment of Cholestatic Liver Diseases and Nonalcoholic Steatohepatitis (NASH)", Journal of Medicinal Chemistry, vol. 60, pp. 9960-9973 (2017).

SUBSTITUTED AMIDE COMPOUNDS USEFUL AS FARNESOID X RECEPTOR MODULATORS

CROSS REFERENCE

This application is a 371 application of International Application No. PCT/US2020/018217, filed on Feb. 14, 2020, which claims the benefit of U.S. Provisional Application Ser. 62/806,047, filed Feb. 15, 2019, the content of each is hereby fully incorporated by reference in its entirety for all purposes.

DESCRIPTION

The present invention relates generally to substituted amide compounds useful as farnesoid X receptor (FXR) modulators, pharmaceutical compositions comprising such compounds and to their use in therapy, especially in the treatment or prophylaxis of diseases, disorders, and conditions for which an FXR modulator is indicated.

BACKGROUND OF THE INVENTION

FXR or NR1H4 (nuclear receptor subfamily 1, group H, member 4) is a nuclear receptor that can activate the expression of specific target genes in a ligand-dependent manner. FXR is expressed in the liver, throughout the gastrointestinal tract, colon, ovary, adrenal gland, kidney, and in the gall bladder and biliary tree in humans. FXR forms a heterodimer with Retinoid X Receptor (RxR) and binds to specific response elements in target genes to regulate gene transcription (B. M. Forman et al., Cell 1995; 81: 687; W. Seol et al., Mol. Endocrinol. 1995; 9: 72). The FXR/RxR heterodimer typically binds to an inverted repeat of a consensus hexanucleotide sequence (AGGTCA) separated by a single nucleotide, i.e. an IR-1 sequence. The relevant physiological ligands of FXR are bile acids including chenodeoxycholic acid and its taurine-conjugate (D. J. Parks et al., Science 1999; 284: 1365; M. Makishima et al., Science 1999; 284: 1362). FXR activation regulates the expression of multiple genes that encode enzymes and transporters involved in bile acid synthesis, influx, and efflux from the liver and intestine resulting in a net decrease in total endogenous bile acids in a negative feedback loop. FXR is involved in paracrine and endocrine signaling by upregulating the expression of the cytokine Fibroblast Growth Factor 15 (rodents) or 19 (primates), which can also contribute to the regulation of bile acid concentrations (Holt et al., Genes Dev. 2003; 17: 1581; Inagaki et al., Cell Metab 2005; 2: 217). Therefore, FXR is considered to be a master regulator of bile acid homeostasis.

One use of FXR agonists is for the treatment of diseases in which bile acids are dysregulated, including cholestatic diseases (e.g. primary biliary cirrhosis and primary sclerosing cholangitis) that can lead to fibrosis, cirrhosis, cholangiocarcinoma, hepatocellular carcinoma, liver failure, and death. While elevated bile acid concentrations in the liver have deleterious effects, bile acids also affect the microflora and integrity of the small intestine. Obstruction of bile flow in humans or rodents causes proliferation of intestinal bacteria and mucosal injury, which can lead to bacterial translocation across the mucosal barrier and systemic infection (Berg, Trends Microbiol. 1995; 3: 149-154). Mice lacking FXR have increased ileal levels of bacteria and a compromised epithelial barrier, while activation of intestinal FXR plays an important role in preventing bacterial overgrowth and maintaining the integrity of the intestinal epithelium (Inagaki et al., Proc Natl Acad Sci 2006; 103: 3920-3925). Over time, FXR null mice spontaneously develop hepatocellular carcinoma, and this can be abrogated by selective re-activation of FXR in the intestine (Degirolamo et al., Hepatology 61: 161-170). Pharmacological activation of FXR with a small molecule agonist or transgenic expression of FXR in the intestine can normalize bile acid concentrations, decrease cellular proliferation in hepatic bile ducts, and reduce inflammatory cell infiltration, necrotic area, and liver fibrosis in rodent models of cholestasis (Liu et al., J. Clin. Invest. 2003; 112:1678-1687; Modica et al., Gastroenterology. 2012; 142: 355-365). Some of these beneficial effects observed in preclinical models of cholestasis have translated to human patients, and the FXR agonist, obeticholic acid (OCA or OCALIVA™), has been approved for the treatment of primary biliary cirrhosis (https://www.fda.gov/newsevents/newsroom/pressannouncements/ucm503964.htm).

In addition to controlling bile acid homeostasis, FXR agonists regulate the hepatic expression of hundreds of genes encoding proteins involved in cholesterol and lipid metabolism and transport, glucose homeostasis, inflammation, chemotaxis, and apoptosis among other pathways (Zhan et al., PLoS One 2014; 9: e105930; Ijssennagger et al., J Hepatol 2016; 64: 1158-1166). Consistent with these broad effects on gene expression, FXR agonists have also been investigated in preclinical models of fibrosis, cancer, inflammatory diseases, and metabolic disorders, including dyslipidemia, obesity, type 2 diabetes, nonalcoholic fatty liver disease (NAFLD) and metabolic syndrome (Crawley, Expert Opin. Ther. Patents 2010; 20:1047-1057).

FXR agonists are also being investigated in human clinical trials for the treatment of NAFLD, a more advanced form of fatty liver disease, nonalcoholic steatohepatitis (NASH), and associated complications. NAFLD is one of the most common causes of chronic liver disease in the world today (Vernon et al., Aliment Pharmacol Ther 2011; 34:274-285). The risk factors for developing NAFLD include obesity, type 2 diabetes mellitus (T2DM), insulin resistance, hypertension, and dyslipidemia. In a 6-week clinical trial in T2DM patients with NAFLD, the FXR agonist OCA statistically significantly improved insulin sensitivity and reduced body weight, showing beneficial effects on some of these risk factors (Mudaliar et al., Gastroenterology 2013; 145: 574-582). NASH is the most severe and progressive form of NAFLD and includes the histological findings of hepatic steatosis, inflammation, and ballooning degeneration with varying amounts of pericellular fibrosis (Sanyal et al., Hepatology 2015; 61:1392-1405). In a 72-week clinical trial in patients with NASH, OCA statistically significantly improved hepatic steatosis, lobular inflammation, hepatocyte ballooning, and fibrosis as assessed by histological analyses of liver biopsies (Neuschwander-Tetri et al., Lancet 2015; 385: 956-965). These data also suggest the potential for FXR agonists to show benefit on clinical outcomes given that NASH is the second leading cause of hepatocellular carcinoma (HCC) and liver transplantation in the United States (Wong et al., Hepatology 2014; 59: 2188-2195).

Applicants have found compounds useful for treating a disease, disorder, or condition associated with farnesoid X receptor (FXR) activity in a patient in need thereof. These compounds are provided to be useful as pharmaceuticals with desirable stability, bioavailability, therapeutic index, and toxicity values that are important to their drugability.

SUMMARY OF THE INVENTION

The present invention provides compounds of Formula (I) as well as the subgenera and species thereof, including stereoisomers, tautomers, pharmaceutically acceptable salts, and solvates thereof, which are useful as FXR modulators.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of Formula (I) and compositions comprising the compounds of Formula (I) may be used in therapy, either alone or in combination with one or more additional therapeutic agents.

The present invention also provides processes and intermediates for making the compounds of Formula (I) and/or salts thereof.

The compounds of the invention may be used in the treatment of a disease, disorder, or condition associated with activity of farnesoid X receptor (FXR) in a patient in need of such treatment by administering a therapeutically effective amount of the compound, or a stereoisomer, a tautomer, or a pharmaceutically acceptable salt or solvate thereof, to the patient. The disease, disorder, or condition may be related to pathological fibrosis. The compounds of the invention can be used alone, in combination with one or more compounds of the present invention, or in combination with one or more, e.g., one to two, other therapeutic agents.

The compounds of the invention may be used, either as a single agent or in combination with other agents, in the treatment of a disease, disorder, or condition selected from nonalcoholic steatohepatitis (NASH), non-alcoholic fatty liver disease (NAFLD), chronic kidney disease, diabetic kidney disease, primary sclerosing cholangitis (PSC), and primary biliary cirrhosis (PBC). The compounds of the invention may be used, either as a single agent or in combination with other agents, in the treatment of idiopathic pulmonary fibrosis (IPF).

The compounds of the invention may be used for the manufacture of a medicament for the treatment of a disease, disorder, or condition in a patient in need of such treatment.

Other features and advantages of the invention will be apparent from the following detailed description and claims.

DETAILED DESCRIPTION

The present application provides compounds, including all stereoisomers, solvates, prodrugs and pharmaceutically acceptable salt and solvate forms thereof, according to Formula (I). The present application also provides pharmaceutical compositions containing at least one compound according to Formula (I), or a stereoisomer, a tautomer, or a pharmaceutically acceptable salt or a solvate thereof, and optionally at least one additional therapeutic agent. Additionally, the present application provides methods for treating a patient suffering from a FXR-modulated disease or disorder such as for example, biliary fibrosis, liver fibrosis, renal fibrosis, Non-Alcoholic Fatty Liver Disease (NAFLD), Non-Alcoholic Steato-Hepatitis (NASH), primary sclerosing cholangitis (PSC), primary biliary cirrhosis (PBC), and pancreatic fibrosis, by administering to a patient in need of such treatment a therapeutically effective amount of a compound of the present invention, or a stereoisomer, a tautomer, or a pharmaceutically acceptable salt or a solvate thereof, and optionally in combination with at least one additional therapeutic agent.

The first aspect of the present invention provides at least one compound of Formula (I):

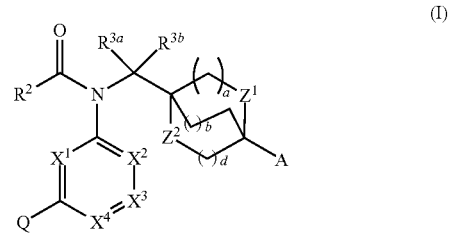

or a stereoisomer, a tautomer, or a salt or solvate thereof, wherein:
$X^1$ is $CR^{5a}$, or N;
$X^2$ is $CR^{5b}$ or N;
$X^3$ is $CR^{5c}$ or N;
$X^4$ is $CR^{5d}$ or N; provided that zero, 1, or 2 of $X^1$, $X^2$, $X^3$, and $X^4$ are N;
$Z^1$ and $Z^2$ are independently $CH_2$ or O; provided that at least one of $Z^1$ and $Z^2$ is $CH_2$;
a is zero or 1;
b is zero, 1, or 2;
d is zero, 1, or 2; provided that $Z^1$ and $Z^2$ are each $CH_2$ when a, b, and d are each zero;
Q is $C_{2-6}$ alkenyl or $C_{2-6}$ alkynyl, each substituted with zero to 2 $R^1$;
each $R^1$ is independently —C(O)OR$^x$, —C(O)NR$^x$R$^x$, $C_{1-4}$ hydroxyalkyl, or a cyclic group selected from 3- to 8-membered carbocyclyl, 6- to 10-membered aryl, 4- to 10-membered heterocyclyl, and 5- to 10-membered heteroaryl, wherein said cyclic group is substituted with zero to 3 $R^{1a}$;
each $R^{1a}$ is independently halo, oxo, cyano, hydroxyl, —NH$_2$, $C_{1-6}$ alkyl, $C_{1-6}$ alkoxy, —NH($C_{1-6}$ alkyl), —N($C_{1-6}$ alkyl)$_2$, or —NR$^x$C(O)($C_{1-6}$ alkyl), wherein each of said alkyl and alkoxy is substituted with zero to 6 $R^{1b}$;
each $R^{1b}$ is independently halo, hydroxyl, —NR$^w$R$^w$, oxo, cyano, $C_{1-3}$ alkoxy, $C_{1-3}$ haloalkoxy, —C(O)OR$^x$, —C(O)NR$^w$R$^w$, or —NR$^x$C(O)R$^y$;
or when $X^1$ is $CR^{5a}$, Q and $R^{5a}$ can be joined together to form a —CR$^{1a}$=CR$^1$CH$_2$CH$_2$— bridge;
$R^2$ is:
(i) $C_{1-6}$ alkyl, $C_{2-6}$ alkenyl, $C_{2-6}$ alkynyl, $C_{1-6}$ alkoxy, or —NR'R$^v$, wherein each of said alkyl, alkenyl, alkynyl, and alkoxy is substituted with zero to 6 $R^{2a}$;
(ii) $C_{3-8}$ carbocyclyl, $C_{6-8}$ spirobicyclyl, 6- to 7-membered heterocyclyl, phenyl, or 5- to 6-membered heteroaryl, wherein each of said carbocyclyl, spirobicyclyl, heterocyclyl, phenyl, and heteroaryl is substituted with zero to 3 $R^{2b}$; or
(iii) —CH$_2$(C$_{3-6}$ cycloalkyl), —CH$_2$(4- to 6-membered heterocyclyl), —NR$^x$(CH$_2$)$_{0-2}$(C$_{3-6}$ cycloalkyl), —NR$^x$(CH$_2$)$_{0-2}$(C$_{5-8}$ bicycloalkyl), —NR$^x$(CH$_2$)$_{0-2}$(C$_{5-8}$ spirobicyclyl), —NR$^x$(CH$_2$)$_{0-2}$(4- to 6-membered heterocyclyl), —NR$^x$(CH$_2$)$_{0-2}$(5- to 6-membered heteroaryl), —NR$^x$(CH$_2$)$_{0-2}$(phenyl), —O(CH$_2$)$_{0-2}$(C$_{3-6}$ cycloalkyl), —O(CH$_2$)$_{0-2}$(C$_{5-8}$ bicycloalkyl), —O(CH$_2$)$_{0-2}$(C$_{5-8}$ spirobicyclyl), —O(CH$_2$)$_{0-2}$(4- to 6-membered heterocyclyl), —O(CH$_2$)$_{0-2}$(5- to 6-membered heteroaryl), or —O(CH$_2$)$_{0-2}$(phenyl), wherein each of said cycloalkyl, heterocyclyl, bicycloalkyl, spirobicyclyl, aryl, and heteroaryl is substituted with zero to 3 $R^{2b}$;
each $R^{2a}$ is independently halo, alkyl, cyano, hydroxyl, oxo, $C_{1-3}$ alkoxy, $C_{1-3}$ haloalkoxy, —NR$^x$R$^x$, $C_{1-3}$ haloalkyl, —C(O)(C$_{1-6}$ alkyl), —C(O)(C$_{3-6}$ cycloalkyl), —NR$^x$C(O)R$^y$, —C(O)(C$_{1-6}$ alkyl), —C(O)OR$^x$, —C(O)NR$^w$R$^w$, —S(O)$_2$R$^y$, —S(O)$_2$(C$_{1-3}$ fluoroalkyl), —NR$^x$S(O)$_2$(C$_{1-3}$ alkyl), —NR$^x$S(O)$_2$(C$_{3-6}$ cycloalkyl), —S(O)$_2$NR$^z$R$^z$, or —P(O)R$^y$R$^y$;

each R$^{2b}$ is independently halo, cyano, hydroxyl, oxo, C$_{1-6}$ alkyl, C$_{1-6}$ alkoxy, —NR$^x$R$^x$, —NR$^x$C(O)O(C$_{1-3}$ alkyl), —C(O)(C$_{1-3}$ alkyl), or —S(O)$_2$(C$_{1-3}$ alkyl), wherein each of said alkyl and alkoxy is substituted with zero to 6 R$^{2a}$;

R$^{3a}$ and R$^{3b}$ are independently hydrogen, C$_{1-3}$ alkyl, C$_{1-3}$ haloalkyl, or C$_{3-6}$ cycloalkyl, or R$^{3a}$ and R$^{3b}$, taken together with the carbon atom to which they are attached, form a C$_{3-6}$ cycloalkyl;

A is:
(i) cyano;
(ii) phenyl or a 5- to 10-membered heteroaryl containing 1 to 4 heteroatoms independently selected from N, O, and S, wherein each of said phenyl and heteroaryl is substituted with zero to 3 R$^{4a}$; or

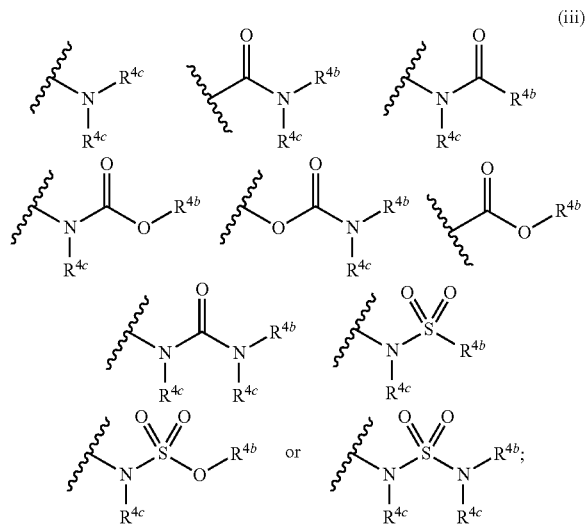

(iii)

each R$^{4a}$ is independently halo, cyano, hydroxyl, —NH$_2$, C$_{1-6}$ alkyl, C$_{2-6}$ alkenyl, C$_{2-6}$ alkynyl, C$_{1-6}$ alkoxy, —(CH$_2$)$_{0-3}$NH(C$_{1-6}$ alkyl), —(CH$_2$)$_{0-2}$N(C$_{1-6}$ alkyl)$_2$, —(CH$_2$)$_{0-3}$(C$_{3-6}$ cycloalkyl), or —(CH$_2$)$_{0-3}$(4- to 6-membered heterocyclyl), wherein each of said alkyl, alkoxy, alkenyl, and alkynyl is substituted with zero to 6 R$^{4d}$ and each of said cycloalkyl and heterocyclyl is substituted with zero to 3 R$^{4e}$;

R$^{4b}$ is C$_{1-6}$ alkyl, —(CH$_2$)$_{0-3}$(C$_{3-6}$ cycloalkyl), or —(CH$_2$)$_{0-3}$(4- to 6-membered heterocyclyl), wherein each of said alkyl is substituted with zero to 6 R$^{4d}$ and each of said cycloalkyl and heterocyclyl is substituted with zero to 3 R$^{4e}$;

each R$^{4c}$ is independently hydrogen, C$_{1-6}$ alkyl, C$_{3-6}$ cycloalkyl, 4- to 6-membered heterocyclyl, phenyl, or 5- to 6-membered heteroaryl;

each R$^{4d}$ is independently halo, hydroxyl, —NR$^x$R$^x$, oxo, cyano, C$_{1-3}$ alkoxy, or C$_{1-3}$ haloalkoxy;

each R$^{4e}$ is independently halo, oxo, cyano, hydroxyl, —NH$_2$, C$_{1-6}$ alkyl, C$_{1-6}$ alkoxy, —NH(C$_{1-6}$ alkyl), or —N(C$_{1-6}$ alkyl)$_2$, wherein each of said alkyl and alkoxy is substituted with zero to 6 R$^{4d}$;

each of R$^{5a}$, R$^{5b}$, R$^{5c}$, and R$^{5d}$ is independently hydrogen, halo, hydroxy, cyano, C$_{1-6}$ alkyl substituted with zero to 6 R$^{5e}$, C$_{1-6}$ alkoxy substituted with zero to 6 R$^{5e}$, —C(O)OR$^x$, —C(O)NR$^w$R$^w$, —S(O)$_2$R$^y$, —S(O)$_2$NR$^z$R$^z$, or phenyl substituted with zero to 3 R$^{5f}$;

each of R$^{5f}$ is independently halo, hydroxyl, —NR$^x$R$^x$, oxo, cyano, C$_{1-3}$ alkoxy, or C$_{1-3}$ haloalkoxy;

each R$^{5f}$ is independently halo, oxo, cyano, hydroxyl, —NR$^x$R$^x$, C$_{1-6}$ alkyl substituted with zero to 6 R$^{5e}$, C$_{1-6}$ alkoxy substituted with zero to 6 R$^{5e}$, or (C$_{1-6}$ alkyl)amino substituted with zero to 6 R$^{5e}$;

each R$^v$ is independently hydrogen, C$_{1-6}$ alkyl, or alternatively, two R$^v$, taken together with the nitrogen atom to which they are attached, form a 4- to 7-membered bicyclic or spirocyclic ring moiety containing zero to 2 additional heteroatoms independently selected from N, O, and S, wherein each ring can be substituted with zero to 6 R$^{2a}$;

each R$^w$ is independently hydrogen, C$_{1-6}$ alkyl, or C$_{3-6}$ cycloalkyl; or alternatively, two R$^w$, taken together with the nitrogen atom to which they are attached, form a 4- to 7-membered ring moiety containing zero to 2 additional heteroatoms independently selected from N, O, and S;

each R$^x$ is independently hydrogen, C$_{1-6}$ alkyl, or C$_{3-6}$ cycloalkyl;

R$^y$ is C$_{1-6}$ alkyl or C$_{3-6}$ cycloalkyl; and each R$^z$ is independently hydrogen, C$_{1-6}$ alkyl, or C$_{3-6}$ cycloalkyl; or alternatively, two R$^z$, taken together with the nitrogen atom to which they are attached, form a 4- to 7-membered ring moiety containing zero to 2 additional heteroatoms independently selected from N, O, and S.

In one embodiment, a compound of Formula (I) or a stereoisomer, a tautomer, or a salt or solvate thereof is provided, wherein X$^1$ is CR$^{5a}$; X$^2$ is CR$^{5b}$; X$^3$ is CR$^{5c}$; X$^4$ is CR$^{5d}$. Compounds of this embodiment have the structure of Formula (Ia):

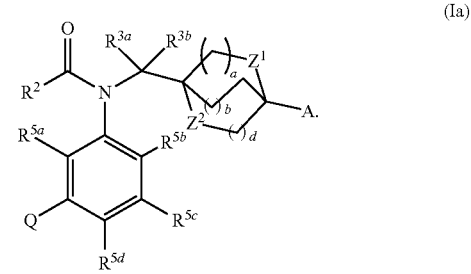

(Ia)

Included in this embodiment are compounds in which each of R$^{5a}$, R$^{5b}$, R$^{5c}$, and R$^{5d}$ is hydrogen.

In one embodiment, a compound of Formula (I) or a stereoisomer, a tautomer, or a salt or solvate thereof is provided, wherein X$^1$ is CR$^{5a}$ or N; X$^2$ is CR$^{5b}$ or N; X$^3$ is CR$^{5c}$ or N; X$^4$ is CR$^{5d}$ or N; and one of X$^1$, X$^2$, X$^3$, and X$^4$ is N. Compounds of this embodiment have one of the following structures: the structure of Formula (Ib), the structure of Formula (Ic), the structure of Formula (Id), and the structure of Formula (Ie):

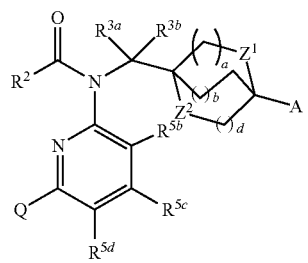
(Ib)

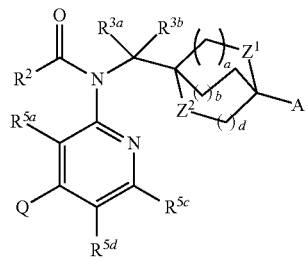
(Ic)

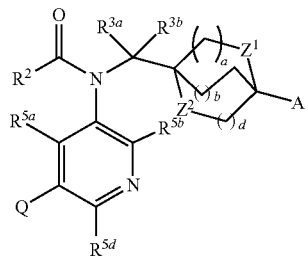
(Id)

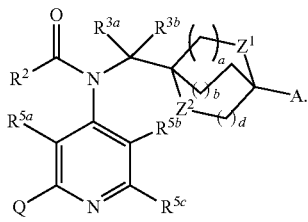
(Ie)

Included in this embodiment are compounds in which each of $R^{5a}$, $R^{5b}$, $R^{5c}$, and $R^{5d}$ is hydrogen.

In one embodiment, a compound of Formula (I) or a stereoisomer, a tautomer, or a salt or solvate thereof is provided, wherein $X^1$ is $CR^{5a}$ or N; $X^2$ is $CR^{5b}$ or N; $X^3$ is $CR^{5c}$ or N; $X^4$ is $CR^{5d}$ or N; and two of $X^1$, $X^2$, $X^3$, and $X^4$ are N. Compounds of this embodiment have one of the following structures: the structure of Formula (If), the structure of Formula (Ig), the structure of Formula (Ih), the structure of Formula (Ii), the structure of Formula (Ij), and the structure of Formula (Ik):

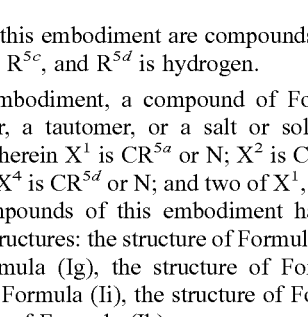
(If)

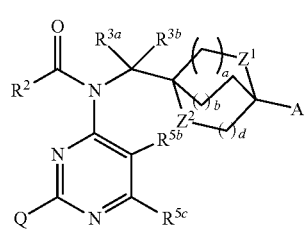
(Ig)

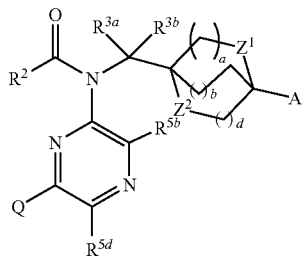
(Ih)

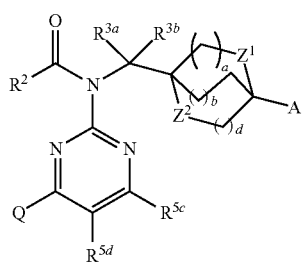
(Ii)

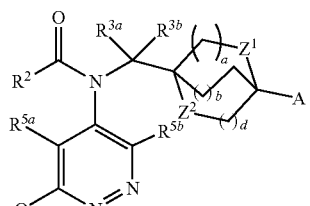
(Ij)

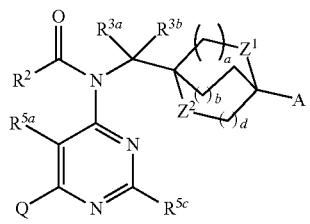
(Ik)

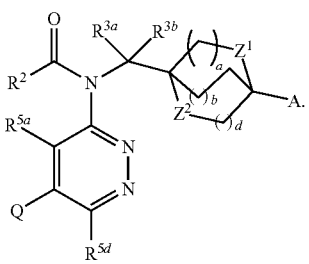

Included in this embodiment are compounds in which each of $R^{5a}$, $R^{5b}$, $R^{5c}$, and $R^{5d}$ is hydrogen.

In one embodiment, a compound of Formula (I) or a stereoisomer, a tautomer, or a salt or solvate thereof is provided, wherein $Z^1$ and $Z^2$ are each $CH_2$. Compounds of this embodiment have the structure of Formula (Il):

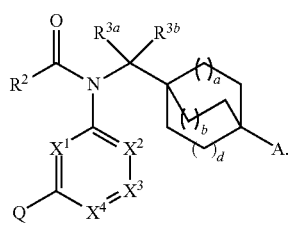

(II)

Included in this embodiment are compounds in which each of a, b, and d are 1. Also included in this embodiment are compounds in which each of a, b, and d are zero. Additionally, included in this embodiment are compounds in which each of a, b, and d are 2.

In one embodiment, a compound of Formula (I) or a stereoisomer, a tautomer, or a salt or solvate thereof is provided, wherein one of $Z^1$ and $Z^2$ is $CH_2$, and the other of $Z^1$ and $Z^2$ is O. Compounds of this embodiment have either the structure of Formula (Im) and the structure of Formula (In):

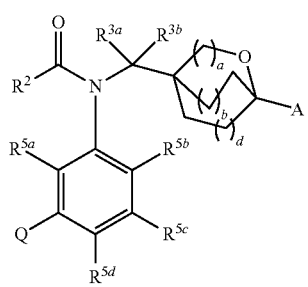

(Im)

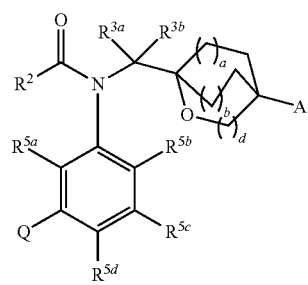

(In)

Included in this embodiment are compounds in which each of a, b, and d are 1. Also included in this embodiment are compounds in which each of a, b, and d are zero. Additionally, included in this embodiment are compounds in which each of a, b, and d are 2.

In one embodiment, a compound of Formula (I) or a stereoisomer, a tautomer, or a salt or solvate thereof is provided, wherein $X^1$ is $CR^{5a}$, and Q and $R^{5a}$ are joined together to form a $-CR^{1a}=CR^1CH_2CH_2-$. Compounds of this embodiment have either the structure of Formula (II):

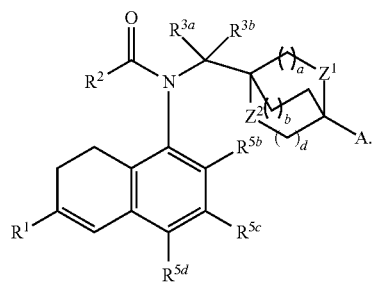

(II)

Included in this embodiment are compounds in which $Z^1$ and $Z^2$ are each $CH_2$. Also included in this embodiment are compounds in which a, b, and d are each 1. Additionally included in this embodiment are compounds in which $R^1$ is $-C(O)OR^x$, $-C(O)NR^xR^x$, or $C_{1-4}$ hydroxyalkyl; and each $R^x$ is independently hydrogen or $-CH_3$.

In one embodiment, a compound of Formula (I) or a stereoisomer, a tautomer, or a salt or solvate thereof is provided, wherein Q is $C_{2-6}$ alkenyl substituted with zero to 2 $R^1$. Included in this embodiment are compounds in which Q is $-CR^{1c}=CR^{1c}R^1$ and each $R^{1c}$ is independently H or $-CH_3$. Also included in this embodiment are compounds in which Q is $-CH=CHC(O)OH$, $-CH=CHC(O)OCH_3$, $-C(CH_3)=CHC(O)OCH_3$, $-CH=CHC(O)N(CH_3)_2$, or $-CH=CH(\text{methyloxadiazolyl})$.

In one embodiment, a compound of Formula (I) or a stereoisomer, a tautomer, or a salt or solvate thereof is provided, wherein Q is $-CR^{1c}=CR^{1c}R^1$ and the compound has the structure of Formula (Ip):

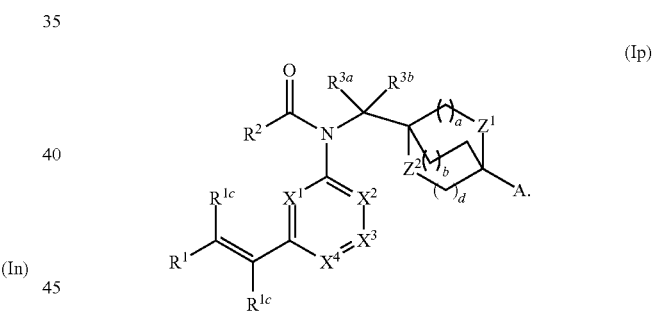

(Ip)

Included in this embodiment are compounds in which $R^1$ is $-C(O)OR^x$, $-C(O)NR^xR^x$, $C_{1-4}$ hydroxyalkyl, or a cyclic group selected from 5- to 6-membered heteroaryl, wherein said cyclic group is substituted with zero to 3 $R^{1a}$. Also included in this embodiment are compounds in which each $R^x$ is independently H, $C_{1-4}$ alkyl, or $C_{3-6}$ cycloalkyl.

In one embodiment, a compound of Formula (I) or a stereoisomer, a tautomer, or a salt or solvate thereof is provided, wherein Q is $C_{2-6}$ alkynyl substituted with zero to 2 $R^1$. Included in this embodiment are compounds in which Q is $-C\equiv CR^1$. Also included in this embodiment are compounds in which Q is $-C\equiv CC(CH_3)_2OH$.

In one embodiment, a compound of Formula (I) or a stereoisomer, a tautomer, or a salt or solvate thereof is provided, wherein A is cyano. Included in this embodiment are compounds in which $X^1$, $X^2$, $X^3$, and $X^4$ are each CH. Also included in this embodiment are compounds in which $Z^1$ and $Z^2$ are each $CH_2$.

In one embodiment, a compound of Formula (I) or a stereoisomer, a tautomer, or a salt or solvate thereof is provided, wherein A is: (i) phenyl or a 5- to 10-membered heteroaryl containing 1 to 4 heteroatoms independently selected from N, O, and S, wherein each of said phenyl and heteroaryl is substituted with zero to 3 $R^{4a}$; or

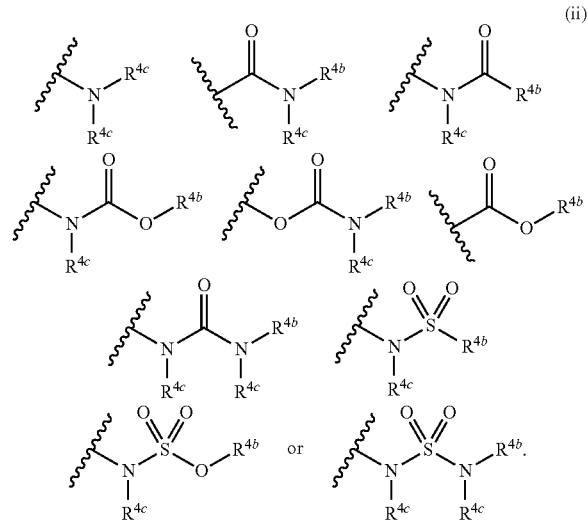

Included in this embodiment are compounds in which A is: (i) phenyl or a 5- to 6-membered heteroaryl containing 1 to 4 heteroatoms independently selected from N, O, and S, wherein each of said phenyl and heteroaryl is substituted with zero to 3 $R^{4a}$; or

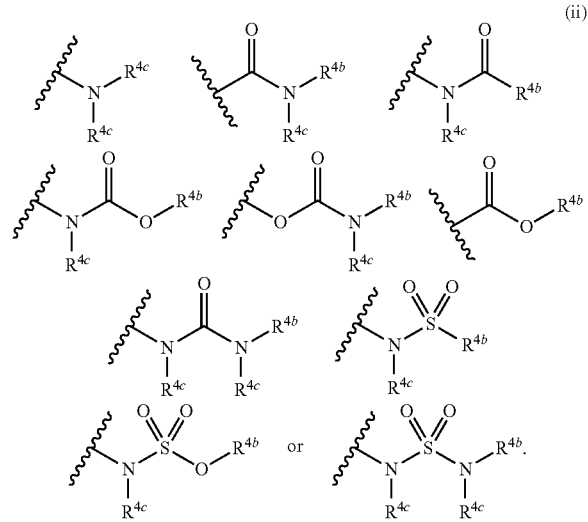

Also included in this embodiment are compounds in which each $R^{4a}$ is independently F, Cl, cyano, hydroxyl, —NH$_2$, $C_{1-4}$ alkyl, $C_{1-4}$ alkoxy, —(CH$_2$)$_{0-3}$NH(C$_{1-6}$ alkyl), —(CH$_2$)$_{0-3}$N(C$_{1-6}$ alkyl)$_2$, —(CH$_2$)$_{0-3}$(C$_{3-6}$ cycloalkyl), or —(CH$_2$)$_{0-3}$(4- to 6-membered heterocyclyl), wherein each of said alkyl and alkoxy is substituted with zero to 4 $R^{4d}$; and each of said cycloalkyl and heterocyclyl is substituted with zero to 3 $R^{4e}$; $R^{4b}$ is $C_{1-4}$ alkyl, —(CH$_2$)$_{0-3}$(C$_{3-6}$ cycloalkyl), or —(CH$_2$)$_{0-3}$(4- to 6-membered heterocyclyl), wherein each of said alkyl is substituted with zero to 4 $R^{4d}$ and each of said cycloalkyl and heterocyclyl is substituted with zero to 3 $R^{4e}$; each $R^{4c}$ is independently hydrogen, $C_{1-3}$ alkyl, or $C_{3-6}$ cycloalkyl; each $R^{4d}$ is independently F, Cl, hydroxyl, —NR$^x$R$^x$, oxo, cyano, $C_{1-3}$ alkoxy, or $C_{1-3}$ fluoroalkoxy; and each $R^{4e}$ is independently F, Cl, oxo, cyano, hydroxyl, —NH$_2$, $C_{1-4}$ alkyl, $C_{1-4}$ alkoxy, or —NH(C$_{1-6}$ alkyl), or —N(C$_{1-6}$ alkyl)$_2$, wherein each of said alkyl and alkoxy is substituted with zero to 4 $R^{4d}$.

In one embodiment, a compound of Formula (I) or a stereoisomer, a tautomer, or a salt or solvate thereof is provided, wherein A is a phenyl or a 5- to 6-membered heteroaryl containing 1 to 4 heteroatoms independently selected from N, O, and S, substituted with zero to 3 $R^{4a}$. Included in this embodiment are compounds in which A is phenyl, furanyl, thiophenyl, pyrrolyl, oxazolyl, thiazolyl, imidazolyl, pyrazolyl, isoxazolyl, isothiazolyl, oxadiazolyl, thiadiazolyl, triazolyl, tetrazolyl, oxatriazolyl, pyridinyl, pyrazinyl, pyrimidinyl, or pyridazinyl, each substituted with zero to 3 $R^{4a}$ Also included in embodiment are compounds in which A is oxadiazolyl, oxazolyl, phenyl, pyrazolyl, pyridinyl, pyrimidinyl, or thiazolyl, each substituted with zero to 2 $R^{4a}$; and each $R^{4a}$ is independently —CH$_3$, —CH(CH$_3$)$_2$, —C(CH$_3$)$_3$, —CH(CH$_3$)$_2$, —CF$_2$CH$_3$, —OCH$_3$, —N(CH$_3$)$_2$, —N(CH$_2$CH$_3$)$_2$, or a cyclic group selected from cyclopropyl, azetidinyl, pyrrolidinyl, tetrahydropyranyl, and morpholinyl. Also included in this embodiment are compounds in which A is oxadiazolyl, phenyl, indazolyl, or benzothiazolyl, each substituted with zero to 1 $R^{4a}$; and each $R^{4a}$ is independently —CH$_3$, —CH(CH$_3$)$_2$, —C(CH$_3$)$_3$, —CH(CH$_3$)$_2$, —CF$_2$CH$_3$, —OCH$_3$, —N(CH$_3$)$_2$, —N(CH$_2$CH$_3$)$_2$, or a cyclic group selected from cyclopropyl, azetidinyl, pyrrolidinyl, tetrahydropyranyl, and morpholinyl.

In one embodiment, a compound of Formula (I) or a stereoisomer, a tautomer, or a salt or solvate thereof is provided, wherein A is:

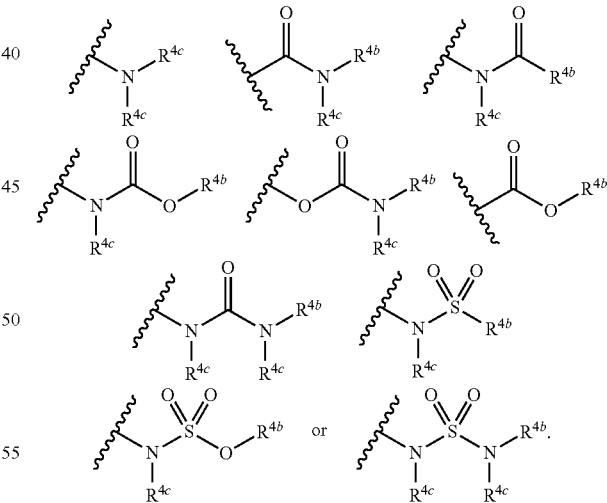

Included in this embodiment are compounds in which $R^{4b}$ is $C_{1-4}$ alkyl, —(CH$_2$)$_{0-3}$(C$_{3-6}$ cycloalkyl), or —(CH$_2$)$_{0-3}$(4- to 6-membered heterocyclyl), wherein each of said alkyl is substituted with zero to 4 $R^{4d}$ and each of said cycloalkyl and heterocyclyl is substituted with zero to 3 $R^{4e}$; each $R^{4c}$ is independently hydrogen, $C_{1-3}$ alkyl, or $C_{3-6}$ cycloalkyl; each $R^{4d}$ is independently F, Cl, hydroxyl, —NR$^x$R$^x$, oxo, cyano, $C_{1-3}$ alkoxy, or $C_{1-3}$ fluoroalkoxy; and each $R^{4e}$ is independently F, Cl, oxo, cyano, hydroxyl, —NH$_2$, $C_{1-4}$ alkyl, $C_{1-4}$ alkoxy, or —NH($C_{1-6}$ alkyl), or —N($C_{1-6}$ alkyl)$_2$, wherein each of said alkyl and alkoxy is substituted with zero to 4 $R^{4d}$.

In one embodiment, a compound of Formula (I) or a stereoisomer, a tautomer, or a salt or solvate thereof is provided, wherein $R^2$ is: (i) $C_{1-6}$ alkyl, $C_{2-6}$ alkenyl, $C_{2-6}$ alkynyl, $C_{1-6}$ alkoxy, or —NR$^v$R$^v$, wherein each of said alkyl, alkenyl, alkynyl, and alkoxy is substituted with zero to 6 $R^{2a}$; or (ii) $C_{3-8}$ carbocyclyl, $C_{6-8}$ spirobicyclyl, 4- to 7-membered heterocyclyl, phenyl, or 5- to 6-membered heteroaryl, wherein each of said carbocyclyl, spirobicyclyl, heterocyclyl, phenyl, and heteroaryl is substituted with zero to 3 $R^{2b}$. Included in this embodiment are compounds in which $R^2$ is: (i) $C_{1-4}$ alkyl, $C_{1-4}$ alkoxy, or —NR$^v$R$^v$, wherein each of said alkyl and alkoxy is substituted with zero to 4 $R^{2a}$; or (ii) $C_{3-8}$ carbocyclyl, $C_{6-8}$ spirobicyclyl, phenyl, or 4- to 7-membered heterocyclyl, wherein each of said carbocyclyl, spirobicyclyl, and heterocyclyl is substituted with zero to 3 $R^{2b}$. Also included in this embodiment are compounds in which $R_2$ is a cyclic group selected from cyclobutyl, cyclohexyl, cycloheptyl, bicyclo[1.1.1]pentyl, piperidinyl, and tetrahydropyranyl, each cyclic group substituted with zero to 1 substituents independently selected from F and —CH$_3$.

In one embodiment, a compound of Formula (I) or a stereoisomer, a tautomer, or a salt or solvate thereof is provided, wherein $R^2$ is —CH$_2$($C_{3-6}$ cycloalkyl), —CH$_2$(4- to 6-membered heterocyclyl), —NR$^x$(CH$_2$)$_{0-2}$($C_{3-6}$ cycloalkyl), —NR$^x$(CH$_2$)$_{0-2}$($C_{5-8}$ bicycloalkyl), —NR$^x$(CH$_2$)$_{0-2}$($C_{5-8}$ spirobicyclyl), —NR$^x$(CH$_2$)$_{0-2}$(4- to 6-membered heterocyclyl), —NR$^x$(CH$_2$)$_{0-2}$(5- to 6-membered heteroaryl), —NR$^x$(CH$_2$)$_{0-2}$(phenyl), —O(CH$_2$)$_{0-2}$($C_{3-6}$ cycloalkyl), —O(CH$_2$)$_{0-2}$($C_{5-8}$ bicycloalkyl), —O(CH$_2$)$_{0-2}$($C_{5-8}$ spirobicyclyl), —O(CH$_2$)$_{0-2}$(4- to 6-membered heterocyclyl), —O(CH$_2$)$_{0-2}$(5- to 6-membered heteroaryl), or —O(CH$_2$)$_{0-2}$(phenyl), wherein each of said cycloalkyl, heterocyclyl, bicycloalkyl, spirobicyclyl, aryl, and heteroaryl is substituted with zero to 3 $R^{2b}$. Included in this embodiment are compounds in which $R^2$ is —CH$_2$($C_{3-5}$ cycloalkyl), —CH$_2$(4- to 6-membered heterocyclyl), —NR$^x$(CH$_2$)$_{0-2}$($C_{3-5}$ cycloalkyl), —NR$^x$(CH$_2$)$_{0-2}$(4- to 6-membered heterocyclyl), —NR$^x$(CH$_2$)$_{0-2}$(phenyl), —O(phenyl), or —S(O)$_2$($C_{3-6}$ cycloalkyl), wherein each of said cycloalkyl, heterocyclyl, phenyl, and pyridinyl is substituted with zero to 3 $R^{2b}$. Also included in this embodiment are compounds in which $R^2$ is —NR$^x$($C_{3-8}$ cycloalkyl), —NR$^x$(phenyl), or —S(O)$_2$($C_{3-6}$ cycloalkyl), wherein each of said phenyl and cycloalkyl is independently substituted with zero to 3 $R^{2b}$.

In one embodiment, a compound of Formula (I) or a stereoisomer, a tautomer, or a salt or solvate thereof is provided, wherein $R^{3a}$ and $R^{3b}$ are independently hydrogen, $C_{1-3}$ alkyl, $C_{1-3}$ fluoroalkyl, or $C_{3-6}$ cycloalkyl; or $R^{3a}$ and $R^{3b}$, taken together with the carbon atom to which they are attached, form a $C_{3-6}$ cycloalkyl. Included in this embodiment are compounds in which $R^{3a}$ and $R^{3b}$ are independently hydrogen, $C_{1-2}$ alkyl, —CH$_2$F, —CHF$_2$, —CF$_3$, or $C_{3-4}$ cycloalkyl; or $R^{3a}$ and $R^{3b}$, taken together with the carbon atom to which they are attached, form a $C_{3-4}$ cycloalkyl. Also included in this embodiment are compounds in which $R^{3a}$ and $R^{3b}$ are independently hydrogen, —CH$_3$, or cyclopropyl; or $R^{3a}$ and $R^{3b}$, taken together with the carbon atom to which they are attached, form a cyclopropyl. Additionally, included in this embodiment are compounds in which one of $R^{3a}$ and $R^{3b}$ is hydrogen or —CH$_3$, and the other of $R^{3a}$ and $R^{3b}$ is hydrogen.

In one embodiment, a compound of Formula (I) or a stereoisomer, a tautomer, or a salt or solvate thereof is provided, wherein:
Q is —CR$^{1c}$=CR$^{1c}$R$^1$ or —C≡CR$^1$;
$R^1$ is —C(O)OR$^x$, —C(O)NR$^x$R$^x$, $C_{1-4}$ hydroxyalkyl, or a cyclic group selected from 5- to 6-membered heteroaryl, wherein said cyclic group is substituted with zero to 3 $R^{1a}$;
each $R^{1a}$ is independently F, Cl, oxo, cyano, hydroxyl, —NH$_2$, $C_{1-4}$ alkyl, $C_{1-4}$ alkoxy, —NH($C_{1-4}$ alkyl), —N($C_{1-4}$ alkyl)$_2$, or —NR$^x$C(O)($C_{1-4}$ alkyl), wherein each of said alkyl and alkoxy is substituted with zero to 4 $R^{1b}$;
each $R^{1b}$ is independently F, Cl, hydroxyl, —NR$^w$R$^w$, cyano, $C_{1-3}$ alkoxy, or $C_{1-3}$ fluoroalkoxy;
each $R^{1c}$ is independently H or —CH$_3$;
or when $X^1$ is CR$^{5a}$, $X^2$ is CR$^{5b}$, $X^3$ is CR$^{5c}$, $X^4$ is CR$^{5d}$, then Q and $R^{5a}$ can be joined together to form a —CR$^{1a}$=CR$^1$CH$_2$CH$_2$— bridge;
$R^2$ is:
(i) $C_{1-4}$ alkyl, $C_{1-4}$ alkoxy, or —NR$^v$R$^v$, wherein each of said alkyl and alkoxy is substituted with zero to 4 $R^{2a}$;
(ii) $C_{3-8}$ carbocyclyl, $C_{6-8}$ spirobicyclyl, phenyl, or 4- to 7-membered heterocyclyl, wherein each of said carbocyclyl, spirobicyclyl, and heterocyclyl is substituted with zero to 3 $R^{2b}$; or
(iii) —CH$_2$($C_{3-5}$ cycloalkyl), —CH$_2$(4- to 6-membered heterocyclyl), —NR$^x$(CH$_2$)$_{0-2}$($C_{3-5}$ cycloalkyl), —NR$^x$(CH$_2$)$_{0-2}$(4- to 6-membered heterocyclyl), —NR$^x$(CH$_2$)$_{0-2}$(phenyl), —O(phenyl), or —S(O)$_2$($C_{3-6}$ cycloalkyl), wherein each of said cycloalkyl, heterocyclyl, and phenyl is substituted with zero to 3 $R^{2b}$;
each $R^{2a}$ is independently F, Cl, hydroxyl, —NR$^x$R$^x$, oxo, cyano, $C_{1-3}$ alkoxy, $C_{1-3}$ haloalkoxy, or —C(O)OH;
each $R^{2b}$ is independently F, Cl, cyano, hydroxyl, $C_{1-4}$ alkyl, $C_{1-3}$ alkoxy, —NR$^x$R$^x$, —NR$^x$C(O)O($C_{1-3}$ alkyl), —C(O)($C_{1-2}$ alkyl), or —S(O)$_2$($C_{1-2}$ alkyl), wherein each of said alkyl and alkoxy is substituted with zero to 4 $R^{2a}$;
A is:
(i) cyano;
(ii) phenyl or a 5- to 6-membered heteroaryl containing 1 to 4 heteroatoms independently selected from N, O, and S, wherein each of said phenyl and heteroaryl is substituted with zero to 3 $R^{4a}$; or

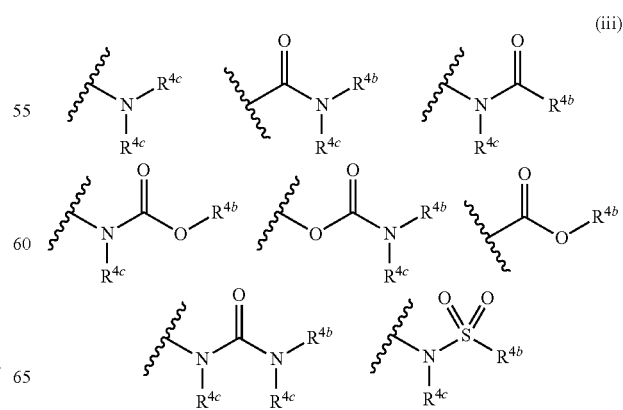

(iii)

-continued

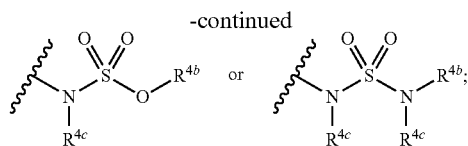

each $R^{4a}$ is independently F, Cl, cyano, hydroxyl, —NH$_2$, C$_{1-4}$ alkyl, C$_{1-4}$ alkoxy, —(CH$_2$)$_{0-3}$NH(C$_{1-6}$ alkyl), —(CH$_2$)$_{0-3}$N(C$_{1-6}$ alkyl)$_2$, —(CH$_2$)$_{0-3}$(C$_{3-6}$ cycloalkyl), or —(CH$_2$)$_{0-3}$(4- to 6-membered heterocyclyl), wherein each of said alkyl and alkoxy is substituted with zero to 4 $R^{4d}$ and each of said cycloalkyl and heterocyclyl is substituted with zero to 3 $R^{4e}$;

$R^{4b}$ is C$_{1-4}$ alkyl, —(CH$_2$)$_{0-3}$(C$_{3-6}$ cycloalkyl), or —(CH$_2$)$_{0-3}$(4- to 6-membered heterocyclyl), wherein each of said alkyl is substituted with zero to 4 $R^{4d}$ and each of said cycloalkyl and heterocyclyl is substituted with zero to 3 $R^{4e}$;

each $R^{4c}$ is independently hydrogen, C$_{1-3}$ alkyl, or C$_{3-6}$ cycloalkyl;

each $R^{4d}$ is independently F, Cl, hydroxyl, —NR$^x$R$^x$, oxo, cyano, C$_{1-3}$ alkoxy, or C$_{1-3}$ fluoroalkoxy;

each $R^{4e}$ is independently F, Cl, oxo, cyano, hydroxyl, —NH$_2$, C$_{1-4}$ alkyl, C$_{1-4}$ alkoxy, or —NH(C$_{1-6}$ alkyl), or —N(C$_{1-6}$ alkyl)$_2$, wherein each of said alkyl and alkoxy is substituted with zero to 4 $R^{4d}$;

each of $R^{5a}$, $R^{5b}$, $R^{5c}$, and $R^{5d}$ is independently hydrogen, F, Cl, hydroxy, cyano, C$_{1-3}$ alkyl substituted with zero to 4 $R^{5e}$, C$_{1-3}$ alkoxy substituted with zero to 4 $R^{5e}$, —C(O)OR$^x$, —C(O)NR$^w$R$^w$, —S(O)$_2$R$^y$, —S(O)$_2$NR$^z$R$^z$, or phenyl substituted with zero to 3 $R^{5f}$;

each $R^w$ is independently hydrogen, C$_{1-4}$ alkyl, or C$_{3-6}$ cycloalkyl; or alternatively, two $R^w$, taken together with the nitrogen atom to which they are attached, form a 4- to 7-membered ring moiety containing zero to 2 additional heteroatoms independently selected from N, O, and S;

each $R^x$ is independently H, C$_{1-4}$ alkyl, or C$_{3-6}$ cycloalkyl; $R^y$ is C$_{1-4}$ alkyl or C$_{3-6}$ cycloalkyl; and each $R^z$ is independently hydrogen, C$_{1-4}$ alkyl, or C$_{3-6}$ cycloalkyl; or alternatively, two $R^z$, taken together with the nitrogen atom to which they are attached, form a 4- to 7-membered ring moiety containing zero to 2 additional heteroatoms independently selected from N, O, and S.

In one embodiment, a compound of Formula (I) or a stereoisomer, a tautomer, or a salt or solvate thereof is provided, wherein: $X^1$ is CH; $X^2$ is CH; $X^3$ is CH; $X^4$ is CH; a is 1; b is 1; d is 1; Q is —CH═CHC(O)OH, —CH═CHC(O)OCH$_3$, —C(CH$_3$)═CHC(O)OCH$_3$, —CH═CHC(O)N(CH$_3$)$_2$, —CH═CH(methyloxadiazolyl), or —C≡CC(CH$_3$)$_2$OH; $R^2$ is —CH(CH$_3$)$_2$ or a cyclic group selected from cyclobutyl, cyclohexyl, cycloheptyl, bicyclo[1.1.1]pentyl, piperidinyl, and tetrahydropyranyl, each cyclic group substituted with zero to 1 substituents independently selected from F and —CH$_3$; $R^{3a}$ is hydrogen or —CH$_3$; $R^{3b}$ is hydrogen; A is oxadiazolyl, phenyl, indazolyl, or benzothiazolyl, each substituted with zero to 1 $R^{4a}$; and each $R^{4a}$ is independently —CH$_3$, —CH(CH$_3$)$_2$, —C(CH$_3$)$_3$, —CH(CH$_3$)$_2$, —CF$_2$CH$_3$, —OCH$_3$, —N(CH$_3$)$_2$, —N(CH$_2$CH$_3$)$_2$, or a cyclic group selected from cyclopropyl, azetidinyl, pyrrolidinyl, tetrahydropyranyl, and morpholinyl.

In one embodiment, a compound of Formula (I) or a stereoisomer, a tautomer, or a salt or solvate thereof is provided, wherein: wherein said compound is: methyl (E)-3-(3-(N-((4-(4-(dimethylamino)phenyl)bicyclo[2.2.2]octan-1-yl)methyl)cyclohexanecarboxamido)phenyl)acrylate (1); (E)-3-(3-(N-((4-(4-dimethylamino)phenyl) bicyclo[2.2.2]octan-1-yl)methyl)cyclohexanecarboxamido)phenyl)acrylic acid (2); (E)-methyl 3-(3-(N-((4-(4-morpholinophenyl)bicyclo[2.2.2]octan-1-yl)methyl)cyclohexanecarboxamido)phenyl)acrylate (3); (E)-methyl 3-(3-(N-((4-(4-(pyrrolidin-1-yl)phenyl)bicyclo[2.2.2]octan-1-yl)methyl)cyclohexanecarboxamido)phenyl)acrylate (4); (E)-methyl 3-(3-(N-((4-(4-(azetidin-1-yl)phenyl)bicyclo[2.2.2]octan-1-yl)methyl)cyclohexanecarboxamido)phenyl)acrylate (5); methyl (E)-3-(3-(N-((4-(4-(dimethylamino)phenyl)bicyclo[2.2.2]octan-1-yl)methyl)tetrahydro-2H-pyran-4-carboxamido)phenyl) acrylate (6); methyl (E)-3-(3-(N-((4-phenylbicyclo[2.2.2]octan-1-yl)methyl)cyclohexanecarboxamido)phenyl) acrylate (7); (E)-methyl 3-(3-(N-((1-(1-methyl-1H-indazol-5-yl)-2-oxabicyclo[2.2.2]octan-4-yl)methyl)tetrahydro-2H-pyran-4-carboxamido)phenyl)acrylate (8); (E)-methyl 3-(3-(1-methyl-N-((1-(1-methyl-1H-indazol-5-yl)-2-oxabicyclo[2.2.2]octan-4-yl)methyl)piperidine-4-carboxamido) phenyl) acrylate (9); methyl (E)-3-(3-(N-((1-(4-methoxyphenyl)-2-oxabicyclo[2.2.2]octan-4-yl)methyl) cyclohexanecarboxamido)phenyl)acrylate (10); methyl (E)-3-(3-(N-((4-(4-morpholinophenyl)bicyclo[2.2.2]octan-1-yl)methyl)cyclohexanecarboxamido)phenyl) but-2-enoate (14); methyl (E)-3-(3-(N-((4-(4-methoxyphenyl)bicyclo[2.2.2]octan-1-yl)methyl)cyclohexanecarboxamido)phenyl) acrylate (15); methyl (E)-3-(3-(N-((4-(4-methoxyphenyl)bicyclo[2.2.2]octan-1-yl)methyl)cyclohexanecarboxamido)phenyl)but-2-enoate (16); methyl (E)-3-(3-(N-((4-(3-methyl-1,2,4-oxadiazol-5-yl)bicyclo[2.2.2]octan-1-yl)methyl)cyclohexanecarboxamido)phenyl)but-2-enoate (19); methyl (E)-3-(3-(N-((4-(3-methyl-1,2,4-oxadiazol-5-yl)bicyclo[2.2.2]octan-1-yl)methyl)cyclohexanecarboxamido)phenyl)acrylate (20); methyl (E)-3-(3-(N-((4-(3-methyl-1,2,4-oxadiazol-5-yl)bicyclo[2.2.2]octan-1-yl)methyl)cyclopropanecarboxamido)phenyl) acrylate (21); methyl (E)-3-(3-(N-((4-(3-methyl-1,2,4-oxadiazol-5-yl) bicyclo[2.2.2]octan-1-yl)methyl)isobutyramido)phenyl)acrylate (22); methyl (E)-3-(3-(N-((4-(3-methyl-1,2,4-oxadiazol-5-yl)bicyclo[2.2.2]octan-1-yl)methyl)tetrahydro-2H-pyran-4-carboxamido)phenyl)acrylate (23); methyl (E)-3-(3-(N-((4-(3-methyl-1,2,4-oxadiazol-5-yl)bicyclo[2.2.2]octan-1-yl)methyl)cycloheptanecarboxamido)phenyl) acrylate (24); methyl (E)-3-(3-(3-fluoro-N-((4-(3-methyl-1,2,4-oxadiazol-5-yl) bicyclo[2.2.2]octan-1-yl)methyl)bicyclo[1.1.1]pentane-1-carboxamido)phenyl)acrylate (25); methyl (E)-3-(3-(3,3-difluoro-N-((4-(3-methyl-1,2,4-oxadiazol-5-yl) bicyclo[2.2.2]octan-1-yl)methyl)cyclobutane-1-carboxamido) phenyl)acrylate (26); (E)-N-(3-(3-(dimethylamino)-3-oxoprop-1-en-1-yl)phenyl)-N-((4-(3-methyl-1,2,4-oxadiazol-5-yl)bicyclo[2.2.2]octan-1-yl)methyl) cyclohexanecarboxamide (27); methyl (E)-3-(3-(N-((4-(4-cyclopropylphenyl)bicyclo[2.2.2]octan-1-yl)methyl) cyclopropanecarboxamido)phenyl)acrylate (28); methyl (E)-3-(3-(N-((4-(4-cyclopropylphenyl)bicyclo[2.2.2]octan-1-yl)methyl)cyclohexanecarboxamido)phenyl)acrylate (29); methyl (E)-3-(3-(N-((4-(benzo[d]thiazol-2-yl)bicyclo[2.2.2]octan-1-yl)methyl)cyclopropanecarboxamido)phenyl)acrylate (33); methyl (E)-3-(3-(N-((4-(benzo[d]thiazol-2-yl)bicyclo[2.2.2]octan-1-yl)methyl)cyclohexanecarboxamido) phenyl)acrylate (34); (E)-N-((4-(4-methoxyphenyl)bicyclo[2.2.2]octan-1-yl)methyl)-N-(3-(2-(3-methyl-1,2,4-oxadiazol-5-yl)vinyl)phenyl)cyclohexanecarboxamide (35); methyl (E)-3-(3-(N-((4-(4-cyclopropylphenyl)bicyclo[2.2.2]octan-1-yl)methyl)cyclopropanecarboxamido)phenyl) but-2-enoate (36); methyl (E)-3-(3-(N-((4-(4-cyclopropylphenyl)bicyclo[2.2.2]octan-1-yl)methyl)cyclohexanecarboxamido)phenyl)but-2-enoate (37); methyl (E)-3-(3-(N-((4-(4-isopropylphenyl)bicyclo[2.2.2]octan-1-yl)methyl)cyclohexanecarboxamido)phenyl) acrylate (38); methyl (E)-3-(3-(N-((4-(4-isopropylphenyl)bicyclo[2.2.2]octan-1-yl)methyl)cyclopropanecarboxamido)phenyl)acrylate (39); methyl (E)-3-(3-(N-((4-(3-cyclopropyl-1,2,4-oxadiazol-5-yl)bicyclo[2.2.2]octan-1-yl)methyl)cyclohexane carboxamido)phenyl)acrylate (41); methyl (E)-3-(3-(N-((4-(3-morpholino-1,2,4-oxadiazol-5-yl)bicyclo[2.2.2]octan-1-yl)methyl)cyclohexanecarboxamido)phenyl) acrylate (42); methyl (E)-3-(3-(N-((4-(3-(tetrahydro-2H-pyran-4-yl)-1,2,4-oxadiazol-5-yl)bicyclo[2.2.2]octan-1-yl)methyl)cyclohexanecarboxamido)phenyl)acrylate (43); methyl (E)-3-(3-(N-((4-(5-methyl-1,2,4-oxadiazol-3-yl)bicyclo[2.2.2]octan-1-yl)methyl)cyclohexanecarboxamido)phenyl)acrylate (44); methyl (E)-3-(3-(N-(1-(4-(3-methyl-1,2,4-oxadiazol-5-yl)bicyclo[2.2.2]octan-1-yl)ethyl)cyclohexanecarboxamido)phenyl) acrylate (46-47); N-((4-(5-(tert-Butyl)-1,3,4-oxadiazol-2-yl)bicyclo[2.2.2]octan-1-yl) methyl)-3-fluoro-N-(3-(3-hydroxy-3-methylbut-1-yn-1-yl)phenyl)bicyclo[1.1.1]pentane-1-carboxamide (48); or N-((4-(5-(1,1-difluoroethyl)-1,2,4-oxadiazol-3-yl) bicyclo[2.2.2]octan-1-yl)methyl)-3-fluoro-N-(3-(3-hydroxy-3-methylbut-1-yn-1-yl)phenyl)bicyclo[1.1.1]pentane-1-carboxamide (49).

In one embodiment, a compound of Formula (I) or a stereoisomer, a tautomer, or a salt or solvate thereof is provided wherein said compound is: methyl 5-(N-((4-(4-morpholinophenyl)bicyclo[2.2.2]octan-1-yl)methyl)cyclohexanecarboxamido)-3,4-dihydronaphthalene-2-carboxylate (11); methyl 5-(N-((4-(4-(dimethylamino)phenyl)bicyclo[2.2.2]octan-1-yl)methyl)cyclohexanecarboxamido)-3,4-dihydronaphthalene-2-carboxylate (12); methyl 5-(N-((4-(4-(diethylamino)phenyl)bicyclo[2.2.2]octan-1-yl)methyl)cyclohexanecarboxamido)-3,4-dihydronaphthalene-2-carboxylate (13); 5-(N-((4-(4-methoxyphenyl)bicyclo[2.2.2]octan-1-yl)methyl)cyclohexanecarboxamido)-3,4-dihydronaphthalene-2-carboxylic acid (17); methyl 5-(N-((4-(4-methoxyphenyl) bicyclo[2.2.2]octan-1-yl)methyl)cyclohexanecarboxamido)-3,4-dihydronaphthalene-2-carboxylate (18); methyl 5-(N-((4-(4-cyclopropylphenyl)bicyclo[2.2.2]octan-1-yl)methyl)cyclohexanecarboxamido)-3,4-dihydronaphthalene-2-carboxylate (30); methyl 5-(N-((4-(4-cyclopropylphenyl)bicyclo[2.2.2]octan-1-yl)methyl)cyclopropanecarboxamido)-3,4-dihydronaphthalene-2-carboxylate (31); methyl 5-(N-((4-(4-cyclopropylphenyl)bicyclo[2.2.2]octan-1-yl)methyl)isobutyramido)-3,4-dihydronaphthalene-2-carboxylate (32); methyl 5-(N-((4-(3-methyl-1,2,4-oxadiazol-5-yl) bicyclo[2.2.2]octan-1-yl)methyl)cyclohexanecarboxamido)-3,4-dihydronaphthalene-2-carboxylate (40); or methyl 5-(N-((1-(1-methyl-1H-indazol-5-yl)-2-oxabicyclo[2.2.2]octan-4-yl)methyl)cyclohexanecarboxamido)-3,4-dihydronaphthalene-2-carboxylate (45).

The present invention may be embodied in other specific forms without departing from the spirit or essential attributes thereof. This invention encompasses all combinations of the aspects and/or embodiments of the invention noted herein. It is understood that any and all embodiments of the present invention may be taken in conjunction with any other embodiment or embodiments to describe additional embodiments. It is also to be understood that each individual element of the embodiments is meant to be combined with any and all other elements from any embodiment to describe an additional embodiment.

Definitions

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phrase "compounds and/or salts thereof" refers to at least one compound, at least one salt of the compounds, or a combination thereof. For example, compounds of Formula (I) and/or salts thereof includes a compound of Formula (I); two compounds of Formula (I); a salt of a compound of Formula (I); a compound of Formula (I) and one or more salts of the compound of Formula (I); and two or more salts of a compound of Formula (I).

Unless otherwise indicated, any atom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The terms "halo" and "halogen," as used herein, refer to F, Cl, Br, and I.

The term "cyano" refers to the group —CN.
The term "hydroxy" refers to the group —OH.
The term "amino" refers to the group —NH$_2$.
The term "oxo" refers to the group =O.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-4}$ alkyl" denotes straight and branched chain alkyl groups with one to four carbon atoms.

The term "haloalkyl" as used herein is intended to include both branched and straight-chain saturated aliphatic hydrocarbon groups substituted with one or more halo atoms. For example, "$C_{1-4}$ haloalkyl" is intended to include $C_1$, $C_2$, $C_3$, and $C_4$ alkyl groups substituted with one or more halo atoms. Representative examples of haloalkyl groups include, but are not limited to, —$CF_3$, —$CCl_3$, —$CHF_2$, and —$CF_2CCl_3$.

The term "fluoroalkyl" as used herein is intended to include both branched and straight-chain saturated aliphatic hydrocarbon groups substituted with one or more fluorine atoms. For example, "$C_{1-4}$ fluoroalkyl" is intended to include $C_1$, $C_2$, $C_3$, and $C_4$ alkyl groups substituted with one or more fluorine atoms. Representative examples of fluoroalkyl groups include, but are not limited to, —$CF_3$ and —$CH_2CF_3$.

The term "hydroxyalkyl" as used herein is intended to include both branched and straight-chain saturated aliphatic hydrocarbon groups substituted with one or more hydroxyl groups. For example, "$C_{1-4}$ hydroxyalkyl" is intended to include $C_1$, $C_2$, $C_3$, and $C_4$ alkyl groups substituted with one or more hydroxyl groups. Representative examples of fluoroalkyl groups include, but are not limited to, —$CH_2OH$, —$CH_2CH_2OH$, and —$C(CH_3)_2OH$.

The term "alkenyl" refers to a straight or branched chain hydrocarbon radical containing from 2 to 12 carbon atoms and at least one carbon-carbon double bond. Exemplary such groups include ethenyl or allyl. For example, "$C_{2-6}$ alkenyl" denotes straight and branched chain alkenyl groups with two to six carbon atoms.

The term "alkynyl" refers to a straight or branched chain hydrocarbon radical containing from 2 to 12 carbon atoms and at least one carbon to carbon triple bond. Exemplary such groups include ethynyl. For example, "$C_{2-6}$ alkynyl" denotes straight and branched chain alkynyl groups with two to six carbon atoms.

The term "alkoxy" as used herein, refers to an alkyl group attached to the parent molecular moiety through an oxygen atom, for example, methoxy group (—$OCH_3$). For example, "$C_{1-3}$ alkoxy" denotes alkoxy groups with one to three carbon atoms.

The terms "haloalkoxy" and "—O(haloalkyl)" represent a haloalkyl group as defined above attached through an oxygen linkage (—O—). For example, "$C_{1-4}$ haloalkoxy" is intended to include $C_1$, $C_2$, $C_3$, and $C_4$ haloalkoxy groups.

The terms "fluoroalkoxy" and "—O(fluoroalkyl)" represent a fluoroalkyl group as defined above attached through an oxygen linkage (—O—). For example, "$C_{1-4}$ fluoroalkoxy" is intended to include $C_1$, $C_2$, $C_3$, and $C_4$ fluoroalkoxy groups.

The term "cycloalkyl," as used herein, refers to a group derived from a non-aromatic monocyclic or polycyclic hydrocarbon molecule by removal of one hydrogen atom from a saturated ring carbon atom. Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "$C_{3-6}$ cycloalkyl" denotes cycloalkyl groups with three to six carbon atoms.

The terms "carbocyclo", "carbocyclic" or "carbocyclyl" may be used interchangeably and refer to cyclic groups having at least one saturated or partially saturated non-aromatic ring wherein all atoms of all rings are carbon, and includes groups having one or more bridged rings in which the bridged ring occurs when one or more carbon atoms link two non-adjacent carbon atoms. The term includes nonaromatic rings such as for example, cycloalkyl and cycloalkenyl, bicyclo[1.1.1]pentyl, bicyclo[2.2.2]octanyl, adamantyl, and tetrahydronaphthyl.

The term "bicycloalkyl," as used herein, refers to a carbocyclyl group having a at least one bridge. Representative examples of bicycloalkyl groups include, but are not limited to, bicyclo[1.1.1]pentyl, bicyclo[2.2.2]octanyl, and adamantyl.

The term "aryl" as used herein, refers to a group of atoms derived from a molecule containing aromatic ring(s) by removing one hydrogen that is bonded to the aromatic ring(s). Representative examples of aryl groups include, but are not limited to, phenyl and naphthyl. The aryl ring may be unsubstituted or may contain one or more substituents as valence allows.

The term "heteroatom" refers to oxygen (O), sulfur (S), and nitrogen (N).

The terms "heterocyclo", "heterocyclic", or "heterocyclyl" may be used interchangeably and refer to cyclic groups having at least saturated or partially saturated non-aromatic ring and wherein one or more of the rings have at least one heteroatom (0, S or N), said heteroatom containing ring preferably having 1 to 3 heteroatoms independently selected from O, S, and/or N. The ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The heterocyclo group may be attached at any available nitrogen or carbon atom. The heterocyclo ring may be unsubstituted or may contain one or more substituents as valence allows.

Exemplary monocyclic heterocyclyl groups include pyrrolidinyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane, tetrahydro-1,1-dioxothienyl, dihydroisoindolyl, and tetrahydroquinolinyl.

The terms "spirobicyclyl" and spirobicyclo" may be used interchangeably and refer to bicyclic groups in which the two rings are attached at a single carbon atom that is a member of each of the two rings. The term includes both spirobicycloalkyls, in which the two rings are cycloalkyl rings attached at a single carbon atom that is a member of each of the two rings, and spirobicycloheteroalkyls, in which one ring is a heterocyclyl ring and the other ring is a cycloalkyl ring attached at a single carbon atom that is a member of each of the two rings, or in which both rings are heterocyclyl rings attached at a single carbon atom that is a member of each of the two rings. Examples of spirobicyclyl groups include spiro[3.3]heptenyl, spiro[3.4]octanyl, azaspiro[3.3]heptanyl, oxaazaspiro[3.3]heptanyl, oxaazaspiro[3.3]heptanyl, and azaspiro[3.4]octanyl.

The term "heteroaryl" refers to substituted and unsubstituted aromatic 5- or 6-membered monocyclic groups and 9- or 10-membered bicyclic groups that have at least one heteroatom (0, S or N) in at least one of the rings, said heteroatom-containing ring preferably having 1, 2, or 3 heteroatoms independently selected from O, S, and/or N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic group are aromatic and may contain only carbon atoms. The nitrogen and sulfur atoms may optionally be oxidized and the nitrogen atoms may optionally be quaternized. Bicyclic heteroaryl groups must include only aromatic rings. The heteroaryl group may be attached at any available nitrogen or carbon atom of any ring. The heteroaryl ring system may be unsubstituted or may contain one or more substituents.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thiophenyl, oxadiazolyl, pyridinyl, pyrazinyl, pyrimidinyl, pyridazinyl, and triazinyl.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, and pyrrolopyridyl.

As used herein, the term "tautomer" refers to each of two or more isomers of a compound that exist together in equilibrium, and are readily interchanged by migration of an atom or group within the molecule. For example, one skilled in the art would readily understand that a 1,2,3-triazole exists in two tautomeric forms as defined above:

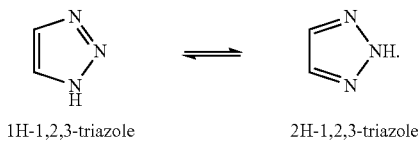 [SMILES: c1c[nH]nn1 ; c1cn[nH]n1]

1H-1,2,3-triazole     2H-1,2,3-triazole

Thus, this disclosure is intended to cover all possible tautomers even when a structure depicts only one of them. For example, the compounds of Formula (Ia) wherein when $R^{5c}$ is hydroxy and each of $R^{5a}$, $R^{5b}$, and $R^{5d}$ are hydrogen, can exist in tautomeric forms:

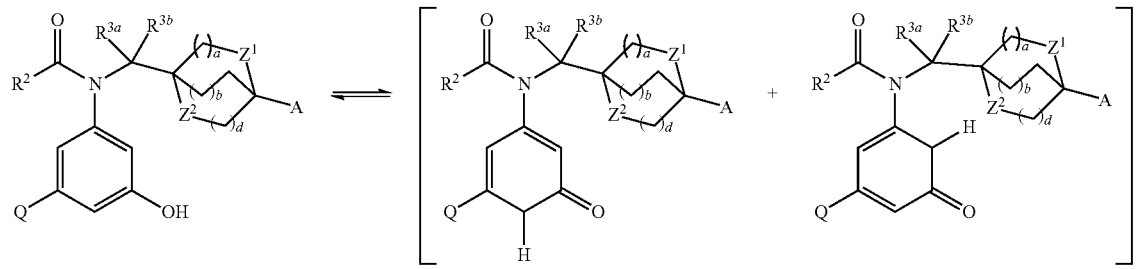

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) can form salts which are also within the scope of this invention. Unless otherwise indicated, reference to an inventive compound is understood to include reference to one or more salts thereof. The term "salt(s)" denotes acidic and/or basic salts formed with inorganic and/or organic acids and bases. In addition, the term "salt(s) may include zwitterions (inner salts), e.g., when a compound of Formula (I) contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula (I) may be formed, for example, by reacting a compound of the Formula (I) with an amount of acid or base, such as an equivalent amount, in a medium such as one in which the salt precipitates or in an aqueous medium followed by lyophilization. Lists of suitable salts are found in *Remington's Pharmaceutical Sciences,* 18th Edition, Mack Publishing Company, Easton, PA (1990), the disclosure of which is hereby incorporated by reference.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, maleates (formed with maleic acid), 2-hydroxyethanesulfonates, lactates, methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-Q-phenethylamine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

The compounds of Formula (I) can be provided as amorphous solids or crystalline solids. Lyophilization can be employed to provide the compounds of Formula (I) as a solid.

It should further be understood that solvates (e.g., hydrates) of the Compounds of Formula (I) are also within the scope of the present invention. The term "solvate" means a physical association of a compound of Formula (I) with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

Various forms of prodrugs are well known in the art and are described in:
a) *The Practice of Medicinal Chemistry*, Camille G. Wermuth et al., Ch 31, (Academic Press, 1996);
b) *Design of Prodrugs*, edited by H. Bundgaard, (Elsevier, 1985);
c) *A Textbook of Drug Design and Development*, P. Krogsgaard-Larson and H. Bundgaard, eds. Ch 5, pgs 113-191 (Harwood Academic Publishers, 1991); and
d) *Hydrolysis in Drug and Prodrug Metabolism*, Bernard Testa and Joachim M. Mayer, (Wiley-VCH, 2003).
e) Rautio, J. et al., *Nature Review Drug Discovery*, 17, 559-587, (2018).

In addition, compounds of Formula (I), subsequent to their preparation, can be isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an agonist of FXR, or effective to treat or prevent disorders associated with dysregulation of bile acids, such as pathological fibrosis, cancer, inflammatory disorders, metabolic, or cholestatic disorders.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

In another embodiment, the present invention provides a composition comprising at least one of the compounds of the present invention, or a stereoisomer, a tautomer, or a pharmaceutically acceptable salt or a solvate thereof.

In another embodiment, the present invention provides a pharmaceutical composition comprising a pharmaceutically acceptable carrier and at least one of the compounds of the present invention or a stereoisomer, a tautomer, or a pharmaceutically acceptable salt or a solvate thereof.

In another embodiment, the present invention provides a pharmaceutical composition, comprising a pharmaceutically acceptable carrier and a therapeutically effective amount of at least one of the compounds of the present invention or a stereoisomer, a tautomer, or a pharmaceutically acceptable salt or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition as defined above further comprising one or more additional therapeutic agents.

Utility

In one embodiment, the present invention provides a method for the treatment of a disease, disorder, or condition associated with dysregulation of bile acids in a patient in need of such treatment, and the method comprises administering a therapeutically effective amount of a compound of the present invention, or a stereoisomer, a tautomer, or a pharmaceutically acceptable salt or solvate thereof, to the patient.

In another embodiment, the present invention provides a method for the treatment of a disease, disorder, or condition associated with activity of farnesoid X receptor (FXR) in a patient in need of such treatment comprising administering a therapeutically effective amount of a compound of the present invention, or a stereoisomer, a tautomer, or a pharmaceutically acceptable salt or solvate thereof, to the patient.

In another embodiment, the present invention provides a method for the treatment of the disease, disorder, or condition comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a method for eliciting an farnesoid X receptor (FXR) agonizing effect in a patient comprising administering a therapeutically effective amount of a compound of the present invention, or a stereoisomer, a tautomer, or a pharmaceutically acceptable salt or solvate thereof, to the patient.

In some embodiments, the disease, disorder, or condition is associated with FXR dysfunction include pathological fibrosis, cancer, inflammatory disorders, metabolic, or cholestatic disorders.

In some embodiments, the disease, disorder, or condition is associated with fibrosis, including liver, biliary, renal, cardiac, dermal, ocular, and pancreatic fibrosis.

In other embodiments, the disease, disorder, or condition is associated with cell-proliferative disorders, such as cancer. In some embodiments, the cancer includes solid tumor growth or neoplasia. In other embodiments, the cancer includes tumor metastasis. In some embodiments, the cancer is of the liver, gall bladder, small intestine, large intestine, kidney, prostate, bladder, blood, bone, brain, breast, central nervous system, cervix, colon, endometrium, esophagus, genitalia, genitourinary tract, head, larynx, lung, muscle tissue, neck, oral or nasal mucosa, ovary, pancreas, skin, spleen, stomach, testicle, or thyroid. In other embodiments, the cancer is a carcinoma, sarcoma, lymphoma, leukemia, melanoma, mesothelioma, multiple myeloma, or seminoma.

Examples of diseases, disorders, or conditions associated with the activity of FXR that can be prevented, modulated, or treated according to the present invention include, but are not limited to, transplant injection, fibrotic disorders (e.g., liver fibrosis, kidney fibrosis), inflammatory disorders (e.g., acute hepatitis, chronic hepatitis, non-alcoholic steatohepatitis (NASH), irritable bowel syndrome (IBS), inflammatory bowel disease (IBD)), as well as cell-proliferative disorders (e.g., cancer, myeloma, fibroma, hepatocellular carcinoma, colorectal cancer, prostate cancer, leukemia, Kaposi's sarcoma, solid tumors).

The fibrotic disorders, inflammatory disorders, as well as cell-proliferative disorders that are suitable to be prevented or treated by the compounds of the present invention include, but are not limited to, non-alcoholic fatty liver disease (NAFLD), alcoholic or non-alcoholic steatohepatitis (NASH), acute hepatitis, chronic hepatitis, liver cirrhosis, primary biliary cirrhosis, primary sclerosing cholangitis, drug-induced hepatitis, biliary cirrhosis, portal hypertension, regenerative failure, liver hypofunction, hepatic blood flow disorder, nephropathy, irritable bowel syndrome (IBS), inflammatory bowel disease (IBD), abnormal pancreatic secretion, benign prostatic hyperplasia, neuropathic bladder disease, diabetic nephropathy, focal segmental glomerulosclerosis, IgA nephropathy, nephropathy induced by drugs or transplantation, autoimmune nephropathy, lupus nephritis, liver fibrosis, kidney fibrosis, chronic kidney disease (CKD), diabetic kidney disease (DKD), skin fibrosis, keloids, systemic sclerosis, scleroderma, virally-induced fibrosis, idiopathic pulmonary fibrosis (IPF), interstitial lung disease, non-specific interstitial pneumonia (NSIP), usual interstitial pneumonia (UIP), radiation-induced fibrosis, familial pulmonary fibrosis, airway fibrosis, chronic obstructive pulmonary disease (COPD), spinal cord tumor, hernia of intervertebral disk, spinal canal stenosis, heart failure, cardiac fibrosis, vascular fibrosis, perivascular fibrosis, foot-and-mouth disease, cancer, myeloma, fibroma, hepatocellular carcinoma, colorectal cancer, prostate cancer, leukemia, chronic lymphocytic leukemia, Kaposi's sarcoma, solid tumors, cerebral infarction, cerebral hemorrhage, neuropathic pain, peripheral neuropathy, age-related macular degeneration (AMD), glaucoma, ocular fibrosis, corneal scarring, diabetic retinopathy, proliferative vitreoretinopathy (PVR), cicatricial pemphigoid glaucoma filtration surgery scarring, Crohn's disease or systemic lupus erythematosus; keloid formation resulting from abnormal wound healing; fibrosis occurring after organ transplantation, myelofibrosis, and fibroids. In one embodiment, the present invention provides a method for the treatment of a fibrotic disorder, an inflammatory disorder, or a cell-proliferative disorder, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a compound of the present invention for use in therapy.

In another embodiment, the present invention provides a compound of the present invention for use in therapy for the treatment of a fibrotic disorder, an inflammatory disorder, or a cell-proliferative disorder thereof.

In another embodiment, the present invention also provides the use of a compound of the present invention for the manufacture of a medicament for the treatment of a fibrotic disorder, an inflammatory disorder, or a cell-proliferative disorder thereof.

In another embodiment, the present invention provides a method for the treatment of a fibrotic disorder, an inflammatory disorder, or a cell-proliferative disorder, comprising administering to a patient in need thereof a therapeutically effective amount of a first and second therapeutic agent, wherein the first therapeutic agent is a compound of the present invention.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment of a fibrotic disorder, an inflammatory disorder, or a cell-proliferative disorder.

The compounds of the present invention may be employed in combination with additional therapeutic agent(s), such as one or more anti-fibrotic and/or anti-inflammatory therapeutic agents.

In one embodiment, additional therapeutic agent(s) used in combined pharmaceutical compositions or combined methods or combined uses, are selected from one or more, preferably one to three, of the following therapeutic agents: TGFβ receptor inhibitors (for example, galunisertib), inhibitors of TGFβ synthesis (for example, pirfenidone), inhibitors of vascular endothelial growth factor (VEGF), platelet-derived growth factor (PDGF) and fibroblast growth factor (FGF) receptor kinases (for example, nintedanib), humanized anti-$α_\nu β6$ integrin monoclonal antibody (for example, 3G9), human recombinant pentraxin-2, recombinant human Serum Amyloid P, recombinant human antibody against TGFβ-1, -2, and -3, endothelin receptor antagonists (for example, macitentan), interferon gamma, c-Jun amino-terminal kinase (INK) inhibitor (for example, 4-[[9-[(3S)-tetrahydro-3-furanyl]-8-[(2,4,6-trifluorophenyl)amino]-9H-purin-2-yl]amino]-trans-cyclohexanol,
3-pentylbenzeneacetic acid (PBI-4050), tetra-substituted porphyrin derivative containing manganese (III), monoclonal antibody targeting eotaxin-2, interleukin-13 (IL-13) antibody (for example, lebrikizumab, tralokinumab), bispecific antibody targeting interleukin 4 (IL-4) and interleukin 13 (IL-13), NK1 tachykinin receptor agonist (for example, $Sar^9$, $Met(O_2)^{11}$-Substance P), Cintredekin Besudotox, human recombinant DNA-derived, IgG1 kappa monoclonal antibody to connective growth factor, and fully human IgG1 kappa antibody, selective for CC-chemokine ligand 2 (for example, carlumab, CCX140), antioxidants (for example, N-acetylcysteine), phosphodiesterase 5 (PDE5) inhibitors (for example, sildenafil), agents for treatment of obstructive airway diseases such as muscarinic antagonists (for example, tiotropium, ipatropium bromide), adrenergic β2 agonists (for example, salbutamol, salmeterol), corticosteroids (for example, triamcinolone, dexamethasone, fluticasone), immunosuppressive agents (for example, tacrolimus, rapamycin, pimecrolimus), and therapeutic agents useful for the treatment of fibrotic conditions, such as liver, biliary, and kidney fibrosis, Non-Alcoholic Fatty Liver Disease (NALFD), Non-Alcoholic Steato-Hepatitis (NASH), cardiac fibrosis, Idiopathic Pulmonary Fibrosis (IPF), and systemic sclerosis. The therapeutic agents useful for the treatment of such fibrotic conditions include, but are not limited to, FXR agonists (for example OCA, GS-9674, and LJN452), LOXL2 inhibitors (for example simtuzumab), LPA1 antagonists (for example, BMS-986020 and SAR 100842), PPAR modulators (for example, elafibrinor, pioglitazone, and saroglitazar, IVA337), SSAO/VAP-1 inhibitors (for example, PXS-4728A and SZE5302), ASK-1 inhibitors (for example GS-4997 or selonsertib), ACC inhibitors (for example, CP-640186 and NDI-010976 or GS-0976), FGF21 mimetics (for example, LY2405319 and BMS-986036), caspase inhibitors (for example, emricasan), NOX4 inhibitors (for example, GKT137831), MGAT2 inhibitor (for example, BMS-963272), αV integrin inhibitors (for example, abituzumab) and bile acid/fatty acid conjugates (for example aramchol). The FXR agonists of various embodiments of the present invention may also be used in combination with one or more therapeutic agents such as CCR2/5 inhibitors (for example, cenicriviroc), Galectin-3 inhibitors (for example, TD-139, GR-MD-02), leukotriene receptor antagonists (for example, tipelukast, montelukast), SGLT2 inhibitors (for example, dapagliflozin, remogliflozin), GLP-1 receptor agonists (for example, liraglutide and semaglutide), FAK inhibitors (for example, GSK-2256098), CB1 inverse agonists (for example, JD-5037), CB2 agonists (for example, APD-371 and JBT-101), autotaxin inhibitors (for example, GLPG1690), prolyl t-RNA synthetase inhibitors (for example, halofugenone), FPR2 agonists (for example, ZK-994), and THR agonists (for example, MGL:3196). In another embodiment, additional therapeutic agent(s) used in combined pharmaceutical compositions or combined methods or combined uses, are selected from one or more, preferably one to three, of immunoncology agents, such as alemtuzumab, atezolizumab, ipilimumab, nivolumab, ofatumumab, pembrolizumab, and rituximab.

The compounds of this invention can be administered for any of the uses described herein by any suitable means, for example, orally, such as tablets, capsules (each of which includes sustained release or timed release formulations), pills, powders, granules, elixirs, tinctures, suspensions, syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, anti-bacterial agents, anti-fungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, well known to those of ordinary skill in the art. Descriptions of suitable pharmaceutically acceptable carriers, and factors involved in their selection, are found in a variety of readily available sources such as, for example, *Remington's Pharmaceutical Sciences,* 18th Edition (1990).

The terms "treating" or "treatment" as used herein refer to an approach for obtaining beneficial or desired results, including clinical results, by using a compound or a composition of the present invention. For purposes of this invention, beneficial or desired clinical results include, but are not limited to, one or more of the following: decreasing the severity and/or frequency one or more symptoms resulting from the disease, disorder, or condition; diminishing the extent of or causing regression of the disease, disorder, or condition; stabilizing the disease, disorder, or condition (e.g., preventing or delaying the worsening of the disease, disorder, or condition); delay or slowing the progression of the disease, disorder, or condition; ameliorating the disease, disorder, or condition state; decreasing the dose of one or more other medications required to treat the disease, disorder, or condition; and/or increasing the quality of life.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, well known to those of ordinary skill in the art. Descriptions of suitable pharmaceutically acceptable carriers, and factors involved in their selection, are found in a variety of readily available sources such as, for example, Allen, L. V. Jr. et al. *Remington: The Science and Practice of Pharmacy* (2 *Volumes*), 22nd Edition (2012), Pharmaceutical Press.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.01 to about 5000 mg per day, preferably between about 0.01 to about 1000 mg per day, and most preferably between about 0.01 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more, preferably one to three, other therapeutic agent(s), e.g., ASK-1 inhibitors, CCR2/5 antagonists, autotaxin inhibitors, LPA1 receptor antagonists or other pharmaceutically active material.

The above other therapeutic agents, when employed in combination with the compounds of the present invention may be used, for example, in those amounts indicated in the *Physicians' Desk Reference*, as in the patents set out above, or as otherwise determined by one of ordinary skill in the art.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The compounds of the present invention can be administered alone or in combination with one or more, preferably one to three, additional therapeutic agents. By "administered in combination" or "combination therapy" it is meant that the compound of the present invention and one or more, preferably one to three, additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The compounds of the present invention are also useful as standard or reference compounds, for example as a quality standard or control, in tests or assays involving FXR agonists. Such compounds may be provided in a commercial kit, for example, for use in pharmaceutical research involving FXR agonist activity. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising a compound of the present invention or a pharmaceutically acceptable salt form thereof; and, (c) a package insert stating that the pharmaceutical composition can be used for the treatment of dyslipidemias and the sequelae thereof. In another embodiment, the package insert states that the pharmaceutical composition can be used in combination (as defined previously) with a second therapeutic agent for the treatment of fibrosis and the sequelae thereof. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic) on which the desired information has been formed (e.g., printed or applied).

Methods of Preparation

The compounds of the present invention may be synthesized by many methods available to those skilled in the art of organic chemistry. General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Examples of compounds of the present invention prepared by methods described in the general schemes are given in the Examples section set out hereinafter. Preparation of homochiral examples may be carried out by techniques known to one skilled in the art. For example, homochiral compounds may be prepared by separation of racemic products or diastereomers by chiral phase preparative HPLC. Alternatively, the example compounds may be prepared by methods known to give enantiomerically or diastereomerically enriched products.

The reactions and techniques described in this section are performed in solvents appropriate to the reagents and materials employed and are suitable for the transformations being effected. Also, in the description of the synthetic methods given below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art, with alternatives required when incompatible substituents are present. This will sometimes require a judgment to modify the order of the synthetic steps or to select one particular process scheme over another in order to obtain a compound of the invention. It will also be recognized that another major consideration in the planning of any synthetic route in this field is the judicious choice of a protecting group used for protection of reactive functional groups present in the compounds described in this invention. An authoritative account describing the many alternatives to the trained practitioner is Wuts and Greene, *Greene's Protective Groups in Organic Synthesis*, Fourth Edition, Wiley and Sons (2007).

EXAMPLES

The following examples illustrate the particular and preferred embodiments of the present invention and do not limit the scope of the present invention. Chemical abbreviations and symbols as well as scientific abbreviations and symbols have their usual and customary meanings unless otherwise specified. Additional abbreviations employed in the Examples and elsewhere in this application are defined below. Common intermediates are generally useful for the preparation of more than one Example and are identified sequentially (e.g., Intermediate 1, Intermediate 2) and are abbreviated as Int. 1 or I1, Int. 2 or I2. Compounds of the Examples are identified by the example and Step in which they were prepared (e.g., "1-A" denotes the Example 1, Step A), or by the example only where the compound is the title compound of the example (for example, "1" denotes the title compound of Example 1). In some instances, alternate preparations of intermediates or examples are described. Frequently chemists skilled in the art of synthesis may devise alternative preparations which may be desirable based on one or more considerations such as shorter reaction time, less expensive starting materials, ease of operation or isolation, improved yield, amenable to catalysis, avoidance of toxic reagents, accessibility of specialized instrumentation, and decreased number of linear Steps. The intent of describing alternative preparations is to further enable the preparation of the examples of this invention. In some instances, some functional groups in the outlined examples and claims may be replaced by well-known bioisosteric replacements known in the art, for example, replacement of a carboxylic acid group with a tetrazole or a phosphate moiety. $^1$H NMR data collected in deuterated dimethyl sulfoxide used water suppression in the data processing. The reported spectra are uncorrected for the effects of water suppression. Protons adjacent to the water suppression frequency of 3.35 ppm exhibit diminished signal intensity.

Abbreviations

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute or minutes, "h" for hour or hours, "rt" for room temperature, "RBF" for round bottom flask, "atm" for atmosphere, "psi" for pounds per square inch, "conc." for concentrated, "RCM" for ring-closing metathesis, "sat" or "sat'd" for saturated, "SFC" for supercritical fluid chromatography, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

The following abbreviations are employed in the Schemes, Examples and elsewhere herein:
EtOAc=ethyl acetate
PE=petroleum ether
DMF=dimethylformamide
THF=tetrahydrofuran
$K_2CO_3$=potassium carbonate
$Na_2CO_3$=sodium carbonate
$MgSO_4$=magnesium sulfate
DCM=$CH_2Cl_2$=methylene chloride
DCE=1,2-dichloroethane
MeOH=methanol
HCl=hydrochloric acid
AcOH=acetic acid
$Cs_2CO_3$=cesium carbonate
DMSO=dimethylsulfoxide
TEA=triethylamine
BOP=(benzotriazol-1-yloxy)tris(dimethylamino)phosphonium hexafluorophosphate
DMAc=dimethyl acetamide
DMAP=4-dimethylaminopyridine
2-DMAP=2-dimethylaminopyridine
PCC=pyridinium chlorochromate
PDC=pyridinium dichromate
DIBAL-H=diisobutylaluminium hydride
rotovap=rotary evaporation
min=minute(s)
h or hr=hour(s)
d=day(s)
rt=room temperature
mL=milliliter
g=gram(s)
mg=milligram(s)
mmol=millimole(s)
LRMS=low resolution mass spectrometry
NMR=nuclear magnetic resonance
HPLC=high performance liquid chromatography Synthesis The compounds of the present invention can be prepared in a number of ways well known to one skilled in the art of organic synthesis. The compounds of the present invention can be synthesized using the methods described below, together with synthetic methods known in the art of organic chemistry, or variations thereon as appreciated by those skilled in the art. Preferred methods include, but are not limited to, those described below. All references cited herein are hereby incorporated in their entirety by reference.

The novel compounds of Formula I may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including solvent, reaction atmosphere, reaction temperature, duration of the experiment and workup procedures, are chosen to be the conditions standard for that reaction, which should be readily recognized by one skilled in the art. One skilled in the art of organic synthesis understands that the functionality present on various portions of the edict molecule must be compatible with the reagents and reactions proposed. Not all compounds of Formula I falling into a given class may be compatible with some of the reaction conditions required in some of the methods described. Such restrictions to the substituents, which are compatible with the reaction conditions, will be readily apparent to one skilled in the art and alternate methods must be used.

SCHEME 1

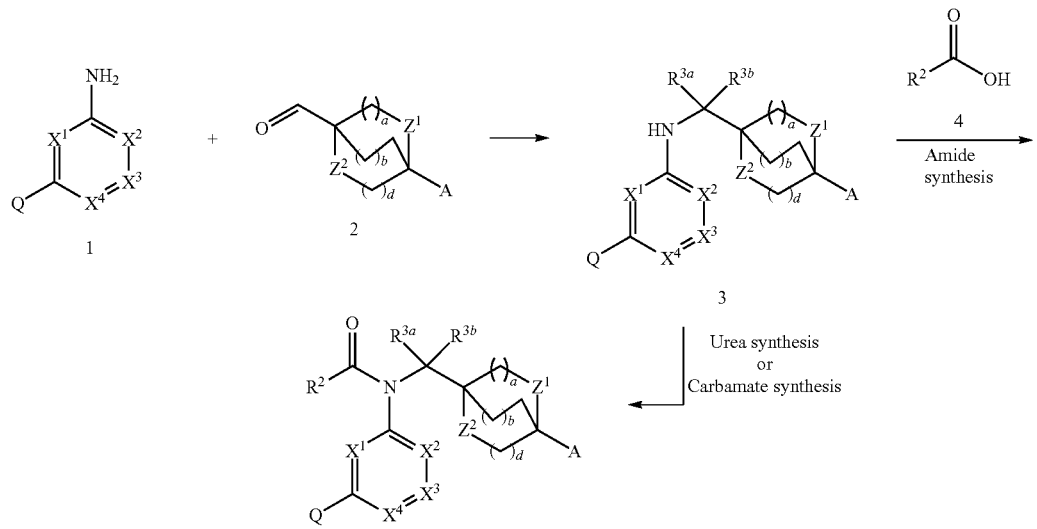

Scheme 1 describes the synthesis of compounds of Formula I. Intermediate 3 can be synthesized by coupling intermediate 1 and intermediate 2 under reductive amination conditions which are known methods recognizable by one skilled in the art. The imine synthesis can occur in presence of acid such as acetic acid in a suitable polar protic solvent (e.g. MeOH, EtOH, etc.) at room temperature or reflux temperature followed by reduction of imine with reducing agents (e.g. sodium cyanoborohydride, sodium triacetoxyborohydride, etc.) to afford intermediate 3. Intermediate 3 can be subjected to a variety of different transformations using numerous known methods recognized by one skilled in the art, including but not limited to the following methods to afford variations of Formula I:

Amides: Intermediate 4 can be obtained from commercial sources or can be synthesized by known methods readily recognizable by one skilled in the art. Intermediate 4 can be activated for acylation using any number of reagents recognizable by one skilled in the art (e.g. phosphorus oxychloride, thionyl chloride, oxalyl chloride, methyl or ethylchloroformate, etc.), in a polar aprotic solvent (e.g. DCM, THF, etc.), at temperatures ranging between −30° C. to 0° C. The activated acid intermediate can then be reacted with intermediate 3 in presence of a base (e.g. pyridine, DMAP, 2-(dimethylamino)pyridine, N-methylmorpholine, etc. or a combination of at least two of these) to generate compounds of Formula I.

Ureas: Intermediate 3 can be subjected to treatment with isocyanates in presence of base (e.g. $Et_3N$, DIPEA, pyridine etc.) in polar aprotic solvent (e.g. DCM, DCE, etc.) at room temperature to afford ureas represented by formula I. Alternatively, the intermediate 3 can be activated by treatment with triphosgene in presence of base (e.g. $Et_3N$, DIPEA, etc.) in solvent (e.g. DCM, DCE, etc.) at 0° C. to room temperature. The activated intermediate 3 can then be treated with substituted alkyl or aryl or heteroaryl amine in presence of base (e.g. $Et_3N$, DIPEA, etc.) in solvent (e.g. DCM, DCE, etc.) at room temperature to afford ureas represented by formula I.

Carbamates: Intermediate 3 can be treated with chloroformates (or alcohols, activated as carbonates) in presence of base (e.g. $Et_3N$, DIPEA, pyridine etc.) in polar aprotic solvent (e.g. DCM, DCE, THF, etc.) at 0° C. to room temperature to afford carbamates represented by formula I.

Intermediates 1(a-h) (Scheme 1) can be accessed in various ways as depicted in schemes 2-10 using numerous known methods recognized by the one skilled in the art including but not limited to the following methods.

SCHEME 2

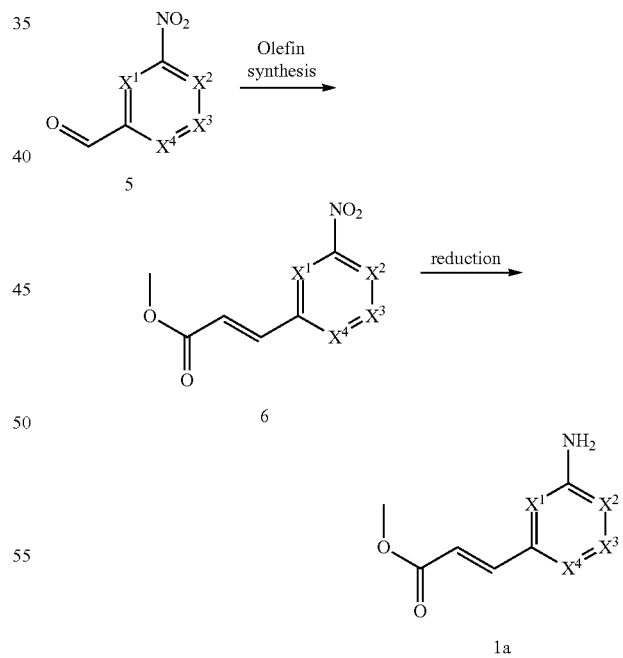

Scheme 2 describes the synthesis of intermediates 1a. Intermediate 5 can be obtained from commercial sources or can be synthesized by known methods readily recognizable by one skilled in the art. Intermediate 5 can be subjected to reaction with alkyl 2-(dimethoxyphosphoryl)acetate in presence of a base (e.g. $K_2CO_3$, $Na_2CO_3$, etc.) in polar protic solvent (e.g. water, methanol, ethanol, etc.) to afford intermediate 6. Intermediate 6 can be reduced to intermediate 1a using the conditions recognized by one skilled in the art including but not limited to one described such as heating in presence of reagent such as tin(II) chloride in polar protic solvent (e.g. water). The intermediate 1a so obtained can be converted compounds of formula I as described in Scheme 1.

SCHEME 3

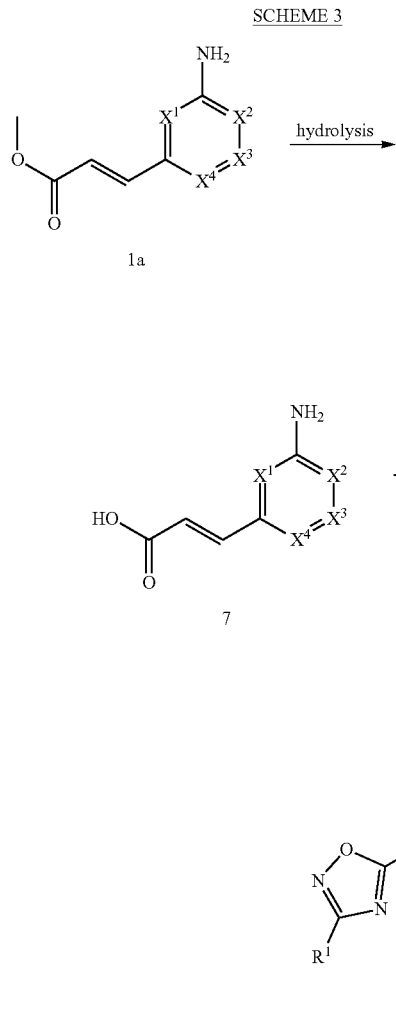

Scheme 3 describes the synthesis of intermediates 1b. Intermediate 1a synthesized as described in Scheme 2 can be subjected to hydrolysis of the methyl ester with an alkali hydroxide base to provide intermediate 7. Intermediate 7 can be coupled with various amide oximes (derived from the corresponding nitriles by reaction with hydroxylamine; see Hirawat, S., et al. WO 2006/110483) using an amide bond coupling reagent (e.g. CDI, BOP, EDC, etc.) in a polar aprotic solvent (e.g. THF, 1,4-dioxane, DMF, etc.) at room temperature. The acyclic intermediate can be subsequently cyclized at elevated temperatures (60° C. to 100° C.). Alternatively, in situ cyclization can be accomplished by conducting the coupling of intermediate 7 with amide oximes at elevated temperatures (60° C. to 100° C.) to afford intermediate 1b.

SCHEME 4

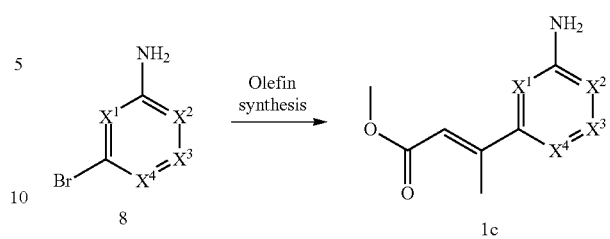

Scheme 4 describes the synthesis of the intermediate 1c. Intermediate 8 can be obtained from commercial sources or can be synthesized by known methods readily recognizable by one skilled in the art. Intermediate 8 can be subjected to olefin synthesis using metal catalyzed cross coupling reactions such as Heck reaction, described in Metal-Catalyzed Cross-Coupling Reactions, Armin de Meijere, François Diederich, 2 Volumes, Second, Revised and Enlarged Edition, 2004, ISBN: 3-527-30518-1, Wiley-VCH and references cited therein. Intermediate 8 can be treated with olefin coupling partner in presence of a metal catalyst such as Dichlorobis(tri-o-tolylphosphine)palladium(II) and tetrabutyl ammonium bromide in presence of base ($Et_3N$, DIPEA, etc.) in solvent (DMAc, DMF, etc.) under heating conditions to afford intermediate 1c.

SCHEME 5

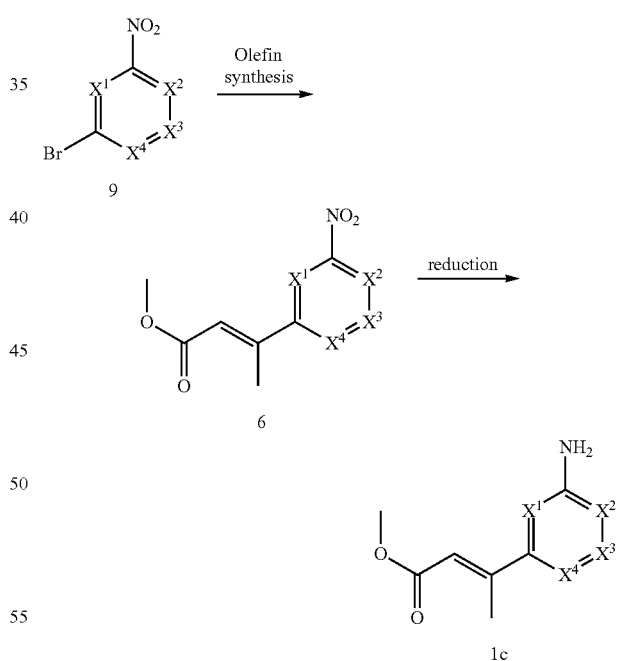

Scheme 5 describes the alternate synthesis of the intermediate 1c. Intermediate 9 can be obtained from commercial sources or can be synthesized by known methods readily recognizable by one skilled in the art. Intermediate 9 can be subjected to olefin synthesis using metal catalyzed cross coupling reactions such as Heck reaction, described in Metal-Catalyzed Cross-Coupling Reactions, Armin de Meijere, François Diederich, 2 Volumes, Second, Revised and Enlarged Edition, 2004, ISBN: 3-527-30518-1, Wiley- VCH and references cited therein. Intermediate 9 can be treated with olefin coupling partner in presence of a metal catalyst such as Dichlorobis(tri-o-tolylphosphine)palladium (II) and tetrabutyl ammonium bromide in presence of base (Et$_3$N, DIPEA, etc.) in solvent (DMAc, DMF, etc.) under heating conditions to afford intermediate 10. Intermediate 10 can be reduced to intermediate 1c using the conditions recognized by one skilled in the art including but not limited to one described such as heating in presence of reagent such as tin(II) chloride in polar protic solvent (e.g. water). The intermediate 1c so obtained can be converted compounds of formula I as described in Scheme 1.

to generate intermediate 13. Intermediates 12 can be obtained from commercial sources or can be synthesized by known methods readily recognizable by one skilled in the art. Intermediate 13 can be reduced to intermediate 1d using the conditions recognized by one skilled in the art including but not limited to one described such as heating in presence of reagent such as tin(II) chloride in polar protic solvent (e.g. water). The intermediate 1d so obtained can be converted compounds of formula I as described in Scheme 1.

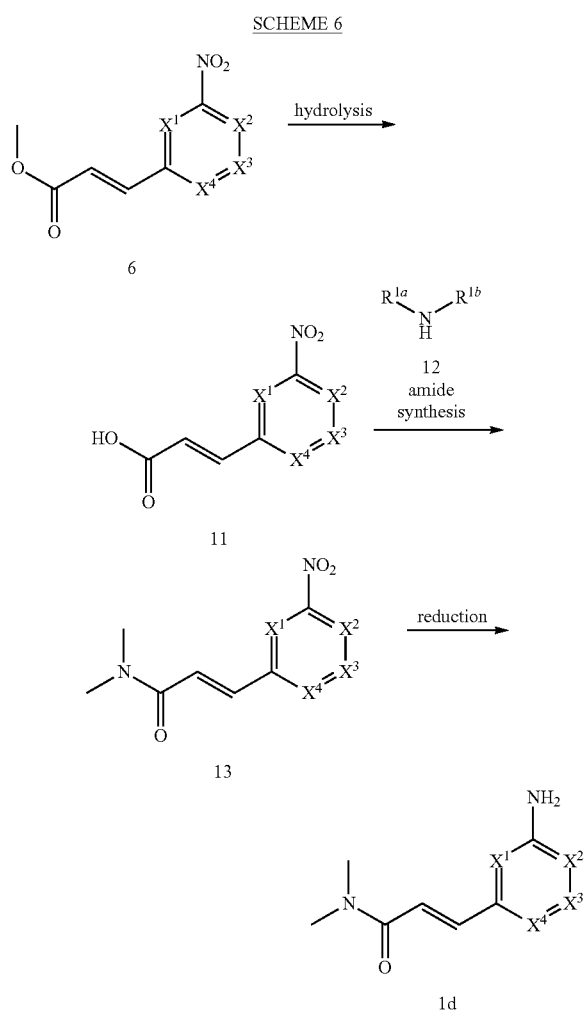

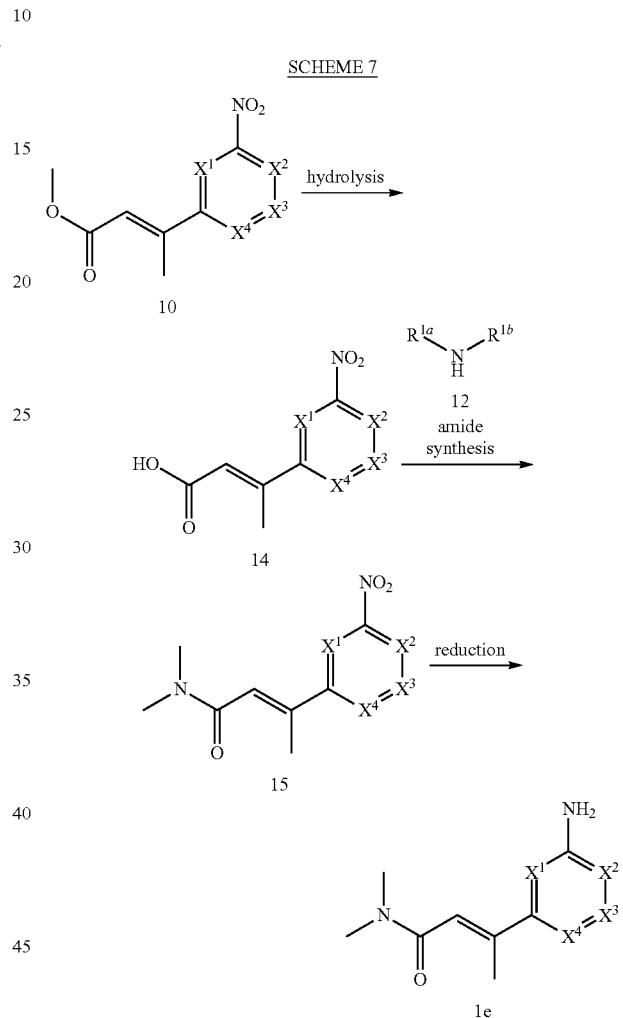

Scheme 6 describes the synthesis of intermediates 1d. Intermediate 6 can be synthesized as described in Scheme 2. Intermediate 6 can be subjected to hydrolysis of the methyl ester with an alkali hydroxide base to provide intermediate 11. Intermediate 11 can be activated for acylation using any number of reagents recognizable by one skilled in the art (e.g. phosphorus oxychloride, thionyl chloride, oxalyl chloride, methyl or alkylchloroformate, etc.), in a polar aprotic solvent (e.g. DCM, THF, etc.), at temperatures ranging between –30° C. to 0° C. The activated acid intermediate can then be reacted with intermediate 12 in presence of a base (e.g. pyridine, DMAP, 2-(dimethylamino)pyridine, N-methylmorpholine, etc. or a combination of at least two of these)

Scheme 7 describes the synthesis of intermediates 1e. Intermediate 10 can be synthesized as described in Scheme 5. Intermediate 10 can be subjected to hydrolysis of the methyl ester with an alkali hydroxide base to provide intermediate 14. Intermediate 14 can be activated for acylation using any number of reagents recognizable by one skilled in the art (e.g. phosphorus oxychloride, thionyl chloride, oxalyl chloride, methyl or alkylchloroformate, etc.), in a polar aprotic solvent (e.g. DCM, THF, etc.), at temperatures ranging between –30° C. to 0° C. The activated acid intermediate can then be reacted with intermediate 12 in presence of a base (e.g. pyridine, DMAP, 2-(dimethylamino)pyridine, N-methylmorpholine, etc. or a combination of at least two of these) to generate intermediate 15. Intermediates 12 can be obtained from commercial sources or can be synthesized by known methods readily recognizable by one skilled in the art. Intermediate 15 can be reduced to intermediate 1e using the conditions recognized by one skilled in the art including but not limited to one described such as heating in presence of reagent such as tin(II) chloride in polar protic solvent (e.g. water). The intermediate 1e so obtained can be converted compounds of formula I as described in Scheme 1.

SCHEME 8

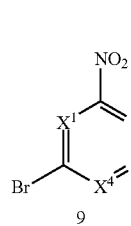

Scheme 8 describes the synthesis of intermediates 1f. Intermediate 9 can be obtained from commercial sources or can be synthesized by known methods readily recognizable by one skilled in the art. Intermediate 9 can be subjected to metal catalyzed Sonogashira coupling reaction using numerous known methods recognized by the one skilled in the art including but not limited to the ones described in Metal-Catalyzed Cross-Coupling Reactions, Armin de Meijere, François Diederich, 2 Volumes, Second, Revised and Enlarged Edition, 2004, ISBN: 3-527-30518-1, Wiley-VCH and references cited therein. Intermediate 9 can be subjected to reaction with suitable alkyne coupling partner in polar aprotic solvent such as DMF in presence of base such as $Et_3N$ and metal catalyst such as bis(triphenylphosphine)palladium(II) dichloride and copper(I) iodide under heating conditions to afford intermediate 16. Intermediate 16 can be reduced to intermediate 1f using the conditions recognized by one skilled in the art including but not limited to one described such as heating in presence of iron with acetic acid and ammonium chloride in polar protic solvent (e.g. water and isopropyl alcohol). The intermediate 1f so obtained can be converted compounds of formula I as described in Scheme 1.

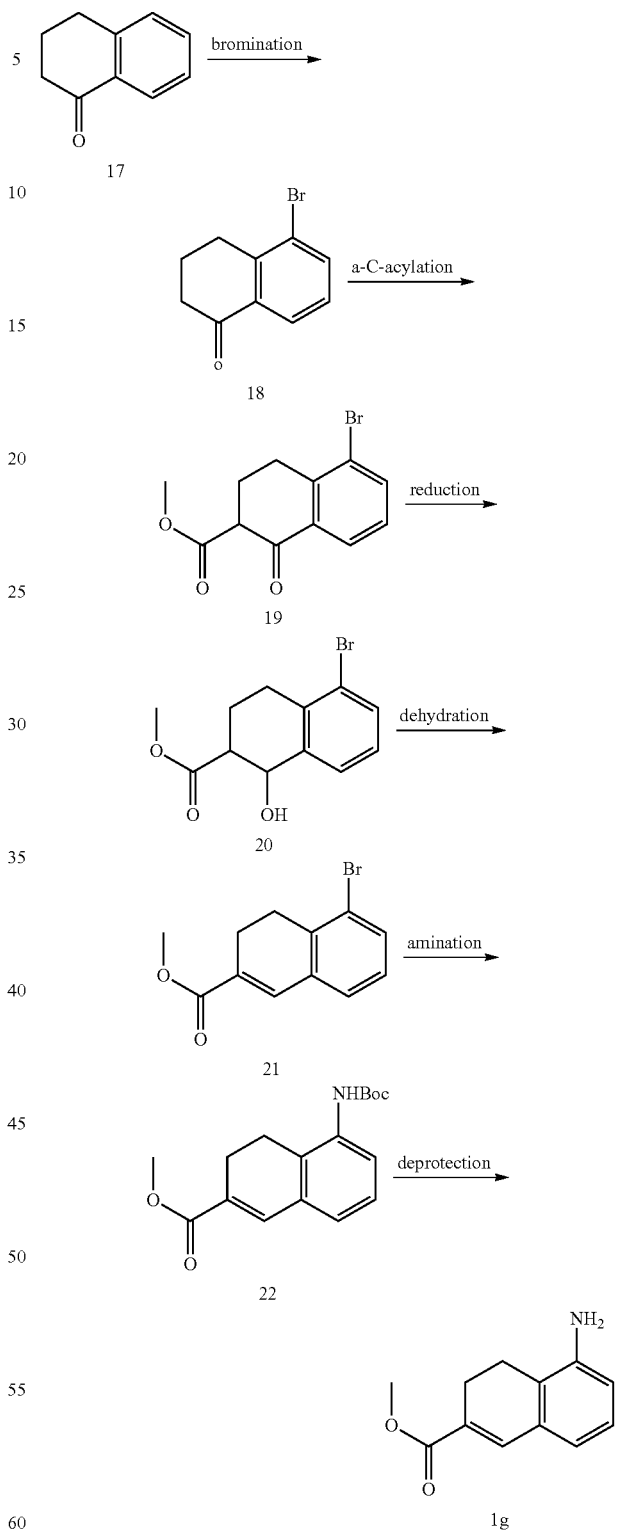

Scheme 9 describes synthesis of intermediate 1g. Intermediate 17 can be obtained from commercial sources or can be synthesized by known methods readily recognizable by one skilled in the art. Intermediate 17 can be subjected to treatment with $AlCl_3$ in presence of bromine under heating conditions to afford corresponding bromo-substituted intermediate 18. The bromo intermediate, 18 can be subjected to acylation in presence of a base such as NaH and dimethyl carbonate in dry toluene under heating conditions to afford intermediate 19. Intermediate 19 can be subjected to reduction by a reducing agent (e.g. $NaBH_4$, DIBAL-H, etc.) in polar protic solvent (e.g. MeOH, EtOH, etc.) to afford sec-alcohol 20, which was subjected to elimination by treatment with p-TSA under heating conditions to yield intermediate 21. Intermediate 21 can be subjected to Buchwald coupling in presence of metal catalyst such as $Pd_2(dba)_3$ and appropriate ligand (including but not limited to ligands such as 4,5-bis(diphenylphosphino)-9,9-dimethylxanthene) with coupling partner tert-butyl carbamate and $Cs_2CO_3$ as a base to afford Boc-protected aniline intermediate 22. The intermediate 22 can be de-protected in solvent (e.g. DCM, THF, etc.) with acid (e.g. TFA, HCl in dioxane, etc.) to afford intermediate 1g.

acid intermediate can then be reacted with intermediate 12 in presence of a base (e.g. pyridine, DMAP, 2-(dimethylamino)pyridine, N-methylmorpholine, etc. or a combination of at least two of these) to generate intermediate 24. Intermediates 12 can be obtained from commercial sources or can be synthesized by known methods readily recognizable by one skilled in the art. Intermediate 24 can be converted to intermediate 1h using the conditions described in Scheme 9 via sequential amination and de-protection steps. The intermediate 1h so obtained can be converted compounds of formula I as described in Scheme 1.

Intermediates 2 (Scheme 1) can be accessed in various ways as depicted in Scheme 11 using numerous known methods recognized by the one skilled in the art including but not limited to the following methods.

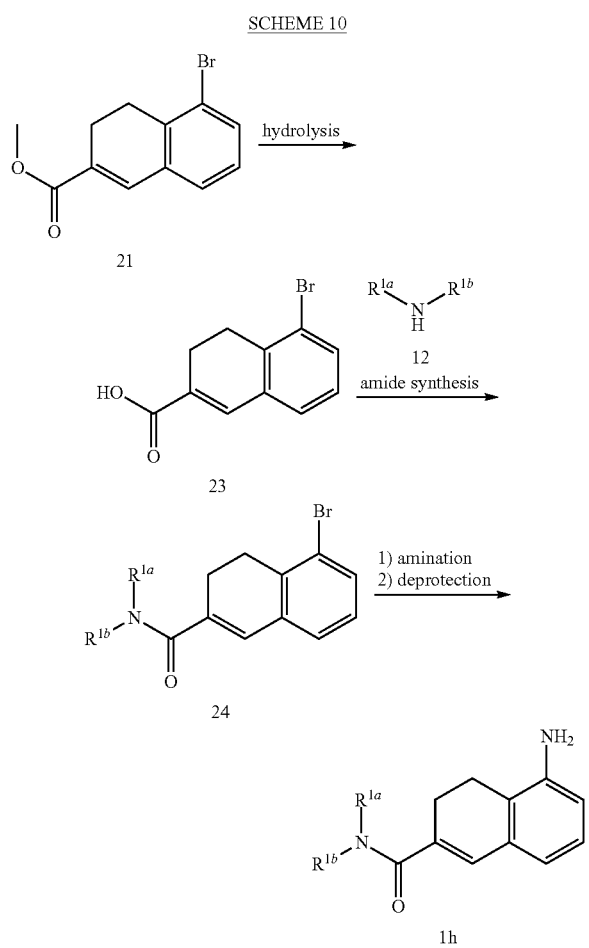

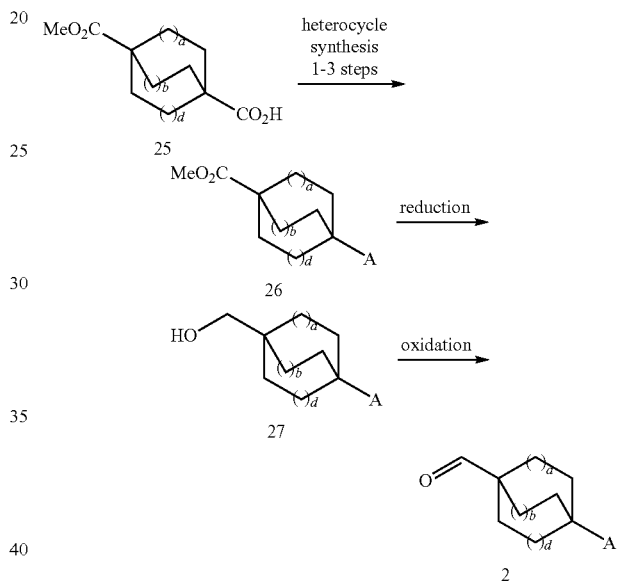

Scheme 10 describes the synthesis of intermediates 1h. Intermediate 21 can be synthesized as described in Scheme 9. Intermediate 21 can be subjected to hydrolysis of the methyl ester with an alkali hydroxide base to provide intermediate 23. Intermediate 23 can be activated for acylation using any number of reagents recognizable by one skilled in the art (e.g. phosphorus oxychloride, thionyl chloride, oxalyl chloride, methyl or alkylchloroformate, etc.), in a polar aprotic solvent (e.g. DCM, THF, etc.), at temperatures ranging between −30° C. to 0° C. The activated Scheme 11 describes the synthesis of intermediate 2. Commercially available 4-(methoxycarbonyl)bicyclo[2.2.2]octane-1-carboxylic acid 25 can be subjected to heterocycle ring synthesis to afford compounds of intermediate 26.

Heterocycle formation (A). The carboxylic acid moiety of compound 25 can be converted to various heterocycles (A) using numerous known methods recognized by one skilled in the art, including but not limited to the following methods:

A=1,2,4-oxadiazole. Intermediate 25 can be coupled with various amide oximes (derived from the corresponding nitriles by reaction with hydroxylamine; see Hirawat, S., et al. WO 2006/110483) using an amide bond coupling reagent (e.g. CDI, BOP, EDC, etc.) in a polar aprotic solvent (e.g. THF, 1,4-dioxane, DMF, etc.) at room temperature. The acyclic intermediate can be subsequently cyclized at elevated temperatures (60° C. to 100° C.). Alternatively, in situ cyclization can be accomplished by conducting the coupling of acid 25 with amide oximes at elevated temperatures (60° C. to 100° C.).

A=1,2,5-oxadiazole. Intermediate 25 can be converted to 1,2,5-oxadiazole as described in Broström, J. et al. *J. Med. Chem.* 2012, 55, 1817-1830 and references described therein.

A=1,3,4-oxadiazole or A=1,3,4-thiadiazole. Intermediate 25 can be coupled with acetic acid hydrazide (described in WO 2014/071247, Bradner, J. E., et al.), using an amide bond coupling reagent (e.g. CDI, BOP, EDC, etc.) in a polar aprotic solvent (e.g. THF, 1,4-dioxane DMF, MeCN, etc.). The acyclic hydrazide intermediate can then be cyclized to either 1,3,4-oxadiazole or 1,3,4-thiadiazole using respectively, 4-toluenesulfonic acid (Stabile, P. et al. *Tetrahedron Lett.* 2010, 51, 4801-4805) or Laweson's reagent (Kitamura, S., et al. PCT Int. Appl., 2008011130, 2008).

A=3-substituted 5-alkyl-1-methyl-1H-pyrazole. Methyl ketones can be treated with base and acid chloride of intermediate 25 to afford a diketone, which upon reaction with substituted or unsubstituted hydrazine salt in polar protic solvent such as ethanol at reflux temperature afforded ester 26 where A is alkyl substituted or unsubstituted pyrazole. (As described in Cadilla, R., et al. WO 03/074495 A1).

A=Isoxazole. The diketone prepared from intermediate 25 as described above can be upon reaction with hydroxyl amine hydrochloride salt in polar protic solvent such as ethanol at reflux temperature afforded ester 26 where A is alkyl substituted isoxazole (as described in Cadilla, R., et al. WO 03/074495 A1).

A=5-(3-alkyl-1-methyl-1H-pyrazole). The diketone prepared from intermediate 25 as described above can be upon reaction with alkyl hydrazine in polar protic solvent such as ethanol at reflux temperature afforded ester 26 where A is alkyl substituted pyrazole.

A=substituted heteroaryl. Intermediate 25 can be subjected to Minisci reaction with substituted heteroaryl compounds such as pyridine, pyrimidine, pyridazine, pyrazine, quinoline, pyrazole, etc in presence of silver nitrate and potassium persulfate or ammonium persulfate in DCM (or any other conditions that can be used to generate carbon-centered radical) and water mixture as a solvent at ambient temperature to afford ester 26 (as described in Ling-Bo, Qu et al. *Org. Biomol. Chem.,* 2015, 13, 2750-2755 and Review: Duncton, M. A. *J. Med. Chem. Commun.,* 2011, 2, 1135-1161 and references described therein).

A=2-Benzothiazole. Method A: Intermediate 25 can be coupled with substituted 2-aminobenzenethiol (See generally Chedekel, M. R., et al. *Synth. Commun.* 1980, 10, 167-173; synthesis of various 2-aminobenzenethiols), using an amide bond coupling reagent (e.g. BOP, T3P, EDC, etc.) in a polar aprotic solvent (e.g. DCE, THF, etc.). The coupling reaction can be conducted at elevated temperatures (60° C. to 80° C.) thereby accomplishing the in situ formation of the cyclized 2-benzothiazole.

Method B: Alternatively, intermediate 25 can be coupled with substituted 2-chloroaniline (commercial available) using an amide bond coupling reagent (e.g. T3P, BOP, etc.), or by activating intermediate 25 for acylation using any number of reagents (e.g. oxalyl chloride, $POCl_3$, etc.). The resultant carboxamide can be treated with Lawesson's reagent at elevated temperature (120° C.), thereby accomplishing an in situ cyclization to 2-benzothiazole.

A=2-Benzoxazole. Intermediate 25 can be coupled with substituted 2-aminophenol (commercial available) using an amide bond coupling reagent (e.g. BOP, EDC, etc.), in a polar aprotic solvent (e.g. DMF, THF, etc.). Cyclization can be accomplished in refluxing toluene in the presence of tosic acid.

A=2-Benzimidazole. Intermediate 25 can be coupled with ethyl 3,4-diaminobenzoate using an amide bond coupling reagent (e.g. TBTU, T3P, PyBOP, etc.) in a polar aprotic solvent (e.g. DMF, NMP, etc.), then cyclized to the 2-benzimidazole under acidic conditions (AcOH neat) at elevated temperatures (115° C.).

A=2-Quinazoline. Intermediate 25 can be coupled with 4-amino-3-(aminomethyl)benzoate dihydrochloride (Pascal, R. et al. *Eur. J. Org. Chem.* 2000, 22, 3755-3761), using an amide bond coupling reagent (e.g. HBTU, EDC, PyBOP, etc.) in a polar aprotic solvent (e.g. MeCN, THF, etc.). Cyclization can be accomplished under acidic conditions (AcOH neat) at elevated temperatures (115° C.). The resultant dihydroquinazoline intermediate can be oxidized to the 2-quinazoline using an oxidizing agent such as DDQ.

A=1-triazole. Intermediate 25 can be converted to corresponding amine via Curtius rearrangement (as described in Shioiri, T. et al. *J. Am. Chem. Soc.* 1972, 94, 6203-6205). The amine upon treatment with reagent such asp-toluene sulfonyl azide can be converted to corresponding azide which upon reaction with suitable alkyne (as described in Boren, B. C. et al *J. Am. Chem. Soc.,* 2008, 130, 8923-8930) afforded triazole.

A=Substituted 1,2,4-triazole. Intermediate 25 can be converted to corresponding hydrazide and can be subjected to reaction with substituted carboxamide in presence of trifluoromethanesulfonic anhydride and 2-fluoropyridine under heating conditions as described by Charette, A. B. et al. *Org. Lett.,* 2015, 17, 1184-1187.

'A' can be other heterocycles such as substituted as well as unsubstituted oxazoles, thiazoles imidazoles, isoxazoles, triazoles, pyrazoles and can be synthesized as described in reference: Wlochal, J. et al *Org. Lett.* 2014, 16, 4094-4097 and references cited therein. Alternatively, acid functional group of intermediate 25 can be converted to heterocycles as described in schemes 2-9 using methods and literature references described therein.

Intermediate 26 can be subjected to reduction by a reducing agent (e.g. LAH, DIBAL-H, $NaBH_4$, etc.) in chlorinated or ethereal solvent (e.g. DCM, ether, 1,4-dioxane, THF, etc.) to afford intermediate 27. Intermediate 27 can be oxidized by methodologies recognized by one skilled in the art using oxidation conditions (e.g. Dess-Martin periodinane, Swern oxidation conditions, PDC, etc.) to afford intermediate 2.

SCHEME 12

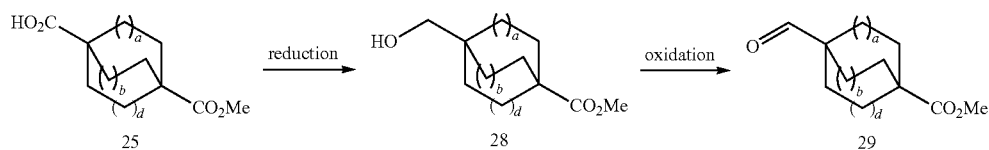

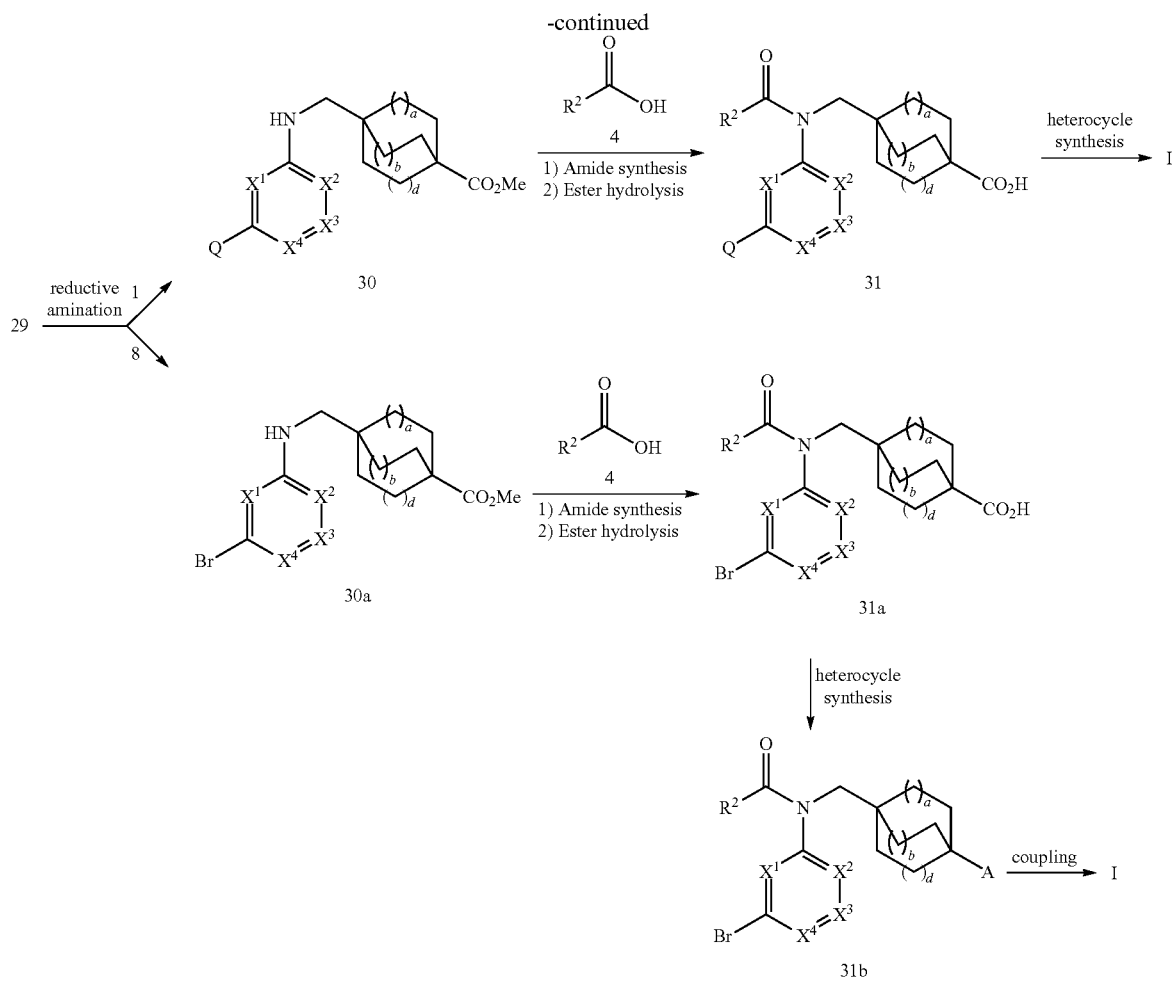

Scheme 12 describes an alternative synthesis of compounds of Formula I with the modified sequence of steps. Commercially available 4-(methoxycarbonyl)bicyclo[2.2.2]octane-1-carboxylic acid 25 can be subjected to reduction in presence of hydride based reducing agent (e.g. LAH, DIBAL-H, NaBH$_4$, etc.) to afford intermediate 28. Intermediate 28 can be oxidized to intermediate 29, by methodologies recognized by one skilled in the art using oxidation conditions (e.g. Dess-Martin periodinane, Swern oxidation conditions, PDC or PCC, etc.). The intermediate 1 and intermediate 29 can be reacted in presence of acid such as acetic acid in a suitable polar protic solvent (e.g. MeOH, EtOH, etc.) at room temperature or reflux temperature followed by reduction with reducing agents (e.g. sodium cyanoborohydride, sodium triacetoxyborohydride, etc.) to afford intermediate 30. Intermediate 4 can be activated for acylation using any number of reagents recognizable by one skilled in the art (e.g. thionyl chloride, phosphorus oxychloride, oxalyl chloride, methyl or ethylchloroformate, etc.), in a polar aprotic solvent (e.g. DCM, THF, etc.), at temperatures ranging between −30° C. to reflux temperatures. The activated acid intermediate can be reacted with intermediate 30 in presence of a base to generate corresponding amide. Subsequent hydrolysis of the methyl ester with an alkali hydroxide base can provide intermediate 31. Intermediate 31 can be converted to various heterocycles (A) using numerous known methods recognized by one skilled in the art, including but not limited to the methods described in Scheme 11 to afford compounds of formula I.

Alternatively, intermediate 29 and intermediate 8 can be subjected to reductive amination using numerous known methods recognizable by one skilled in the art. The imine synthesis in presence of acid such as acetic acid in a suitable polar protic solvent (e.g. MeOH, EtOH, etc.) at room temperature or reflux temperature followed by reduction of imine with reducing agents (e.g. sodium cyanoborohydride, sodium triacetoxyborohydride, etc.) afforded intermediate 30a. Intermediate 4 can be activated for acylation using any number of reagents recognizable by one skilled in the art (e.g. thionyl chloride, phosphorus oxychloride, oxalyl chloride, methyl or ethylchloroformate, etc.), in a polar aprotic solvent (e.g. DCM, THF, etc.), at temperatures ranging between −30° C. to reflux temperatures. The activated acid intermediate can be reacted with intermediate 30a in presence of a base to generate corresponding amide. Subsequent hydrolysis of the methyl ester with an alkali hydroxide base can provide intermediate 31a. Intermediate 31a can be converted to various heterocycles (A) using numerous known methods recognized by one skilled in the art, including but not limited to the methods described in Scheme 11 to afford intermediate 31b. Intermediate 31b can be subjected to metal catalyzed cross coupling reactions using numerous known methods recognized by the one skilled in the art including but not limited to the ones described in Metal-Catalyzed Cross-Coupling Reactions, Armin de Meijere, François Diederich, 2 Volumes, Second, Revised and Enlarged Edition, 2004, ISBN: 3-527-30518-1, Wiley-VCH and references cited therein. Intermediate 31b can be subjected to metal catalyzed Sonogashira coupling. These coupling reactions can be carried out in presence of metal catalyst $Pd(PPh_3)_2Cl_2$ and CuI in presence of base such as triethylamine in polar aprotic solvent such as DMF at 90° C. The coupling reactions of intermediate 31b can be carried out with various appropriate coupling partners such substituted alkynes to afford compounds represented by formula I. Intermediate 31b can be subjected to metal catalyzed Heck coupling. These coupling reactions can be carried out in presence of metal catalyst such as Dichlorobis(tri-o-tolylphosphine)palladium(II) and tetrabutyl ammonium bromide in presence of base ($Et_3N$, DIPEA, etc.) in solvent (DMAc, DMF, etc.) under heating conditions. The coupling reactions of intermediate 31b can be carried out with various appropriate coupling partners such substituted alkenes, alkenyl halides or triflates to afford compounds represented by formula I. Intermediate 31b can be converted to organoboron reagent using bis(pinacolato)diboron, bis(neopentyl glycolato)diboron, etc in presence of a palladium catalyst such as $Pd(dppf)Cl_2$ and base such as potassium acetate in solvent (e.g. dioxane, DMSO etc.) at reflux temperature, which upon coupling with suitable coupling partners such as alkenes, alkenyl halides or triflates etc. in a Suzuki coupling afforded compounds represented by formula I. Alternatively, intermediate 31b can be converted to organotin reagent using hexamethylditin in presence of a palladium catalyst and in solvent (e.g. toluene, THF etc.) at reflux temperature, which upon coupling with suitable coupling partners such as alkenyl halides or triflates etc. in a Stille coupling (Sherer, B., et al. PCT Int. Appl., 2016/039734, 2016) afforded compounds represented by formula I.

SCHEME 13

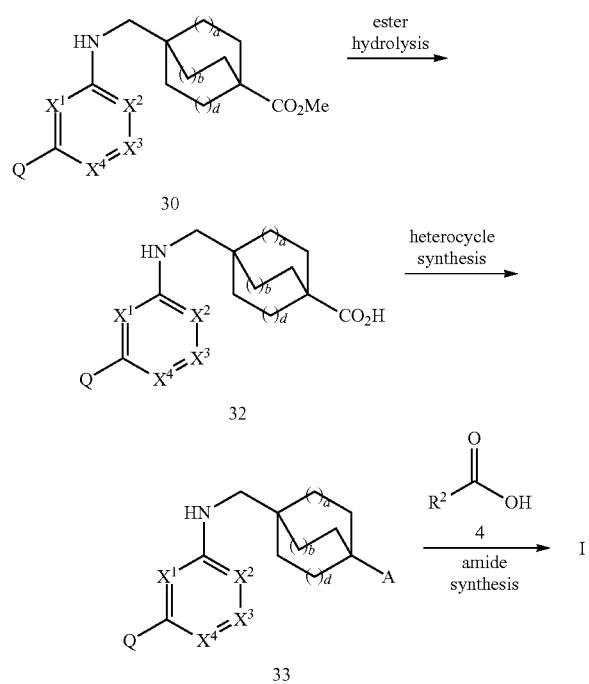

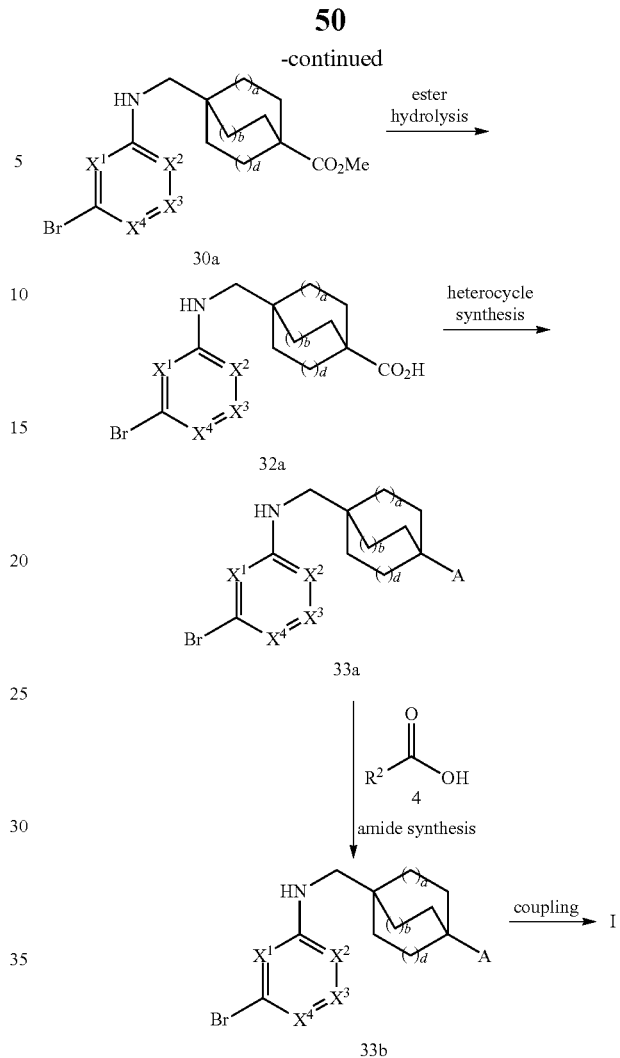

Scheme 13 describes an alternative synthesis of compounds of Formula I with the modified sequence of steps.

Intermediate 30 (described in Scheme 12) can be subjected to hydrolysis of the methyl ester with an alkali hydroxide base to provide intermediate 32. Intermediate 32 can be converted to various heterocycles (A) using numerous known methods recognized by one skilled in the art, including but not limited to the methods described in Scheme 11 to afford compounds of formula 33. Intermediate 4 can be activated for acylation using any number of reagents recognizable by one skilled in the art (e.g. thionyl chloride, phosphorus oxychloride, oxalyl chloride, methyl or ethylchloroformate, etc.), in a polar aprotic solvent (e.g. DCM, THF, etc.), at temperatures ranging between −30° C. to reflux temperatures. The activated acid intermediate can be reacted with intermediate 33 in presence of a base to generate compounds of formula I.

Alternatively, intermediate 30a (described in Scheme 12) can be subjected to hydrolysis of the methyl ester with an alkali hydroxide base to provide intermediate 32a. Intermediate 32a can be converted to various heterocycles (A) using numerous known methods recognized by one skilled in the art, including but not limited to the methods described in Scheme 11 to afford compounds of formula 33a. Intermediate 4 can be activated for acylation using any number of reagents recognizable by one skilled in the art (e.g. thionyl chloride, phosphorus oxychloride, oxalyl chloride, methyl or ethylchloroformate, etc.), in a polar aprotic solvent (e.g. DCM, THF, etc.), at temperatures ranging between −30° C. to reflux temperatures. The activated acid intermediate can be reacted with intermediate 33a in presence of a base to generate intermediate 33b. Intermediate 33b can be subjected to metal catalyzed cross coupling reactions using numerous known methods recognized by the one skilled in the art including but not limited to the ones described in Metal-Catalyzed Cross-Coupling Reactions, Armin de Meijere, François Diederich, 2 Volumes, Second, Revised and Enlarged Edition, 2004, ISBN: 3-527-30518-1, Wiley-VCH and references cited therein. Intermediate 33b can be subjected to metal catalyzed Sonogashira coupling. These coupling reactions can be carried out in presence of metal catalyst Pd(PPh$_3$)$_2$Cl$_2$ and CuI in presence of base such as triethylamine in polar aprotic solvent such as DMF at 90° C. The coupling reactions of intermediate 33b can be carried out with various appropriate coupling partners such substituted alkynes to afford compounds represented by formula I. Intermediate 33b can be subjected to metal catalyzed Heck coupling. These coupling reactions can be carried out in presence of metal catalyst such as dichlorobis(tri-o-tolylphosphine)palladium(II) and tetrabutyl ammonium bromide in presence of base (Et$_3$N, DIPEA, etc.) in solvent (DMAc, DMF, etc.) under heating conditions. The coupling reactions of intermediate 33b can be carried out with various appropriate coupling partners such substituted alkenes, alkenyl halides or triflates to afford compounds represented by formula I. Intermediate 33b can be converted to organoboron reagent using bis(pinacolato)diboron, bis(neopentyl glycolato)diboron, etc in presence of a palladium catalyst such as Pd(dppf)Cl$_2$ and base such as potassium acetate in solvent (e.g. dioxane, DMSO etc.) at reflux temperature, which upon coupling with suitable coupling partners such as alkenes, alkenyl halides or triflates etc. in a Suzuki coupling afforded compounds represented by formula I. Alternatively, intermediate 33b can be converted to organotin reagent using hexamethylditin in presence of a palladium catalyst and in solvent (e.g. toluene, THF etc.) at reflux temperature, which upon coupling with suitable coupling partners such as alkenyl halides or triflates etc. in a Stille coupling (Sherer, B., et al. PCT Int. Appl., 2016/039734, 2016) afforded compounds represented by formula I.

SCHEME 14

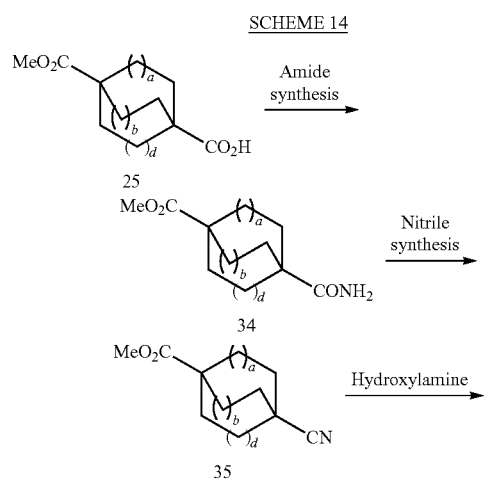

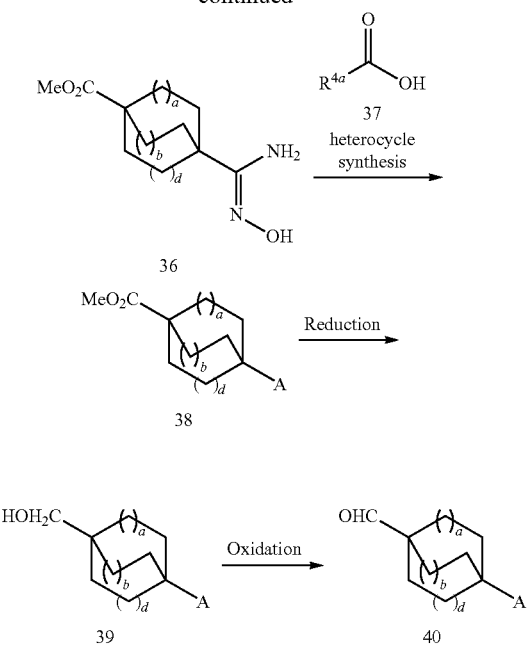

Scheme 14 describes the synthesis of intermediate 40 where A is 3-(5-substituted-1,2,4-oxadiazolyl) ring. Commercially available 4-(methoxycarbonyl)bicyclo[2.2.2]octane-1-carboxylic acid 25 can be subjected to amide synthesis by treating with activation agent such as BOP, HATU, etc. in presence of solvent such as DCM, DMF, etc. and an organic base such as Et$_3$N, DIPEA, etc. at ambient temperature in presence of ammonium chloride to afford intermediate 34. Intermediate 34 can be converted to intermediate 35 by treatment with trifluoroacetic anhydride in pyridine at 0° C. or by treatment with POCl$_3$ and a base such as imidazole. Intermediate 36 can be synthesized by reaction of intermediate 35 with hydroxylamine; see Hirawat, S., et al. WO 2006/110483. Variously substituted intermediates 37 can be coupled with intermediates 36 using an amide bond coupling reagent (e.g. CDI, BOP, EDC, etc.) in a polar aprotic solvent (e.g. THF, 1,4-dioxane, DMF, etc.) at room temperature. The acyclic intermediate can be subsequently cyclized at elevated temperatures (60° C. to 100° C.). Alternatively, in situ cyclization can be accomplished by conducting the coupling of acids 37 with amide oximes 36 at elevated temperatures (60° C. to 100° C.) to afford intermediates of formula 38. Reduction of intermediate 38 can be accomplished in presence of hydride based reducing agents (e.g. LAH, DIBAL-H, NaBH$_4$, etc.) in chlorinated or ethereal solvent such as DCM, ether, 1,4-dioxane, THF, etc. to afford intermediate 39. Intermediate 39 can be oxidized to intermediate 40, by methodologies recognized by one skilled in the art using oxidation conditions (e.g. Dess-Martin periodinane, Swern oxidation conditions, PDC or PCC, etc.). Intermediates 40 can be converted to compounds of formula I by steps described in Scheme 1.

SCHEME 15

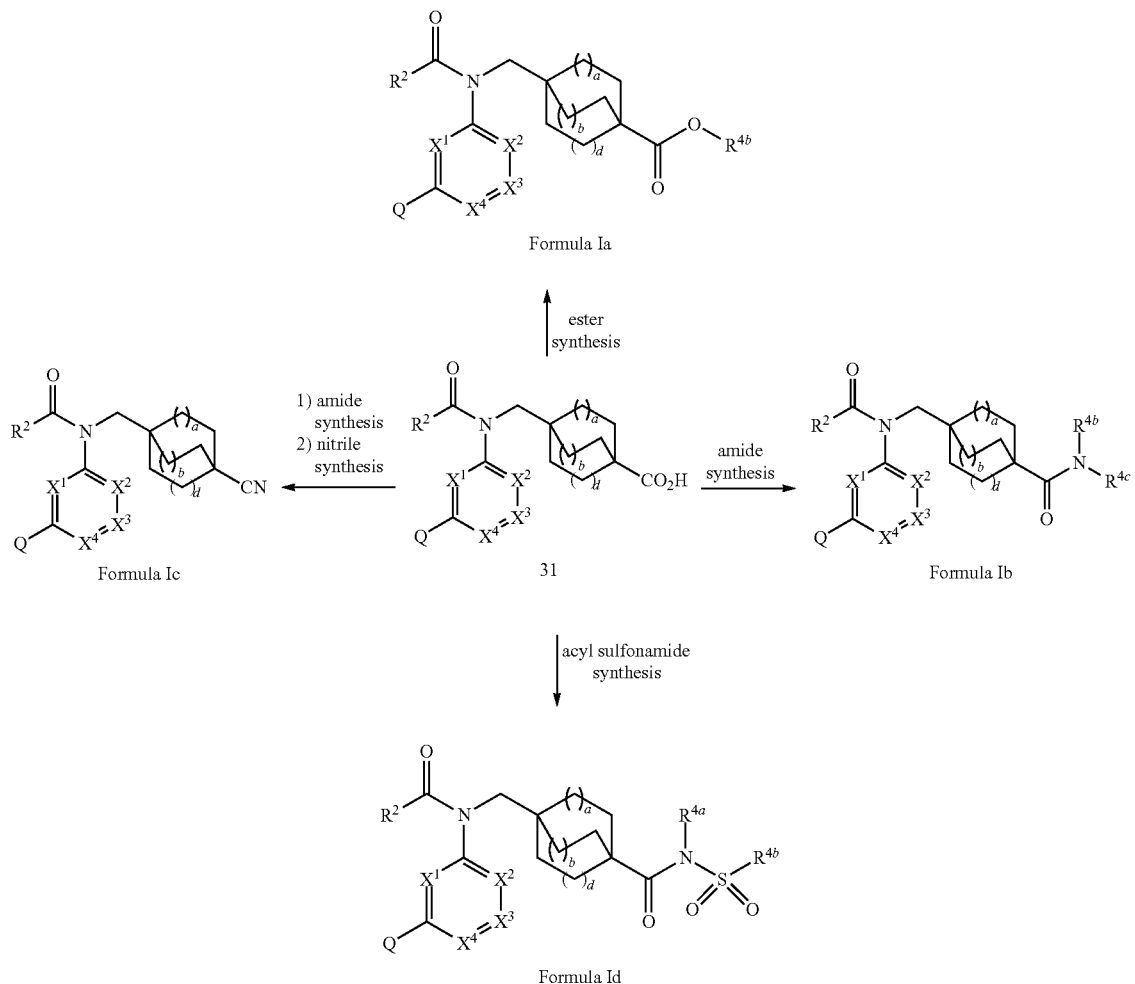

Scheme 15 describes the synthesis of compounds of formula I(a-d). The intermediates represented by formula 31 (synthesis described in Scheme 12) can be subjected to esterification. Intermediate 31 can be activated for acylation using any number of reagents recognizable by one skilled in the art (e.g. thionyl chloride, phosphorus oxychloride, oxalyl chloride, methyl or ethylchloroformate, etc.), in a polar aprotic solvent (e.g. DCM, THF, etc.), at temperatures ranging between −30° C. to reflux temperatures. The activated acid intermediate can be reacted with alcohols in presence of a base to generate compounds of formula Ia. Intermediate 31 can be subjected to amide synthesis by activating acid with activation agent (e.g. BOP, CDI, HATU, etc.) in solvent (e.g. DCM, DMF, etc.) in presence of base (e.g. Et$_3$N, DIPEA, etc.) at ambient temperature or heating conditions in presence of ammonium chloride or substituted amine (e.g. alkyl, cycloalkyl, aryl, heteroaryl, etc.) to afford amides of formula Ib. Intermediate 31 can be subjected to primary amide synthesis by treating with activation agent (e.g. BOP, CDI, HATU, etc.) in solvent (e.g. DCM, DMF, etc.) in presence of base (e.g. Et$_3$N, DIPEA, etc.) and ammonium chloride at ambient temperature. The primary amide so obtained can be treated with i) trifluoroacetic anhydride in pyridine at 0° C. or ii) POCl$_3$ and imidazole to afford nitriles of formula Ic. Intermediate 31 can be activated using any number of reagents recognizable by one skilled in the art (e.g. thionyl chloride, phosphorus oxychloride, oxalyl chloride, methyl or ethylchloroformate, etc.), in a polar aprotic solvent (e.g. DCM, THF, etc.), at temperatures ranging between −30° C. to reflux temperatures. The activated acid intermediate can be reacted with a sulfonamides in presence of a base (e.g. pyridine, DMAP, 2-(dimethylamino)pyridine, N-methylmorpholine, etc.) in a polar aprotic solvent (e.g. DCM, THF, etc.), at temperatures ranging between 0° C. to 90° C. to generate acyl sulfonamides of formula Id.

SCHEME 16

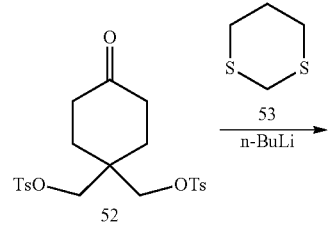

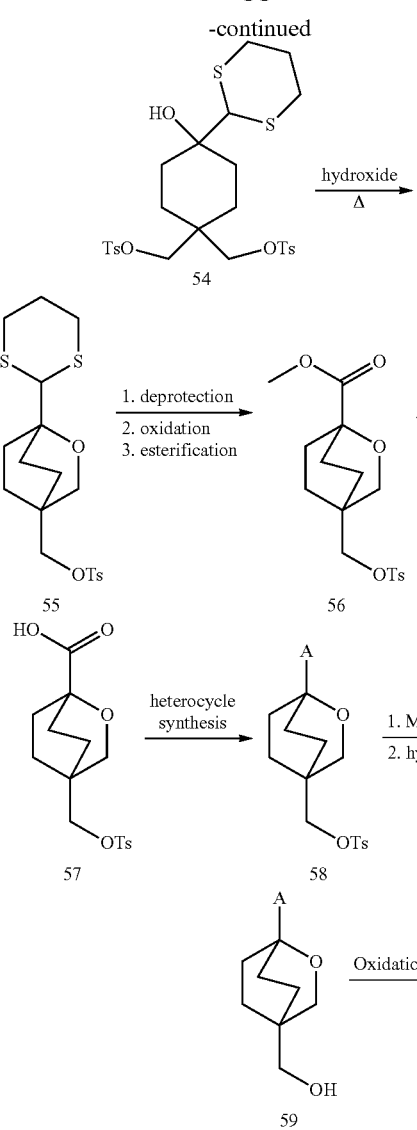

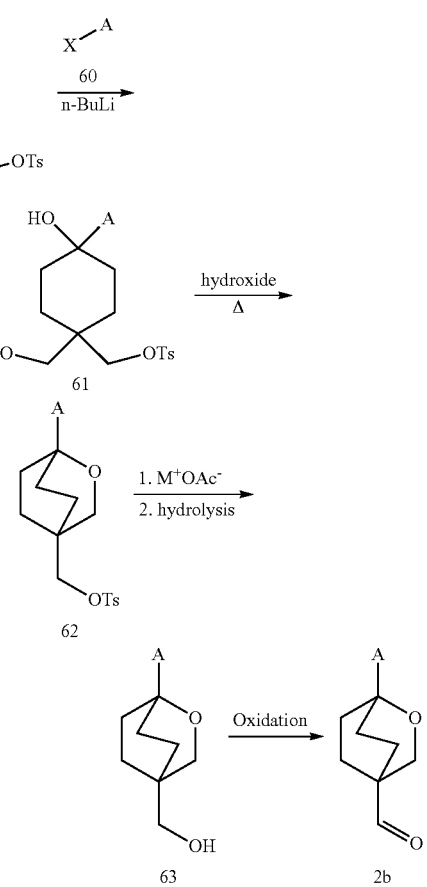

temperatures (120° C.) to provide corresponding acetate, which upon subsequent hydrolysis under acidic conditions (HCl) afforded intermediate 59. Intermediate 59 can be oxidized by methodologies recognized by one skilled in the art using oxidation conditions (e.g. Dess-Martin periodinane, Swern oxidation conditions, PDC or PCC, etc.) to afford compounds of formula 2a. The intermediates 2a can be converted to compounds of formula I by using steps described in Scheme 1.

Scheme 16 describes the synthesis of intermediate 2a. Intermediate 52 can be synthesized according to methods described by Singh, S. B. et al. (*ACS Med. Chem. Lett.* 2014, 5, 609-614). Intermediate 53 can be deprotonated with n-BuLi in an ethereal solvent (e.g. THF, 1,4-dioxane, etc.) with temperature varying between −78° C. and 0° C., then reacted with intermediate 52 to yield intermediate 54. Intermediate 54 can be cyclized in the presence of an alkali hydroxide base at elevated temperature (70° C.) to form intermediate 55. Thioacetal deprotection can be accomplished using any number of reagents (e.g. NCS, Hg(ClO₄)₂, DDQ, etc.) to provide the aldehyde, which can be oxidized to the acid by use of an oxidizing agent (NaClO₂, PCC or PDC, KMnO₄, etc.) then subsequently esterified by reaction with iodomethane to provide intermediate 56. Subsequent hydrolysis of the intermediate 56 with an alkali hydroxide base can provide intermediate 57. Intermediate 57 can be converted to various heterocycles (A) using numerous known methods recognized by one skilled in the art, including but not limited to the methods described in Scheme 11 to afford compounds of intermediate 58. Intermediate 58 can be treated with an acetate salt (e.g. CsOAc, KOAc, etc.) in a polar aprotic solvent (e.g. DMF, NMP, etc.) at elevated Scheme 17 describes an alternative synthesis of intermediate 2b. Intermediate 52 can be synthesized according to methods described by Singh, S. B. et al. (*ACS Med. Chem. Lett.* 2014, 5, 609-614). Halogenated heterocycles, 60, (commercially available or obtained by methods known by one skilled in the art) can be treated with base such as (n-BuLi, s-BuLi, MeLi, etc.) in an ethereal solvent (e.g. THF, 1,4-dioxane, etc.) with temperature varying between −78° C. and 0° C., and then reacted with ketone 52 to afford intermediate 61. Intermediate 61 can be cyclized in the presence of an alkali hydroxide base at elevated temperature (70° C.) to afford intermediate 62. Intermediate 62 can be treated with an acetate salt (e.g. CsOAc, KOAc, etc.) in a polar aprotic solvent (e.g. DMF, NMP, etc.) at elevated temperatures (120° C.) to provide corresponding acetate, which upon subsequent hydrolysis under acidic conditions (HCl) afforded intermediate 63. Intermediate 63 can be oxidized by methodologies recognized by one skilled in the art using oxidation conditions (e.g. Dess-Martin periodinane, Swern oxidation conditions, PDC or PCC, etc.) to afford intermediate 2b. Intermediate 2b can be converted to compounds of formula I by using steps described in Scheme 1.

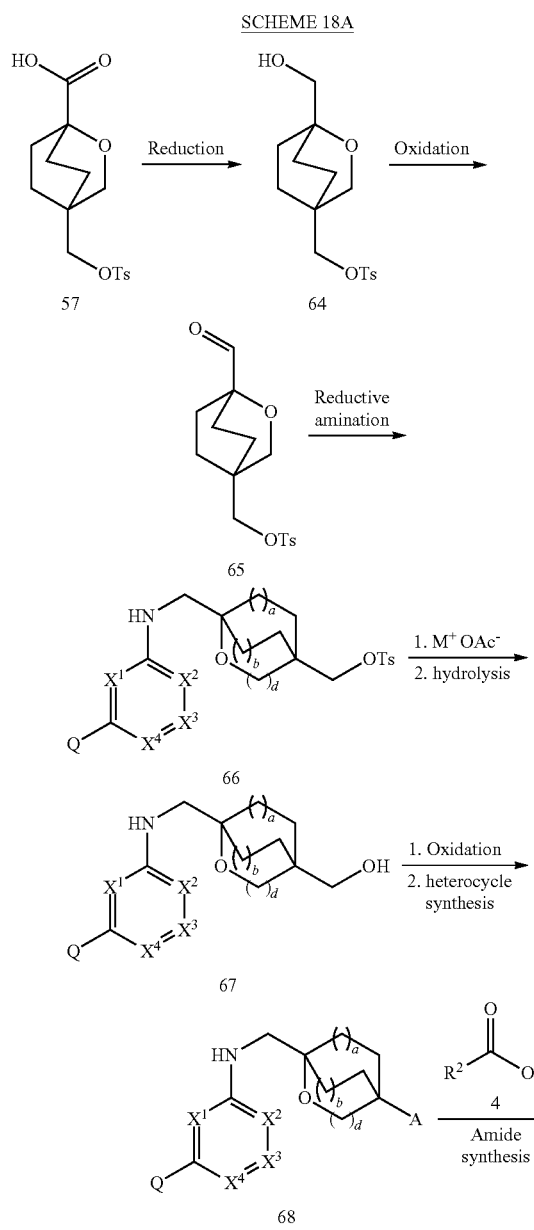

solvent (e.g. MeOH, EtOH, etc.) at room temperature or reflux temperature followed by reduction of imine with reducing agents (e.g. sodium cyanoborohydride, sodium triacetoxyborohydride, etc.) afforded intermediate 66. Intermediate 66 can be treated with an acetate salt (e.g. CsOAc, KOAc, etc.) in a polar aprotic solvent (e.g. DMF, NMP, etc.) at elevated temperatures (120° C.) to provide corresponding acetate, which upon subsequent hydrolysis under acidic conditions (HCl) afforded intermediate 67. The intermediate 67 can be oxidized to the acid by use of an oxidizing agent ($NaClO_2$, PCC or PDC, $KMnO_4$, etc.) followed by synthesis of various heterocycles (A) using numerous known methods recognized by one skilled in the art, including but not limited to the methods described in Scheme 11 to afford intermediate 68. Intermediate 4 can be activated for acylation using any number of reagents recognizable by one skilled in the art (e.g. thionyl chloride, phosphorus oxychloride, oxalyl chloride, methyl or ethylchloroformate, etc.), in a polar aprotic solvent (e.g. DCM, THF, etc.), at temperatures ranging between −30° C. to reflux temperatures. The activated acid intermediate can be reacted with intermediate 68 in presence of a base to generate compounds of formula I.

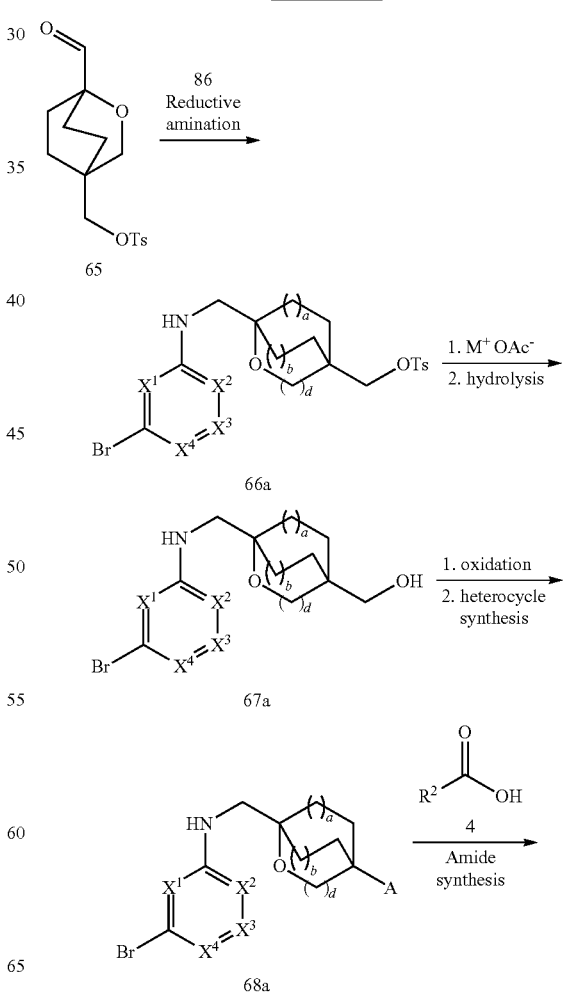

Scheme 18A describes an alternative synthesis of compounds of Formula I. Intermediate 57 (synthesis described in Scheme 16) can be subjected to reduction in presence of hydride based reducing agent (e.g. LAH, DIBAL-H, $NaBH_4$, etc.) to afford intermediate 64. The intermediate 64 can be oxidized to aldehyde 65, by methodologies recognized by one skilled in the art using oxidation conditions (e.g. Dess-Martin periodinane, Swern oxidation conditions, PDC or PCC, etc.). The intermediate 1 and intermediate 65 can be subjected to reductive amination, using numerous known methods recognizable by one skilled in the arts, in presence of acid such as acetic acid in a suitable polar protic

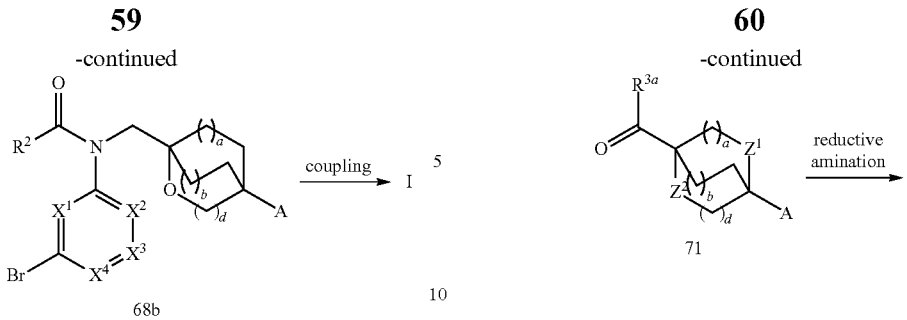

68b

Scheme 18B describes an alternative synthesis of compounds of Formula I. The intermediate 86 and intermediate 65 (as described in Scheme 18A) can be subjected to reductive amination, using numerous known methods recognizable by one skilled in the art, in presence of acid such as acetic acid in a suitable polar protic solvent (e.g. MeOH, EtOH, etc.) at room temperature or reflux temperature followed by reduction of imine with reducing agents (e.g. sodium cyanoborohydride, sodium triacetoxyborohydride, etc.) afforded intermediate 66a. Intermediate 66a can be treated with an acetate salt (e.g. CsOAc, KOAc, etc.) in a polar aprotic solvent (e.g. DMF, NMP, etc.) at elevated temperatures (120° C.) to provide corresponding acetate, which upon subsequent hydrolysis under acidic conditions (HCl) afforded intermediate 67a. The intermediate 67a can be oxidized to the acid by use of an oxidizing agent (NaClO$_2$, PCC or PDC, KMnO$_4$, etc.) followed by synthesis of various heterocycles (A) using numerous known methods recognized by one skilled in the art, including but not limited to the methods described in Scheme 11 to afford intermediate 68a. Intermediate 68a can be converted via sequential amide synthesis and coupling to compounds of formula I by following steps described in Scheme 13.

SCHEME 19

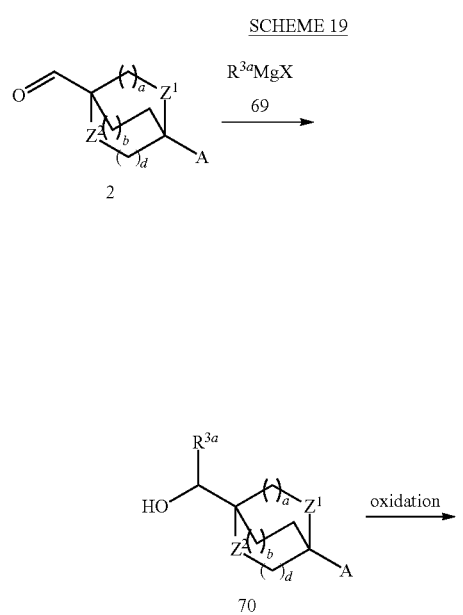

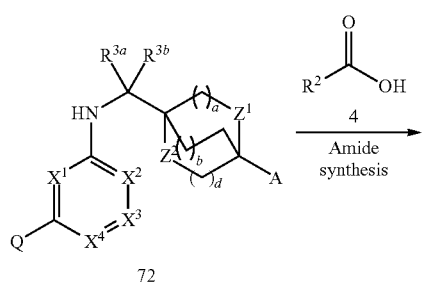

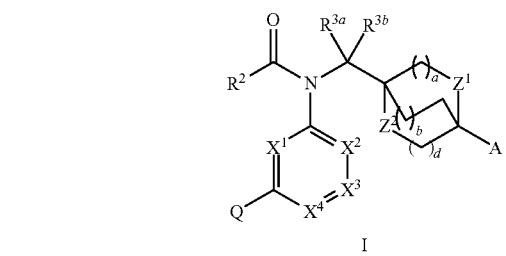

Scheme 19 describes an alternative synthesis of compounds of Formula I. Intermediate 2 can be subjected to treatment with organo magnesium reagents in ethereal solvent (such as Et$_2$O, THF, etc.) with temperature varying between −78° C. and 0° C. to afford intermediate 70. The intermediate 70 can be oxidized to intermediate 71, by methodologies recognized by one skilled in the art under oxidation conditions using oxidizing agents such as Dess-Martin periodinane, PDC or PCC, etc. Intermediate 71 and intermediate 1 in polar protic solvent such as (MeOH, EtOH, etc.) can be treated with triethyl silane and indium chloride at ambient temperature to afford intermediates of formula 72. Intermediate 4 can be activated for acylation using any number of reagents recognizable by one skilled in the art (e.g. thionyl chloride, phosphorus oxychloride, oxalyl chloride, methyl or ethylchloroformate, etc.), in a polar aprotic solvent (e.g. DCM, THF, etc.), at temperatures ranging between −30° C. to reflux temperatures. The activated acid intermediate can be reacted with intermediate 72 in presence of a base to generate compounds of formula I.

SCHEME 20

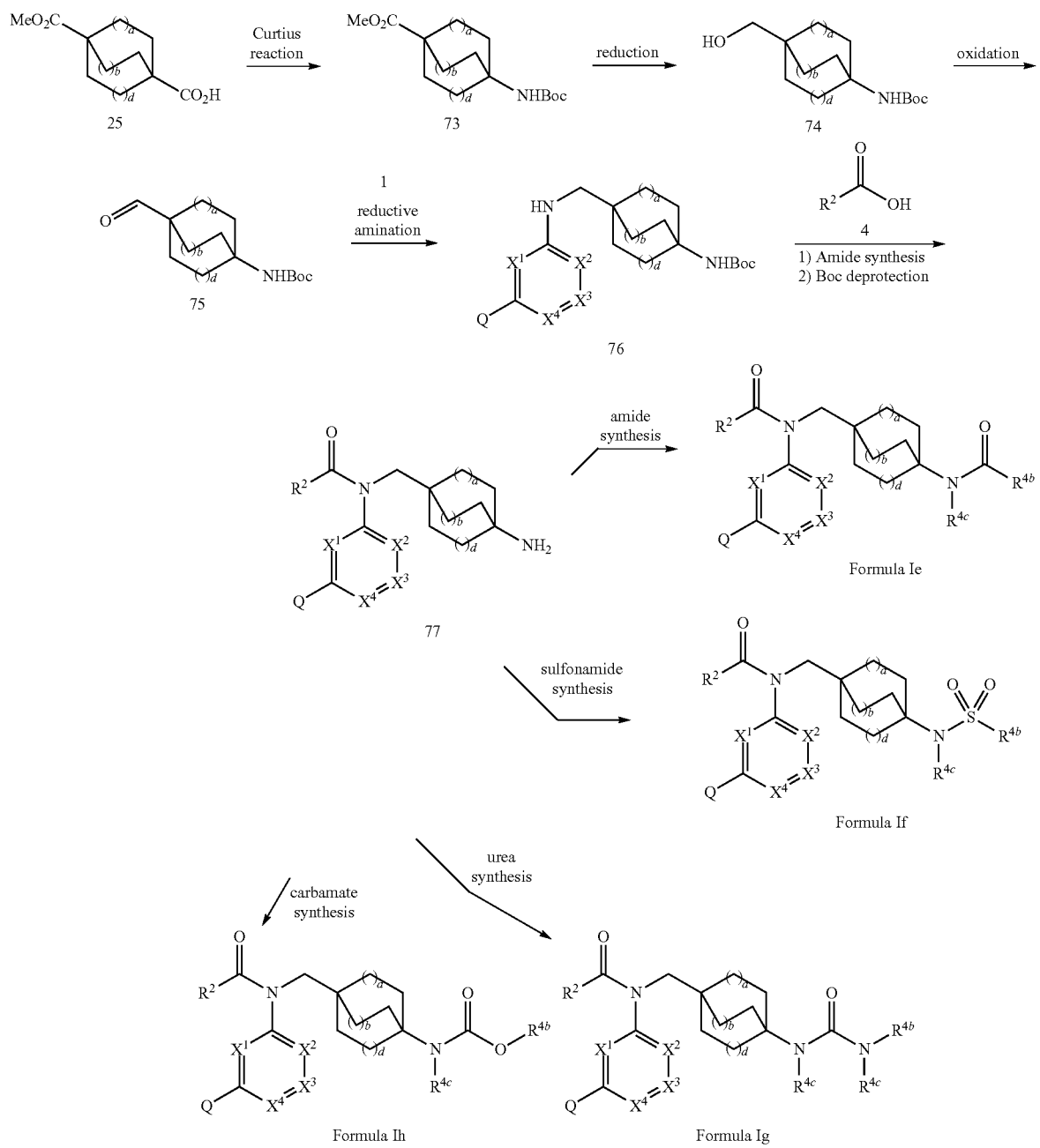

Scheme 20 describes synthesis of compounds of formula I(e-g) (where 'A' is amide, sulfonamide, urea or carbamate). Intermediate 25 can be converted to intermediate 73 via Curtius rearrangement (as described in Shioiri, T. et al. J. Am. Chem. Soc. 1972, 94, 6203-6205). Intermediate 73 can be subjected to reduction in presence of hydride based reducing agent (e.g. LAH, DIBAL-H, $NaBH_4$, etc.) to afford intermediate 74. The intermediate 74 can be oxidized to aldehyde 75, by methodologies recognized by one skilled in the art using oxidation conditions (e.g. Dess-Martin periodinane, Swern oxidation conditions, PDC or PCC, etc.). The intermediate 1 and intermediate 75 can be subjected to reductive amination, using numerous known methods recognizable by one skilled in the art, in presence of acid such as acetic acid in a suitable polar protic solvent (e.g. MeOH, EtOH, etc.) at room temperature or reflux temperature followed by reduction of imine with reducing agents (e.g. sodium cyanoborohydride, sodium triacetoxyborohydride, etc.) to afford intermediate 76. Intermediate 4 can be activated for acylation using any number of reagents recognizable by one skilled in the art (e.g. thionyl chloride, phosphorus oxychloride, oxalyl chloride, methyl or ethylchloroformate, etc.), in a polar aprotic solvent (e.g. DCM, THF, etc.), at temperatures ranging between –30° C. to reflux temperatures. The activated acid intermediate can be reacted with intermediate 76 in presence of a base to generate corresponding amide. The amide intermediate can be subjected to Boc-deprotection in polar aprotic solvent (e.g. DCM, THF, etc.) using trifluoroacetic acid at room temperature to afford intermediate 77. Intermediate 77 can be subjected to a variety of different transformations using numerous known methods recognized by one skilled in the art, including but not limited to the following methods to afford variations of Formula I:

Amides: Intermediate 77 can be reacted with activated acid intermediates in presence of base (e.g. pyridine, DMAP, 2-(dimethylamino)pyridine, N-methylmorpholine, etc.) in polar aprotic solvent (e.g. DCM, THF, etc.) to generate amides of Formula Ie.

Sulfonamides: Intermediate 77 can be treated with sulfonyl chlorides in presence of a base (e.g. pyridine, DMAP, 2-(dimethylamino)pyridine, N-methylmorpholine, etc.) in a polar aprotic solvent (e.g. DCM, THF, etc.), at temperatures ranging between 0° C. to 90° C. to generate sulfonamides of Formula If.

Ureas: Intermediate 77 can be subjected to treatment with isocyanates in presence of base (e.g. Et$_3$N, DIPEA, pyridine etc.) in polar aprotic solvent (e.g. DCM, DCE, etc.) at room temperature to afford ureas represented by formula Ig. Alternatively, intermediate 77 can be activated by treatment with triphosgene in presence of base (e.g. Et$_3$N, DIPEA, etc.) in solvent (e.g. DCM, DCE, etc.) at 0° C. to room temperature. The activated intermediate 77 can then be treated with substituted alkyl or aryl or heteroaryl amine in presence of base (e.g. Et$_3$N, DIPEA, etc.) in solvent (e.g. DCM, DCE, etc.) at room temperature to afford ureas represented by formula Ig.

Carbamates: Intermediate 77 can be treated with chloroformates (or alcohols, activated as carbonates) in presence of base (e.g. Et$_3$N, DIPEA, pyridine, t-BuOK etc.) in polar aprotic solvent (e.g. DCM, DCE, THF, etc.) at 0° C. to room temperature to afford carbamates represented by formula Ih.

SCHEME 21

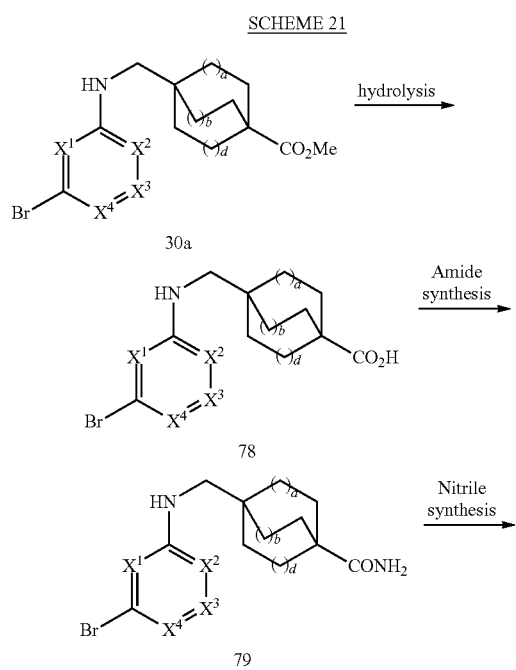

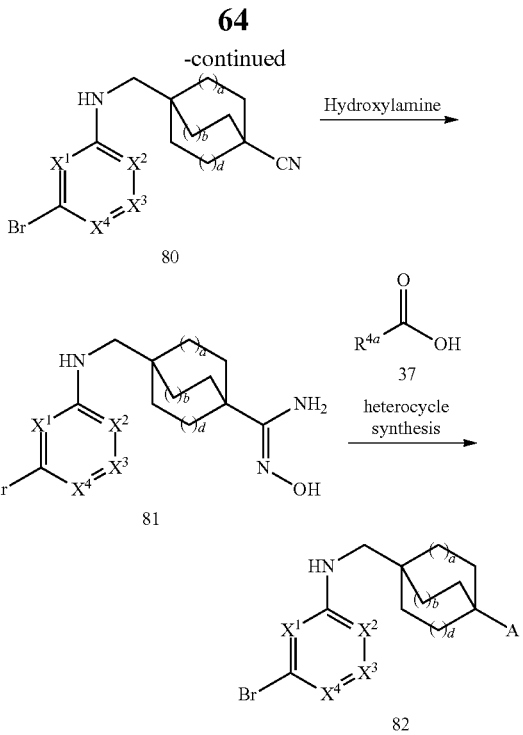

Scheme 21 describes the synthesis of intermediates 82 where A is 3-(5-substituted-1,2,4-oxadiazolyl) ring. Intermediate 30a (synthesized as described in Scheme 12) can be hydrolyzed with an alkali hydroxide base to afford intermediate 78. Intermediate 78 can be subjected to primary amide synthesis by activating acid with activation agent (BOP, CDI, HATU, etc.) in polar aprotic solvent (DCM, DMF, etc.) in presence of base (e.g. Et$_3$N, DIPEA, etc.) at ambient temperature in presence of ammonium chloride to afford intermediate 79. Intermediate 79 can be converted to intermediate 80 using various methods recognized by those skilled in the art including but not limited to the treatment with reagent (POCl$_3$, SOCl$_2$, TFAA, etc.) and base (imidazole, Et$_3$N, DIPEA, etc.). Intermediate 81 can be synthesized by reaction of intermediate 80 with hydroxylamine; see Hirawat, S., et al. WO 2006/110483. Intermediate 37 can be obtained from commercial sources or can be synthesized by known methods readily recognizable by one skilled in the art. Intermediates 37 can be coupled with intermediates 81 using an amide bond coupling reagent (e.g. CDI, BOP, EDC, etc.) in a polar aprotic solvent (e.g. THF, 1,4-dioxane, DMF, etc.) at room temperature. The acyclic intermediate can be subsequently cyclized at elevated temperatures (60° C. to 100° C.). Alternatively, in situ cyclization can be accomplished by conducting the coupling of intermediates 37 with intermediates 81 at elevated temperatures (60° C. to 100° C.) to afford oxadiazoles 82. Intermediates 82 can be converted to compounds of formula I via a sequential amide synthesis and coupling as described in Scheme 13.

SCHEME 22

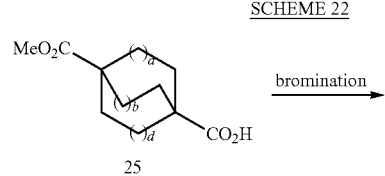

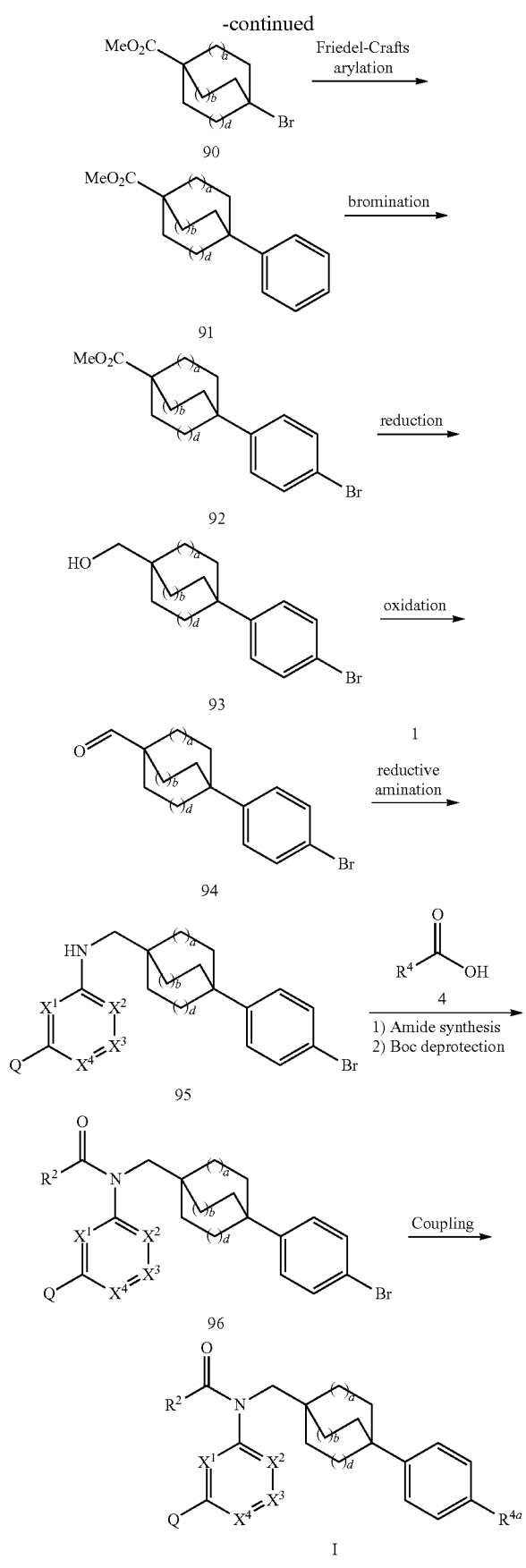

Scheme 22 describes synthesis of compounds of formula I (where 'A' is phenyl). Commercially available 4-(methoxycarbonyl)bicyclo[2.2.2] octane-1-carboxylic acid 25 can be subjected to bromination reaction with bromine in presence of mercuric oxide in dibromomethane as a solvent under heating conditions to afford intermediate 90 (as described by Owen et. al. PCT Int. Appl., 2014113485, 2014). Intermediate 90 can be converted to intermediate 91 in benzene in presence of $AlCl_3$ under conditions described by Piyasena et. al. PCT Int. Appl., 2015005901, 2015. Intermediate 91 can be subjected to bromination in presence of silver trifluoroacetate and bromine in $CHCl_3$ at room temperature to afford intermediate 92 (described by Piyasena et. al. PCT Int. Appl., 2015005901, 2015). Intermediate 92 can be subjected to reduction in presence of hydride based reducing agent (e.g. LAH, DIBAL-H, $NaBH_4$, etc.) to afford intermediate 93. The intermediate 93 can be oxidized to aldehyde 94, by methodologies recognized by one skilled in the art using oxidation conditions (e.g. Dess-Martin periodinane, Swern oxidation conditions, PDC or PCC, etc.). The intermediate 1 and intermediate 94 can be subjected to reductive amination, using numerous known methods recognizable by one skilled in the art, in presence of acid such as acetic acid in a suitable polar protic solvent (e.g. MeOH, EtOH, etc.) at room temperature or reflux temperature followed by reduction of imine with reducing agents (e.g. sodium cyanoborohydride, sodium triacetoxyborohydride, etc.) afforded intermediate 95. Intermediate 4 can be activated for acylation using any number of reagents recognizable by one skilled in the art (e.g. thionyl chloride, phosphorus oxychloride, oxalyl chloride, methyl or ethylchloroformate, etc.), in a polar aprotic solvent (e.g. DCM, THF, etc.), at temperatures ranging between −30° C. to reflux temperatures. The activated acid intermediate can be reacted with intermediate 95 in presence of a base to generate intermediate 96. Intermediate 96 can be subjected to various metal catalyzed reactions (including but not limited to reactions such as Ullmann, Suzuki, Buchwald, Stille coupling, etc.) in presence of metal catalyst (e.g. CuBr, $Pd(OAc)_2$, $Pd_2(dba)_3$, $Pd(PPh_3)_4$, $Pd(PPh_3)_2Cl_2$, $Pd(dppf)Cl_2$, etc.) and appropriate ligand (including but not limited to ligands such as tricyclohexylphosphine, dppf, etc.) when necessary. The Ullmann and Buchwald coupling reactions of intermediate 96 can be carried out with various coupling partners such as alkyl or aryl or heteroaryl amines, thiols and alcohols, etc. The Suzuki, Stille coupling reaction of intermediate 96 can be carried out with various coupling partners such as alkenyl, aryl or heteroaryl boronic acids, boronic acid esters, organotin reagents, etc. The coupling reactions can be carried out in presence of base whenever necessary (including but not limited to $Na_2CO_3$, $K_2CO_3$, $NaHCO_3$, $K_3PO_4$, $NaO^tBu$, etc.) and solvent (e.g. dioxane, THF, DME, toluene, methanol, DMF, water, etc. or the mixture of two or three of these solvents) under heating conditions to afford compounds of formula I.

SCHEME 23

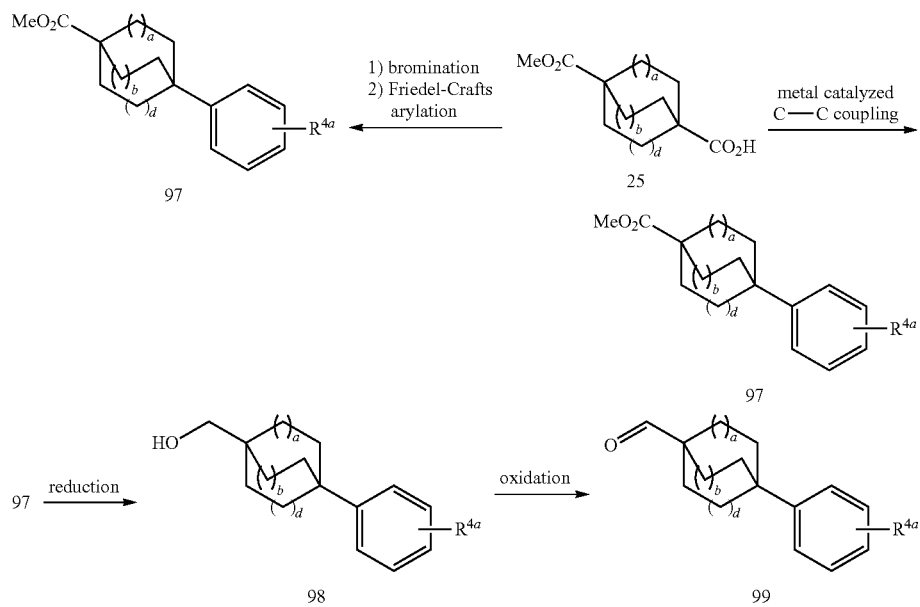

Scheme 23 describes the synthesis of intermediates 99. Commercially available 4-(methoxycarbonyl)bicyclo[2.2.2]octane-1-carboxylic acid 25 can be subjected to bromination followed by Friedel-Crafts arylation in presence of suitably substituted arenes as described in Scheme 22 to afford intermediate 97. Alternatively, intermediate 97 can be synthesized via decarboxylative Negishi- or Suzuki type cross coupling reactions. Intermediate 25 can be activated as N-hydroxyphthalimide ester or N-hydroxybenzotriazole ester, etc., as redox-active ester and can be treated with organozincs or organoboronic acids or Grignard reagents of variously substituted aryls in presence of metal catalysts (e.g. Fe(acac)$_3$, FeCl$_3$, NiCl$_2$.glyme, etc.) as described by Torriyama, F. et al *J. Am. Chem. Soc.* 2016, 138, 11132-11135 and references cited therein to afford intermediate 97. Intermediate 97 can be subjected to reduction in presence of hydride based reducing agent (e.g. LAH, DIBAL-H, NaBH$_4$, etc.) to afford intermediate 98. The intermediate 98 can be oxidized to aldehyde 99, by methodologies recognized by one skilled in the art using oxidation conditions (e.g. Dess-Martin periodinane, Swern oxidation conditions, PDC or PCC, etc.). Intermediate 99 can be converted to compounds of formula I (where 'A' is phenyl) by using steps described in Scheme 1.

SCHEME 24

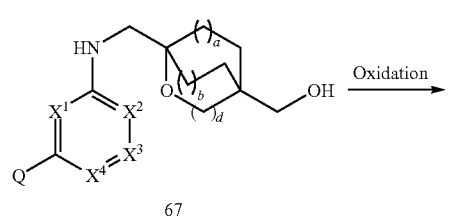

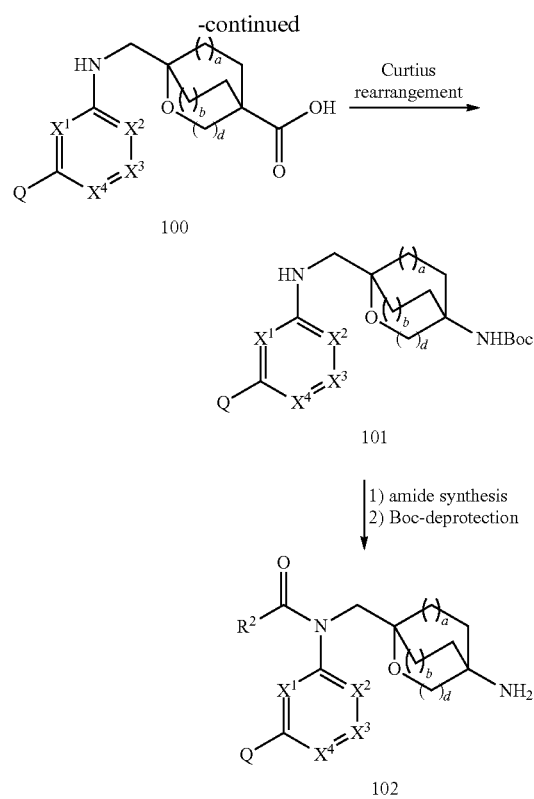

Scheme 24 describes alternative synthesis of compounds of formula I (where 'A' is amide, sulfonamide, urea or carbamate). Intermediate 67 (synthesized as described in Scheme 18A) can be oxidized by use of an oxidizing agent (NaClO$_2$, PCC or PDC, KMnO$_4$, etc.) to afford intermediate 100. Intermediate 100 can be converted to intermediate 101 via Curtius rearrangement (as described in Shioiri, T. et al. *J. Am. Chem. Soc.* 1972, 94, 6203-6205). Intermediates 101 can be subjected to sequential amide synthesis and boc-deprotection as described in Scheme 20 to afford the amine intermediate 102. Intermediate 102 can be subjected to a variety of different transformations using numerous known methods recognized by one skilled in the art, including but not limited to the methods described in Scheme 20 to afford variations of Formula I (where 'A' is amide, sulfonamide, urea or carbamate).

Scheme 25 describes synthesis of compounds of formula I(i,j,k,m) (where 'A' is amide, sulfonamide, urea or carbamate). Intermediate 67a (synthesized as described in Scheme 18B) can be oxidized by use of an oxidizing agent (NaClO$_2$, PCC or PDC, KMnO$_4$, etc.) to afford intermediate 100a. Intermediate 100a can be converted to intermediate 101a via Curtius rearrangement (as described in Shioiri, T. et al. *J. Am. Chem. Soc.* 1972, 94, 6203-6205). Intermediates 101a

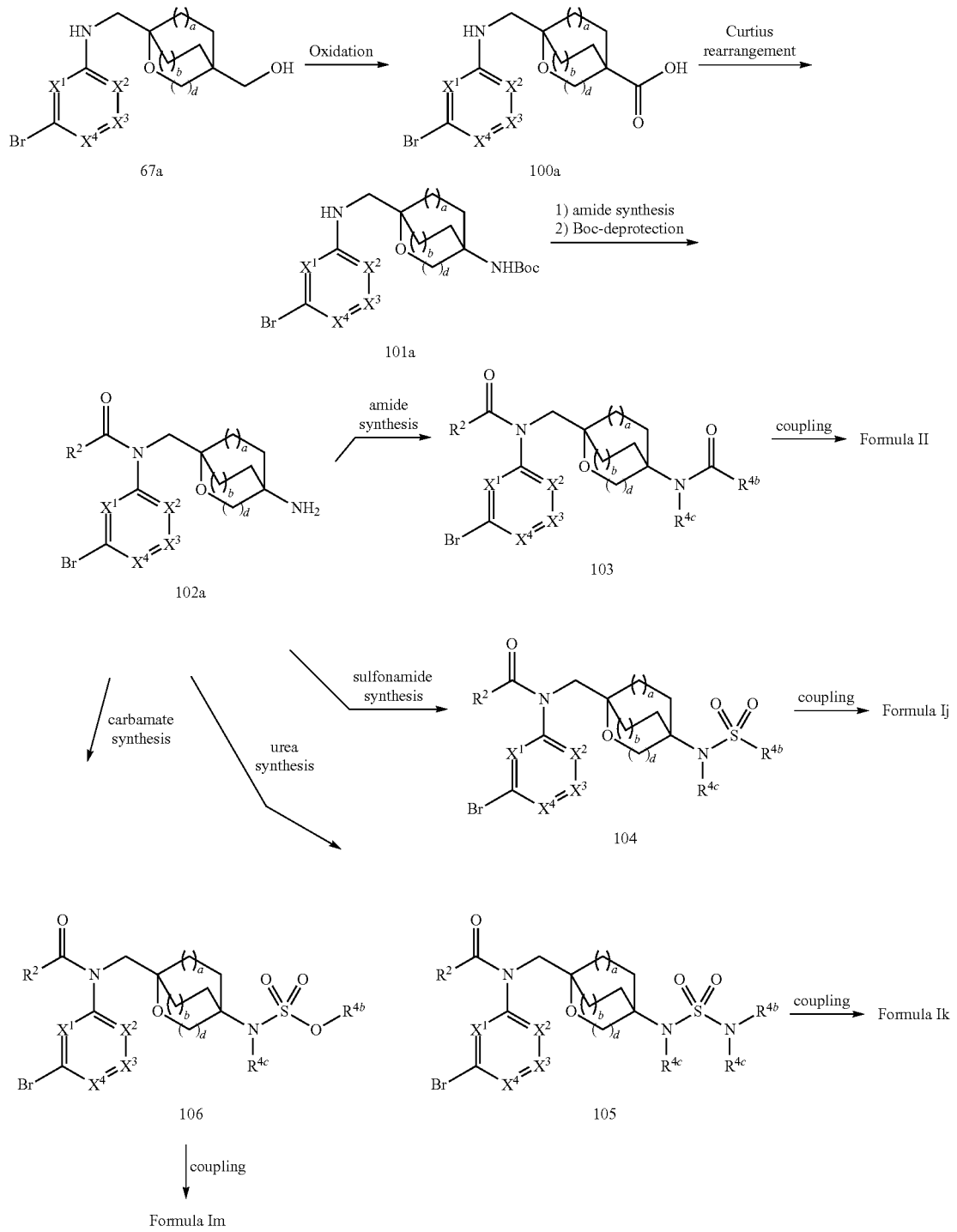

can be subjected to sequential amide synthesis and boc-deprotection as described in Scheme 20 to afford the amine intermediate 102a.

Intermediate 102a can be subjected to a variety of different transformations using numerous known methods recognized by one skilled in the art, including but not limited to the following methods to afford variations of Formula I:

Amides: Intermediate 102a can be reacted with activated acid intermediates in presence of base (e.g. pyridine, DMAP, 2-(dimethylamino)pyridine, N-methylmorpholine, etc.) in polar aprotic solvent (e.g. DCM, THF, etc.) to generate intermediate 103.

Sulfonamides: Intermediate 102a can be treated with sulfonyl chlorides in presence of a base (e.g. pyridine, DMAP, 2-(dimethylamino)pyridine, N-methylmorpholine, etc.) in a polar aprotic solvent (e.g. DCM, THF, etc.), at temperatures ranging between 0° C. to 90° C. to generate intermediate 104.

Ureas: Intermediate 102a can be subjected to treatment with isocyanates in presence of base (e.g. Et$_3$N, DIPEA, pyridine etc.) in polar aprotic solvent (e.g. DCM, DCE, etc.) at room temperature to afford intermediate 105. Alternatively, intermediate 102a can be activated by treatment with triphosgene in presence of base (e.g. Et$_3$N, DIPEA, etc.) in solvent (e.g. DCM, DCE, etc.) at 0° C. to room temperature. The activated intermediate 102a can then be treated with substituted alkyl or aryl or heteroaryl amine in presence of base (e.g. Et$_3$N, DIPEA, etc.) in solvent (e.g. DCM, DCE, etc.) at room temperature to afford intermediate 105.

Carbamates: Intermediate 102a can be treated with chloroformates (or alcohols, activated as carbonates) in presence of base (e.g. Et$_3$N, DIPEA, pyridine, t-BuOK etc.) in polar aprotic solvent (e.g. DCM, DCE, THF, etc.) at 0° C. to room temperature to afford intermediate 106.

Intermediates 103-106 can be subjected to metal catalyzed cross coupling reactions using numerous known methods recognized by the one skilled in the art including but not limited to the ones described in Metal-Catalyzed Cross-Coupling Reactions, Armin de Meijere, François Diederich, 2 Volumes, Second, Revised and Enlarged Edition, 2004, ISBN: 3-527-30518-1, Wiley-VCH and references cited therein. Intermediates 103-106 can be subjected to metal catalyzed Sonogashira coupling. These coupling reactions can be carried out in presence of metal catalyst Pd(PPh$_3$)$_2$Cl$_2$ and CuI in presence of base such as triethylamine in polar aprotic solvent such as DMF at 90° C. The coupling reactions of intermediates 103-106 can be carried out with various appropriate coupling partners such substituted alkynes to afford compounds represented by formula I(i,j,k,m). Intermediate 103-106 can be subjected to metal catalyzed Heck coupling. These coupling reactions can be carried out in presence of metal catalyst such as Dichlorobis(tri-o-tolylphosphine)palladium(II) and tetrabutyl ammonium bromide in presence of base (Et$_3$N, DIPEA, etc.) in solvent (DMAc, DMF, etc.) under heating conditions. The coupling reactions of intermediate 103-106 can be carried out with various appropriate coupling partners such substituted alkenes, alkenyl halides or triflates to afford compounds represented by formula I(i,j,k,m). Intermediate 103-106 can be converted to organoboron reagent using bis(pinacolato)diboron, bis(neopentyl glycolato)diboron, etc in presence of a palladium catalyst such as Pd(dppf)Cl$_2$ and base such as potassium acetate in solvent (e.g. dioxane, DMSO etc.) at reflux temperature, which upon coupling with suitable coupling partners such as alkenes, alkenyl halides or triflates etc. in a Suzuki coupling afforded compounds represented by formula I(i,j,k,m). Alternatively, intermediate 103-106 can be converted to organotin reagent using hexamethylditin in presence of a palladium catalyst and in solvent (e.g. toluene, THE etc.) at reflux temperature, which upon coupling with suitable coupling partners such as alkenyl halides or triflates etc. in a Stille coupling (Sherer, B., et al. PCT Int. Appl., 2016/039734, 2016) afforded compounds represented by formula I(i,j,k,m).

General Notes: The sequence of the steps involving installation of groups 'Q' and 'A' can be interchangeably performed in the scheme as appropriate. The oxadiazole regio-isomers can be generated by using sequence described in schemes 11 and 14 attached to the oxabicyclo ring system.

Examples 1 and 2

Methyl (E)-3-(3-(N-((4-(4-(dimethylamino)phenyl)bicyclo[2.2.2]octan-1-yl)methyl)cyclohexanecarboxamido)phenyl)acrylate (1) and (E)-3-(3-(N-((4-(4-(dimethylamino)phenyl)bicyclo[2.2.2]octan-1-yl)methyl)cyclohexanecarboxamido)phenyl)acrylic Acid (2)

(1)

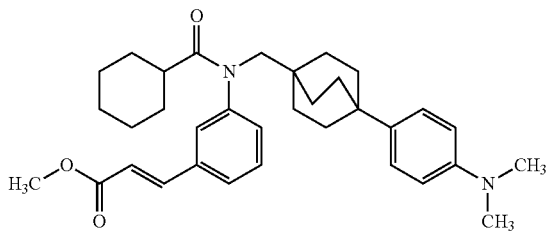

(2)

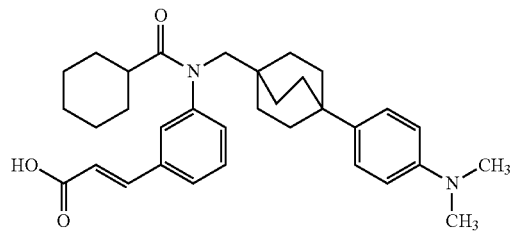

Step A. Intermediate 1A. Preparation of methyl 4-bromobicyclo[2.2.2]octane-1-carboxylate

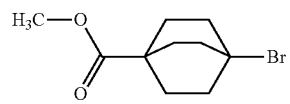

To a stirred solution of 4-(methoxycarbonyl)bicyclo[2.2.2]octane-1-carboxylic acid (commercially available) (1 g, 4.71 mmol) in CH$_2$Br$_2$ (10 mL) was added mercuric oxide (1.73 g, 8.01 mmol) at room temperature. The reaction mixture was heated at 80° C. Bromine (0.36 mL, 7.07 mmol) was added drop wise to the reaction mixture at the same temperature and continued stirring for 3 h. The reaction mixture was cooled to room temperature, filtered through Celite. The filtrate was concentrated under reduced pressure to afford the title compound (1 g, 4.05 mmol, 86% yield).

This compound was taken to the next step as such. $^1$H NMR (300 MHz, DMSO-$d_6$) δ 3.56 (s, 3H), 2.25-2.15 (m, 6H), 1.94-1.85 (m, 6H).

Step B. Intermediate 1B. Preparation of methyl 4-phenylbicyclo[2.2.2]octane-1-carboxylate

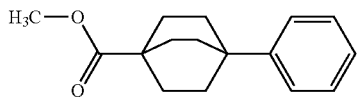

Benzene (12 mL, 142 mmol) was cooled to −10° C. and was added aluminum chloride (2.70 g, 20.23 mmol) under nitrogen atmosphere. The solution was stirred for 5 min at the same temperature. Intermediate 1A (1 g, 4.05 mmol) as a solution in benzene (12 mL) was added to the reaction mixture at −10° C. The reaction mixture was allowed to warm to room temperature and stirred for 12 h. The reaction mixture was poured into crushed ice and diluted with water (50 mL). The organic layer was separated, washed with water (2×10 mL), dried over MgSO$_4$ and concentrated under reduced pressure to afford the title compound (0.82 g, 2.10 mmol, 52% yield). This compound was taken to the next step as such. $^1$H NMR (300 MHz, chloroform-d) δ 7.34-7.30 (m, 4H), 7.21 (dt, J=5.8, 2.6 Hz, 1H), 3.73 (s, 3H), 1.99-1.84 (m, 12H). MS (ESI) 445 (M+H).

Step C. Intermediate 1C. Preparation of methyl 4-(4-bromophenyl)bicyclo[2.2.2]octane-1-carboxylate

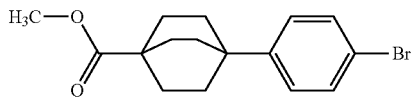 [SMILES: COC(=O)C12CCC(c3ccc(Br)cc3)(CC1)CC2]

A stirred solution of Intermediate 1B (0.8 g, 3.27 mmol) and silver trifluoro acetate (0.86 g, 3.93 mmol) was stirred at room temperature for 5 min under nitrogen atmosphere. A solution of Br$_2$ (0.17 mL, 3.27 mmol) in CHCl$_3$ (40 mL) was added to the reaction mixture. The reaction mixture was stirred at room temperature for 2 h. The reaction mixture was filtered through Celite. The filtrate was evaporated under reduced pressure, the residue was washed with n-hexane and dried in vacuo to afford the title compound (0.74 g, 1.580 mmol, 48% yield). MS (ESI) 323 (M+H). $^1$H NMR (300 MHz, chloroform-d) δ 7.43 (d, J=8.7 Hz, 2H), 7.20 (d, J=8.7 Hz, 2H), 3.69 (s, 3H), 1.99-1.78 (m, 12H).

Step D. Intermediate 1D. Preparation of (4-(4-bromophenyl)bicyclo[2.2.2]octan-1-yl) methanol

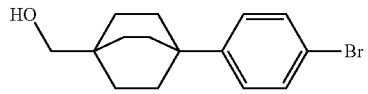 [SMILES: OCC12CCC(c3ccc(Br)cc3)(CC1)CC2]

A stirred solution of Intermediate 1C (0.65 g, 2.011 mmol) in DCM (5 mL) was cooled to −78° C. DIBAL-H (4.0 mL, 4.02 mmol) was added to the reaction mixture. The reaction mixture was allowed to warm to room temperature and stirred for 2 h. The reaction mixture was poured into crushed ice and diluted with water (10 mL). The aqueous layer was extracted with ethyl acetate (2×20 mL). The organic layers were combined, dried over anhydrous sodium sulphate and concentrated under reduced pressure. The crude material was purified by flash chromatography (24 g silica gel cartridge; A=Hex, B=EtOAc; 30 min grad.; 0% B to 40% B; flow rate=30 mL/min). The pure fractions were combined, concentrated under reduced pressure and dried in vacuo to afford the title compound (0.59 g, 1.999 mmol, 99% yield). $^1$H NMR (300 MHz, DMSO-$d_6$) δ 7.44 (d, J=8.7 Hz, 2H), 7.28 (d, J=8.7 Hz, 2H), 4.35 (t, J=5.3 Hz, 1H), 3.08 (d, J=5.3 Hz, 2H), 1.78-1.66 (m, 6H), 1.51-1.39 (m, 6H).

Step E. Intermediate 1E. Preparation of 4-(4-bromophenyl)bicyclo[2.2.2]octane-1-carbaldehyde

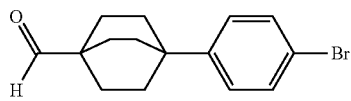

To a stirred solution of oxalyl chloride (0.12 mL, 1.219 mmol) in anhydrous DCM (3 mL) was added drop wise a solution of DMSO (0.21 mL, 3.05 mmol) in anhydrous DCM (2.5 mL) at −78° C. under nitrogen atmosphere. The reaction mixture was stirred for 15 min. A solution of Intermediate 1D (0.3 g, 1.016 mmol) in DCM (5 ml) was added to the reaction mixture over a period of 10 min. The reaction mixture was stirred at −78° C. for 3 h. Et$_3$N (0.85 mL, 6.10 mmol) was added to the reaction and continued stirring for another 5 min. at −78° C. The reaction mixture was allowed to warm to 0° C. and stirred for 1 h. The reaction mixture was poured into crushed ice and diluted with cold water (20 mL). The organic layer was separated and the aqueous layer was extracted with DCM (2×30 mL). The combined organic layers were dried over anhydrous sodium sulphate and concentrated under reduced pressure to afford the title compound (220 mg, 0.750 mmol, 74% yield). $^1$H NMR (300 MHz, chloroform-d) δ 9.53 (s, 1H), 7.44 (d, J=8.7 Hz, 2H), 7.20 (d, J=8.7 Hz, 2H), 1.95-1.73 (m, 12H).

Step F. Intermediate 1F. Preparation of methyl (E)-3-(3-nitrophenyl)acrylate

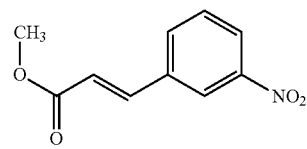

To a stirred solution of methyl 2-(dimethoxyphosphoryl) acetate (commercially available) (1.29 mL, 7.94 mmol) in water (6 mL) was added K$_2$CO$_3$ (1.82 g, 13.23 mmol) followed by 3-nitrobenzaldehyde (commercially available) (1 g, 6.62 mmol) at room temperature. The reaction mixture was stirred at room temperature for 30 min. The reaction mixture was diluted with water (10 mL) and extracted with EtOAc (2×25 mL). The combined organic layers were dried over anhydrous sodium sulphate and concentrated under reduced pressure to afford the title compound (1 g, 4.83 mmol, 73% yield). ¹H NMR (300 MHz, DMSO-d₆) δ 8.56 (t, J=1.7 Hz, 1H), 8.27-8.18 (m, 2H), 7.81 (d, J=16.2 Hz, 1H), 7.71 (t, J=8.1 Hz, 1H), 6.87 (d, J=16.2 Hz, 1H), 3.75 (s, 3H).

Step G. Intermediate 1G. Preparation of methyl (E)-3-(3-aminophenyl)acrylate

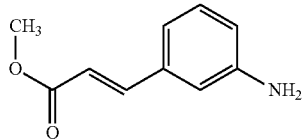

To a stirred solution of Intermediate 1F (1.300 g, 6.27 mmol) in water (15 mL) was added tin(II) chloride dihydrate (8.50 g, 37.6 mmol) at room temperature. The reaction mixture was heated at 80° C. 3 h. The reaction mixture was allowed to warm to room temperature. The reaction volume was reduced to half under reduced pressure and the remaining solution was poured into crushed ice. The aqueous solution was neutralized (pH~7) using aqueous saturated Na₂CO₃ solution and extracted with ethyl acetate (2×30 mL). The combined organic layers were dried over anhydrous sodium sulphate and concentrated under reduced pressure to afford the title compound (1 g, 3.84 mmol, 61% yield) as a light yellow solid. ¹H NMR (400 MHz, DMSO-d₆) δ 7.49 (d, J=15.6 Hz, 1H), 7.12-7.01 (m, 1H), 6.87-6.77 (m, 2H), 6.67-6.59 (m, 1H), 6.41 (d, J=16.1 Hz, 1H), 5.18 (s, 2H), 3.71 (s, 3H). MS (ESI) 178 (M+H).

Step H. Intermediate 1H. Preparation of methyl (E)-3-(3-(((4-(4-bromophenyl) bicyclo[2.2.2]octan-1-yl)methyl)amino)phenyl)acrylate

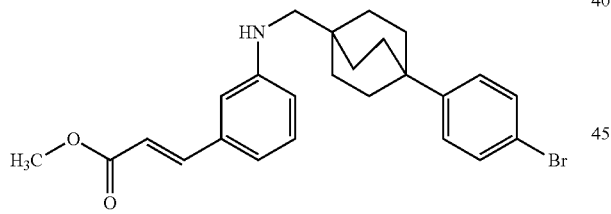

To a stirred solution of Intermediate 1E (150 mg, 0.512 mmol) in anhydrous MeOH (3 mL) was added Intermediate 1G (100 mg, 0.563 mmol) followed by acetic acid (0.015 mL, 0.256 mmol) and molecular sieves 4 Å (15 mg) at room temperature. The reaction mixture was heated at 60° C. overnight. The reaction mixture was cooled to 0° C. and was added sodium cyanoborohydride (96 mg, 1.535 mmol). The reaction mixture was allowed to warm to room temperature and stirred for 2 h. The reaction mixture was concentrated under reduced pressure, residue was diluted with water and extracted with EtOAc (2×50 mL). The combined organic layers were dried over anhydrous sodium sulphate and concentrated under reduced pressure. The crude material was purified by flash chromatography (40 g silica gel cartridge; A=Hex, B=EtOAc; 30 min grad.; 0% B to 50% B; flow rate=30 mL/min). The pure fractions were combined, concentrated under reduced pressure and dried in vacuo to afford the title compound (100 mg, 0.178 mmol, 35% yield).

¹H NMR (400 MHz, DMSO-d₆) δ 7.53 (d, J=16.1 Hz, 1H), 7.46 (d, J=8.00 Hz, 2H), 7.30 (d, J=8.00 Hz, 2H), 7.09 (t, J=7.8 Hz, 1H), 6.89 (s, 1H), 6.85-6.79 (m, 1H), 6.72 (d, J=8.3 Hz, 1H), 6.50 (d, J=15.9 Hz, 1H), 5.60-5.54 (m, 1H), 3.72 (s, 3H), 3.18 (d, J=5.4 Hz, 2H), 1.80-1.72 (m, 6H), 1.63-1.53 (m, 6H). MS (ESI) 455 (M+H).

Step I. Intermediate 1I. Preparation of methyl (E)-3-(3-(N-((4-(4-bromophenyl)bicyclo[2.2.2]octan-1-yl)methyl)cyclohexanecarboxamido)phenyl)acrylate

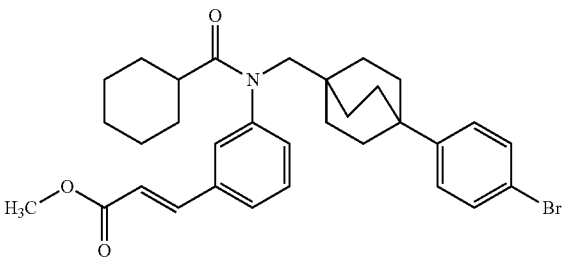 [SMILES: COC(=O)/C=C/c1cccc(N(CC23CCC(c4ccc(Br)cc4)(CC2)CC3)C(=O)C2CCCCC2)c1]

To a stirred solution of Intermediate 1H (100 mg, 0.220 mmol) in anhydrous DCM (2 mL) was added Et₃N (0.123 mL, 0.880 mmol) followed by cyclohexanecarbonyl chloride (commercially available) (0.06 mL, 0.440 mmol) at 0° C. The reaction mixture was allowed to warm to room temperature and stirred for 3 h. The reaction mixture was diluted with water and extracted with DCM (2×50 mL). The organic layers were combined, dried over anhydrous sodium sulphate and concentrated under reduced pressure. The crude material was purified by flash chromatography (12 g silica gel cartridge; A=Hex, B=EtOAc; 30 min grad.; 0% B to 30% B; flow rate=30 mL/min). The pure fractions were combined, concentrated under reduced pressure and dried in vacuo to afford the title compound (120 mg, 0.172 mmol, 78% yield). MS (ESI) 564 (M+H).

Step J. Example 1 and Example 2. Preparation of methyl (E)-3-(3-(N-((4-(4-(dimethylamino)phenyl) bicyclo[2.2.2]octan-1-yl)methyl)cyclohexanecarboxamido) phenyl)acrylate & (E)-3-(3-(N-((4-(4-(dimethylamino)phenyl)bicyclo[2.2.2]octan-1-yl) methyl)cyclohexanecarboxamido)phenyl)acrylic acid To a stirred solution of Intermediate 1I (100 mg, 0.177 mmol) in toluene (5 mL) were added dimethylamine (0.094 mL, 1.771 mmol), 2-di-tert-butylphosphino-2',4',6'-triisopropylbiphenyl (7.52 mg, 0.018 mmol) and sodium tert-butoxide (51 mg, 0.531 mmol) at room temperature. The reaction mixture was degassed and back-filled with argon. Pd₂(dba)₃ (8 mg, 8.86 µmol) was added to the reaction and the vial was sealed (Pressure release vial). The reaction mixture was heated at 80° C. for 12 h. The reaction mixture was diluted with water (10 mL) and extracted with EtOAc (2×50 mL). The combined organic layers were dried over anhydrous sodium sulphate and concentrated under reduced pressure. The crude material was purified via preparative HPLC using following conditions: (Column: waters XBridge C18, 19×150 mm, 5-µm particles; Mobile Phase A: 10-mM ammonium acetate; Mobile Phase B: acetonitrile; Gradient: 40-80% B over 20 minutes, then a 5-minute hold at 100% B; Flow: 15 mL/min). Fractions containing the desired product were combined and dried via centrifugal evaporation to afford the title compound (Example 1); (9 mg, 0.016 mmol, 9% yield); $^1$H NMR (400 MHz, DMSO-$d_6$) δ 7.79 (s, 1H), 7.75-7.66 (m, 2H), 7.53-7.37 (m, 2H), 7.10-7.00 (m, J=8.8 Hz, 2H), 6.76 (d, J=16.1 Hz, 1H), 6.65-6.58 (m, J=8.8 Hz, 2H), 3.74 (s, 3H), 3.58 (br. s., 2H), 2.81 (s, 6H), 1.66-1.53 (m, 12H), 1.42-1.28 (m, 8H), 0.86 (d, J=6.1 Hz, 3H). FXR EC$_{50}$ (nM) 78; MS (ESI) 529 (M+H) and Example 2 (2.7 mg, 4.98 μmol, 3% yield); $^1$H NMR (400 MHz, DMSO-$d_6$) δ 12.44 (bs, 1H), 7.74 (s, 1H), 7.68-7.62 (m, 2H), 7.60 (s, 1H), 7.47 (t, J=7.8 Hz, 1H), 7.40 (d, J=7.8 Hz, 1H), 7.06 (d, J=9.0 Hz, 2H), 6.61 (d, J=9.0 Hz, 2H), 3.58 (br. s., 2H), 2.81 (s, 6H), 2.20 (br. s., 1H), 1.65-1.54 (m, 8H), 1.49 (d, J=12.2 Hz, 2H), 1.41-1.33 (m, 7H), 1.32 (br. s., 1H), 1.24 (s, 1H), 1.08 (d, J=7.1 Hz, 1H), 0.94-0.79 (m, 2H). FXR EC$_{50}$ (nM) 1517, MS (ESI) 515 (M+H).

The following compounds were prepared according to the method described for the synthesis of Example 1 by substituting Intermediate 11 and corresponding amines.

| Ex. No. | Structure & Name | MS (ESI) (M + H) | FXR EC$_{50}$ (nM) |
|---|---|---|---|
| 3 | 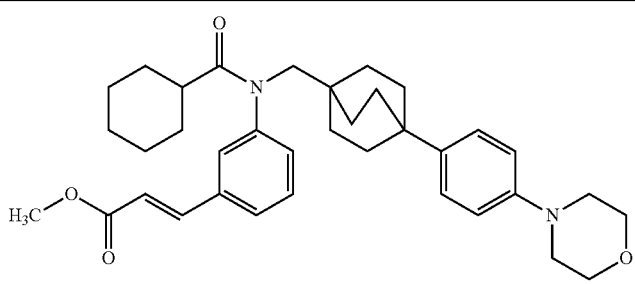 (E)-methyl 3-(3-(N-((4-(4-morpholinophenyl) bicyclo[2.2.2]octan-1-yl)methyl) cyclohexanecarboxamido)phenyl)acrylate | 571 | 165 |
| 4 | 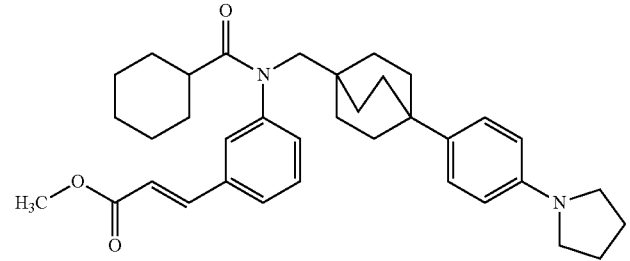 (E)-methyl 3-(3-(N-((4-(4-(pyrrolidin-1-yl)phenyl) bicyclo[2.2.2]octan-1-yl)methyl) cyclohexanecarboxamido)phenyl)acrylate | 555 | 520 |
| 5 | 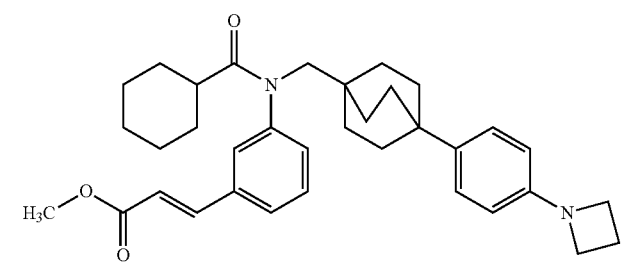 (E)-methyl 3-(3-(N-((4-(4-(azetidin-1-yl)phenyl) bicyclo[2.2.2]octan-1-yl)methyl) cyclohexanecarboxamido)phenyl)acrylate | 541 | 168 |

3   $^1$H NMR (400 MHz, DMSO-$d_6$) δ 7.64-7.83 (m, 3 H) 7.38-7.54 (m, 2 H) 7.06-7.15 (m, 2 H) 6.70-6.88 (m, 3 H) 3.74 (s, 6 H) 3.55-3.64 (m, 2 H) 2.97-3.07 (m, 4 H) 1.45-1.68 (m, 12 H) 1.24-1.44 (m, 8 H) 1.02-1.14 (m, 1 H) 0.78-0.95 (m, 2 H).

4   $^1$H NMR (400 MHz, DMSO-$d_6$) δ 7.78 (s, 1H), 7.73-7.64 (m, 2H), 7.51-7.38 (m, 2H), 7.02 (d, J = 9.0 Hz, 2H), 6.75 (d, J = 16.1 Hz, 1H), 6.41 (d, J = 9.0 Hz, 2H), 3.73 (s, 3H), 3.57 (br. s., 2H), 3.17-3.10 (m, 4H), 2.23-2.13 (m, 1H), 1.94-1.86 (m, 4H), 1.66-1.53 (m, 10H), 1.48 (d, J = 12.5 Hz, 1H), 1.40-1.31 (m, 7H), 1.31-1.25 (m, 1H), 1.15-1.01 (m, 1H), 0.86 (d, J = 9.0 Hz, 2H).

| Ex. No. | Structure & Name | MS (ESI) (M + H) | FXR EC$_{50}$ (nM) |
|---|---|---|---|
| 5 | $^1$H NMR (400 MHz, DMSO-d$_6$) δ 7.79 (br. s., 1H), 7.75-7.66 (m, 2H), 7.53-7.39 (m, 2H), 7.04 (d, J = 8.5 Hz, 2H), 6.76 (d, J = 16.1 Hz, 1H), 6.29 (d, J = 8.5 Hz, 2H), 3.77-3.68 (m, 6H), 3.58 (br. s., 2H), 2.89 (s, 1H), 2.73 (s, 1H), 2.29-2.14 (m, 3H), 1.66-1.54 (m, 8H), 1.49 (d, J = 11.5 Hz, 1H), 1.41-1.21 (m, 9H), 1.08 (d, J = 11.5 Hz, 1H), 0.86 (d, J = 6.5 Hz, 2H). | | |

Example 6

Methyl (E)-3-(3-(N-((4-(4-(dimethylamino)phenyl) bicyclo[2.2.2]octan-1-yl)methyl) tetrahydro-2H-pyran-4-carboxamido)phenyl)acrylate (6)

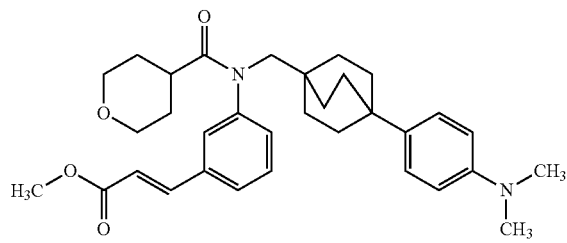

Step A. Intermediate 6A. Preparation of methyl (E)-3-(3-(N-((4-(4-bromophenyl) bicyclo[2.2.2]octan-1-yl)methyl)tetrahydro-2H-pyran-4-carboxamido)phenyl)acrylate

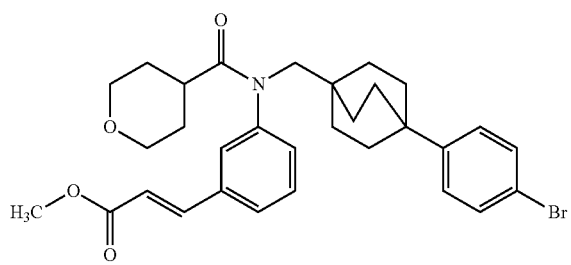 [SMILES: COC(=O)/C=C/c1cccc(N(CC23CCC(c4ccc(Br)cc4)(CC2)CC3)C(=O)C2CCOCC2)c1]

To a stirred solution of tetrahydro-2H-pyran-4-carboxylic acid (commercially available) (100 mg, 0.768 mmol) in DCM (5 mL) was added oxalyl chloride (0.13 mL, 1.537 mmol) followed by DMF (catalytic amount) at 0° C. The reaction mixture was stirred at the same temperature for 1 h. The reaction mixture was allowed to warm to room temperature and concentrated under reduced pressure to afford corresponding acid chloride. To a stirred solution of Intermediate 1H (120 mg, 0.264 mmol)) in DCM (20 mL) was added TEA (0.64 mL, 4.61 mmol) and stirred for 5 min. The acid chloride prepared was added to the reaction mixture and stirred for overnight. The reaction mixture was diluted with DCM (20 mL), washed with water (2×20 mL), brine solution (2×10 mL) and concentrated under reduced pressure. The crude material was purified by flash chromatography (24 g silica gel cartridge; A=Hex, B=EtOAc; 30 min grad.; 0% B to 45% B; flow rate=30 mL/min). The pure fractions were combined, concentrated and dried in vacuo to afford the title compound (50 mg, 0.077 mmol, 10% yield). MS (ESI) 568 (M+H).

Step B. Intermediate 6B. Preparation of (E)-3-(3-(N-((4-(4-(dimethylamino)phenyl) bicyclo[2.2.2] octan-1-yl)methyl)tetrahydro-2H-pyran-4-carboxamido)phenyl)acrylic Acid

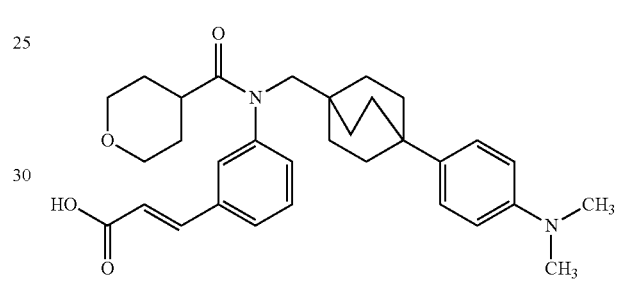

To a stirred solution of Intermediate 6A (35 mg, 0.062 mmol) in toluene (2 mL) were added dimethylamine (0.927 mL, 0.927 mmol), 2-di-tert-butylphosphino-2',4',6'-triisopropylbiphenyl (2.62 mg, 6.18 µmol) and sodium tert-butoxide (17.81 mg, 0.185 mmol) at room temperature. The reaction mixture was degassed and back-filled with argon. Pd$_2$(dba)$_3$ (2.8 mg, 3.09 µmol) was added to the reaction and the vial was sealed (Pressure release vial). The reaction mixture was heated at 80° C. for 4 h. The reaction mixture was cooled to room temperature and concentrated under reduced pressure. The residue was diluted with water and extracted with ethyl acetate (2×10 mL). The organic layers were combined, dried over anhydrous sodium sulphate and concentrated under reduced pressure to afford the title compound (30 mg, 0.058 mmol, 94% yield). MS (ESI) 517 (M+H).

Step C. Example 6. Preparation of methyl (E)-3-(3-(N-((4-(4-(dimethylamino)phenyl) bicyclo[2.2.2] octan-1-yl)methyl)tetrahydro-2H-pyran-4-carboxamido)phenyl)acrylate To a stirred solution of Intermediate 6B (35 mg, 0.068 mmol) in DCM (5 mL) was added (trimethylsilyl)diazomethane (0.17 mL, 0.339 mmol) at 0° C. The reaction mixture was allowed to warm to room temperature and stirred for 12 h. The reaction was quenched with acetic acid (0.5 mL) and the reaction mixture was concentrated under reduced pressure. The crude material was purified via preparative LC/MS using following conditions: (Column: InertsilODS, 19×250 mm, 5-µm particles; Mobile Phase A: 10-mM ammonium acetate; Mobile Phase B: acetonitrile;

Gradient: 50-100% B over 24 minutes, then a 0-minute hold at 0% B; Flow: 17 mL/min). Fractions containing the desired product were combined and dried via centrifugal evaporation to afford the title compound (1.1 mg, 1.886 μmol, 3% yield) as a gummy liquid. $^1$H NMR (400 MHz, DMSO-$d_6$) δ 7.82 (s, 1H), 7.74-7.63 (m, 2H), 7.55-7.44 (m, 2H), 7.20 (br. s., 2H), 7.06 (d, J=8.6 Hz, 2H), 6.77 (d, J=15.9 Hz, 1H), 6.61 (d, J=8.8 Hz, 2H), 3.74 (s, 6H), 3.64-3.54 (m, 3H), 3.07-2.91 (m, 2H), 2.89-2.76 (m, 7H), 1.60 (d, J=8.8 Hz, 9H), 1.50-1.31 (m, 9H), 1.23 (s, 2H), 1.13 (t, J=7.5 Hz, 2H). FXR $EC_{50}$ (nM)=212; MS (ESI) 531 (M+H).

Example 7

Methyl (E)-3-(3-(N-((4-phenylbicyclo[2.2.2]octan-1-yl)methyl)cyclohexanecarboxamido)phenyl)acrylate

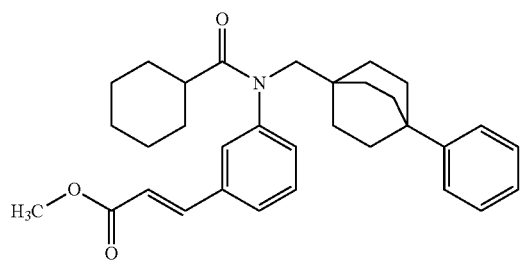

(7)

Step A. Intermediate 7A. Preparation of (4-phenyl-bicyclo[2.2.2]octan-1-yl)methanol

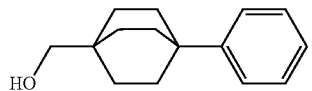 [SMILES: OCC12CCC(c3ccccc3)(CC1)CC2]

The title compound was prepared according to the method described for the synthesis of Intermediate 1D by substituting Intermediate 1B where appropriate. (0.2 g, 0.925 mmol, 64% yield) as an off-white solid. $^1$H NMR (400 MHz, DMSO-$d_6$) δ 7.39-7.21 (m, 4H), 7.20-7.10 (m, 1H), 4.36 (t, J=5.5 Hz, 1H), 3.09 (d, J=5.6 Hz, 2H), 1.83-1.66 (m, 6H), 1.52-1.38 (m, 6H).

Step B. Intermediate 7B. Preparation of 4-phenylbi-cyclo[2.2.2]octane-1-carbaldehyde

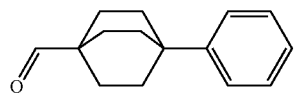 [SMILES: O=CC12CCC(c3ccccc3)(CC1)CC2]

To a solution of Intermediate 7A (0.1 g, 0.462 mmol) in DCM (5 mL) was added Dess-Martin periodinane (0.196 g, 0.462 mmol) under nitrogen atmosphere at 0° C. The reaction mixture was allowed to warm to room temperature and stirred for 30 min. The reaction mixture was diluted with dichloromethane (20 mL), washed with aqueous 10% NaHCO$_3$ solution, brine solution (5 mL), dried over anhydrous sodium sulphate and concentrated under reduced pressure to afford the title compound (0.1 g, 0.397 mmol, 86% yield). $^1$H NMR (400 MHz, DMSO-$d_6$) δ 9.48 (s, 1H), 7.36-7.25 (m, 4H), 7.19-7.13 (m, 1H), 1.85-1.78 (m, 6H), 1.73-1.66 (m, 6H).

Step C. Intermediate 7C. Preparation of methyl (E)-3-(3-(((4-phenylbicyclo[2.2.2]octan-1-yl)methyl)amino)phenyl)acrylate

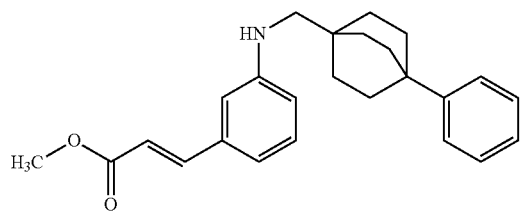 [SMILES: COC(=O)/C=C/c1cccc(NCC23CCC(c4ccccc4)(CC2)CC3)c1]

The title compound was prepared according to the method described for the synthesis of Intermediate 1H by substituting Intermediate 1G and Intermediate 7B where appropriate. (0.05 g, 0.126 mmol, 34% yield) as pale yellow solid. $^1$H NMR (400 MHz, DMSO-$d_6$) δ 7.53 (d, J=16.1 Hz, 1H), 7.37-7.23 (m, 4H), 7.19-7.05 (m, 2H), 6.89 (s, 1H), 6.81 (d, J=7.6 Hz, 1H), 6.73 (dd, J=7.9, 1.6 Hz, 1H), 6.51 (d, J=15.9 Hz, 1H), 5.58 (t, J=5.9 Hz, 1H), 3.72 (s, 3H), 2.87 (d, J=5.9 Hz, 2H), 1.85-1.71 (m, 6H), 1.65-1.52 (m, 6H). MS (ESI) 376 (M+H).

Step C. Example 7. Preparation of methyl (E)-3-(3-(N-((4-phenylbicyclo[2.2.2]octan-1-yl)methyl)cyclohexanecarboxamido)phenyl)acrylate The title compound was prepared according to the method described for the synthesis of Intermediate 1I by substituting Intermediate 7C and corresponding acid chloride where appropriate. (9 mg, 0.018 mmol, 27% yield). $^1$H NMR (400 MHz, DMSO-$d_6$) δ 7.80 (s, 1H), 7.75-7.63 (m, 2H), 7.53-7.38 (m, 2H), 7.32-7.18 (m, 4H), 7.16-7.06 (m, 1H), 6.76 (d, J=16.1 Hz, 1H), 3.74 (s, 3H), 3.59 (br. s., 2H), 2.20 (br. s., 1H), 1.73-1.54 (m, 10H), 1.48 (br. s., 1H), 1.44-1.28 (m, 8H), 1.09 (d, J=13.2 Hz, 1H), 0.88 (br. s., 2H).
FXR $EC_{50}$ (nM) 395; MS (ESI) 486 (M+H).

Example 8

(E)-Methyl 3-(3-(N-((1-(1-methyl-1H-indazol-5-yl)-2-oxabicyclo[2.2.2]octan-4-yl)methyl)tetrahydro-2H-pyran-4-carboxamido)phenyl)acrylate (8)

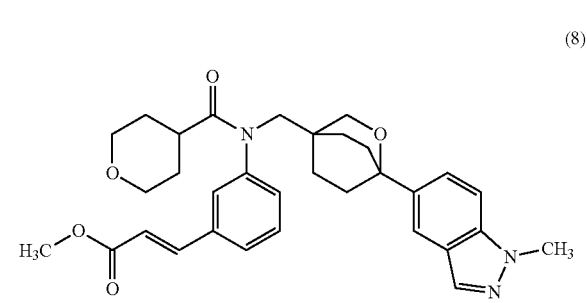

Step A. Intermediate 8A1 & 8A2. Preparation of (5-bromo-1-methyl-1H-indazole & 5-bromo-2-methyl-2H-indazole

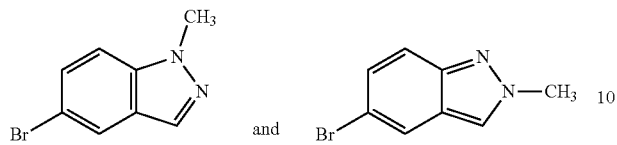

To a stirred solution of 5-bromo-1H-indazole (commercially available) (2 g, 10.15 mmol) in DMSO (20 mL) was added methyl iodide (0.82 mL, 13.20 mmol) followed by potassium carbonate (7.0 g, 50.8 mmol). The reaction mixture was stirred at room temperature for overnight. The reaction mixture was diluted with water and extracted with EtOAc (3×20). The organic layers were combined, dried over anhydrous sodium sulphate and concentrated under reduced pressure. The crude material was purified by flash chromatography (40 g silica gel cartridge; A=Hex, B=EtOAc; 30 min grad.; 0% B to 40% B; flow rate=30 mL/min). The pure fractions were combined, concentrated under reduced pressure and dried in vacuo to afford Intermediate 8A1 (1.2 g, 5.40 mmol, 53% yield) as a white solid and Intermediate 8A2 (0.6 g, 2.70 mmol, 27% yield) as an off-white solid. The required compound was confirmed NOE studies. MS (ESI) 213 (M+H).

Step B. Intermediate 8B. Preparation of 5-iodo-1-methyl-1H-indazole

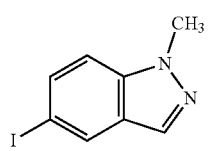

To a solution of Intermediate 8A1 (1 g, 4.74 mmol) in 1,4-dioxane (5 mL) were added sodium iodide (1.42 g, 9.48 mmol), copper(I) iodide (0.05 g, 0.237 mmol) and (1r,2r)-n,n'-dimethyl-1,2-cyclohexanediamine (0.07 g, 0.474 mmol) under argon atmosphere. The reaction mixture was heated at 110° C. for overnight. The reaction mixture was cooled to room temperature, diluted with water (30 mL) and extracted with DCM (3×20 mL). The organic layers were combined, dried over anhydrous sodium sulphate and concentrated under reduced pressure. The crude material was purified by flash chromatography (40 g silica gel cartridge; B=EtOAc; 30 min grad.; 0% B to 30% B; flow rate=30 mL/min). The pure fractions were combined, concentrated and dried in vacuo to afford the title compound (1 g, 3.60 mmol, 76% yield) as an off-white crystalline solid. MS (ESI) 259 (M+H).

Step C. Intermediate 8C. Preparation of (4-hydroxy-4-(1-methyl-1H-indazol-5-yl) cyclohexane-1,1-diyl)bis(methylene)bis(4-methylbenzenesulfonate)

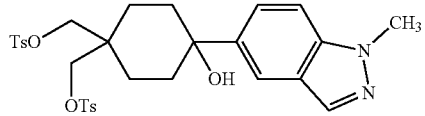 [SMILES: Cc1ccc(S(=O)(=O)OCC2(COS(=O)(=O)c3ccc(C)cc3)CCC(O)(c3ccc4c(cnn4C)c3)CC2)cc1]

A stirred solution of Intermediate 8B (0.3 g, 1.163 mmol) in tetrahydrofuran (5 mL) was cooled to −78° C. n-BuLi (0.93 mL, 2.325 mmol) in hexane was added drop wise to the reaction mixture. The reaction mixture was stirred at −78° C. for 1 h. A solution of (4-oxocyclohexane-1,1-diyl) bis(methylene)bis(4-methylbenzenesulfonate) (see *ACS Med. Chem. Lett.*, 5(5), 609-614; 2014) (0.70 g, 1.511 mmol) in 2 mL dry THF was added to the reaction. The reaction mixture was allowed to warm to room temperature. The reaction mixture was quenched with aqueous saturated ammonium chloride solution. The reaction mixture was extracted with EtOAc (2×20 mL). The organic layers were combined, dried over anhydrous sodium sulphate and concentrated under reduced pressure. The crude material was purified by flash chromatography (24 g silica gel cartridge; A=Hex, B=EtOAc; 30 min grad.; 0% B to 100% B; flow rate=30 mL/min). The pure fractions were combined, concentrated under reduced pressure and dried in vacuo to afford the title compound (0.25 g, 0.397 mmol, 34% yield) as an off-white solid. MS (ESI) 599 (M+H).

Step D. Intermediate 8D. Preparation of (1-(1-methyl-1H-indazol-5-yl)-2-oxabicyclo [2.2.2]octan-4-yl)methyl 4-methylbenzenesulfonate

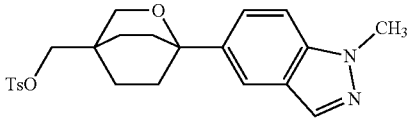 [SMILES: Cc1ccc(S(=O)(=O)OCC23CCC(c4ccc5c(cnn5C)c4)(CC2)OC3)cc1]

To a stirred solution of Intermediate 8C (0.25 g, 0.418 mmol) in anhydrous 1,2-dimethoxyethane (10 mL) was added sodium hydride (0.050 g, 1.253 mmol) at 0° C. under nitrogen atmosphere. The reaction mixture was stirred at the same temperature for 30 min. and then heated at reflux for 12 h. The reaction mixture was quenched with aqueous saturated ammonium chloride solution. The reaction mixture was extracted with EtOAc (2×10 mL). The organic layers were combined, dried over anhydrous sodium sulphate and concentrated under reduced pressure. The crude material was purified by flash chromatography (40 g silica gel cartridge; A=Hex, B=EtOAc; 30 min grad.; 0% B to 50% B; flow rate=30 mL/min). The pure fractions were combined, concentrated under reduced pressure and dried in vacuo to afford the title compound (0.18 g, 0.401 mmol, 96% yield) as white solid. MS (ESI) 427 (M+H).

Step E. Intermediate 8E. Preparation of (1-(1-methyl-1H-indazol-5-yl)-2-oxabicyclo[2.2.2]octan-4-yl)methyl acetate

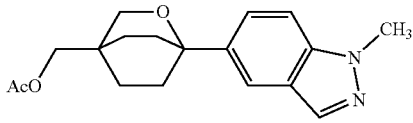

To a solution of Intermediate 8D (2.5 g, 5.86 mmol) in DMF (30 mL) in a pressure tube was added sodium acetate (2.88 g, 35.2 mmol). The reaction mixture was heated at 120° C. for overnight. The reaction mixture was cooled to room temperature and diluted with water (50 mL). The aqueous solution was extracted with EtOAc (2×20 mL). The organic layers were combined, dried over anhydrous sodium sulphate and concentrated under reduced pressure. The crude material was purified by flash chromatography (40 g silica gel cartridge; A=Hex, B=EtOAc; 30 min grad.; 0% B to 50% B; flow rate=30 mL/min). The pure fractions were combined, concentrated and dried in vacuo to afford the title compound (0.6 g, 1.813 mmol, 31% yield) as an off-white solid. MS (ESI) 315 (M+H).

Step F. Intermediate 8F. Preparation of (1-(1-methyl-1H-indazol-5-yl)-2-oxabicyclo[2.2.2]octan-4-yl)methanol

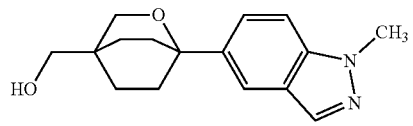 [SMILES: Cn1ncc2cc(C34CCC(CO)(CC3)CO4)ccc21]

To a stirred solution of Intermediate 8E (0.6 g, 1.909 mmol) in methanol (10 mL) was added a solution of potassium carbonate (1.32 g, 9.54 mmol) in water (15 mL) at 0° C. The reaction mixture was stirred at room temperature for 2 h. The solvent was removed under reduced pressure and the residue was diluted with water (15 mL). The aqueous solution was extracted with EtOAc (2×20 mL). The organic layers were combined, dried over anhydrous sodium sulphate, concentrated under reduced pressure and dried in vacuo to afford the title compound (0.45 g, 1.570 mmol, 82% yield) as white solid. MS (ESI) 273 (M+H).

Step G. Intermediate 8G. Preparation of 1-(1-methyl-1H-indazol-5-yl)-2-oxabicyclo[2.2.2]octane-4-carbaldehyde

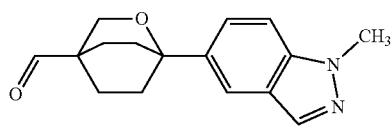 [SMILES: Cn1ncc2cc(C34CCC(C=O)(CC3)CO4)ccc21]

To a stirred solution of Intermediate 8F (0.4 g, 1.469 mmol) in dichloromethane (2 mL) was added Dess-Martin periodinane (0.748 g, 1.762 mmol) at 0° C. The reaction mixture was stirred for 2 h at room temperature. The reaction mixture was diluted with DCM, washed with water (10 mL), aqueous sodium bicarbonate solution (10 mL), dried over anhydrous sodium sulphate and concentrated under reduced pressure. The crude material was purified by flash chromatography (24 g silica gel cartridge; A=Hex, B=EtOAc; 30 min grad.; 0% B to 30% B; flow rate=30 mL/min). The pure fractions were combined, concentrated and dried in vacuo to afford the title compound (0.4 g, 1.406 mmol, 96% yield) as semi solid. $^1$H NMR (400 MHz, DMSO-$d_6$) δ 9.53 (s, 1H), 7.98 (s, 1H), 7.87 (d, J=7.5 Hz, 1H), 7.74-7.71 (m, 1H), 7.57-7.53 (m, 1H), 4.03 (s, 2H), 4.01 (s, 3H), 2.23-2.12 (m, 2H), 2.01-1.85 (m, 6H).

Step H. Intermediate 8H. Preparation of (E)-methyl 3-(3-(((1-(1-methyl-1H-indazol-5-yl)-2-oxabicyclo[2.2.2]octan-4-yl)methyl)amino)phenyl)acrylate

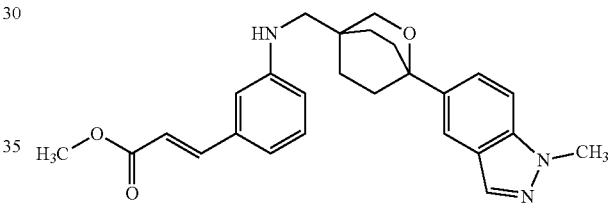

The title compound was prepared according to the method described for the synthesis of Intermediate 1H by substituting Intermediate 8G and Intermediate 1G. (0.035 g, 0.077 mmol, 42% yield) as black color solid. MS (ESI) 432 (M+H).

Step I. Example 8. Preparation of (E)-methyl 3-(3-(N-((1-(1-methyl-1H-indazol-5-yl)-2-oxabicyclo[2.2.2]octan-4-yl)methyl)tetrahydro-2H-pyran-4-carboxamido)phenyl)acrylate The title compound was prepared according to the method described for the synthesis of Intermediate 6A by substituting Intermediate 8H and corresponding acid where appropriate. (4.5 mg, 7.78 μmol, 10% yield). $^1$H NMR (400 MHz, DMSO-$d_6$) δ 7.94 (s, 1H), 7.87 (s, 1H), 7.69 (s, 1H), 7.73 (s, 1H), 7.64 (s, 1H), 7.56-7.43 (m, 3H), 7.39 (dd, J=8.9, 1.6 Hz, 1H), 6.78 (d, J=15.9 Hz, 1H), 3.99 (s, 3H), 3.80-3.71 (m, 6H), 3.66 (d, J=15.9 Hz, 3H), 2.99 (t, J=11.5 Hz, 2H), 2.08-1.96 (m, 2H), 1.81 (d, J=5.1 Hz, 2H), 1.69-1.53 (m, 5H), 1.47 (d, J=11.5 Hz, 4H). FXR $EC_{50}$ (nM) 1595.92; MS (ESI) 544 (M+H).

Example 9

(E)-Methyl 3-(3-(1-methyl-N-((1-(1-methyl-1H-indazol-5-yl)-2-oxabicyclo[2.2.2]octan-4-yl)methyl)piperidine-4-carboxamido)phenyl)acrylate

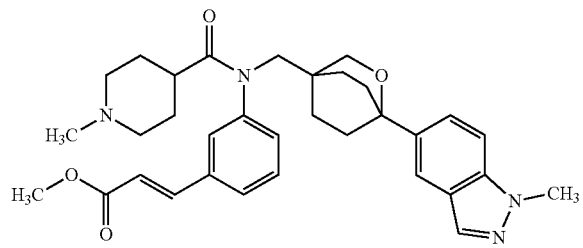

(9)

The title compound was prepared according to the method described for the synthesis of Intermediate 6A by substituting Intermediate 8H and corresponding acid where appropriate. (1.5 mg, 2.64 µmol, 6% yield). $^1$H NMR (400 MHz, DMSO-$d_6$) δ 8.05-7.92 (m, 2H), 7.69 (s, 1H), 7.73 (s, 1H), 7.65 (s, 1H), 7.50 (d, J=7.8 Hz, 3H), 7.44-7.33 (m, 1H), 6.79 (d, J=16.1 Hz, 1H), 3.99 (s, 3H), 3.74 (s, 3H), 3.71-3.55 (m, 4H), 2.65 (br. s., 1H), 2.12 (br. s., 1H), 2.02 (s, 5H), 1.87-1.73 (m, 2H), 1.68-1.50 (m, 9H), 1.50-1.38 (m, 2H). FXR $EC_{50}$ (nM) 4718; MS (ESI) 557 (M+H).

Example 10

Methyl (E)-3-(3-(N-((1-(4-methoxyphenyl)-2-oxabicyclo[2.2.2]octan-4-yl)methyl)cyclohexanecarboxamido)phenyl)acrylate

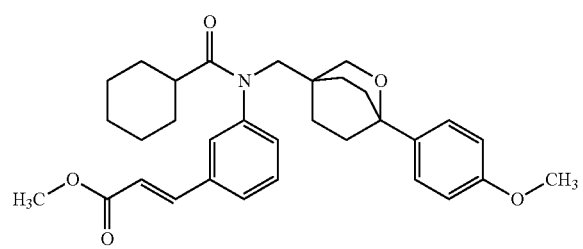

(10)

Step A. Intermediate 10A. Preparation of (4-hydroxy-4-(4-methoxyphenyl)cyclohexane-1,1-diyl)bis(methylene)bis(4-methylbenzenesulfonate)

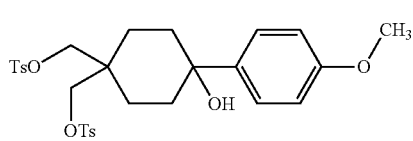

To a stirred solution of (4-oxocyclohexane-1,1-diyl)bis(methylene)bis(4-methylbenzenesulfonate) (0.5 g, 1.072 mmol) in THF (15 mL) was added (4-methoxyphenyl) magnesium bromide (commercially available) (3.21 mL, 3.21 mmol) at −78° C. The reaction mixture was allowed to warm to room temperature and stirred for 2 h. The reaction mixture was quenched with aqueous saturated ammonium chloride solution. The reaction mixture was extracted with EtOAc (2×20 mL). The organic layers were combined, dried over anhydrous sodium sulphate and concentrated under reduced pressure. The crude material was purified by flash chromatography (40 g silica gel cartridge; A=Hex, B=EtOAc; 30 min grad.; 0% B to 100% B; flow rate=30 mL/min). The pure fractions were combined, concentrated under reduced pressure and dried in vacuo to afford the title compound (0.6 g, 0.992 mmol, 93% yield) as white solid. $^1$H NMR (400 MHz, chloroform-d) δ 7.81-7.71 (m, 4H), 7.37 (d, J=8.5 Hz, 4H), 7.27-7.24 (m, 2H), 6.90-6.83 (m, 2H), 4.00 (s, 1H), 3.84-3.77 (m, 5H), 2.49-2.44 (m, 6H), 1.70-1.60 (m, 5H), 1.58-1.48 (m, 2H), 1.30-1.27 (m, 1H).

Step B. Intermediate 10B. Preparation of (1-(4-methoxyphenyl)-2-oxabicyclo[2.2.2]octan-4-yl)methyl 4-methylbenzenesulfonate

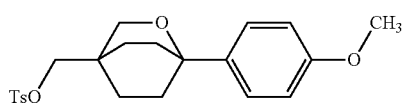

The title compound was prepared according to the method described for the synthesis of Intermediate 8D by substituting Intermediate 10A where appropriate. (0.4 g, 0.944 mmol, 90% yield) as white solid. MS (ESI) 403 (M+H).

Step C. Intermediate 10C. Preparation of (1-(4-methoxyphenyl)-2-oxabicyclo[2.2.2]octan-4-yl) methyl acetate

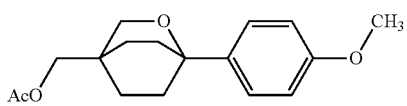

The title compound was prepared according to the method described for the synthesis of Intermediate 8E by substituting Intermediate 10B where appropriate. (0.3 g, 0.982 mmol, 99% yield) as an off-white solid. MS (ESI) 291 (M+H).

Step D. Intermediate 10D. Preparation of (1-(4-methoxyphenyl)-2-oxabicyclo[2.2.2]octan-4-yl) methanol

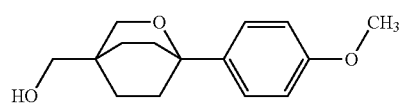 [SMILES: COc1ccc(C23CCC(CO)(CC2)CO3)cc1]

The title compound was prepared according to the method described for the synthesis of Intermediate 8F by substituting Intermediate 10C where appropriate. (0.25 g, 0.906 mmol, 88% yield) as an off-white solid. MS (ESI) 249 (M+H).

Step E. Intermediate 10E. Preparation of 1-(4-methoxyphenyl)-2-oxabicyclo[2.2.2]octane-4-carbaldehyde

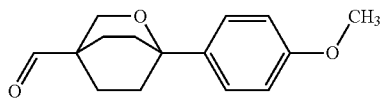

The title compound was prepared according to the method described for the synthesis of Intermediate 8G by substituting Intermediate 10D where appropriate. (0.1 g, 0.386 mmol, 96% yield) as an off-white solid. $^1$H NMR (400 MHz, DMSO-$d_6$) δ 9.51 (s, 1H), 7.32-7.25 (m, 2H), 6.89-6.81 (m, 2H), 3.98 (s, 2H), 3.73 (s, 3H), 2.14-2.00 (m, 2H), 1.93-1.83 (m, 6H).

Step F. Intermediate 10F. Preparation of (E)-methyl 3-(3-(((1-(4-methoxyphenyl)-2-oxabicyclo[2.2.2]octan-4-yl)methyl)amino)phenyl)acrylate

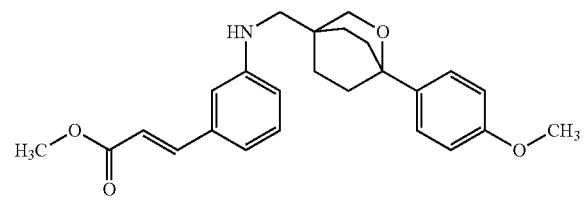

The title compound was prepared according to the method described for the synthesis of Intermediate 1H by substituting Intermediate 10E and Intermediate 1G where appropriate. (0.25 g, 0.386 mmol, 96% yield) as black color solid. MS (ESI) 408 (M+H).

Step G. Example 10. Preparation of methyl (E)-3-(3-(N-((1-(4-methoxyphenyl)-2-oxabicyclo[2.2.2]octan-4-yl)methyl)cyclohexanecarboxamido)phenyl)acrylate The title compound was prepared according to the method described for the synthesis of Intermediate 11 by substituting Intermediate 10F where appropriate. (13 mg, 0.025 mmol, 41% yield). $^1$H NMR (400 MHz, DMSO-$d_6$) δ 7.83 (s, 1H), 7.76-7.64 (m, 2H), 7.55-7.39 (m, 2H), 7.22 (d, J=8.8 Hz, 2H), 6.87-6.72 (m, 2H), 3.74 (s, 3H), 3.70 (s, 3H), 3.62 (d, J=10.5 Hz, 4H), 2.19 (br. s., 1H), 1.98-1.87 (m, 2H), 1.75 (br. s., 2H), 1.58 (br. s., 7H), 1.49 (br. s., 3H), 1.33 (d, J=13.9 Hz, 2H), 1.07 (s, 1H), 0.88 (br. s., 2H); FXR EC$_{50}$ (nM) 318.73; MS (ESI) 518 (M+H).

Example 11

Methyl 5-(N-((4-(4-morpholinophenyl)bicyclo[2.2.2]octan-1-yl)methyl)cyclohexanecarboxamido)-3,4-dihydronaphthalene-2-carboxylate

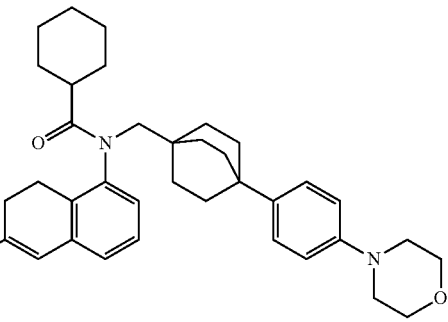

(11)

Step A. Intermediate 11A. Preparation of 5-bromo-3,4-dihydronaphthalen-1(2H)-one

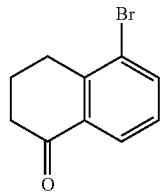 [SMILES: O=C1CCCc2c(Br)cccc21]

3,4-Dihydronaphthalen-1(2H)-one (commercially available) (8.5 g, 58.1 mmol) was added to aluminum chloride (19.38 g, 145 mmol) in a 2-neck 250 mL flask at 0° C. under nitrogen atmosphere. The reaction mixture was heated at 90° C. 45 min. Bromine (3.6 ml, 69.8 mmol) was added dropwise to the reaction mixture at the same temperature and stirred for 1 h. The reaction mixture was poured into crushed ice and neutralized by using aqueous NaHCO$_3$ solution. The aqueous solution was extracted with EtOAc (2×100 mL). The organic layers were combined, dried over anhydrous sodium sulphate and concentrated under and dried in vacuo to afford the title compound 3,4-dihydronaphthalen-1(2H)-one (8.5 g, 58.1 mmol) and the combined organic layers were dried over MgSO$_4$, filtered, concentrated under reduced pressure to afford the title compound (5.2 g, 15.48 mmol, 27% yield). $^1$H NMR (400 MHz, DMSO-$d_6$) δ 7.89 (ddd, J=9.2, 7.7, 1.3 Hz, 2H), 7.31 (t, J=7.8 Hz, 1H), 2.95 (t, J=6.0 Hz, 2H), 2.67-2.57 (m, 2H), 2.13-2.03 (m, 2H). MS (ESI) 225/227 (M+H).

Step B. Intermediate 11B. Preparation of methyl 5-bromo-1-oxo-1,2,3,4-tetrahydronaphthalene-2-carboxylate

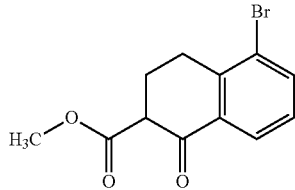 [SMILES: COC(=O)C1CCc2c(Br)cccc2C1=O]

To a stirred solution of NaH (0.88 g, 22.21 mmol) and dimethyl carbonate (4.53 mL, 53.3 mmol) in dry toluene (20 mL) was added a solution of Intermediate 11A (2 g, 8.89 mmol) in toluene (20 mL) at 60° C. The reaction mixture was stirred at the same temperature for 16 h. The reaction mixture was poured into crushed ice and extracted with EtOAc (3×30 mL). The organic layers were combined, dried over anhydrous sodium sulphate, concentrated under reduced pressure and dried in vacuo to afford the title compound (2.4 g, 7.63 mmol, 86% yield). $^1$H NMR (400 MHz, chloroform-d) δ 8.06-8.00 (m, 1H), 7.81-7.75 (m, 1H), 7.57 (dd, J=8.0, 1.0 Hz, 1H), 3.78 (s, 3H), 3.62 (dd, J=10.3, 4.8 Hz, 1H), 2.59 (t, J=8.00 Hz, 2H), 2.94 (t, J=8.00 Hz, 2H). MS (ESI) 283/285 (M+H).

Step C. Intermediate 11C. Preparation of methyl 5-bromo-1-hydroxy-1,2,3,4-tetrahydronaphthalene-2-carboxylate

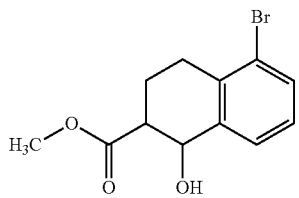 [SMILES: COC(=O)C1CCc2c(Br)cccc2C1O]

To a stirred solution of Intermediate 11B (2.4 g, 8.48 mmol) in MeOH (20 mL) was added NaBH$_4$ (0.45 g, 11.87 mmol) at 0° C. The reaction mixture was allowed to warm to room temperature and stirred for 5 h. The reaction mixture was concentrated under reduced pressure and the residue was poured into crushed ice. The aqueous solution was extracted with EtOAc (2×150 mL). The organic layers were combined, dried over anhydrous sodium sulphate, concentrated under reduced pressure and dried in vacuo to afford the title compound (1.7 g, 5.60 mmol, 66% yield). $^1$H NMR (400 MHz, chloroform-d) δ 7.55-7.48 (m, 1H), 7.39 (d, J=7.5 Hz, 1H), 7.17-7.06 (m, 1H), 5.06-4.97 (m, 1H), 3.78 (s, 3H), 3.13 (d, J=5.0 Hz, 1H), 3.01-2.94 (m, 1H), 2.79 (dt, J=11.5, 3.3 Hz, 1H), 2.73-2.62 (m, 1H), 2.36-2.21 (m, 1H), 2.17 (ddd, J=6.8, 3.3, 1.0 Hz, 1H). MS (ESI) 304 (M+NH$_3$).

Step D. Intermediate 11D. Preparation of methyl 5-bromo-3,4-dihydronaphthalene-2-carboxylate

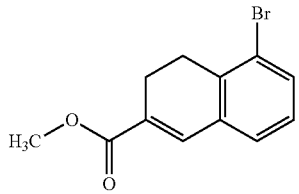

To a stirred solution of Intermediate 11C (1.7 g, 5.96 mmol) in toluene (20 mL) was added p-toluenesulfonic acid monohydrate (0.057 g, 0.298 mmol) at 0° C. The reaction mixture was heated at 110° C. for 3 h. The reaction mixture was diluted with DCM (100 mL) and washed with water (2×50 mL), dried over anhydrous sodium sulphate and concentrated under reduced pressure. The crude material was purified by flash chromatography (24 g silica gel cartridge; A=Hex, B=EtOAc; 30 min grad.; 0% B to 30% B; flow rate=30 mL/min). The pure fractions were combined, concentrated under reduced pressure and dried in vacuo to afford the title compound (900 mg, 3.37 mmol, 56% yield). $^1$H NMR (300 MHz, chloroform-d) δ 7.55-7.43 (m, 2H), 7.20-7.04 (m, 2H), 3.85 (s, 3H), 3.09-2.95 (m, 2H), 2.72-2.61 (m, 2H). MS (ESI) 284 (M+H) NH3 adduct.

Step E. Intermediate 11E. Preparation of methyl 5-((tert-butoxycarbonyl)amino)-3,4-dihydronaphthalene-2-carboxylate

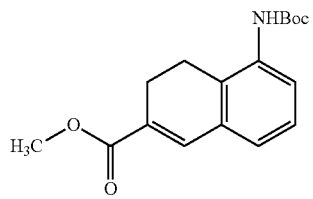 [SMILES: COC(=O)C1=Cc2cccc(NC(=O)OC(C)(C)C)c2CC1]

To a solution of Intermediate 11D (0.7 g, 2.62 mmol) in toluene were added tert-butyl carbamate (0.338 g, 2.88 mmol), cesium carbonate (2.56 g, 7.86 mmol) and 4,5-bis(diphenylphosphino)-9,9-dimethylxanthene (0.152 g, 0.262 mmol). The reaction mixture was degassed and back-filled with argon. Pd$_2$(dba)$_3$ (0.120 g, 0.131 mmol) was added to the reaction mass and the vial was sealed (pressure release vial). The reaction mixture was stirred 100° C. for overnight. The reaction mixture was diluted with water and extracted with EtOAc (2×30 mL). The organic layers were combined, dried over anhydrous sodium sulphate and concentrated under reduced pressure. The crude material was purified by flash chromatography (40 g silica gel cartridge; A=Hex, B=EtOAc; 30 min grad.; 0% B to 20% B; flow rate=30 mL/min). The pure fractions were combined, concentrated under reduced pressure and dried in vacuo to afford the title compound (0.42 g, 1.315 mmol, 50% yield) as an off-white solid. MS (ESI) 304 (M+H).

Step F. Intermediate 11F. Preparation of methyl 5-amino-3,4-dihydronaphthalene-2-carboxylate

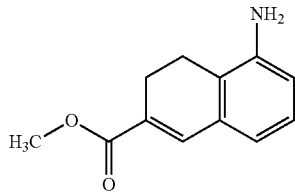

To a solution of Intermediate 11E (0.42 g, 1.385 mmol) in dichloromethane (10 mL) was added TFA (0.53 mL, 6.92 mmol) at room temperature. The reaction mixture was stirred at room temperature for 4 h. The reaction mixture was diluted with DCM (10 mL), washed with aqueous 10% NaHCO$_3$ solution, dried over anhydrous sodium sulphate and concentrated under reduced pressure. The crude material was purified by flash chromatography (40 g silica gel cartridge; A=Hex, B=EtOAc; 30 min grad.; 0% B to 40% B; flow rate=30 mL/min). The pure fractions were combined, concentrated under reduced pressure and dried in vacuo to afford the title compound (0.28 g, 1.309 mmol, 95% yield) as oil. MS (ESI) 204 (M+H).

Step G. Intermediate 11G. Preparation of methyl 5-(((4-(4-bromophenyl) bicyclo[2.2.2]octan-1-yl)methyl)amino)-3,4-dihydronaphthalene-2-carboxylate

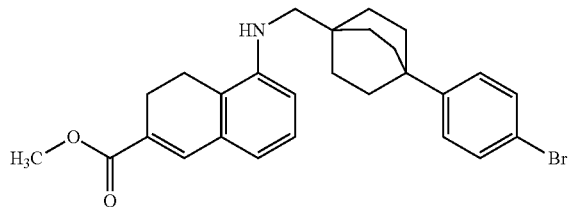 [SMILES: COC(=O)C1=Cc2cccc(NCC34CCC(c5ccc(Br)cc5)(CC3)CC4)c2CC1]

The title compound was prepared according to the method described for the synthesis of Intermediate 1H by substituting Intermediate 11F and Intermediate 1E. (0.21 g, 0.415 mmol, 61% yield) as an off-white solid. MS (ESI) 482 (M+H).

Step H. Intermediate 11H. Preparation of methyl 5-(N-((4-(4-bromophenyl) bicyclo[2.2.2]octan-1-yl)methyl)cyclohexanecarboxamido)-3,4-dihydronaphthalene-2-carboxylate

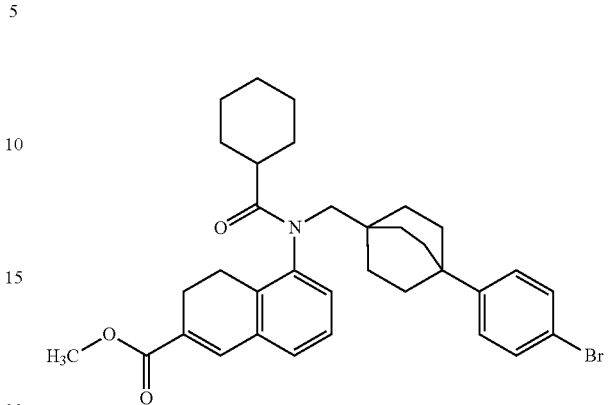

The title compound was prepared according to the method described for the synthesis of Intermediate 11 by substituting Intermediate 11G and corresponding acid chloride. (0.18 g, 0.274 mmol, 63% yield) as an off-white solid. MS (ESI) 590 (M+H).

Step I. Example 11. Preparation of methyl 5-(N-((4-(4-morpholinophenyl) bicyclo[2.2.2]octan-1-yl)methyl)cyclohexanecarboxamido)-3,4-dihydronaphthalene-2-carboxylate To a stirred solution of Intermediate 11H (0.02 g, 0.034 mmol) in toluene (1 mL) and THF (0.2 mL) were added, cesium carbonate (0.03 g, 0.102 mmol), morpholine (5.9 mg, 0.068 mmol) and 2-di-tert-butylphosphino-2',4',6'-triisopropylbiphenyl (2.88 mg, 6.77 µmol) at room temperature. The reaction mixture was degassed and back-filled with argon. Pd$_2$(dba)$_3$ (3.1 mg, 3.39 µmol) was added to the reaction and the vessel was sealed (Pressure release vial). The reaction mixture was heated at 90° C. for 5 h. The reaction mixture was concentrated under reduced pressure. The crude material was purified via preparative LC/MS using following conditions: (Column: Waters XBridge C18, 19×150 mm, 5-µm particles; Mobile Phase A: 10-mM ammonium acetate; Mobile Phase B: acetonitrile; Gradient: 15-55% B over 20 minutes, then a 5-minute hold at 100% B; Flow: 15 mL/min). Fractions containing the desired product were combined and dried via centrifugal evaporation to afford the title compound (5.4 mg, 8.60 µmol, 25% yield). $^1$H NMR (400 MHz, DMSO-d$_6$) δ 7.59 (s, 1H), 7.44-7.40 (m, 2H), 7.36-7.32 (m, 1H), 7.12 (d, J=8.80 Hz, 2H), 6.82 (d, J=8.80 Hz, 2H), 3.81 (d, J=4.80 Hz, 1H), 3.75 (s, 3H), 3.72-3.69 (m, 4H), 3.03-2.97 (m, 5H), 2.74-2.70 (m, 1H), 2.55-2.50 (m, 2H), 2.43-2.40 (m, 1H), 1.97 (s, 1H), 1.67-1.60 (m, 9H), 1.49-1.47 (m, 3H), 1.41-1.38 (m, 4H), 1.28-1.19 (m, 3H), 1.06-1.05 (m, 1H), 0.92-0.81 (m, 2H). FXR EC$_{50}$ (nM) 2738; MS (ESI) 597 (M+H).

The following compounds were prepared according to the method described for the synthesis Example 11 (Step I) by substituting Intermediate 11H and corresponding amines where appropriate.

| Ex. No. | Structure & Name | MS (ESI) (M + H) | FXR EC$_{50}$ (nM) |
|---|---|---|---|
| 12 | 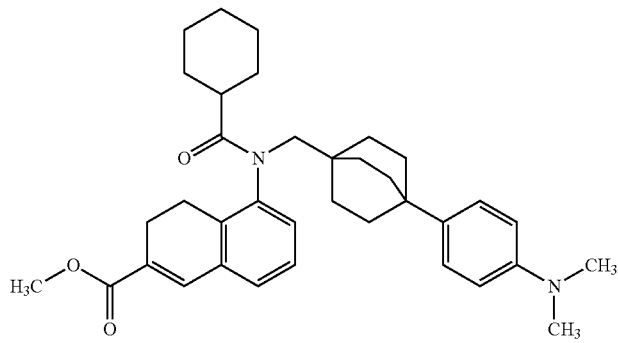<br>Methyl 5-(N-((4-(4-(dimethylamino)phenyl)bicyclo[2.2.2]octan-1-yl)methyl)cyclohexanecarboxamido)-3,4-dihydronaphthalene-2-carboxylate | 555 | 2581 |
| 13 | 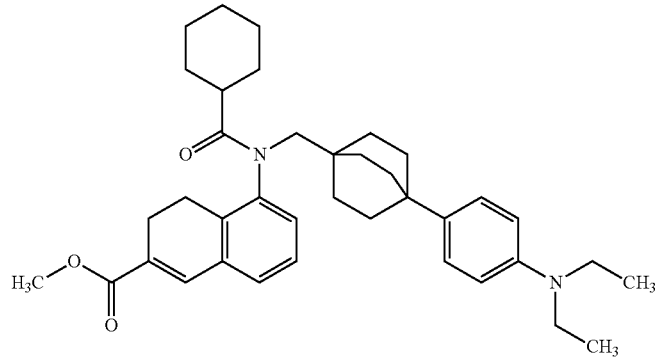<br>Methyl 5-(N-((4-(4-(diethylamino)phenyl)bicyclo[2.2.2]octan-1-yl)methyl)cyclohexanecarboxamido)-3,4-dihydronaphthalene-2-carboxylate | 583 | 912 |

12 $^1$H NMR (400 MHz, DMSO-d$_6$) δ 7.59 (s, 1H), 7.49-7.30 (m, 3H), 7.16-7.01 (m, 2H), 6.69 (br. s., 2H), 3.83 (d, J = 13.7 Hz, 1H), 3.75 (s, 3H), 2.98 (d, J = 13.4 Hz, 1H), 2.84 (s, 6H), 2.73 (dd, J = 15.3, 5.5 Hz, 1H), 2.62-2.55 (m, 1H), 2.41 (d, J = 11.2 Hz, 1H), 1.98 (br. s., 1H), 1.73-1.59 (m, 8H), 1.57 (br. s., 1H), 1.48 (d, J = 7.8 Hz, 3H), 1.39 (d, J = 7.8 Hz, 6H), 1.33-1.19 (m, 2H), 1.07 (d, J = 12.7 Hz, 1H), 0.94-0.70 (m, 2H).

13 $^1$H NMR (400 MHz, DMSO-d$_6$) δ 7.59 (s, 1H), 7.46-7.38 (m, 2H), 7.37-7.31 (m, 1H), 7.07-7.00 (m, J = 9.0 Hz, 2H), 6.57-6.51 (m, J = 9.0 Hz, 2H), 3.82 (d, J = 13.6 Hz, 1H), 3.75 (s, 3H), 3.25 (q, J = 6.7 Hz, 4H), 2.98 (d, J = 13.6 Hz, 1H), 2.73 (dd, J = 15.1, 6.0 Hz, 1H), 2.62-2.54 (m, 3H), 2.45-2.35 (m, 2H), 2.00 (br. s., 1H), 1.70-1.54 (m, 8H), 1.47 (d, J = 8.0 Hz, 4H), 1.37 (s, 2H), 1.40 (s, 3H), 1.30-1.19 (m, 2H), 1.10-0.99 (m, 5H), 0.94-0.79 (m, 2H).

Example 14

Methyl (E)-3-(3-(N-((4-(4-morpholinophenyl)bicyclo[2.2.2]octan-1-yl)methyl)cyclohexanecarboxamido)phenyl)but-2-enoate (14)

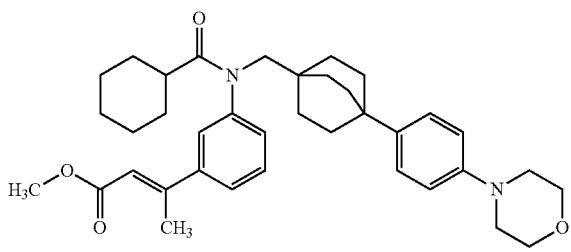

Step A. Intermediate 14A. Preparation of methyl (E)-3-(3-aminophenyl)but-2-enoate

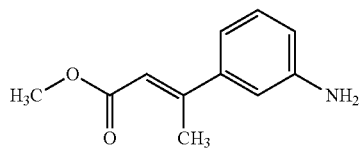

To a stirred solution of 3-bromoaniline (commercially available) (1 g, 5.81 mmol) in DMF (10 mL) were added (E)-methyl but-2-enoate (commercially available) (1.74 g, 17.44 mmol), tetrabutylammonium bromide (0.37 g, 1.163 mmol) and TEA (2.431 mL, 17.44 mmol) in a pressure release vial. The reaction mixture was degassed and backfilled with argon. Dichlorobis(tri-o-tolylphosphine)palladium(II) (0.457 g, 0.581 mmol) was added to the reaction and the vial was sealed. The reaction mixture was heated at 110° C. for 12 h. The reaction mixture was cooled to room temperature, diluted with water (30 mL) and extracted with EtOAc (2×30 mL). The organic layers were combined, dried over anhydrous sodium sulphate and concentrated under reduced pressure. The crude material was purified by flash chromatography (24 g silica gel cartridge; A=Hex, B=EtOAc; 30 min grad.; 0% B to 50% B; flow rate=30 mL/min). The pure fractions were combined, concentrated and dried in vacuo to afford the title compound (0.7 g, 3.48 mmol, 60% yield) as pale yellow oil. MS (ESI) 192 (M+H).

Step B. Intermediate 14B. Preparation of methyl (E)-3-(3-(((4-(4-bromophenyl) bicyclo[2.2.2]octan-1-yl)methyl)amino)phenyl)but-2-enoate

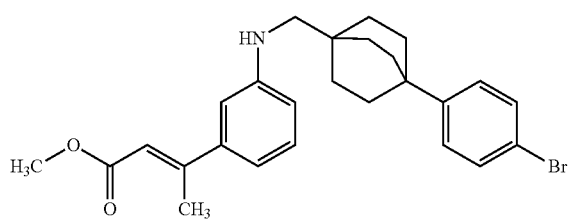 [SMILES: COC(=O)/C=C(\C)c1cccc(NCC23CCC(c4ccc(Br)cc4)(CC2)CC3)c1]

The title compound was prepared according to the method described for the synthesis of Intermediate 1H by substituting Intermediate 14A and Intermediate 1E. (0.06 g, 0.125 mmol, 22% yield) as an off-white solid. MS (ESI) 468 (M+H).

Step C. Intermediate 14C. Preparation of methyl (E)-3-(3-(N-((4-(4-bromophenyl) bicyclo[2.2.2]octan-1-yl)methyl)cyclohexanecarboxamido)phenyl)but-2-enoate

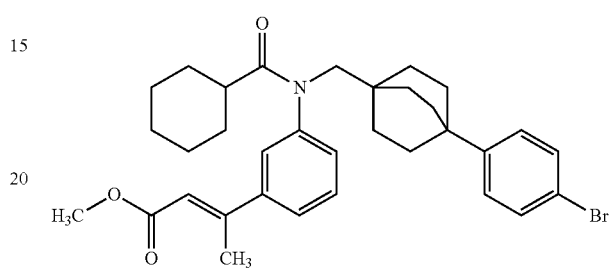

The title compound was prepared according to the method described for the synthesis of Intermediate 1I by substituting Intermediate 14B. (0.045 g, 0.070 mmol, 54% yield) as an off-white solid. MS (ESI) 578 (M+H).

Step D. Example 14. Preparation of methyl (E)-3-(3-(N-((4-(4-morpholinophenyl) bicyclo[2.2.2]octan-1-yl)methyl)cyclohexanecarboxamido)phenyl)but-2-enoate The title compound was prepared according to the method described for the synthesis of Example 11 by substituting Intermediate 14C and morpholine. (12 mg, 0.020 mmol, 47% yield). $^1$H NMR (400 MHz, DMSO-$d_6$) δ 7.61-7.50 (m, 2H), 7.48 (t, J=7.6 Hz, 1H), 7.41 (d, J=7.6 Hz, 1H), 7.18 (d, J=8.8 Hz, 2H), 6.90 (d, J=8.8 Hz, 2H), 6.23 (s, 1H), 3.74-3.67 (m, 7H), 3.59 (br. s., 2H), 3.07-2.98 (m, 4H), 2.19 (br. s., 1H), 1.70-1.55 (m, 10H), 1.50 (d, J=10.3 Hz, 1H), 1.43-1.27 (m, 8H), 1.16-0.97 (m, 1H), 0.87 (d, J=13.7 Hz, 2H). (Methyl 3 protons were buried under the solvent peak). FXR EC$_{50}$ (nM) 1153. MS (ESI) 585 (M+H).

Example 15

Methyl (E)-3-(3-(N-((4-(4-methoxyphenyl)bicyclo[2.2.2]octan-1-yl)methyl)cyclohexanecarboxamido)phenyl)acrylate (15)

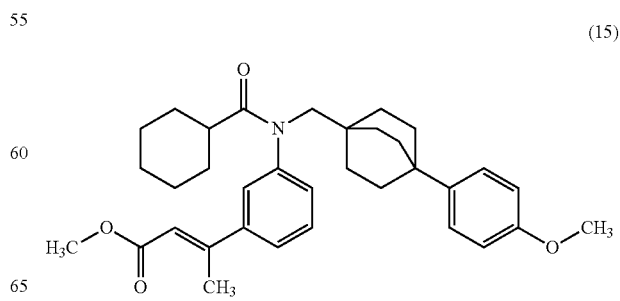

Step A. Intermediate 15A. Preparation of (4-(4-methoxyphenyl)bicycle[2.2.2]octan-1-yl)methanol

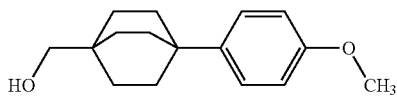

To a stirred solution of Intermediate 1D (0.15 g, 0.508 mmol) in methanol (1 mL) and DMF (2 mL) was added a solution of sodium methoxide (0.08 g, 1.524 mmol) in methanol at room temperature under nitrogen atmosphere. The reaction mixture was heated at 110° C. for 1 h. The reaction mixture was cooled to room temperature and was added copper(I) bromide (0.073 g, 0.508 mmol). The resulting reaction mixture was heated at 110° C. for 16 h. The reaction mixture was diluted with water and extracted with EtOAc (3×25 mL). The organic layers were combined, dried over anhydrous sodium sulphate and concentrated under reduced pressure. The crude material was purified by flash chromatography (12 g silica gel cartridge; A=Hex, B=EtOAc; 30 min grad.; 0% B to 30% B; flow rate=30 mL/min). The pure fractions were combined, concentrated under reduced pressure and dried in vacuo to afford the title compound (0.1 g, 0.325 mmol, 64% yield) as an off-white solid. $^1$H NMR (400 MHz, DMSO-$d_6$) δ 7.35-7.25 (m, 2H), 7.25-7.21 (m, 1H), 6.86-6.79 (m, 1H), 4.36 (q, J=5.4 Hz, 1H), 3.71 (s, 3H), 3.08 (dd, J=5.3, 4.3 Hz, 2H), 1.80-1.65 (m, 6H), 1.50-1.39 (m, 6H).

Step B. Intermediate 15 B. Preparation of 4-(4-methoxyphenyl)bicyclo[2.2.2]octane-1-carbaldehyde

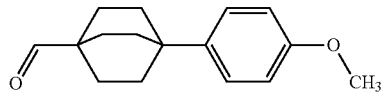

The title compound was prepared according to the method described for the synthesis of Intermediate 8G by substituting Intermediate 15A where appropriate. (0.09 g, 0.295 mmol, 86% yield). $^1$H NMR (400 MHz, DMSO-$d_6$) δ 9.48 (s, 1H), 7.23 (d, J=9.0 Hz, 2H), 6.84 (d, J=9.0 Hz, 2H), 3.72 (s, 3H), 1.80-1.70 (m, 12H).

Step C. Intermediate 15 C. Preparation of methyl (E)-3-(3-(((4-(4-methoxyphenyl)bicyclo[2.2.2]octan-1-yl)methyl)amino)phenyl)acrylate

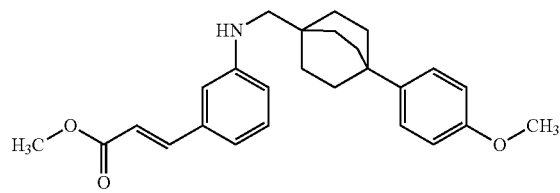

The title compound was prepared according to the method described for the synthesis of Intermediate 1H by substituting Intermediate 15B and Intermediate 1G where appropriate. (0.03 g, 0.078 mmol, 30% yield) as pale yellow solid. MS (ESI) 406 (M+H).

Step D. Example 15. Preparation of methyl (E)-3-(3-(N-((4-(4-methoxyphenyl) bicyclo[2.2.2]octan-1-yl)methyl)cyclohexanecarboxamido)phenyl)acrylate The title compound was prepared according to the method described for the synthesis of Intermediate 11 by substituting Intermediate 15C where appropriate. (25 mg, 0.048 mmol, 55% yield). $^1$H NMR (400 MHz, DMSO-$d_6$) δ 7.79 (s, 1H), 7.75-7.60 (m, 2H), 7.48 (t, J=7.7 Hz, 1H), 7.42 (d, J=8.1 Hz, 1H), 7.21-7.08 (m, 2H), 6.86-6.65 (m, 3H), 3.74 (s, 3H), 3.71-3.66 (m, 3H), 3.59 (br. s., 2H), 2.20 (br. s., 1H), 1.73-1.53 (m, 10H), 1.48 (br. s., 1H), 1.43-1.26 (m, 8H), 1.08 (d, J=12.2 Hz, 1H), 0.88 (br. s., 2H). FXR $EC_{50}$ (nM) 243; MS (ESI) 516 (M+H).

Example 16

Methyl (E)-3-(3-(N-((4-(4-methoxyphenyl)bicyclo[2.2.2]octan-1-yl)methyl)cyclohexanecarboxamido)phenyl)but-2-enoate (16)

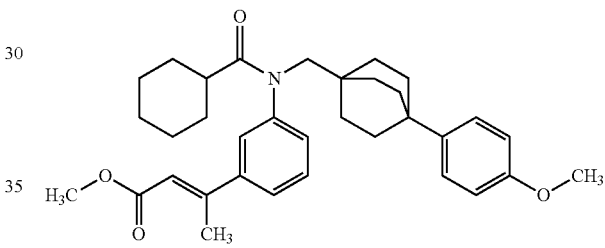

Step A. Intermediate 16A. Preparation of methyl (E)-3-(3-(((4-(4-methoxyphenyl) bicyclo[2.2.2]octan-1-yl)methyl)amino)phenyl)but-2-enoate

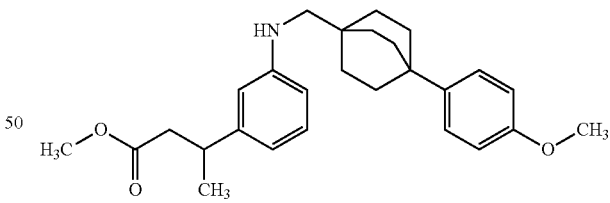

The title compound was prepared according to the method described for the synthesis of Intermediate 1H by substituting Intermediate 14A and Intermediate 15B where appropriate. (0.016 g, 0.036 mmol, 36% yield). MS (ESI) 420 (M+H).

Step B. Example 16. Preparation of methyl (E)-3-(3-(N-((4-(4-methoxyphenyl) bicyclo[2.2.2]octan-1-yl)methyl)cyclohexanecarboxamido)phenyl)but-2-enoate The title compound was prepared according to the method described for the synthesis of Intermediate 11 by substituting Intermediate 16A where appropriate. (2.8 mg, 5.23 μmol, 15% yield). $^1$H NMR (400 MHz, DMSO-$d_6$) δ 7.62-7.51 (m, 2H), 7.48 (t, J=7.6 Hz, 1H), 7.45-7.37 (m, 1H), 7.23 (d, J=8.8 Hz, 2H), 6.87 (d, J=8.8 Hz, 2H), 6.23 (s, 1H), 3.69 (s, 6H), 3.59 (br. s., 2H), 2.53 (s, 3H), 2.17-2.15 (m, 1H), 1.69-1.55 (m, 10H), 1.52 (br. s., 1H), 1.44-1.26 (m, 8H), 1.09 (d, J=11.0 Hz, 1H), 0.87 (d, J=13.7 Hz, 2H). FXR $EC_{50}$ (nM) 575.63 MS (ESI) 530 (M+H).

Example 17

5-(N-((4-(4-methoxyphenyl)bicyclo[2.2.2]octan-1-yl)methyl)cyclohexanecarboxamido)-3,4-dihydronaphthalene-2-carboxylic Acid (17)

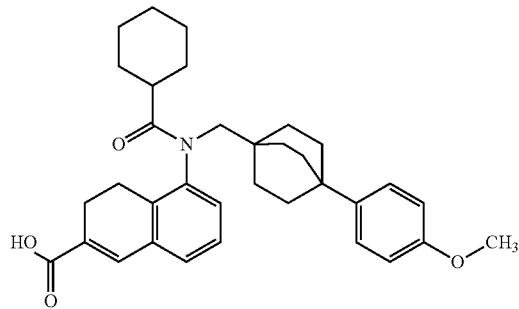

To a stirred solution of Intermediate 11H (15 mg, 0.025 mmol) in toluene (0.5 mL) were added methanol (8.14 mg, 0.254 mmol), cesium carbonate (24 mg, 0.076 mmol) and 2-di-tert-butylphosphino-2',4',6'-triisopropylbiphenyl (2.1 mg, 5.08 μmol) at room temperature. The reaction mixture was degassed and back-filled with argon. $Pd_2(dba)_3$ (2.32 mg, 2.54 μmol) was added to the reaction mixture and the vial was sealed (Pressure release vial). The reaction mixture was heated at 75° C. for 6 h. The reaction mixture was cooled to room temperature and concentrated under reduced pressure. The crude material was purified via preparative LC/MS using following conditions: (Column: Waters XBridge C18, 19×150 mm, 5-μm particles; Mobile Phase A: 10-mM ammonium acetate; Mobile Phase B: acetonitrile; Gradient: 20-80% B over 20 minutes, then a 10-minute hold at 80% B; Flow: 15 mL/min). Fractions containing the desired product were combined and dried via centrifugal evaporation to afford the title compound (3 mg, 9% yield). FXR $EC_{50}$ (nM) 2243. MS (ESI) 528 (M+H). $^1$H NMR (400 MHz, DMSO-$d_6$) δ 7.47 (s, 1H), 7.42-7.28 (m, 3H), 7.21-7.16 (m, 2H), 6.83-6.78 (m, 2H), 4.32 (br d, J=4.0 Hz, 1H), 3.87-3.74 (m, 2H), 3.69 (s, 3H), 3.00 (d, J=13.6 Hz, 1H), 2.76-2.68 (m, 1H), 2.46-2.33 (m, 1H), 2.04 (s, 1H), 1.74-1.54 (m, 9H), 1.49 (br d, J=5.5 Hz, 4H), 1.39 (br d, J=14.1 Hz, 5H), 1.29 (br s, 2H), 0.86 (br d, J=7.5 Hz, 2H).

Example 18

Methyl 5-(N-((4-(4-methoxyphenyl)bicyclo[2.2.2]octan-1-yl)methyl)cyclohexanecarboxamido)-3,4-dihydronaphthalene-2-carboxylate (18)

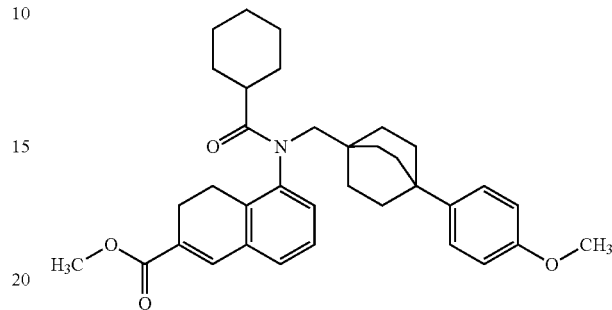

To a stirred solution of Intermediate 11H (18 mg, 0.030 mmol) in toluene (0.5 mL) were added methanol (0.02 mL, 0.494 mmol), cesium carbonate (19 mg, 0.061 mmol) and 2-di-tert-butylphosphino-2',4',6'-triisopropylbiphenyl (2.5 mg, 6.10 μmol) at room temperature. The reaction mixture was degassed and back-filled with argon. $Pd_2(dba)_3$ (2.79 mg, 3.05 μmol) was added to the reaction mixture and the vial was sealed (Pressure release vial). The reaction mixture was heated at 75° C. for 3 h. The reaction mixture was cooled and the crude material was purified via preparative LC/MS using following conditions: (Column: Waters XBridge C18, 19×150 mm, 5-μm particles; Mobile Phase A: 10-mM ammonium acetate; Mobile Phase B: acetonitrile; Gradient: 25-80% B over 20 minutes, then a 10-minute hold at 80% B; Flow: 15 mL/min). Fractions containing the desired product were combined and dried via centrifugal evaporation to afford the title compound (4 mg, 9% yield). $^1$H NMR (400 MHz, DMSO-$d_6$) δ 7.59 (s, 1H), 7.32-7.44 (m, 3H), 7.17 (d, J=8.40 Hz, 2H), 6.80 (d, J=8.80 Hz, 2H), 3.80-3.84 (m, 1H), 3.75 (s, 3H), 3.70 (s, 3H), 3.17 (d, J=5.20 Hz, 1H), 3.00 (d, J=13.20 Hz, 1H), 2.71-2.75 (m, 1H), 1.98-1.99 (m, 1H), 1.64-1.67 (m, 9H), 1.28-1.56 (m, 12H), 1.05-1.09 (m, 1H), 0.85-0.91 (m, 2H). FXR $EC_{50}$ (nM) 1805. MS (ESI) 542 (M+H).

Example 19

Methyl (E)-3-(3-(N-((4-(3-methyl-1,2,4-oxadiazol-5-yl)bicyclo[2.2.2]octan-1-yl)methyl)cyclohexanecarboxamido)phenyl)but-2-enoate (19)

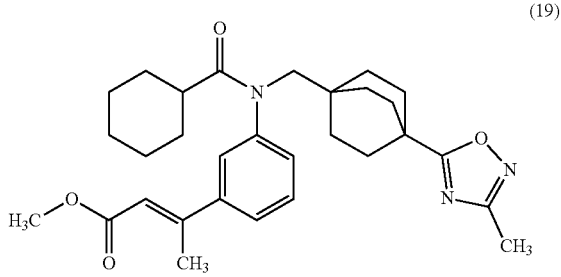 [SMILES: COC(=O)/C=C(\C)c1cccc(N(CC23CCC(c4nc(C)no4)(CC2)CC3)C(=O)C2CCCCC2)c1]

Step A. Intermediate 19A. Preparation of methyl 4-(3-methyl-1,2,4-oxadiazol-5-yl) bicyclo[2.2.2]octane-1-carboxylate

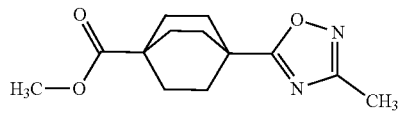

To a stirred solution of 4-(methoxycarbonyl)bicyclo[2.2.2]octane-1-carboxylic acid (2 g, 9.42 mmol) in DMF (20 mL) were added (E)-N'-hydroxyacetimidamide (commercially available) (1.39 g, 18.85 mmol), BOP (4.17 g, 9.42 mmol) and TEA (3.94 mL, 28.3 mmol) at room temperature. The reaction mixture was stirred at room temperature for 2 h and heated at 110° C. for overnight. The reaction mixture was cooled to room temperature, diluted with water and extracted with EtOAc (2×30 mL). The organic layers were combined, dried over anhydrous sodium sulphate and concentrated under reduced pressure. The crude material was purified by flash chromatography (40 g silica gel cartridge; A=Hex, B=EtOAc; 30 min grad.; 0% B to 40% B; flow rate=30 mL/min). The pure fractions were combined, concentrated under reduced pressure and dried in vacuo to afford the title compound (0.6 g, 2.277 mmol, 24% yield) as white solid. H NMR (400 MHz, DMSO-$d_6$) δ 3.60 (s, 3H), 2.29 (s, 3H), 1.95-1.86 (m, 6H), 1.86-1.78 (m, 6H).

Step B. Intermediate 19B. Preparation of methyl 4-(3-methyl-1,2,4-oxadiazol-5-yl) bicyclo[2.2.2]octane-1-carboxylate

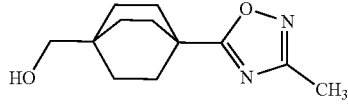 [SMILES: Cc1noc(C23CCC(CO)(CC2)CC3)n1]

To a stirred solution of Intermediate 19A (0.6 g, 2.397 mmol) in tetrahydrofuran (20 mL) was added DIBAL-H (6 mL, 5.99 mmol) at −78° C. under nitrogen atmosphere. The reaction mixture was allowed to warm to room temperature and stirred for 1 h. The reaction mixture was cooled to 0° C., and the reaction was quenched with aqueous 1.5 N HCl solution. The reaction mixture was extracted with EtOAc (2×25 mL). The organic layers were combined, dried over anhydrous sodium sulphate and concentrated under reduced pressure. The crude material was purified by flash chromatography (24 g silica gel cartridge; A=Hex, B=EtOAc; 30 min grad.; 0% B to 30% B; flow rate=30 mL/min). The pure fractions were combined, concentrated under reduced pressure and dried in vacuo to afford the title compound (0.58 g, 2.348 mmol, 98% yield) as an off-white solid. $^1$H NMR (400 MHz, DMSO-$d_6$) δ 4.41 (br. s., 1H), 3.08 (s, 2H), 2.29 (s, 3H), 1.90-1.80 (m, 6H), 1.50-1.40 (m, 6H).

Step C. Intermediate 19C. Preparation of 4-(3-methyl-1,2,4-oxadiazol-5-yl) bicyclo[2.2.2]octane-1-carbaldehyde

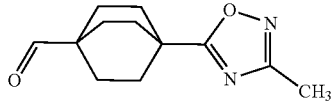

To a stirred solution of Intermediate 19B (0.58 g, 2.61 mmol) in dichloromethane (10 mL) was added Dess-Martin periodinane (2.21 g, 5.22 mmol) at 0° C. under nitrogen atmosphere. The reaction mixture was stirred at the same temperature for 1 h. The reaction mixture was allowed to warm to room temperature, diluted with DCM (20 mL) and filtered through Celite. The filtrate was washed with aqueous 10% sodium bicarbonate solution (2×20 mL). The organic layer was dried over anhydrous sodium sulphate and concentrated under reduced pressure. The crude material was purified by flash chromatography (24 g silica gel cartridge; A=Hex, B=EtOAc; 30 min grad.; 0% B to 30% B; flow rate=30 mL/min). The pure fractions were combined, concentrated under reduced pressure and dried in vacuo to afford the title compound (0.46 g, 1.98 mmol, 76% yield) as white solid. $^1$H NMR (400 MHz, DMSO-$d_6$) δ 9.46 (s, 1H), 2.30 (s, H), 1.96-1.84 (m, 6H), 1.73-1.66 (m, 6H).

Step D. Intermediate 19D. Preparation of 4-(3-methyl-1,2,4-oxadiazol-5-yl)bicyclo [2.2.2]octane-1-carbaldehyde

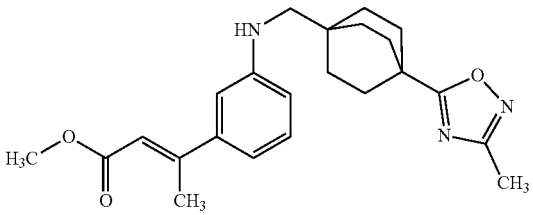 [SMILES: COC(=O)/C=C(\C)c1cccc(NCC23CCC(c4nc(C)no4)(CC2)CC3)c1]

The title compound was prepared according to the method described for the synthesis of Intermediate 1H by substituting Intermediate 14A and Intermediate 19C where appropriate. (50 mg, 0.101 mmol, 44% yield) as pale yellow solid. MS (ESI) 396 (M+H).

Step F. Example 19. Preparation of methyl (E)-3-(3-(N-((4-(3-methyl-1,2,4-oxadiazol-5-yl)bicyclo[2.2.2]octan-1-yl)methyl)cyclohexanecarboxamido)phenyl)but-2-enoate To a stirred solution of Intermediate 19D (50 mg, 0.126 mmol) in dichloromethane (2 mL) was added TEA (0.053 mL, 0.379 mmol) at room temperature. The reaction mixture was cooled to 0° C. Cyclohexanecarbonyl chloride (18 mg, 0.126 mmol) was added to the reaction mixture and stirred at the same temperature for 1 h. The reaction mixture was allowed to warm to room temperature and concentrated under reduced pressure. The crude material which was purified via preparative HPLC using following conditions: (Column: Waters XBridge C18, 19×150 mm, 5-μm particles; Mobile Phase A: 10-mM ammonium acetate; Mobile Phase B: acetonitrile; Gradient: 10-45% B over 25 minutes, then a 5-μminute hold at 100% B; Flow: 15 mL/min). Fractions containing the desired product were combined and dried via centrifugal evaporation to afford the title compound (42 mg, 0.080 mmol, 63% yield). $^1$H NMR (400 MHz, DMSO-d$_6$) δ 7.58 (s, 1H), 7.56-7.51 (m, 1H), 7.51-7.31 (m, 2H), 6.24 (s, 1H), 3.69 (s, 3H), 3.60 (br. s., 2H), 2.53 (s, 4H), 2.27 (s, 3H), 2.18 (br. s., 1H), 1.87-1.70 (m, 6H), 1.60 (d, J=11.0 Hz, 4H), 1.50 (d, J=13.7 Hz, 1H), 1.44-1.26 (m, 7H), 1.16-1.01 (m, 1H), 0.87 (d, J=10.8 Hz, 2H). FXR EC$_{50}$ (nM) 551; MS (ESI) 506 (M+H).

Example 20

Methyl (E)-3-(3-(N-((4-(3-methyl-1,2,4-oxadiazol-5-yl)bicyclo[2.2.2]octan-1-yl)methyl)cyclohexanecarboxamido)phenyl)acrylate (20)

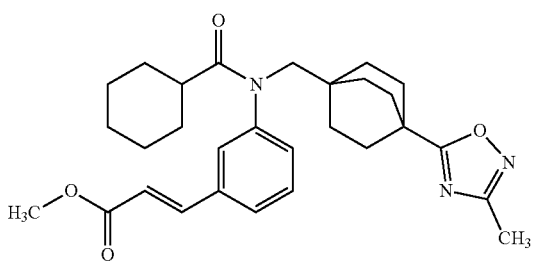

Step A. Intermediate 20A. Preparation of methyl (E)-3-(3-(((4-(3-methyl-1,2,4-oxadiazol-5-yl)bicyclo[2.2.2]octan-1-yl)methyl)amino)phenyl)acrylate

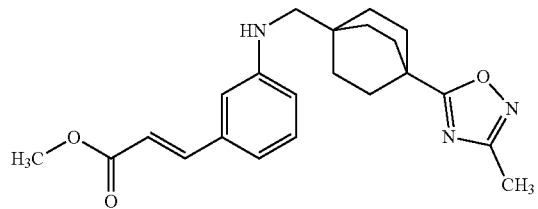 [SMILES: COC(=O)/C=C/c1cccc(NCC23CCC(c4nc(C)no4)(CC2)CC3)c1]

The title compound was prepared according to the method described for the synthesis of Intermediate 1H by substituting Intermediate 1G and Intermediate 19C where appropriate. (0.18 g, 0.236 mmol, 26% yield) as pale yellow solid. MS (ESI) 382 (M+H).

Step B. Example 20. Preparation of methyl (E)-3-(3-(N-((4-(3-methyl-1,2,4-oxadiazol-5-yl)bicyclo[2.2.2]octan-1-yl)methyl)cyclohexanecarboxamido)phenyl)acrylate The title compound was prepared according to the method described for the synthesis of Example 19 (Step F) by substituting Intermediate 20A and cyclohexanecarbonyl chloride where appropriate. (6 mg, 0.012 mmol, 22% yield) as white solid. $^1$H NMR (400 MHz, DMSO-d$_6$) δ 7.80 (s, 1H), 7.75-7.63 (m, 2H), 7.54-7.37 (m, 2H), 6.76 (d, J=16.1 Hz, 1H), 3.74 (s, 3H), 3.65-3.53 (m, 2H), 2.26 (s, 3H), 2.18 (br. s., 1H), 1.83-1.72 (m, 6H), 1.59 (d, J=11.0 Hz, 4H), 1.47 (br. s., 1H), 1.44-1.35 (m, 6H), 1.35-1.21 (m, 2H), 1.08 (d, J=12.7 Hz, 1H), 0.87 (br. s., 2H). FXR EC$_{50}$ (nM) 56; MS (ESI) 492 (M+H).

The below compounds were prepared according to the method described for the synthesis of Example 19 (Step F) by substituting Intermediate 20A and corresponding acid chlorides where appropriate.

| Ex. No. | Structure & Name | MS (ESI) (M + H) | FXR EC$_{50}$ (nM) |
|---|---|---|---|
| 21 | 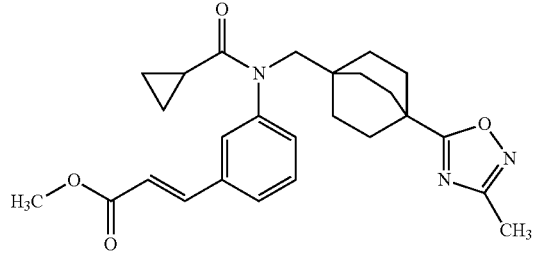<br>methyl (E)-3-(3-(N-((4-(3-methyl-1,2,4-oxadiazol-5-yl)bicyclo[2.2.2]octan-1-yl)methyl)cyclopropanecarboxamido)phenyl)acrylate | 450 | 2436 |

| Ex. No. | Structure & Name | MS (ESI) (M + H) | FXR EC$_{50}$ (nM) |
|---|---|---|---|
| 22 | methyl (E)-3-(3-(N-((4-(3-methyl-1,2,4-oxadiazol-5-yl)bicyclo[2.2.2]octan-1-yl)methyl)isobutyramido)phenyl)acrylate | 452 | 849 |

21 $^1$H NMR (400 MHz, DMSO-d$_6$) δ 7.85 (s, 1H), 7.68 (s, 1H), 7.72 (s, 1H), 7.49 (d, J = 4.4 Hz, 2H), 6.76 (d, J = 16.1 Hz, 1H), 3.74 (s, 3H), 3.66 (br. s., 2H), 2.26 (s, 3H), 1.87-1.66 (m, 6H), 1.47-1.26 (m, 7H), 0.78 (br. s., 2H), 0.62 (br. s., 2H)

22 $^1$H NMR (400 MHz, DMSO-d$_6$) δ 7.83 (s, 1H), 7.74-7.60 (m, 2H), 7.53-7.35 (m, 2H), 6.77 (d, J = 16.4 Hz, 1H), 3.74 (s, 3H), 3.59 (s, 2H), 2.27 (s, 3H), 1.89-1.67 (m, 6H), 1.50-1.29 (m, 6H), 0.90 (d, J = 6.6 Hz, 6H)

Example 23

Methyl (E)-3-(3-(N-((4-(3-methyl-1,2,4-oxadiazol-5-yl)bicyclo[2.2.2]octan-1-yl)methyl)tetrahydro-2H-pyran-4-carboxamido)phenyl)acrylate (23)

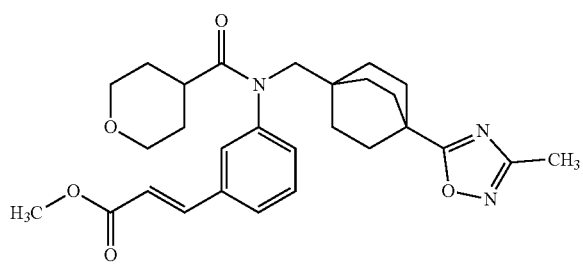

To a stirred solution of Intermediate 20A (0.02 g, 0.052 mmol) in dichloromethane (1 mL) was added tetrahydro-2H-pyran-4-carboxylic acid (6.8 mg, 0.052 mmol) followed by pyridine (0.013 mL, 0.157 mmol). The reaction mixture was cooled to 0° C. and was added POCl$_3$ (9.77 µL, 0.105 mmol). The reaction mixture was allowed to warm to room temperature and stirred for 1 h. The reaction was quenched with water (5 mL). The reaction mixture was extracted with DCM (2×5 mL). The organic layers were combined, dried over anhydrous sodium sulphate and concentrated under reduced pressure. The crude material was purified via preparative LC/MS using following conditions: (Column: Waters XBridge C18, 19×150 mm, 5-µm particles; Mobile Phase A: 10-mM ammonium acetate; Mobile Phase B: acetonitrile; Gradient: 15-52% B over 25 minutes, then a 5-minute hold at 100% B; Flow: 15 mL/min). Fractions containing the desired product were combined and dried via centrifugal evaporation to afford the title compound (8.8 mg, 0.017 mmol, 33% yield). $^1$H NMR (400 MHz, DMSO-d$_6$) δ 7.83 (s, 1H), 7.77-7.63 (m, 2H), 7.55-7.41 (m, 2H), 6.77 (d, J=16.4 Hz, 1H), 3.74 (s, 5H), 3.66-3.55 (m, 2H), 2.98 (t, J=11.5 Hz, 2H), 2.27 (s, 3H), 1.85-1.73 (m, 7H), 1.65-1.52 (m, 2H), 1.50-1.31 (m, 8H). FXR EC$_{50}$ (nM) 920; MS (ESI) 494 (M+H).

The following compounds were prepared according to the method described for the synthesis of Example 23 by substituting Intermediate 20A and corresponding acids where appropriate.

| Ex. No. | Structure & Name | MS (ESI) (M + H) | FXR EC$_{50}$ (nM) |
|---|---|---|---|
| 24 | Methyl (E)-3-(3-(N-((4-(3-methyl-1,2,4-oxadiazol-5-yl)bicyclo[2.2.2]octan-1-yl)methyl)cyclopropanecarboxamido)phenyl)acrylate | 506 | 150 |

-continued

| Ex. No. | Structure & Name | MS (ESI) (M + H) | FXR EC$_{50}$ (nM) |
|---|---|---|---|
| 25 | methyl (E)-3-(3-(3-fluoro-N-((4-(3-methyl-1,2,4-oxadiazol-5-yl)bicyclo[2.2.2]octan-1-yl)methyl)bicyclo[1.1.1]pentane-1-carboxamido)phenyl)acrylate | 494 | 123 |
| 26 | methyl (E)-3-(3-(3,3-difluoro-N-((4-(3-methyl-1,2,4-oxadiazol-5-yl)bicyclo[2.2.2]octan-1-yl)methyl)cyclobutane-1-carboxamido)phenyl)acrylate | 500 | 302 |

24  $^1$H NMR (400 MHz, DMSO-d$_6$) δ 7.82 (s, 1H), 7.74-7.60 (m, 2H), 7.49 (t, J = 7.8 Hz, 1H), 7.44 (d, J = 8.3 Hz, 1H), 6.78 (d, J = 16.1 Hz, 1H), 3.75 (s, 3H), 3.59 (s, 2H), 2.38-2.32 (m, 1H), 2.28 (s, 3H), 1.85-1.75 (m, 6H), 1.62 (br. s., 3H), 1.59-1.47 (m, 4H), 1.45-1.28 (m, 9H), 1.07 (br. s., 2H).

25  $^1$H NMR (400 MHz, DMSO-d$_6$) δ 7.84 (s, 1H), 7.80-7.68 (m, 2H), 7.57-7.48 (m, 1H), 7.48-7.41 (m, 1H), 6.81 (d, J = 16.1 Hz, 1H), 3.75 (s, 3H), 3.57 (d, J = 13.2 Hz, 2H), 2.28 (s, 3H), 1.95-1.68 (m, 12H), 1.48-1.40 (m, 6H).

26  $^1$H NMR (400 MHz, DMSO-d$_6$) δ 7.82 (s, 1H), 7.76-7.64 (m, 2H), 7.53-7.40 (m, 2H), 6.79 (d, J = 16.1 Hz, 1H), 3.75 (s, 3H), 3.64 (s, 2H), 2.89 (d, J = 7.8 Hz, 2H), 2.75 (d, J = 9.5 Hz, 2H), 2.33-2.19 (m, 4H), 1.93-1.69 (m, 6H), 1.62-1.33 (m, 6H).

Example 27

(E)-N-(3-(3-(dimethylamino)-3-oxoprop-1-en-1-yl)phenyl)-N-((4-(3-methyl-1,2,4-oxadiazol-5-yl)bicyclo[2.2.2]octan-1-yl)methyl)cyclohexanecarboxamide

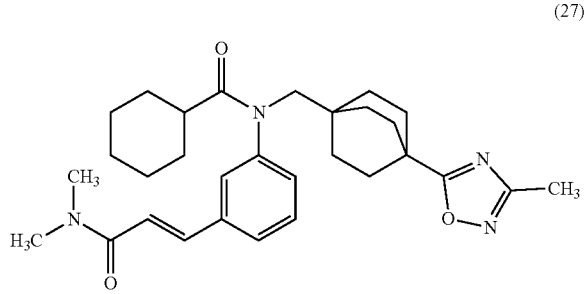

(27)

Step A. Intermediate 27A. Preparation of (E)-3-(3-(N-((4-(3-methyl-1,2,4-oxadiazol-5-yl)bicyclo[2.2.2]octan-1-yl)methyl)cyclohexanecarboxamido)phenyl)acrylic Acid

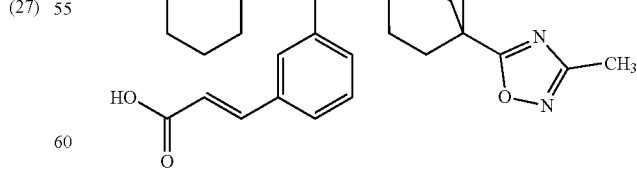

To a stirred solution of Example 24 (0.06 g, 0.122 mmol) in methanol (2 mL) was added a solution of LiOH (0.015 g, 0.610 mmol) in water (1 mL). The reaction mixture was stirred at room temperature for 2 h. The reaction mixture was concentrated under reduced pressure. The residue was acidified to pH~2 by using aqueous 1.5N HCl solution. The precipitated solid was filtered and dried in vacuo to afford the title compound (0.06 g, 0.119 mmol, 98% yield) as an off-white solid. MS (ESI) 478 (M+H).

Step B. Example 27. Preparation of (E)-N-(3-(3-(dimethylamino)-3-oxoprop-1-en-1-yl)phenyl)-N-((4-(3-methyl-1,2,4-oxadiazol-5-yl)bicyclo[2.2.2]octan-1-yl)methyl)cyclohexanecarboxamide To a stirred solution of Intermediate 27A (15 mg, 0.031 mmol) in dichloromethane (2 mL) was added DIPEA (0.016 mL, 0.094 mmol) followed by isobutyl chloroformate (8.25 µl, 0.063 mmol) at 0° C. The reaction mixture was allowed to warm to room temperature and stirred for 30 min. Dimethylamine (7.08 mg, 0.157 mmol) was added to the reaction mixture and stirred for 5 min. The reaction mixture was concentrated under reduced pressure. The crude material was purified via preparative LC/MS using following conditions: (Column: Waters XBridge C18, 19×150 mm, 5-µm particles; Mobile Phase A: 10-mM ammonium acetate; Mobile Phase B: acetonitrile; Gradient: 15-55% B over 20 minutes, then a 5-minute hold at 100% B; Flow: 20 mL/min). Fractions containing the desired product were combined and dried via centrifugal evaporation to afford the title compound (5.5 mg, 10.68 µmol, 34% yield). $^1$H NMR (400 MHz, DMSO-d$_6$) δ 7.76 (s, 1H), 7.67 (d, J=6.6 Hz, 1H), 7.52-7.42 (m, 2H), 7.41-7.35 (m, 1H), 7.33-7.22 (m, 1H), 3.60 (br. s., 2H), 3.17 (s, 3H), 2.93 (s, 3H), 2.27 (s, 3H), 2.21 (br. s., 1H), 1.83-1.74 (m, 6H), 1.59 (br. s., 4H), 1.48 (br. s., 1H), 1.44-1.26 (m, 8H), 1.06 (s, 1H), 0.86 (br. s., 2H). FXR EC$_{50}$ (nM) 4462; MS (ESI) 505 (M+H).

Example 28

Methyl (E)-3-(3-(N-((4-(4-cyclopropylphenyl)bicyclo[2.2.2]octan-1-yl)methyl)cyclopropanecarboxamido)phenyl)acrylate (28)

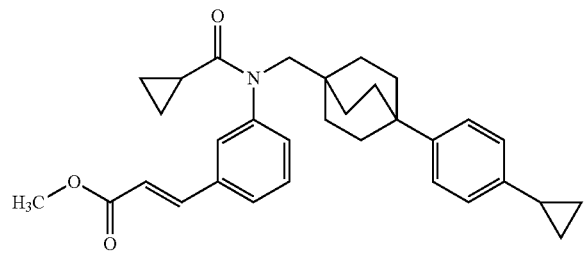

Step A. Intermediate 28A. Preparation of methyl 4-(4-cyclopropylphenyl)bicyclo[2.2.2]octane-1-carboxylate

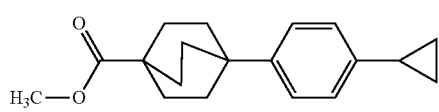

To a stirred solution of Intermediate 1C (500 mg, 1.547 mmol) in 1,4-dioxane (10 mL) were added cyclopropylboronic acid (200 mg, 2.320 mmol), potassium phosphate tribasic (985 mg, 4.64 mmol), palladium(II) acetate (34.7 mg, 0.155 mmol) and tricyclohexylphosphine (87 mg, 0.309 mmol). The reaction mixture was degassed and back-filled with argon. The reaction mixture was heated at 100° C. for 12 h. The reaction mixture was cooled to room temperature, diluted with water (20 mL) and extracted with ethyl acetate (2×10 mL). The organic layers were combined, dried over anhydrous sodium sulphate and concentrated under reduced pressure. The crude material was purified by flash chromatography (24 g silica gel cartridge; A=Hex, B=EtOAc; 30 min grad.; 0% B to 30% B; flow rate=30 mL/min). The pure fractions were combined, concentrated under reduced pressure and dried in vacuo to afford the title compound (330 mg, 0.580 mmol, 37% yield). MS (ESI) 285 (M+H).

Step B. Intermediate 28B. Preparation of (4-(4-cyclopropylphenyl)bicyclo[2.2.2]octan-1-yl)methanol

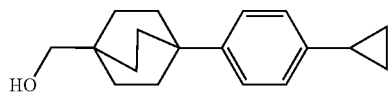 [SMILES: OCC12CCC(c3ccc(C4CC4)cc3)(CC1)CC2]

The title compound was prepared according to the method described for the synthesis of Intermediate 19B by substituting Intermediate 28A where appropriate. (250 mg, 0.975 mmol, 84% yield). $^1$H NMR (400 MHz, DMSO-d$_6$) δ 7.17 (d, J=8.3 Hz, 2H), 6.96 (d, J=8.3 Hz, 2H), 4.34 (d, J=5.5 Hz, 1H), 3.07 (d, J=5.4 Hz, 2H), 1.91-1.79 (m, 1H), 1.78-1.64 (m, 6H), 1.49-1.36 (m, 6H), 0.89 (dd, J=2.2, 8.4 Hz, 2H), 0.65-0.51 (m, 2H).

Step C. Intermediate 28C. Preparation of 4-(4-cyclopropylphenyl)bicyclo[2.2.2]octane-1-carbaldehyde

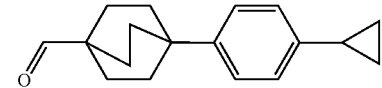

The title compound was prepared according to the method described for the synthesis of Intermediate 8G by substituting Intermediate 28B where appropriate. (200 mg, 0.786 mmol, 78% yield). $^1$H NMR (400 MHz, chloroform-d) δ 9.61-9.42 (m, 1H), 7.20 (d, J=8.3 Hz, 2H), 7.02 (d, J=8.3 Hz, 2H), 1.91-1.83 (m, 7H), 1.81-1.73 (m, 6H), 0.95-0.91 (m, 2H), 0.67 (dd, J=1.6, 5.0 Hz, 2H).

Step D. Intermediate 28D. Preparation of methyl (E)-3-(3-(((4-(4-cyclopropylphenyl) bicyclo[2.2.2]octan-1-yl)methyl)amino)phenyl)acrylate

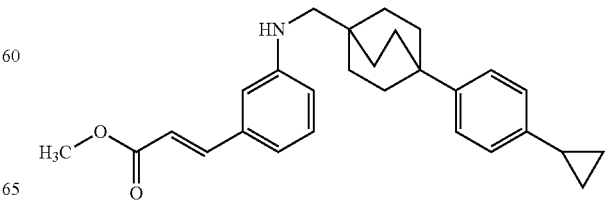

The title compound was prepared according to the method described for the synthesis of Intermediate 1H by substituting Intermediate 1G and Intermediate 28C where appropriate. (40 mg, 0.044 mmol, 22% yield). MS (ESI) 416 (M+H).

Step E. Example 28. Preparation of methyl (E)-3-(3-(N-((4-(4-cyclopropylphenyl) bicyclo[2.2.2]octan-1-yl)methyl)cyclopropanecarboxamido)phenyl)acrylate The title compound was prepared according to the method described for the synthesis of Example 19 (Step F) by substituting Intermediate 28D and cyclopropanecarbonyl chloride where appropriate. (4.6 mg, 9.42 μmol, 19% yield). $^1$H NMR (400 MHz, DMSO-d$_6$) δ 7.84 (s, 1H), 7.68 (s, 1H), 7.72 (s, 1H), 7.48 (br. s., 2H), 7.11 (d, J=8.1 Hz, 2H), 6.93 (d, J=8.3 Hz, 2H), 6.75 (d, J=16.1 Hz, 1H), 3.74 (s, 3H), 3.66 (s, 2H), 1.86-1.76 (m, 1H), 1.70-1.52 (m, 6H), 1.48-1.30 (m, 7H), 0.93-0.83 (m, 2H), 0.78 (d, J=3.9 Hz, 2H), 0.69-0.51 (m, 4H). FXR EC$_{50}$ (nM) 947; MS (ESI) 484 (M+H).

Example 29

Methyl (E)-3-(3-(N-((4-(4-cyclopropylphenyl)bicyclo[2.2.2]octan-1-yl)methyl)cyclohexanecarboxamido)phenyl)acrylate (29)

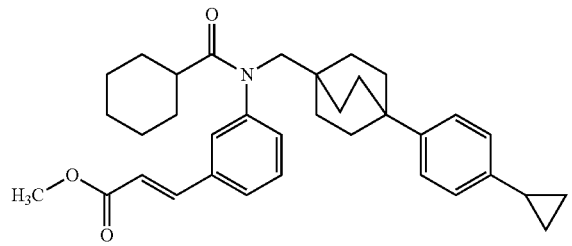

The title compound was prepared according to the method described for the synthesis of Example 19 (Step F) by substituting Intermediate 28D and cyclohexanecarbonyl chloride where appropriate. (3.0 mg, 5.68 μmol, 11% yield). $^1$H NMR (400 MHz, DMSO-d$_6$) δ 7.79 (s, 1H), 7.74-7.60 (m, 2H), 7.54-7.31 (m, 2H), 7.17-7.06 (m, J=8.3 Hz, 2H), 7.01-6.88 (m, J=8.3 Hz, 2H), 6.76 (d, J=16.1 Hz, 1H), 3.74 (s, 3H), 3.58 (br. s., 2H), 2.19 (br. s., 1H), 1.87-1.77 (m, 1H), 1.69-1.54 (m, 11H), 1.48 (br. s., 1H), 1.42-1.28 (m, 8H), 1.24 (s, 1H), 1.07 (br. s., 1H), 0.97-0.75 (m, 4H), 0.62-0.54 (m, 2H). FXR EC$_{50}$ (nM) 161; MS (ESI) 526 (M+H).

Example 30

Methyl 5-(N-((4-(4-cyclopropylphenyl)bicyclo[2.2.2]octan-1-yl)methyl)cyclohexanecarboxamido)-3,4-dihydronaphthalene-2-carboxylate (30)

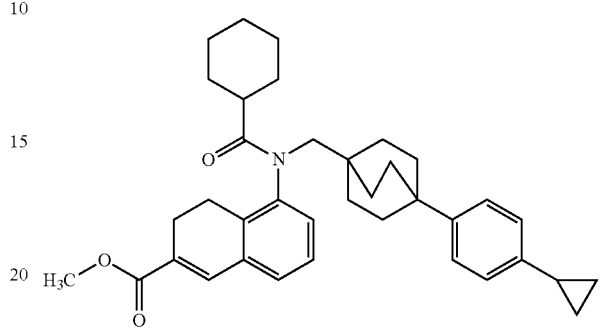

Step A. Intermediate 30A. Preparation of methyl 5-(((4-(4-cyclopropylphenyl) bicyclo[2.2.2]octan-1-yl)methyl)amino)-3,4-dihydronaphthalene-2-carboxylate

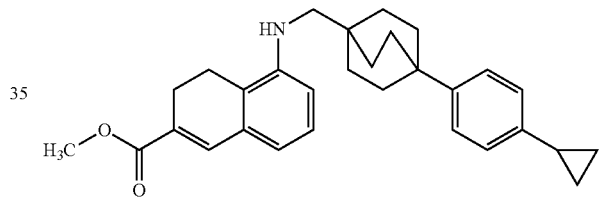

The title compound was prepared according to the method described for the synthesis of Intermediate 1H by substituting Intermediate 11F and Intermediate 28C where appropriate. (45 mg, 0.043 mmol, 22% yield). MS (ESI) 442 (M+H).

Step B. Example 30. Preparation of methyl 5-(N-((4-(4-cyclopropylphenyl)bicyclo[2.2.2]octan-1-yl)methyl)cyclohexanecarboxamido)-3,4-dihydronaphthalene-2-carboxylate The title compound was prepared according to the method described for the synthesis of Example 19 (Step F) by substituting Intermediate 30A and cyclohexanecarbonyl chloride where appropriate. (7.0 mg, 0.013 mmol, 28% yield). $^1$H NMR (400 MHz, DMSO-d$_6$) δ 7.59 (s, 1H), 7.49-7.38 (m, 2H), 7.37-7.29 (m, 1H), 7.21-7.06 (m, J=8.1 Hz, 2H), 7.02-6.84 (m, J=8.3 Hz, 2H), 3.83 (d, J=13.9 Hz, 1H), 3.75 (s, 3H), 2.99 (d, J=13.7 Hz, 1H), 2.79-2.71 (m, 1H), 2.62-2.54 (m, 2H), 2.45-2.37 (m, 1H), 2.00 (br. s., 1H), 1.89-1.78 (m, 1H), 1.71-1.55 (m, 9H), 1.49 (d, J=5.9 Hz, 4H), 1.41 (br. s., 5H), 1.26 (d, J=18.3 Hz, 2H), 1.07 (d, J=13.7 Hz, 1H), 0.94-0.76 (m, 4H), 0.63-0.53 (in, 2H); FXR EC$_5$O (nM) 195; MS (ESI) 552 (M+H).

The following compounds were prepared according to the method described for the synthesis Example 19 (Step F) by substituting Intermediate 30A and corresponding Acid chlorides where appropriate.

| Ex. No. | Structure & Name | MS (ESI) (M + H) | FXR EC$_{50}$ (nM) |
|---|---|---|---|
| 31 | 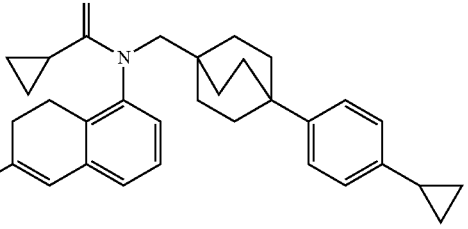<br>methyl 5-(N-((4-(4-cyclopropylphenyl)bicyclo[2.2.2]octan-1-yl)methyl)cyclopropanecarboxamido)-3,4-dihydronaphthalene-2-carboxylate | 510 | 796 |
| 32 | 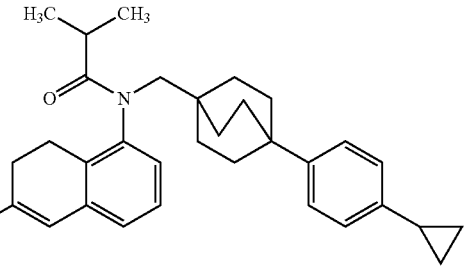<br>methyl 5-(N-((4-(4-cyclopropylphenyl)bicyclo[2.2.2]octan-1-yl)methyl)isobutyramido)-3,4-dihydronaphthalene-2-carboxylate | 512 | 466 |

31 $^1$H NMR (400 MHz, DMSO-d$_6$) δ 7.59 (s, 1H), 7.47 (d, J = 8.1 Hz, 1H), 7.42-7.29 (m, 2H), 7.13 (d, J = 8.3 Hz, 2H), 6.94 (d, J = 8.1 Hz, 2H), 3.76 (s, 3H), 3.66 (d, J = 13.7 Hz, 2H), 3.36 (s, 1H), 2.86-2.75 (m, 1H), 2.71 (d, J = 8.3 Hz, 1H), 1.90-1.78 (m, 1H), 1.73-1.56 (m, 6H), 1.41 (d, J = 7.6Hz, 3H), 1.45 (d, J = 7.6 Hz, 3H), 1.27-1.07 (m, 2H), 0.92-0.82 (m, 2H), 0.77 (br. s., 1H), 0.70 (br. s., 1H), 0.65-0.44 (m, 4H)

32 $^1$H NMR (400 MHz, DMSO-d$_6$) δ 7.58 (s, 1H), 7.45 (d, J = 8.1 Hz, 1H), 7.42-7.37 (m, 1H), 7.37-7.28 (m, 1H), 7.19-7.07 (m, J = 8.1 Hz, 2H), 7.00-6.86 (m, J = 8.3 Hz, 2H), 3.87 (d, J = 13.7 Hz, 1H), 3.75 (s, 3H), 2.97 (d, J = 13.7 Hz, 1H), 2.78-2.71 (m, 1H), 2.56 (d, J = 5.9 Hz, 2H), 2.43 (d, J = 9.3 Hz, 1H), 2.32-2.23 (m, 1H), 1.88-1.78 (m, 1H), 1.73-1.59 (m, 6H), 1.50 (d, J = 6.6 Hz, 3H), 1.40 (br. s., 3H), 0.93 (d, J = 6.6 Hz, 3H), 0.90-0.80 (m, 2H), 0.62-0.55 (m, 2H)

Example 33

Methyl (E)-3-(3-(N-((4-(benzo[d]thiazol-2-yl)bicyclo[2.2.2]octan-1-yl)methyl)cyclopropanecarboxamido)phenyl)acrylate (33)

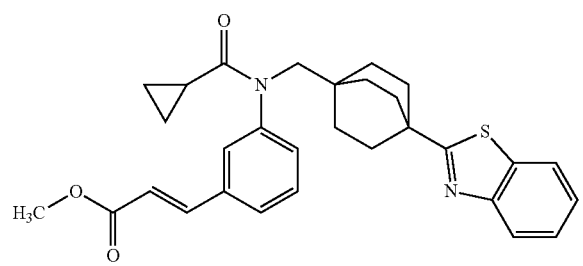

Step A. Intermediate 33A. Preparation of methyl 4-(benzo[d]thiazol-2-yl) bicyclo[2.2.2]octane-1-carboxylate

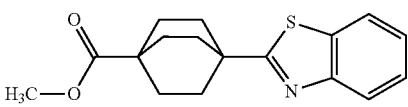

To a solution of 4-(methoxycarbonyl)bicyclo[2.2.2]octane-1-carboxylic acid (0.25 g, 1.178 mmol) in dichloromethane (10 mL) and Water (10 mL) were added benzo[d]thiazole (commercially available) (0.16 g, 1.178 mmol), silver nitrate (0.040 g, 0.236 mmol) and potassium persulfate (1.27 g, 4.71 mmol). The reaction mixture was stirred at room temperature for 12 h. The reaction mixture was diluted with DCM (10 mL), washed with water (10 mL), brine solution (10 mL), dried over anhydrous sodium sulphate and concentrated under reduced pressure. The crude material was purified by flash chromatography (12 g silica gel cartridge; A=Hex, B=EtOAc; 30 min grad.; 0% B to 30% B; flow rate=30 mL/min). The pure fractions were combined, concentrated under reduced pressure and dried in vacuo to afford the title compound (0.07 g, 0.232 mmol, 20% yield) as pale yellow solid. MS (ESI) 302 (M+H).

Step B. Intermediate 33B. Preparation of (4-(benzo[d]thiazol-2-yl)bicyclo[2.2.2]octan-1-yl)methanol

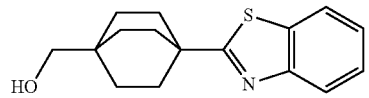 [SMILES: OCC12CCC(c3nc4ccccc4s3)(CC1)CC2]

The title compound was prepared according to the method described for the synthesis of Intermediate 19B by substituting Intermediate 33A where appropriate. (0.06 g, 0.208 mmol, 90% yield) as an off-white solid. MS (ESI) 274 (M+H).

Step C. Intermediate 33C. Preparation of 4-(benzo[d]thiazol-2-yl)bicyclo[2.2.2]octane-1-carbaldehyde

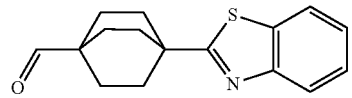 [SMILES: O=CC12CCC(c3nc4ccccc4s3)(CC1)CC2]

The title compound was prepared according to the method described for the synthesis of Intermediate 19C by substituting Intermediate 33B where appropriate. (0.07 g, 0.155 mmol, 85% yield). $^1$H NMR (400 MHz, DMSO-$d_6$) δ 9.50 (s, 1H), 7.65-7.73 (m, 2H), 7.45-7.49 (m, 2H), 1.95-2.12 (m, 6H), 1.82-1.85 (m, 3H), 1.79-1.81 (m, 3H).

Step D. Intermediate 33D. Preparation of methyl (E)-3-(3-(((4-(benzo[d]thiazol-2-yl)bicyclo[2.2.2]octan-1-yl)methyl)amino)phenyl)acrylate

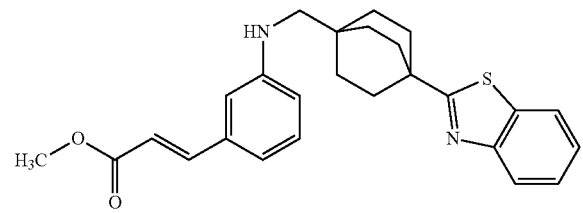 [SMILES: COC(=O)/C=C/c1cccc(NCC23CCC(c4nc5ccccc5s4)(CC2)CC3)c1]

The title compound was prepared according to the method described for the synthesis of Intermediate 1H by substituting Intermediate 1G and Intermediate 33C where appropriate. (30 mg, 0.069 mmol, 47% yield) as pale yellow solid. MS (ESI) 433 (M+H).

Step E. Example 33. Preparation of methyl (E)-3-(3-(N-((4-(benzo[d]thiazol-2-yl)bicyclo[2.2.2]octan-1-yl)methyl)cyclopropanecarboxamido)phenyl)acrylate The title compound was prepared according to the method described for the synthesis of Example 19 (Step F) by substituting Intermediate 33D and cyclopropanecarbonyl chloride. (2.8 mg, 5.59 μmol, 20% yield). $^1$H NMR (400 MHz, DMSO-$d_6$) δ 8.02 (d, J=7.8 Hz, 1H), 7.94-7.81 (m, 2H), 7.77-7.61 (m, 2H), 7.50 (d, J=4.6 Hz, 2H), 7.45 (t, J=7.7 Hz, 1H), 7.40-7.32 (m, 1H), 6.77 (d, J=16.1 Hz, 1H), 3.74 (s, 3H), 3.69 (br. s., 2H), 1.96-1.79 (m, 6H), 1.52-1.40 (m, 6H), 1.37 (br. s., 1H), 0.80 (br. s., 2H), 0.62 (br. s., 2H). FXR $EC_{50}$ (nM) 414; MS (ESI) 501 (M+H).

Example 34

Methyl (E)-3-(3-(N-((4-(benzo[d]thiazol-2-yl)bicyclo[2.2.2]octan-1-yl)methyl)cyclohexanecarboxamido)phenyl)acrylate (34)

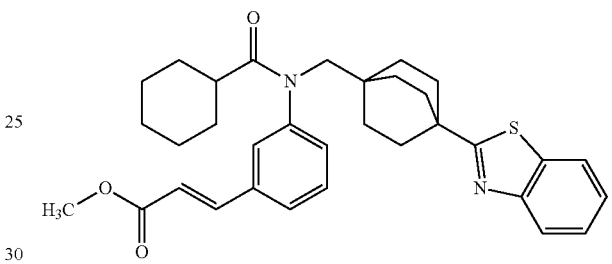

The title compound was prepared according to the method described for the synthesis of Example 19 (Step F) by substituting Intermediate 33D and cyclohexanecarbonyl chloride. (3.3 mg, 6.08 μmol, 22% yield). $^1$H NMR (400 MHz, DMSO-$d_6$) δ 8.02 (d, J=7.8 Hz, 1H), 7.90 (d, J=8.1 Hz, 1H), 7.82 (s, 1H), 7.76-7.60 (m, 2H), 7.55-7.42 (m, 3H), 7.37 (t, J=7.8 Hz, 1H), 6.77 (d, J=16.1 Hz, 1H), 3.74 (s, 3H), 3.62 (br. s., 2H), 2.19 (br. s., 1H), 1.92-1.87 (d, J=8.6 Hz, 6H), 1.59 (br. s., 4H), 1.53-1.40 (m, 7H), 1.39-1.27 (m, 2H), 1.07 (br. s., 1H), 0.88 (br. s., 2H). FXR $EC_{50}$ (nM) 222; MS (ESI) 543 (M+H).

Example 35

(E)-N-((4-(4-methoxyphenyl)bicyclo[2.2.2]octan-1-yl)methyl)-N-(3-(2-(3-methyl-1,2,4-oxadiazol-5-yl)vinyl)phenyl)cyclohexanecarboxamide (35)

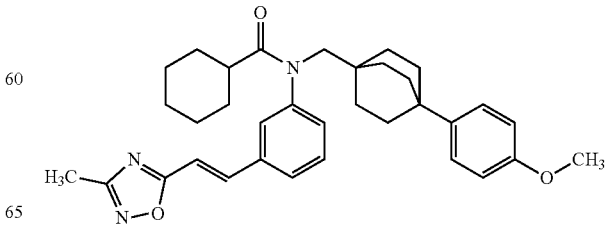

Step A. Intermediate 35A. Preparation of (E)-3-(3-amino phenyl)acrylic acid

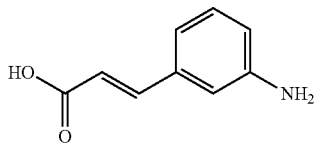 [SMILES: Nc1cccc(/C=C/C(=O)O)c1]

To a stirred solution of Intermediate 1G (0.1 g, 0.564 mmol) in methanol (1 mL), tetrahydrofuran (1 mL) and water (1 mL) was added LiOH (0.041 g, 1.693 mmol). The reaction mixture was stirred at room temperature for 12 h. The reaction mixture was concentrated under reduced pressure. The residue was diluted with water and acidified using aqueous saturated citric acid solution. The aqueous solution was extracted with EtOAc (2×20 mL). The organic layers were combined, dried over anhydrous sodium sulphate and concentrated under reduced pressure to afford the title compound (0.08 g, 0.466 mmol, 83% yield). $^1$H NMR (400 MHz, DMSO-$d_6$) δ 12.32 (s, 1H), 7.41 (d, J=16.00 Hz, 1H), 7.06 (t, J=8.00 Hz, 1H), 6.79 (d, J=6.00 Hz, 2H), 6.61 (d, J=7.60 Hz, 1H), 6.30 (d, J=15.60 Hz, 1H), 5.20 (br. s, 2H). MS (ESI) 164 (M+H).

Step B. Intermediate 35B. Preparation of (E)-3-(2-(3-methyl-1,2,4-oxadiazol-5-yl) vinyl)aniline

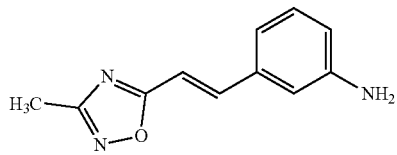

To a stirred solution of Intermediate 35A (0.08 g, 0.490 mmol) in DMF (2 mL) were added (E)-N'-hydroxyacetimidamide (0.073 g, 0.981 mmol), BOP (0.217 g, 0.490 mmol) followed by TEA (0.205 mL, 1.471 mmol). The reaction mixture was stirred at room temperature for 1 h and at 100° C. for 12 h. The reaction mixture was cooled to room temperature, diluted with water (10 mL) and extracted with EtOAc (2×20 mL). The organic layers were combined, dried over anhydrous sodium sulphate and concentrated under reduced pressure. The crude material was purified by flash chromatography (12 g silica gel cartridge; A=Hex, B=EtOAc; 30 min grad.; 0% B to 50% B; flow rate=30 mL/min). The pure fractions were combined, concentrated under reduced pressure and dried in vacuo to afford the title compound (0.055 g, 0.260 mmol, 53% yield) as yellow solid. $^1$H NMR (400 MHz, DMSO-$d_6$) δ 7.65 (d, J=16.1 Hz, 1H), 7.13-7.06 (m, 2H), 6.97-6.86 (m, 2H), 6.68-6.63 (m, 1H), 5.21 (s, 2H), 2.35 (s, 3H). MS (ESI) 164 (M+H).

Step C. Intermediate 35C. Preparation of (E)-N-((4-(4-methoxyphenyl) bicyclo[2.2.2]octan-1-yl)methyl)-3-(2-(3-methyl-1,2,4-oxadiazol-5-yl)vinyl)aniline

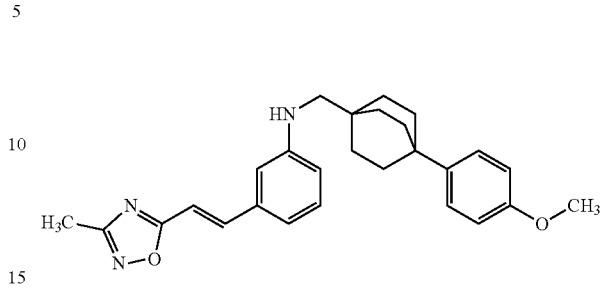

The title compound was prepared according to the method described for the synthesis of Intermediate 1H by substituting Intermediate 35B and Intermediate 15B where appropriate. (0.03 g, 0.035 mmol, 28% yield) as pale yellow solid. MS (ESI) 430 (M+H).

Step D. Example 35. Preparation of (E)-N-((4-(4-methoxyphenyl)bicyclo[2.2.2]octan-1-yl)methyl)-N-(3-(2-(3-methyl-1,2,4-oxadiazol-5-yl)vinyl)phenyl) cyclohexanecarboxamide The title compound was prepared according to the method described for the synthesis of Example 19 (Step F) by substituting Intermediate 35C and cyclohexanecarbonyl chloride where appropriate. (2.8 mg, 5.19 µmol, 18% yield). $^1$H NMR (400 MHz, DMSO-$d_6$) δ 7.96-7.83 (m, 2H), 7.77 (d, J=7.1 Hz, 1H), 7.57-7.35 (m, 3H), 7.24 (d, J=8.8 Hz, 2H), 6.89 (d, J=8.8 Hz, 2H), 3.69 (s, 3H), 3.60 (br. s, 2H), 2.37 (s, 3H), 2.22 (br. s, 1H), 1.72-1.53 (m, 12H), 1.48 (br. s, 1H), 1.40 (d, J=8.1 Hz, 6H), 1.09 (d, J=12.5 Hz, 1H), 0.87 (d, J=13.2 Hz, 2H). FXR EC$_{50}$ (nM) 446; MS (ESI) 540 (M+H).

Example 36

Methyl (E)-3-(3-(N-((4-(4-cyclopropylphenyl)bicyclo[2.2.2]octan-1-yl)methyl)cyclopropanecarboxamido)phenyl)but-2-enoate (36)

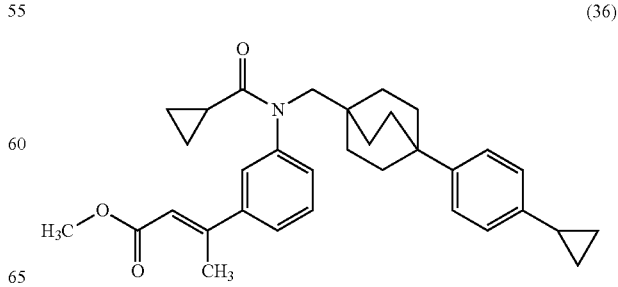

Step A. Intermediate 36A. Preparation of methyl (E)-3-(3-(((4-(4-cyclopropylphenyl)bicyclo[2.2.2]octan-1-yl)methyl)amino)phenyl)but-2-enoate

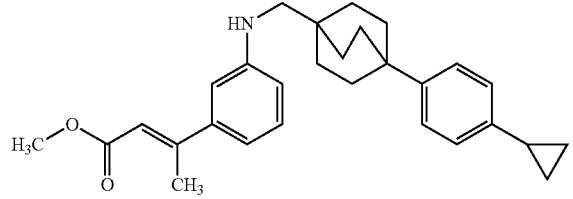 [SMILES: COC(=O)/C=C(\C)c1cccc(NCC23CCC(c4ccc(C5CC5)cc4)(CC2)CC3)c1]

The title compound was prepared according to the method described for the synthesis of Intermediate 1H by substituting Intermediate 14A and Intermediate 28C where appropriate. (30 mg, 0.024 mmol, 12% yield). MS (ESI) 430 (M+H).

Step B. Example 36. Preparation of methyl (E)-3-(3-(N-((4-(4-cyclopropylphenyl) bicyclo[2.2.2]octan-1-yl)methyl)cyclopropanecarboxamido)phenyl)but-2-enoate The title compound was prepared according to the method described for the synthesis of Example 19 (Step F) by substituting Intermediate 36A and cyclopropanecarbonyl chloride where appropriate. (6.6 mg, 0.013 mmol, 37% yield). $^1$H NMR (400 MHz, DMSO-$d_6$) δ 7.63 (s, 1H), 7.57-7.40 (m, 3H), 7.11 (d, J=8.3 Hz, 2H), 6.93 (d, J=8.3 Hz, 2H), 6.24 (s, 1H), 3.78-3.57 (m, 5H), 2.53 (s, 3H), 1.90-1.75 (m, 1H), 1.71-1.53 (m, 6H), 1.45-1.28 (m, 7H), 1.24 (s, 1H), 0.93-0.83 (m, 2H), 0.80 (d, J=2.9 Hz, 2H), 0.69-0.52 (m, 4H); FXR EC$_{50}$ (nM) 1785; MS (ESI) 498 (M+H).

Example 37

Methyl (E)-3-(3-(N-((4-(4-cyclopropylphenyl)bicyclo[2.2.2]octan-1-yl)methyl)cyclohexanecarboxamido)phenyl)but-2-enoate (37)

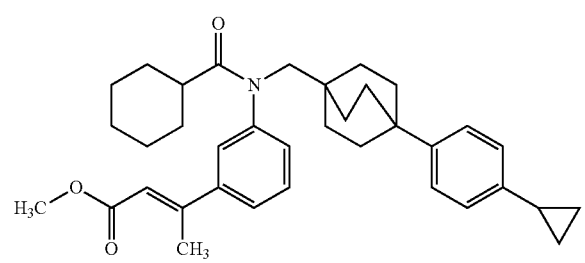

The title compound was prepared according to the method described for the synthesis of Example 19 (Step F) by substituting Intermediate 36A and cyclohexanecarbonyl chloride. (7.4 mg, 0.014 mmol, 39% yield). $^1$H NMR (400 MHz, DMSO-$d_6$) δ 7.60-7.40 (m, 4H), 7.12 (d, J=8.3 Hz, 2H), 6.94 (d, J=8.6 Hz, 2H), 6.23 (s, 1H), 3.69 (s, 3H), 3.59 (br. s., 2H), 2.53 (s, 3H), 2.19 (br. s., 1H), 1.89-1.75 (m, 1H), 1.71-1.53 (m, 10H), 1.48 (br. s., 1H), 1.44-1.28 (m, 8H), 1.09 (d, J=13.9 Hz, 1H), 0.95-0.74 (m, 4H), 0.64-0.49 (m, 2H); FXR EC$_{50}$ (nM) 498; MS (ESI) 540 (M+H).

Example 38

Methyl (E)-3-(3-(N-((4-(4-isopropylphenyl)bicyclo[2.2.2]octan-1-yl)methyl)cyclohexanecarboxamido)phenyl)acrylate (38)

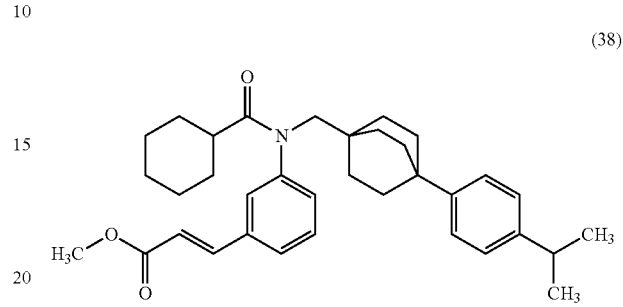

Step A. Intermediate 38A. Preparation of methyl 4-(4-(prop-1-en-2-yl)phenyl) bicyclo[2.2.2]octane-1-carboxylate

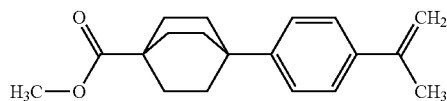

To a stirred solution of Intermediate 1C (0.35 g, 1.083 mmol) in 1,4-dioxane (6 mL) and Water (1.5 mL) were added 4,4,5,5-tetramethyl-2-(prop-1-en-2-yl)-1,3,2-dioxaborolane (0.72 g, 4.33 mmol), sodium carbonate (0.34 g, 3.25 mmol). The reaction mixture was degassed and backfilled with argon. PdCl$_2$(dppf)-CH$_2$Cl$_2$ adduct (0.088 g, 0.108 mmol) was added to the reaction and the vial was sealed (Pressure release vial). The reaction mixture was heated at 90° C. for 12 h. The reaction mixture was cooled to room temperature and diluted with water (10 mL) and extracted with ethyl acetate (2×10 mL). The organic layers were combined, dried over anhydrous sodium sulphate and concentrated under reduced pressure. The crude material was purified by flash chromatography (12 g silica gel cartridge; A=Hex, B=EtOAc; 30 min grad.; 0% B to 30% B; flow rate=30 mL/min). The pure fractions were combined, concentrated under reduced pressure and dried in vacuo to afford the title compound (0.25 g, 0.791 mmol, 73% yield) as an off-white solid. $^1$H NMR (400 MHz, DMSO-$d_6$) δ 7.39-7.47 (m, 2H), 7.27-7.30 (m, 2H), 5.37 (d, J=0.40 Hz, 1H), 5.04 (d, J=1.60 Hz, 1H), 3.60 (s, 3H), 2.04 (s, 3H), 1.72-1.83 (m, 12H).

Step B. Intermediate 38B. Preparation of methyl 4-(4-isopropylphenyl) bicyclo[2.2.2]octane-1-carboxylate

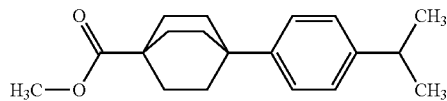

To a stirred solution of Intermediate 38A (0.2 g, 0.703 mmol) in methanol (3 mL) was degassed and back-filled with nitrogen. Palladium on carbon (0.075 g, 0.070 mmol) was added to the reaction mixture and hydrogenated under hydrogen atmosphere (balloon pressure) at room temperature for 12 h. The reaction mixture was filtered through Celite. The filtrate was concentrated under reduced pressure to afford the title compound (0.18 g, 0.534 mmol, 76% yield) as an off-white solid. MS (ESI) 287 (M+H).

Step C. Intermediate 38C. Preparation of (4-(4-isopropylphenyl)bicyclo[2.2.2]octan-1-yl)methanol

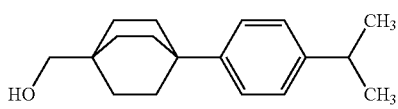

The title compound was prepared according to the method described for the synthesis of Intermediate 19B by substituting Intermediate 38B where appropriate. (0.13 g, 0.478 mmol, 95% yield) as white solid. $^1$H NMR (400 MHz, DMSO-$d_6$) δ 7.21-7.24 (m, 2H), 7.11-7.15 (m, 2H), 4.30-4.34 (m, 1H), 3.08 (d, J=5.20 Hz, 2H), 2.80-2.84 (m, 1H), 1.70-1.74 (m, 6H), 1.43-1.46 (m, 6H), 1.18 (d, J=17.60 Hz, 6H).

Step D. Intermediate 38D. Preparation of 4-(4-isopropylphenyl)bicycle[2.2.2]octane-1-carbaldehyde

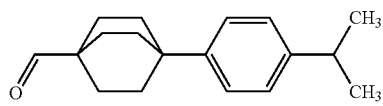

The title compound was prepared according to the method described for the synthesis of Intermediate 19C by substituting Intermediate 38C where appropriate. (0.1 g, 0.390 mmol, 78% yield) as an oil. $^1$H NMR (400 MHz, DMSO-$d_6$) δ 9.48 (s, 1H), 7.21-7.29 (m, 2H), 7.14-7.16 (m, 2H), 2.80-2.84 (m, 1H), 1.66-1.91 (m, 12H), 1.17 (d, J=7.20 Hz, 6H).

Step E. Intermediate 38E. Preparation of methyl (E)-3-(3-(((4-(4-isopropylphenyl) bicyclo[2.2.2]octan-1-yl)methyl)amino)phenyl)acrylate

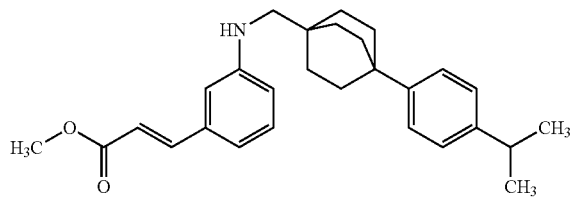 [SMILES: COC(=O)/C=C/c1cccc(NCC23CCC(c4ccc(C(C)C)cc4)(CC2)CC3)c1]

The title compound was prepared according to the method described for the synthesis of Intermediate 1H by substituting Intermediate 1G and Intermediate 38D where appropriate. (0.07 g, 0.134 mmol, 43% yield) as pale yellow solid. MS (ESI) 418 (M+H).

Step E. Example 38. Preparation of methyl(E)-3-(3-(N-((4-(4-isopropylphenyl) bicyclo[2.2.2]octan-1-yl)methyl)cyclohexanecarboxamido)phenyl)acrylate The title compound was prepared according to the method described for the synthesis of Example 19 (Step F) by substituting Intermediate 38E and cyclohexanecarbonyl chloride. (6.8 mg, 0.012 mmol, 23% yield). $^1$H NMR (400 MHz, DMSO-$d_6$) δ 7.79 (s, 1H), 7.76-7.64 (m, 2H), 7.54-7.39 (m, 2H), 7.16 (d, J=8.4 Hz, 2H), 7.10 (d, J=8.4 Hz, 2H), 6.76 (d, J=16 Hz, 1H), 3.74 (s, 3H), 3.59 (br. s., 2H), 2.80 (dt, J=13.7, 6.8 Hz, 1H), 2.20 (br. s., 1H), 1.76-1.75 (m, 1H), 1.69-1.54 (m, 9H), 1.43-1.34 (m, 7H), 1.32 (br. s., 2H), 1.19 (d, J=8.4 Hz, 6H), 1.09 (d, J=9.8 Hz, 1H), 0.85 (br. s., 2H). FXR EC$_{50}$ (nM) 196; MS (ESI) 528 (M+H).

Example 39

Methyl (E)-3-(3-(N-((4-(4-isopropylphenyl)bicyclo[2.2.2]octan-1-yl)methyl)cyclopropanecarboxamido)phenyl)acrylate (39)

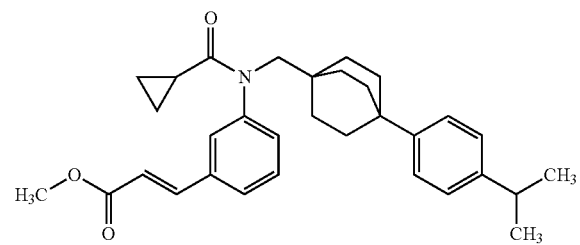

The title compound was prepared according to the method described for the synthesis of Example 19 (Step F) by substituting Intermediate 38E and cyclopropanecarbonyl chloride. (2.3 mg, 4.64 μmol, 9% yield). $^1$H NMR (400 MHz, DMSO-$d_6$) δ 7.84 (s, 1H), 7.76-7.58 (m, 2H), 7.48 (d, J=5.4 Hz, 2H), 7.16 (d, J=8.4 Hz, 2H), 7.09 (d, J=8.4 Hz, 2H), 6.75 (d, J=16 Hz, 1H), 3.74 (s, 3H), 3.66 (br. s., 2H), 2.80 (dt, J=13.9, 6.9 Hz, 1H), 1.73-1.58 (m, 6H), 1.48-1.27 (m, 7H), 1.15 (d, J=6.8 Hz, 6H), 0.84-0.74 (m, 2H), 0.62 (br. s., 2H). FXR EC$_{50}$ (nM) 1427; MS (ESI) 486 (M+H).

Example 40

Methyl 5-(N-((4-(3-methyl-1,2,4-oxadiazol-5-yl)bicyclo[2.2.2]octan-1-yl)methyl)cyclohexanecarboxamido)-3,4-dihydronaphthalene-2-carboxylate

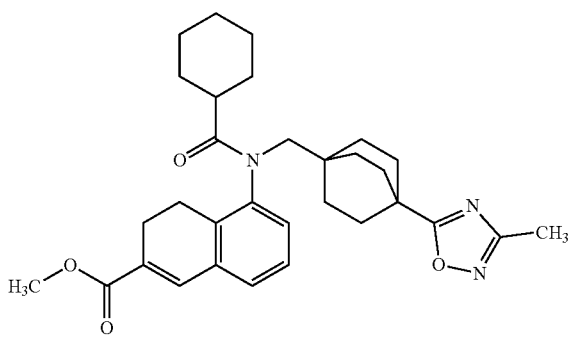

(40)

Step A. Intermediate 40A. Preparation of methyl 5-(((4-(3-methyl-1,2,4-oxadiazol-5-yl) bicyclo[2.2.2]octan-1-yl)methyl)amino)-3,4-dihydronaphthalene-2-carboxylate

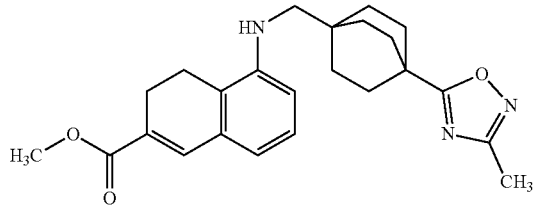 [SMILES: COC(=O)C1=Cc2cccc(NCC34CCC(c5nc(C)no5)(CC3)CC4)c2CC1]

The title compound was prepared according to the method described for the synthesis of Intermediate 1H by substituting Intermediate 11F and Intermediate 19C. (50 mg, 0.086 mmol, 38% yield) as pale yellow solid. MS (ESI) 408 (M+H).

Step B. Example 40. Preparation of methyl 5-(N-((4-(3-methyl-1,2,4-oxadiazol-5-yl) bicyclo[2.2.2]octan-1-yl)methyl)cyclohexanecarboxamido)-3,4-dihydronaphthalene-2-carboxylate The title compound was prepared according to the method described for the synthesis of Example 19 (Step F) by substituting Intermediate 40A and cyclohexanecarbonyl chloride. (27 mg, 0.051 mmol, 69% yield). $^1$H NMR (400 MHz, DMSO-d$_6$) δ 7.58 (s, 1H), 7.51-7.38 (m, 2H), 7.37-7.29 (m, 1H), 3.84 (d, J=13.7 Hz, 1H), 3.75 (s, 3H), 3.17 (d, J=5.4 Hz, 1H), 2.99 (d, J=13.9 Hz, 1H), 2.78-2.68 (m, 1H), 2.61-2.53 (m, 2H), 2.43-2.33 (m, 1H), 2.27 (s, 3H), 1.99 (br. s., 1H), 1.81 (t, J=7.9 Hz, 6H), 1.71-1.53 (m, 4H), 1.53-1.44 (m, 3H), 1.40 (br. s., 3H), 1.36-1.17 (m, 2H), 1.07 (d, J=12.2 Hz, 1H), 0.93-0.74 (m, 2H). FXR EC$_{50}$ (nM) 1069; MS (ESI) 518 (M+H).

Example 41

Methyl (E)-3-(3-(N-((4-(3-cyclopropyl-1,2,4-oxadiazol-5-yl)bicyclo[2.2.2]octan-1-yl)methyl)cyclohexane carboxamido)phenyl)acrylate

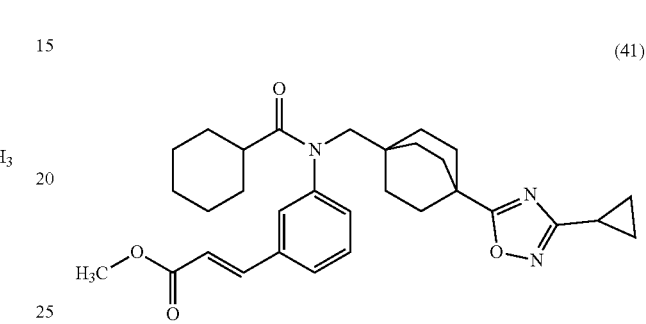

(41)

Step A. Intermediate 41A. Preparation of methyl 4-(3-cyclopropyl-1,2,4-oxadiazol-5-yl) bicyclo[2.2.2]octane-1-carboxylate

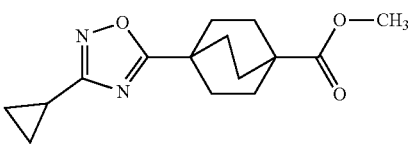 [SMILES: COC(=O)C12CCC(c3nc(C4CC4)no3)(CC1)CC2]

The title compound was prepared according to the method described for the synthesis of Intermediate 19A by substituting 4-(methoxycarbonyl)bicyclo[2.2.2]octane-1-carboxylic acid and (Z)—N'-hydroxycyclopropanecarboximidamide. (490 mg, 1.667 mmol, 71% yield). MS (ESI) 277 (M+H).

Step B. Intermediate 41B. Preparation of (4-(3-cyclopropyl-1,2,4-oxadiazol-5-yl)bicyclo[2.2.2]octan-1-yl)methanol

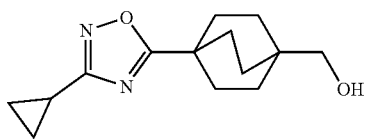 [SMILES: OCC12CCC(c3nc(C4CC4)no3)(CC1)CC2]

The title compound was prepared according to the method described for the synthesis of Intermediate 19B by substituting Intermediate 41A where appropriate. (500 mg, 1.087 mmol, 61% yield). MS (ESI) 249 (M+H).

Step C. Intermediate 41C. Preparation of 4-(3-cyclopropyl-1,2,4-oxadiazol-5-yl) bicyclo[2.2.2]octane-1-carbaldehyde

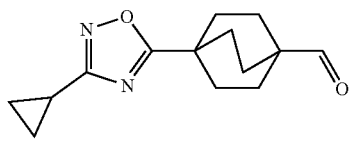 [SMILES: O=CC12CCC(c3nc(C4CC4)no3)(CC1)CC2]

The title compound was prepared according to the method described for the synthesis of Intermediate 8G by substituting Intermediate 41B where appropriate. (350 mg, 1.421 mmol, 71% yield). MS (ESI) 247 (M+H).

Step D. Intermediate 41D. Preparation of methyl (E)-3-(3-(((4-(3-cyclopropyl-1,2,4-oxadiazol-5-yl) bicyclo[2.2.2]octan-1-yl)methyl)amino)phenyl)acrylate

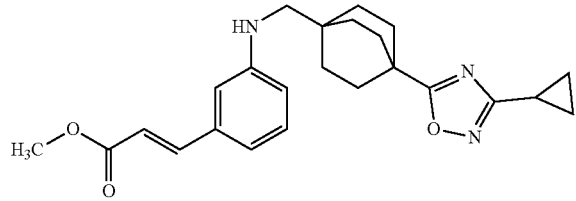 [SMILES: COC(=O)/C=C/c1cccc(NCC23CCC(c4nc(C5CC5)no4)(CC2)CC3)c1]

The title compound was prepared according to the method described for the synthesis of Intermediate 1H by substituting Intermediate 1G and Intermediate 41C where appropriate. (130 mg, 0.319 mmol, 79% yield) as yellow gummy liquid. MS (ESI) 408 (M+H).

Step E. Example 41. Preparation of methyl (E)-3-(3-(N-((4-(3-cyclopropyl-1,2,4-oxadiazol-5-yl)bicyclo[2.2.2]octan-1-yl)methyl)cyclohexane carboxamido)phenyl) acrylate The title compound was prepared according to the method described for the synthesis of Example 19 (Step F) by substituting Intermediate 41D and cyclohexanecarbonyl chloride where appropriate. (22 mg, 0.042 mmol, 58% yield); $^1$H NMR (400 MHz, DMSO-$d_6$) δ 7.79 (s, 1H), 7.74-7.59 (m, 2H), 7.54-7.33 (m, 2H), 6.76 (d, J=16.1 Hz, 1H), 3.74 (s, 3H), 3.58 (s, 2H), 2.17 (br. s., 1H), 2.08-1.98 (m, 1H), 1.84-1.68 (m, 6H), 1.59 (d, J=9.0 Hz, 4H), 1.47 (br. s., 1H), 1.42-1.23 (m, 8H), 1.15-0.97 (m, 3H), 0.93-0.75 (m, 4H). FXR EC$_{50}$ (nM)=47; MS (ESI) 518 (M+H).

Example 42

Methyl (E)-3-(3-(N-((4-(3-morpholino-1,2,4-oxadiazol-5-yl)bicyclo[2.2.2]octan-1-yl) methyl)cyclohexanecarboxamido)phenyl)acrylate (42)

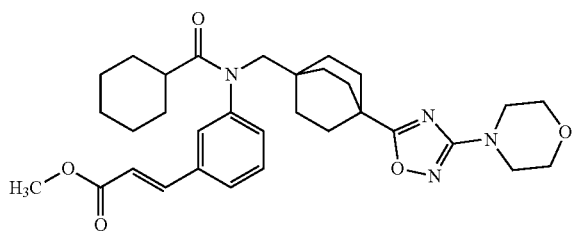

Step A. Intermediate 42A. Preparation of (Z)—N'-hydroxymorpholine-4-carboximidamide

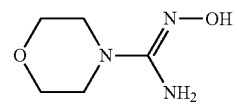

To a stirred solution of morpholine-4-carbonitrile (commercially available) (0.902 mL, 8.92 mmol) in ethanol (12 mL) was added hydroxylamine (2.73 mL, 44.6 mmol). The reaction mixture was stirred at reflux temperature for 1.5 h. The reaction mixture was cooled to room temperature and diluted with water (20 mL), extracted with ethyl acetate (3×20 ml). The organic layers were combined, dried over anhydrous sodium sulphate and concentrated under reduced pressure to afford the title compound (500 mg, 3.41 mmol, 38% yield) as gummy liquid. MS (ESI) 146 (M+H).

Step B. Intermediate 42B. Preparation of methyl 4-(3-morpholino-1,2,4-oxadiazol-5-yl) bicyclo[2.2.2]octane-1-carboxylate

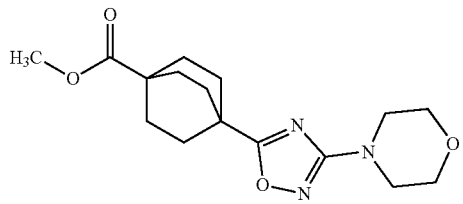 [SMILES: COC(=O)C12CCC(c3nc(N4CCOCC4)no3)(CC1)CC2]

The title compound was prepared according to the method described for the synthesis of Intermediate 19A by substituting Intermediate 42A where appropriate. (450 mg, 1.400 mmol, 93% yield) with minor impurities. MS (ESI) 322 (M+H).

Step C. Intermediate 42C. Preparation of (4-(3-morpholino-1,2,4-oxadiazol-5-yl)bicyclo[2.2.2]octan-1-yl)methanol

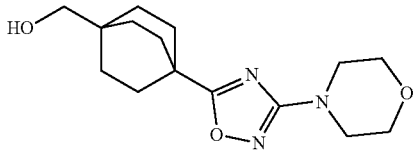 [SMILES: OCC12CCC(c3nc(N4CCOCC4)no3)(CC1)CC2]

The title compound was prepared according to the method described for the synthesis of Intermediate 19B by substituting Intermediate 42B where appropriate. (200 mg, 0.443 mmol, 57% yield) as yellow solid. MS (ESI) 294 (M+H).

Step D. Intermediate 42D. Preparation of 4-(3-morpholino-1,2,4-oxadiazol-5-yl)bicyclo[2.2.2]octane-1-carbaldehyde

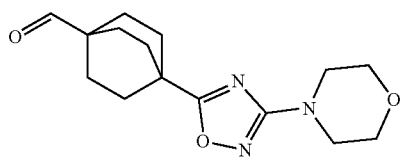 [SMILES: O=CC12CCC(c3nc(N4CCOCC4)no3)(CC1)CC2]

To a stirred solution of Intermediate 42C (170 mg, 0.579 mmol) in DCM (3 mL) was added DMP (295 mg, 0.695 mmol) at 0° C. The reaction mixture was stirred at 0° C. for 1 h. The reaction mixture was allowed to warm to room temperature, diluted with DCM (10 ml), washed with aqueous sodium bicarbonate solution (10 mL), dried over anhydrous sodium sulphate and concentrated under reduced pressure. The crude material was purified by flash chromatography (12 g silica gel cartridge; A=Hex, B=EtOAc; 30 min grad.; 0% B to 30% B; flow rate=30 mL/min). The pure fractions were combined, concentrated under reduced pressure and dried in vacuo to afford the title compound (90 mg, 0.238 mmol, 41% yield) as gummy liquid. MS (ESI) 292 (M+H).

Step E. Intermediate 42E. Preparation of methyl (E)-3-(3-(((4-(3-morpholino-1,2,4-oxadiazol-5-yl)bicyclo[2.2.2]octan-1-yl)methyl)amino)phenyl)acrylate

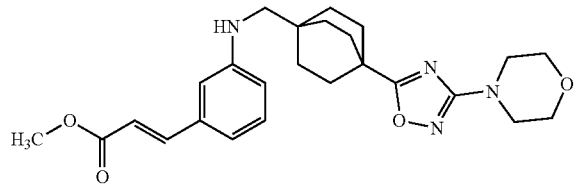 [SMILES: COC(=O)/C=C/c1cccc(NCC23CCC(c4nc(N5CCOCC5)no4)(CC2)CC3)c1]

The title compound was prepared according to the method described for the synthesis of Intermediate 1H by substituting Intermediate 1G and Intermediate 42D where appropriate. (100 mg, 0.208 mmol, 67% yield). MS (ESI) 453 (M+H).

Step F. Example 42. Preparation of methyl (E)-3-(3-(N-((4-(3-morpholino-1,2,4-oxadiazol-5-yl)bicyclo[2.2.2]octan-1-yl)methyl)cyclohexanecarboxamido)phenyl) acrylate The title compound was prepared according to the method described for the synthesis of Example 19 (Step F) by substituting Intermediate 42E and cyclohexanecarbonyl chloride. (11.56 mg, 0.021 mmol, 31% yield). $^1$H NMR (400 MHz, DMSO-$d_6$) δ 7.80 (s, 1H), 7.74-7.62 (m, 2H), 7.54-7.37 (m, 2H), 6.76 (d, J=16.1 Hz, 1H), 3.74 (s, 3H), 3.68-3.61 (m, 4H), 3.58 (s, 2H), 3.28-3.20 (m, 4H), 2.17 (br. s., 1H), 1.82-1.70 (m, 6H), 1.59 (d, J=11.0 Hz, 4H), 1.42-1.18 (m, 9H), 1.08 (d, J=12.0 Hz, 1H), 0.85 (d, J=11.5 Hz, 2H) FXR $EC_{50}$ (nM)=118. MS (ESI) 563 (M+H).

Example 43

Methyl (E)-3-(3-(N-((4-(3-(tetrahydro-2H-pyran-4-yl)-1,2,4-oxadiazol-5-yl) bicyclo[2.2.2]octan-1-yl)methyl)cyclohexanecarboxamido)phenyl)acrylate (43)

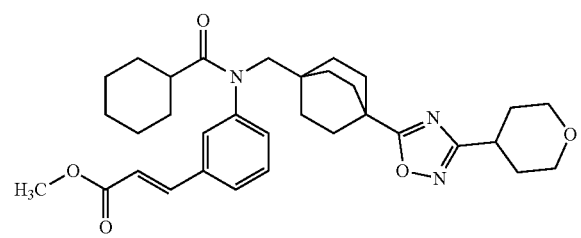

Step A. Intermediate 43A. Preparation of N'-hydroxytetrahydro-2H-pyran-4-carboximidamide

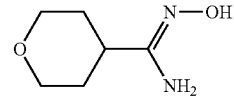

To a stirred solution of tetrahydro-2H-pyran-4-carbonitrile (commercially available) (0.988 mL, 9.00 mmol) in ethanol (12 mL) was added hydroxylamine (2.7 mL, 45.0 mmol) at room temperature. The reaction mixture was stirred at reflux temperature for 2 h. The reaction cooled to room temperature and concentrated under reduced pressure The residue was diluted with water (20 mL) and stirred for 5 min. The precipitated solid was filtered, washed with water and dried in vacuo to afford the title compound (1280 mg, 6.21 mmol, 69% yield) as white solid. MS (ESI) 145 (M+H).

Step B. Intermediate 43B. Preparation of methyl 4-(3-(tetrahydro-2H-pyran-4-yl)-1,2,4-oxadiazol-5-yl)bicyclo[2.2.2]octane-1-carboxylate

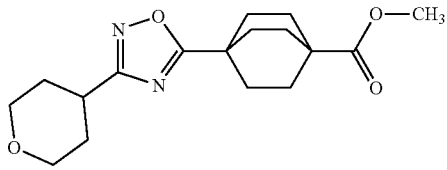 [SMILES: COC(=O)C12CCC(c3nc(C4CCOCC4)no3)(CC1)CC2]

The title compound was prepared according to the method described for the synthesis of Intermediate 19A by substituting Intermediate 43A where appropriate. (350 mg, 0.983 mmol, 42% yield). MS (ESI) 320 (M+H).

Step C. Intermediate 43C. Preparation of (4-(3-(tetrahydro-2H-pyran-4-yl)-1,2,4-oxadiazol-5-yl)bicyclo[2.2.2]octan-1-yl)methanol

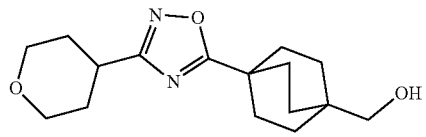 [SMILES: OCC12CCC(c3nc(C4CCOCC4)no3)(CC1)CC2]

The title compound was prepared according to the method described for the synthesis of Intermediate 19B by substituting Intermediate 43B where appropriate. (160 mg, 0.465 mmol, 43% yield) as white solid. MS (ESI) 293 (M+H).

Step D. Intermediate 43D. Preparation of 4-(3-(tetrahydro-2H-pyran-4-yl)-1,2,4-oxadiazol-5-yl)bicyclo[2.2.2]octane-1-carbaldehyde

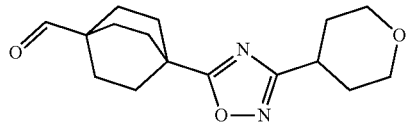 [SMILES: O=CC12CCC(c3nc(C4CCOCC4)no3)(CC1)CC2]

The title compound was prepared according to the method described for the synthesis of Intermediate 28C by substituting Intermediate 43C where appropriate. (230 mg, 0.776 mmol, 76% yield). MS (ESI) 291 (M+H).

Step E. Intermediate 43E. Preparation of methyl (E)-3-(3-(((4-(3-(tetrahydro-2H-pyran-4-yl)-1,2,4-oxadiazol-5-yl)bicyclo[2.2.2]octan-1-yl)methyl)amino)phenyl)acrylate

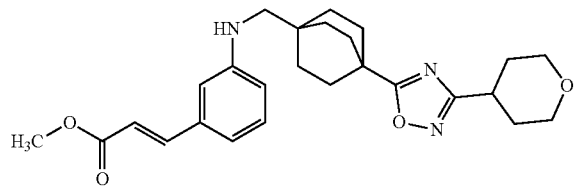 [SMILES: COC(=O)/C=C/c1cccc(NCC23CCC(c4nc(C5CCOCC5)no4)(CC2)CC3)c1]

The title compound was prepared according to the method described for the synthesis of Intermediate 1H by substituting Intermediate 1G and Intermediate 43D where appropriate. (220 mg, 0.487 mmol, 61% yield) as pale yellow solid. MS (ESI) 453 (M+H).

Step C. Example 43. Preparation of methyl (E)-3-(3-(N-((4-(3-(tetrahydro-2H-pyran-4-yl)-1,2,4-oxadiazol-5-yl)bicyclo[2.2.2]octan-1-yl)methyl)cyclohexanecarboxamido)phenyl)acrylate The title compound was prepared according to the method described for the synthesis of Example 19 (Step F) by substituting Intermediate 43E and cyclohexanecarbonyl chloride where appropriate. (26 mg, 0.046 mmol, 69% yield). $^1$H NMR (400 MHz, DMSO-d$_6$) δ 7.80 (s, 1H), 7.76-7.62 (m, 2H), 7.55-7.32 (m, 2H), 6.76 (d, J=15.9 Hz, 1H), 3.91-3.79 (m, 2H), 3.74 (s, 3H), 3.59 (s, 2H), 3.49-3.38 (m, 2H), 3.00 (tt, J=11.5, 3.8 Hz, 1H), 2.18 (br. s., 1H), 1.88-1.72 (m, 8H), 1.71-1.53 (m, 6H), 1.49 (d, J=11.5 Hz, 1H), 1.44-1.24 (m, 8H), 1.08 (d, J=13.0 Hz, 1H), 0.86 (d, J=11.7 Hz, 2H); FXR EC$_{50}$ (nM)=107. MS (ESI) 562 (M+H).

Example 44

Methyl (E)-3-(3-(N-((4-(5-methyl-1,2,4-oxadiazol-3-yl)bicyclo[2.2.2]octan-1-yl)methyl)cyclohexanecarboxamido)phenyl)acrylate (44)

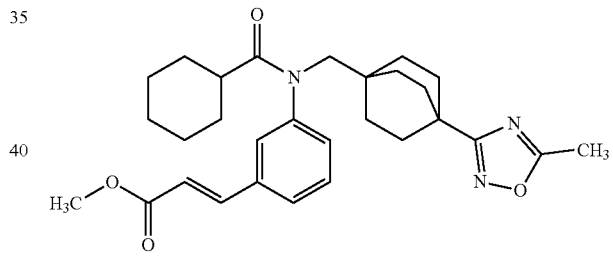

Step A. Intermediate 44A. Preparation of methyl 4-carbamoylbicyclo[2.2.2]octane-1-carboxylate

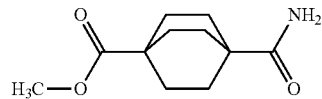

To a stirred solution of 4-(methoxycarbonyl)bicyclo[2.2.2]octane-1-carboxylic acid (0.5 g, 2.356 mmol) in DMF (10 mL) were added ammonium chloride (1.26 g, 23.56 mmol), TEA (1.3 mL, 9.42 mmol) and BOP (1.04 g, 2.356 mmol) at room temperature under nitrogen atmosphere. The reaction mixture was stirred at room temperature for 12 h. The reaction mixture was diluted with water (30 mL) and extracted with EtOAc (2×30 mL). The organic layers were combined, dried over anhydrous sodium sulphate and concentrated under reduced pressure. The crude material was purified by flash chromatography (40 g silica gel cartridge;

A=Hex, B=EtOAc; 30 min grad.; 0% B to 100% B; flow rate=30 mL/min). The pure fractions were combined, concentrated under reduced pressure and dried in vacuo to afford the title compound (0.4 g, 1.89 mmol, 80% yield) as white solid. $^1$H NMR (400 MHz, DMSO-d$_6$) δ 6.95 (br. s., 1H), 6.74 (br. s., 1H), 3.57 (s, 3H), 1.74-1.61 (m, 12H). MS (ESI) 212 (M+H).

Step B. Intermediate 44B. Preparation of methyl 4-cyanobicyclo[2.2.2]octane-1-carboxylate

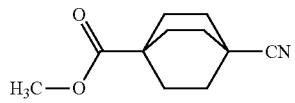

To a stirred solution of Intermediate 44A (0.35 g, 1.657 mmol) in pyridine (7 mL) was added trifluoroacetic anhydride (1.74 g, 8.28 mmol) drop wise at 0° C. The reaction mixture was stirred at the same temperature for 30 min. The reaction was quenched with aqueous 10% NaHCO$_3$ solution. The reaction mixture was extracted with EtOAc (2×20 mL). The organic layers were combined, dried over anhydrous sodium sulphate and concentrated under reduced pressure. The crude material was purified by flash chromatography (24 g silica gel cartridge; A=Hex, B=EtOAc; 30 min grad.; 0% B to 30% B; flow rate=30 mL/min). The pure fractions were combined, concentrated under reduced pressure and dried in vacuo to afford the title compound (0.25 g, 1.23 mmol, 74% yield) as an off-white solid. $^1$H NMR (400 MHz, DMSO-d$_6$) δ 3.58 (s, 3H), 1.93-1.83 (m, 6H), 1.78-1.68 (m, 6H).

Step C. Intermediate 44C. Preparation of methyl 4-cyanobicyclo[2.2.2]octane-1-carboxylate

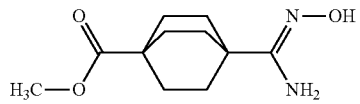

To a stirred solution of Intermediate 44B (0.25 g, 1.294 mmol) in ethanol (5 mL) was added hydroxylamine in water (0.319 mL, 5.17 mmol) at room temperature. The reaction mixture was heated at reflux for 2 h. The reaction mixture was cooled to room temperature and concentrated under reduced pressure. The residue was diluted with water (5 mL) and stirred for 5 min. The precipitated solid was filtered, washed with water, dried in vacuo to afford the title compound (0.28 g, 1.17 mmol, 91% yield) as white solid. $^1$H NMR (400 MHz, chloroform-d) δ 8.88 (s, 1H), 5.15 (s, 2H), 3.57 (s, 3H), 1.73-1.62 (m, 12H). MS (ESI) 227 (M+H).

Step D. Intermediate 44D. Preparation of methyl 4-(5-methyl-1,2,4-oxadiazol-3-yl) bicyclo[2.2.2]octane-1-carboxylate

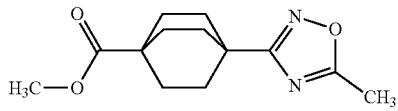

A stirred solution Intermediate 44C (0.23 g, 1.016 mmol) in acetic anhydride (1.91 ml, 20.33 mmol) was heated at 120° C. for 30 min. The reaction mixture was cooled to room temperature and concentrated under reduced pressure. The residue was diluted with water (5 mL) and stirred for 5 min. as added to the residue. The precipitated solid was filtered, washed with water, dried in vacuo to afford the title compound (0.21 g, 0.79 mmol, 78% yield) as an off-white solid. $^1$H NMR (400 MHz, DMSO-d$_6$) δ 3.59 (s, 3H), 2.53 (s, 3H), 1.87-1.77 (m, 12H). MS (ESI) 251 (M+H).

Step E. Intermediate 44E. Preparation of (4-(5-methyl-1,2,4-oxadiazol-3-yl)bicyclo[2.2.2]octan-1-yl)methanol

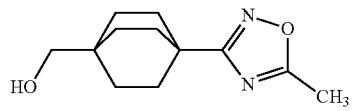 [SMILES: Cc1nc(C23CCC(CO)(CC2)CC3)no1]

The title compound was prepared according to the method described for the synthesis of Intermediate 19B by substituting Intermediate 44D where appropriate. (0.155 g, 0.66 mmol, 79% yield) as white solid. $^1$H NMR (400 MHz, DMSO-d$_6$) δ 4.37 (t, J=5.5 Hz, 1H), 3.07 (d, J=5.5 Hz, 2H), 2.52 (s, 3H), 1.82-1.73 (m, 6H), 1.48-1.38 (m, 6H).

Step F. Intermediate 44F. Preparation of 4-(5-methyl-1,2,4-oxadiazol-3-yl)bicyclo[2.2.2]octane-1-carbaldehyde

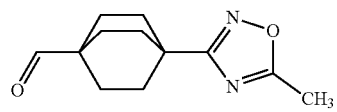

The title compound was prepared according to the method described for the synthesis of Intermediate 19C by substituting Intermediate 44E where appropriate. (0.12 g, 0.218 mmol, 44% yield) as an off-white solid. $^1$H NMR (400 MHz, DMSO-d$_6$) δ 9.45 (s, 1H), 2.54 (s, 3H), 1.79-1.87 (m, 6H), 1.66-1.70 (m, 6H).

Step G. Intermediate 44G. Preparation of methyl (E)-3-(3-(((4-(5-methyl-1,2,4-oxadiazol-3-yl)bicyclo [2.2.2]octan-1-yl)methyl)amino)phenyl)acrylate

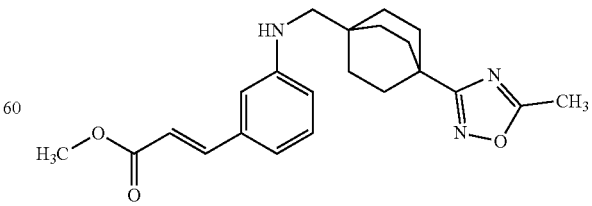

The title compound was prepared according to the method described for the synthesis of Intermediate 1H by substituting Intermediate 1G and Intermediate 44F where appropriate. (20 mg, 0.050 mmol, 23% yield) as an off-white solid. MS (ESI) 382 (M+H).

Step H. Example 44. Preparation of methyl (E)-3-(3-(N-((4-(5-methyl-1,2,4-oxadiazol-3-yl)bicyclo[2.2.2]octan-1-yl)methyl)cyclohexanecarboxamido)phenyl)acrylate The title compound was prepared according to the method described for the synthesis of Example 19 (Step F) by substituting Intermediate 44G and cyclohexanecarbonyl chloride. (9.3 mg, 0.019 mmol, 36% yield). $^1$H NMR (400 MHz, DMSO-$d_6$) δ 7.80 (s, 1H), 7.75-7.60 (m, 2H), 7.54-7.37 (m, 2H), 6.76 (d, J=16.1 Hz, 1H), 3.74 (s, 3H), 3.58 (br. s., 2H), 2.18 (br. s., 1H), 1.78-1.66 (m, 6H), 1.59 (d, J=9.8 Hz, 4H), 1.48 (br. s., 1H), 1.42-1.25 (m, 8H), 1.08 (d, J=14.4 Hz, 1H), 0.87 (br. s., 2H), (3 protons of the methyl were buried under the solvent peak). FXR $EC_{50}$ (nM) 87; MS (ESI) 492 (M+H).

Example 45

Methyl 5-(N-((1-(1-methyl-1H-indazol-5-yl)-2-oxabicyclo[2.2.2]octan-4-yl)methyl)cyclohexanecarboxamido)-3,4-dihydronaphthalene-2-carboxylate (45)

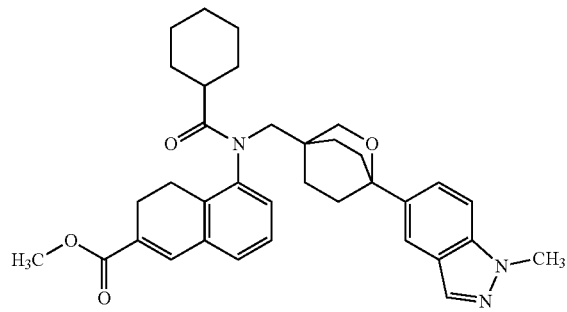

Step A. Intermediate 45A. Preparation of methyl 5-(((1-(1-methyl-1H-indazol-5-yl)-2-oxabicyclo[2.2.2]octan-4-yl)methyl)amino)-3,4-dihydronaphthalene-2-carboxylate

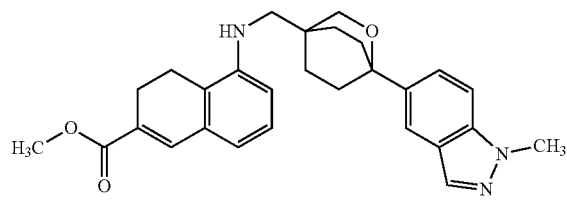

The title compound was prepared according to the method described for the synthesis of Intermediate 1H by substituting Intermediate 11F and Intermediate 8G where appropriate. (0.12 g, 0.249 mmol, 33% yield) as black color solid. MS (ESI) 458 (M+H).

Step B. Example 45. Preparation of methyl 5-(N-((1-(1-methyl-1H-indazol-5-yl)-2-oxabicyclo[2.2.2]octan-4-yl)methyl)cyclohexanecarboxamido)-3,4-dihydronaphthalene-2-carboxylate The title compound was prepared according to the method described for the synthesis of Example 19 (Step F) by substituting Intermediate 45A and cyclohexanecarbonyl chloride. (0.06 g, 0.100 mmol, 92% yield) as an off-white solid. $^1$H NMR (400 MHz, DMSO-$d_6$) δ 7.95 (s, 1H), 7.66 (s, 1H), 7.60 (s, 1H), 7.52-7.48 (m, 2H), 7.40-7.34 (m, 3H), 3.99 (s, 3H), 3.95-3.90 (m, 1H), 3.84-3.81 (m, 1H), 3.76 (s, 3H), 3.69-3.67 (m, 1H), 2.97-2.93 (m, 1H), 2.67-2.68 (m, 1H), 2.56-2.55 (m, 2H), 2.45-2.36 (m, 2H), 2.05-2.02 (m, 4H), 1.83-1.25 (m, 10H), 1.12-1.05 (m, 1H), 0.89-0.83 (m, 3H). FXR $EC_{50}$ (nM) 1150; MS (ESI) 568.3 (M+H).

Examples 46 and 47

Methyl (E)-3-(3-(N-(1-(4-(3-methyl-1,2,4-oxadiazol-5-yl)bicyclo[2.2.2]octan-1-yl)ethyl)cyclohexanecarboxamido)phenyl)acrylate (46-47)

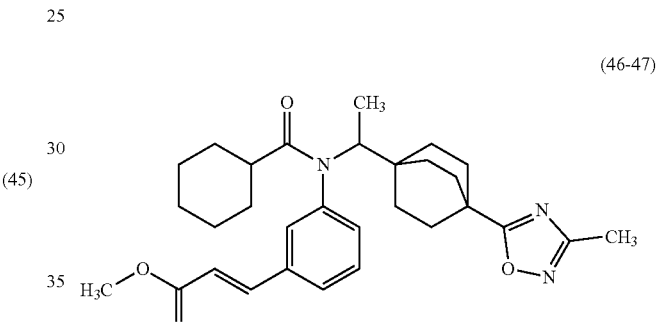

Step A. Intermediate 46A. Preparation of 1-(4-(3-methyl-1,2,4-oxadiazol-5-yl) bicyclo[2.2.2]octan-1-yl)ethan-1-ol

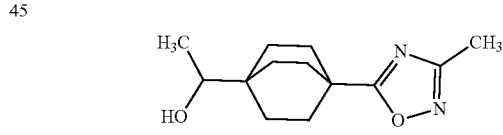

A stirred solution of Intermediate 19C (0.5 g, 2.270 mmol) in dry tetrahydrofuran (15 mL) was cooled to −78° C. Methyl magnesium bromide in diethyl ether (1.135 mL, 3.40 mmol) was added to the reaction under nitrogen. The reaction mixture was stirred at the same temperature for 1 h. The reaction mixture was allowed to warm to 0° C. The reaction was quenched with aqueous saturated NH$_4$Cl solution. The reaction mixture was extracted with EtOAc (2×10 mL). The organic layers were combined, dried over anhydrous sodium sulphate and concentrated under reduced pressure. The crude material was purified by flash chromatography (24 g silica gel cartridge; A=Hex, B=EtOAc; 30 min grad.; 0% B to 50% B; flow rate=30 mL/min). The pure fractions were combined, concentrated under reduced pressure and dried in vacuo to afford the title compound (0.51 g, 2.050 mmol, 90% yield) as an oil. $^1$H NMR (400 MHz, DMSO-d$_6$) δ 4.28 (d, J=5.20 Hz, 1H), 3.24-3.26 (m, 1H), 2.29 (s, 3H), 1.83-1.87 (m, 6H), 1.40-1.55 (m, 6H), 0.96 (d, J=6.40 Hz, 3H).

Step B. Intermediate 46B. Preparation of 1-(4-(3-methyl-1,2,4-oxadiazol-5-yl) bicyclo[2.2.2]octan-1-yl)ethan-1-one

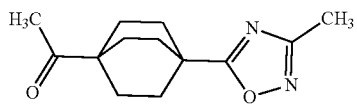 [SMILES: CC(=O)C12CCC(c3nc(C)no3)(CC1)CC2]

To a stirred solution of Intermediate 46A (0.4 g, 1.693 mmol) in dichloromethane (5 mL) was added Dess-Martin periodinane (1.79 g, 4.23 mmol) at 0° C. The reaction mixture was allowed to warm to room temperature and stirred for 1 h. The reaction mixture was diluted with DCM (10 mL), washed with aqueous 10% NaHCO$_3$ solution (10 mL), brine solution (10 mL), dried over anhydrous sodium sulphate and concentrated under reduced pressure. The crude material was purified by flash chromatography (24 g silica gel cartridge; A=Hex, B=EtOAc; 30 min grad.; 0% B to 40% B; flow rate=30 mL/min). The pure fractions were combined, concentrated under reduced pressure and dried in vacuo to afford the title compound (0.3 g, 1.216 mmol, 72% yield) as white solid. $^1$H NMR (400 MHz, DMSO-d$_6$) δ 2.31 (s, 3H), 2.00 (s, 3H), 1.89-1.93 (m, 6H), 1.74-1.78 (m, 6H).

Step C. Intermediate 46C. Preparation of methyl (E)-3-(3-((1-(4-(3-methyl-1,2,4-oxadiazol-5-yl)bicyclo[2.2.2]octan-1-yl)ethyl)amino)phenyl)acrylate

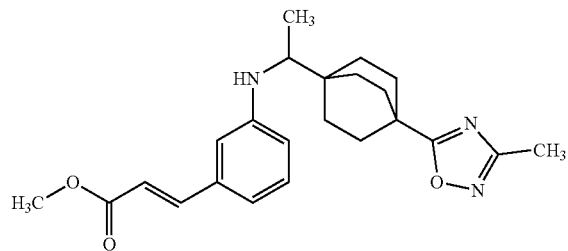

The title compound was prepared according to the method described for the synthesis of Intermediate 1H by substituting Intermediate 1G and Intermediate 46B where appropriate. (100 mg, 0.152 mmol, 47% yield) as pale yellow oil. MS (ESI) 396 (M+H).

Step D. Examples 46 and 47. Preparation of methyl (E)-3-(3-(N-(1-(4-(3-methyl-1,2,4-oxadiazol-5-yl) bicyclo[2.2.2]octan-1-yl)ethyl)cyclohexanecarboxamido)phenyl)acrylate To a stirred solution of Intermediate 46A (70 mg, 0.177 mmol) in pyridine (2 mL) was added DMAP (23 mg, 0.177 mmol) followed by cyclohexanecarbonyl chloride (130 mg, 0.885 mmol) at room temperature. The reaction mixture was heated at 90° C. for 3 days. The reaction mixture was diluted with DCM (10 mL), washed with aqueous 10% NaHCO$_3$ solution (10 mL), brine solution (10 mL), dried over anhydrous sodium sulphate and concentrated under reduced pressure. The crude material was purified by reverse phase followed by chiral HPLC using following conditions: (Column: DAD-1 Cellulose-2 (250×4.6) 5.0 m; Isocratic Mode, Mobile phase: MeOH, Column Temperature: 30° C.; Total Flow: 2 mL/min). Enantiomer 1 (RT=7.97 min.) Example-46 (7.5 mg, 0.015 mmol, 8% yield); $^1$H NMR (400 MHz, DMSO-d$_6$) δ 7.83-7.27 (m, 5H), 6.76 (dd, J=16.3, 7.2 Hz, 1H), 4.80 (br. s., 1H), 3.75 (d, J=2.7 Hz, 3H), 2.29 (s, 3H), 1.83 (br. s., 7H), 1.61 (br. s., 3H), 1.53 (br. s., 6H), 1.45 (br. s., 2H), 1.41-1.28 (m, 2H), 1.07 (d, J=12.2 Hz, 2H), 0.97 (br. s., 2H), 0.78 (br. s., 2H). FXR EC$_{50}$ (nM) 302; MS (ESI) 506 (M+H); and Enantiomer 2 (RT=9.7 min) Example-47 (9.1 mg, 0.018 mmol, 10% yield). $^1$H NMR (400 MHz, DMSO-d$_6$) δ 7.83-7.27 (m, 5H), 6.76 (dd, J=16.3, 7.2 Hz, 1H), 4.80 (br. s., 1H), 3.75 (d, J=2.7 Hz, 3H), 2.29 (s, 3H), 1.83 (br. s., 7H), 1.61 (br. s., 3H), 1.53 (br. s., 6H), 1.45 (br. s., 2H), 1.41-1.28 (m, 2H), 1.07 (d, J=12.2 Hz, 2H), 0.97 (br. s., 2H), 0.78 (br. s., 2H). FXR EC$_{50}$ (nM) 152. MS (ESI) 506 (M+H).

Example 48

N-((4-(5-(tert-Butyl)-1,3,4-oxadiazol-2-yl)bicyclo[2.2.2]octan-1-yl)methyl)-3-fluoro-N-(3-(3-hydroxy-3-methylbut-1-yn-1-yl)phenyl)bicyclo[1.1.1]pentane-1-carboxamide (48)

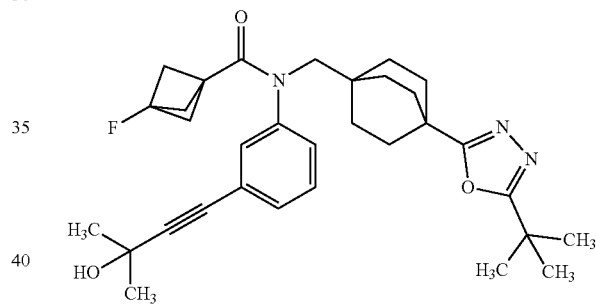

Step A. Intermediate 48A. Preparation of methyl 4-(2-pivaloylhydrazine-1-carbonyl) bicyclo[2.2.2]octane-1-carboxylate

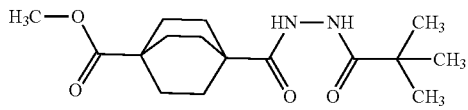

To a stirred solution of 4-(methoxycarbonyl)bicyclo[2.2.2]octane-1-carboxylic acid (1 g, 4.71 mmol) and pivalohydrazide (commercially available) (0.602 g, 5.18 mmol) in DMF (10 mL) were added HATU (2.329 g, 6.12 mmol) and DIPEA (2.469 mL, 14.13 mmol) at 0° C. and reaction mixture was stirred at room temperature for 12 h. The reaction mixture was poured onto ice water and extracted with ethyl acetate (2×150 mL). The combined organic layers were dried over MgSO$_4$ and concentrated under reduced pressure. The crude residue so obtained was purified by flash silica gel column chromatography (30% EtOAc in hexane as an eluent, 40 g column) to afford the title compound (900 mg, 2.90 mmol, 62% yield). ¹H NMR (300 MHz, DMSO-d₆) δ 9.21 (d, J=0.90 Hz, 1H), 9.15 (s, 1H), 3.57 (s, 3H), 1.85-1.60 (m, 12H), 1.12 (s, 9H). MS (ESI) 311 (M+H).

Step B. Intermediate 48B. Preparation of methyl 4-(5-(tert-butyl)-1,3,4-oxadiazol-2-yl) bicyclo[2.2.2]octane-1-carboxylate

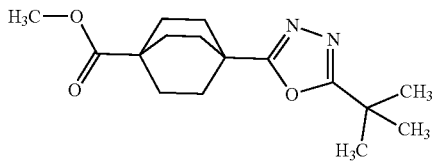 [SMILES: COC(=O)C12CCC(c3nnc(C(C)(C)C)o3)(CC1)CC2]

To a stirred solution of Intermediate 48A (700 mg, 2.255 mmol) in MeCN (1 mL) were added triphenylphosphine (1242 mg, 4.74 mmol) and CCl₄ (0.239 mL, 2.481 mmol) at room temperature and reaction mixture was stirred at 90° C. for 12 h. The reaction mixture was concentrated under reduced pressure and the residue was diluted with EtOAc (50 mL) and washed with water (30 mL). The organic layer was dried over sodium sulphate, filtered and concentrated under reduced pressure. The crude product was purified by flash silica gel column chromatography (24 g silica gel column, EtOAc/PE, 0-60% EA, gradient elution) to afford the title compound (650 mg, 2.223 mmol, 99% yield). ¹H NMR (300 MHz, DMSO-d₆) δ 3.60 (s, 3H), 1.89-1.80 (m, 12H), 1.32 (s, 9H). MS (ESI) 293 (M+H).

Step C. Intermediate 48C. Preparation of (4-(5-(tert-butyl)-1,3,4-oxadiazol-2-yl) bicyclo[2.2.2]octan-1-yl)methanol

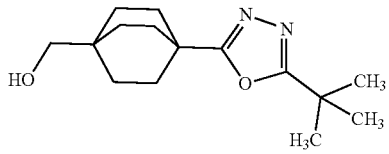

The title compound was prepared according to the method described for the synthesis of Intermediate 19B by substituting Intermediate 48B where appropriate. (720 mg, 2.72 mmol, 100% yield). ¹H NMR (400 MHz, DMSO-d₆) δ 4.40 (t, J=5.5 Hz, 1H), 3.08 (d, J=5.5 Hz, 2H), 1.89-1.75 (m, 6H), 1.51-1.37 (m, 6H), 1.38 (s, 9H).

Step D. Intermediate 48D. Preparation of 4-(5-(tert-butyl)-1,3,4-oxadiazol-2-yl) bicyclo[2.2.2]octane-1-carbaldehyde

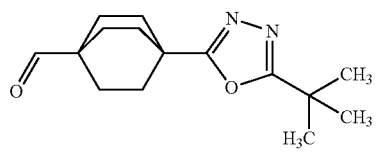 [SMILES: CC(C)(C)c1nnc(C23CCC(C=O)(CC2)CC3)o1]

The title compound was prepared according to the method described for the synthesis of Intermediate 19C by substituting Intermediate 48C where appropriate. (600 mg, 2.287 mmol, 86% yield). ¹H NMR (400 MHz, DMSO-d₆) δ 9.46 (s, 1H), 1.96-1.83 (m, 6H), 1.75-1.63 (m, 6H), 1.33 (s, 9H). MS (ESI) 263 (M+H).

Step E. Intermediate 48E. Preparation of 3-bromo-N-((4-(5-(tert-butyl)-1,3,4-oxadiazol-2-yl)bicyclo[2.2.2]octan-1-yl)methyl)aniline

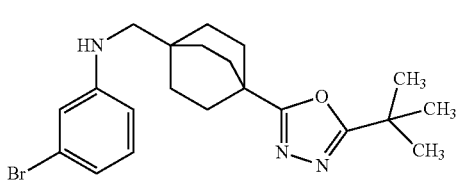 [SMILES: CC(C)(C)c1nnc(C23CCC(CNc4cccc(Br)c4)(CC2)CC3)o1]

The title compound was prepared according to the method described for the synthesis of Intermediate 1H by substituting Intermediate 48D where appropriate. (200 mg, 0.478 mmol, 33% yield). ¹H NMR (300 MHz, DMSO-d₆) δ 7.00-6.93 (m, 1H), 6.76 (d, J=2.3 Hz, 1H), 6.60 (dd, J=8.1, 2.1 Hz, 2H), 5.76 (d, J=2.6 Hz, 1H), 2.80 (d, J=5.9 Hz, 2H), 1.90-1.80 (m, 6H), 1.60-1.50 (m, 6H), 1.32 (s, 9H). MS (ESI) 418 (M+H).

Step F. Intermediate 48F. Preparation of N-(3-bromophenyl)-N-((4-(5-(tert-butyl)-1,3,4-oxadiazol-2-yl)bicyclo[2.2.2]octan-1-yl)methyl)-3-fluorobicyclo[1.1.1]pentane-1-carboxamide

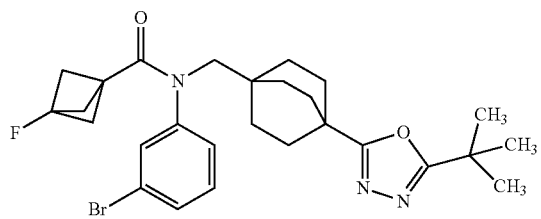 [SMILES: CC(C)(C)c1nnc(C23CCC(CN(C(=O)C45CC(F)(C4)C5)c4cccc(Br)c4)(CC2)CC3)o1]

To a stirred solution of Intermediate 48E (300 mg, 0.717 mmol) and 3-fluorobicyclo[1.1.1]pentane-1-carboxylic acid (112 mg, 0.860 mmol) in DCM (5 mL) were added pyridine (0.290 mL, 3.59 mmol) and POCl₃ (0.134 mL, 1.434 mmol) at room temperature. The reaction mixture was stirred for 2 h at room temperature and was poured into ice water. The aqueous layer was extracted with EtOAc (2×150 mL) and combined organic layers were dried over MgSO₄. The solvent was removed under reduced pressure. The residue was purified via flash silica gel column chromatography using 50% EtOAC in hexane as eluent (24 g column) to afford the title compound (250 mg, 0.471 mmol, 66% yield). ¹H NMR (300 MHz, DMSO-d₆) δ 7.71 (s, 1H), 7.61 (d, J=7.6 Hz, 1H), 7.42 (d, J=8.9 Hz, 2H), 1.87 (br. s., 6H), 1.80-1.72 (m, 6H), 1.45-1.36 (m, 6H), 1.30 (s, 9H). MS (ESI) 530 (M+H).

Step G. Example 48. Preparation of N-((4-(5-(tert-Butyl)-1,3,4-oxadiazol-2-yl) bicyclo[2.2.2]octan-1-yl)methyl)-3-fluoro-N-(3-(3-hydroxy-3-methylbut-1-yn-1-yl)phenyl)bicyclo[1.1.1]pentane-1-carboxamide To a stirred solution of intermediate 48F (20 mg, 0.038 mmol) in DMF (1 mL) was added 2-methylbut-3-yn-2-ol (3.81 mg, 0.045 mmol) and Et$_3$N (0.016 mL, 0.113 mmol) at room temperature. The reaction mixture was degassed with argon for 5 min and bis(triphenylphosphine)palladium (II) dichloride (2.65 mg, 3.77 μmol) was added followed by addition of copper(I) iodide (0.359 mg, 1.885 μmol). The reaction mixture was stirred at 90° C. for 12 h. The reaction mixture was cooled to room temperature and concentrated under reduced pressure. The crude residue so obtained was purified via preparative LC/MS using following conditions: Column: Waters XBridge C18, 150 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 10% B, 10-40% B over 25 minutes, then a 5-minute hold at 100% B; Flow Rate: 15 mL/min; Column Temperature: 25 C. Fraction collection was triggered by signals. Fractions containing the desired product were combined and dried via centrifugal evaporation to afford the title compound (3.7 mg, 18% yield). $^1$H NMR (400 MHz, DMSO-d$_6$) δ 7.56-7.27 (m, 4H), 5.51 (s, 1H), 3.72-3.55 (m, 1H), 3.50-3.39 (m, 1H), 1.97-1.63 (m, 12H), 1.54-1.34 (m, 12H), 1.30 (s, 9H). FXR EC$_{50}$ (nM)=30. MS (ESI) 534 (M+H).

Example 49

N-((4-(5-(1,1-difluoroethyl)-1,2,4-oxadiazol-3-yl) bicyclo[2.2.2]octan-1-yl)methyl)-3-fluoro-N-(3-(3-hydroxy-3-methylbut-1-yn-1-yl)phenyl)bicyclo [1.1.1]pentane-1-carboxamide

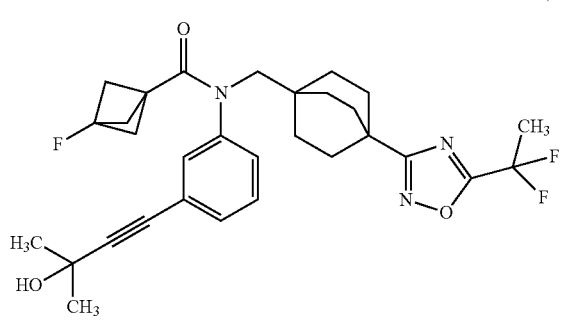

(49)

Step A. Intermediate 49A. Preparation of methyl 4-(hydroxymethyl)bicycle[2.2.2]octane-1-carboxylate

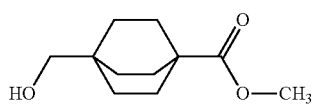

To a stirred solution of 4-(methoxycarbonyl)bicyclo [2.2.2]octane-1-carboxylic acid (1.5 g, 7.1 mmol) in THF (17 mL), was added borane dimethyl sulfide complex (2.0 mL, 21 mmol) at 0° C. The reaction mixture was warmed to room temperature and stirred. After 4 h, the reaction was quenched with MeOH (drop wise addition over 15 minutes with cooling). the reaction mixture was stirred at room temperature for 2 h. The reaction mixture was concentrated under and the crude product was purified by flash silica gel column chromatography (80 g silica gel cartridge; A=PE, B=EtOAc; 25 min grad.; 0% to 50% B; flow rate=60 mL/min; TLC visualized with KMnO$_4$). The pure fractions were combined, concentrated and dried in vacuo to afford the title compound (1.3 g, 6.6 mmol, 93% yield) as a white solid. $^1$H NMR (400 MHz, DMSO-d$_6$) δ 3.56 (s, 3H), 3.36 (s, 2H), 3.05 (s, 1H), 1.78-1.64 (m, 6H), 1.37-1.27 (m, 6H).

Step B. Intermediate 49B. Preparation of methyl 4-formylbicyclo[2.2.2]octane-1-carboxylate

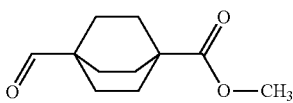

The title compound was prepared according to the method described for the synthesis of Intermediate 19C by substituting Intermediate 49A where appropriate. (0.070 g, 0.34 mmol, 67% yield) as colorless oil. $^1$H NMR (400 MHz, CHCl$_3$-d) δ 9.4 (s, 1H), 3.66 (s, 3H), 1.86-1.82 (m, 7H), 1.69-1.66 (m, 5H)

Step C. Intermediate 49C. Preparation of methyl 4-(((3-bromophenyl)amino)methyl) bicyclo[2.2.2] octane-1-carboxylate

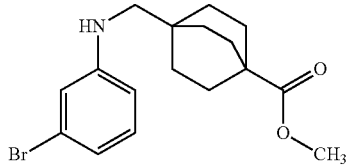 [SMILES: COC(=O)C12CCC(CNc3cccc(Br)c3)(CC1)CC2]

The title compound was prepared according to the method described for the synthesis of Intermediate 1H by substituting Intermediate 49B and 3-bromoaniline where appropriate. (900 mg, 2.55 mmol, 44% yield). MS (ESI) 353 (M+H).

Step D. Intermediate 49D. Preparation of methyl 4-((N-(3-bromophenyl)-3-fluorobicyclo[1.1.1]pentane-1-carboxamido)methyl)bicyclo[2.2.2]octane-1-carboxylate

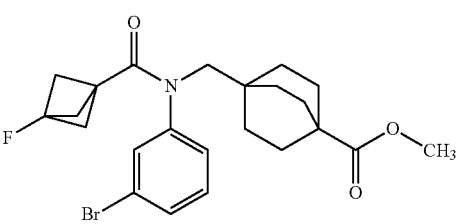 [SMILES: COC(=O)C12CCC(CN(C(=O)C34CC(F)(C3)C4)c3cccc(Br)c3)(CC1)CC2]

The title compound was prepared according to the method described for the synthesis of Example 23 by substituting Intermediate 49C where appropriate. (850 mg, 1.830 mmol, 71.6% yield). MS (ESI) 464 (M+H).

Step E. Intermediate 49E. Preparation of 4-((N-(3-bromophenyl)-3-fluorobicyclo[1.1.1]pentane-1-carboxamido)methyl)bicyclo[2.2.2]octane-1-carboxylic Acid

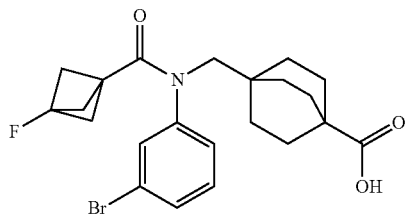 [SMILES: O=C(O)C12CCC(CN(C(=O)C34CC(F)(C3)C4)c3cccc(Br)c3)(CC1)CC2]

To a stirred solution of Intermediate 49D (850 mg, 1.830 mmol) in THF (5 mL), MeOH (5 mL) and H$_2$O (5 mL) was added LiOH (263 mg, 10.98 mmol) at room temperature. The reaction mixture was stirred at room temperature for 12 h. The reaction mixture was concentrated under reduced pressure to afford crude product. Ice water was added to this residue and the aqueous layer was acidified with aqueous HCl till the pH of the solution was around 2. The product was extracted with EtOAc (2×50 mL) and combined organic layers were dried over sodium sulphate, concentrated under reduced pressure to afford the title compound (750 mg, 1.649 mmol, 90% yield). MS (ESI) 450 (M+H).

Step F. Intermediate 49F. Preparation of 4-((N-(3-bromophenyl)-3-fluorobicyclo[1.1.1]pentane-1-carboxamido)methyl)bicyclo[2.2.2]octane-1-carboxamide

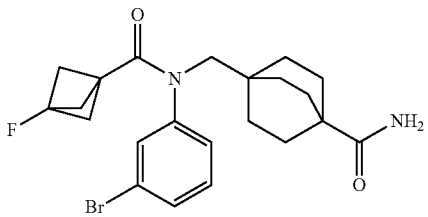 [SMILES: NC(=O)C12CCC(CN(C(=O)C34CC(F)(C3)C4)c3cccc(Br)c3)(CC1)CC2]

To a stirred solution of Intermediate 49E (1.65 g, 3.66 mmol) in DMF (15 mL) were added ammonium chloride (235 mg, 4.40 mmol), TEA (1.5 mL, 10.99 mmol) and BOP (1.78 g, 4.03 mmol). The reaction mixture was stirred at room temperature for 1 h. The reaction mixture was concentrated under reduced pressure and the residue was diluted with water (50 mL) and extracted with ethyl acetate (2×20 mL). The organic layers were combined, dried over anhydrous sodium sulphate, concentrated under reduced pressure and dried in vacuo to afford the title compound (1.6 g, 3.56 mmol, 97% yield). MS (ESI) 449 (M+H).

Step G Intermediate 49G. Preparation of N-(3-bromophenyl)-N-((4-cyanobicyclo[2.2.2]octan-1-yl)methyl)-3-fluorobicyclo[1.1.1]pentane-1-carboxamide

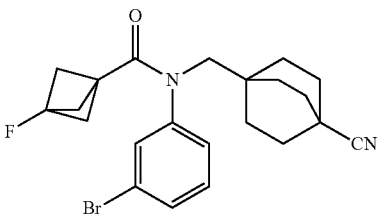 [SMILES: N#CC12CCC(CN(C(=O)C34CC(F)(C3)C4)c3cccc(Br)c3)(CC1)CC2]

A stirred solution of Intermediate 49F (1.6 g, 3.56 mmol) in pyridine (15 mL) was cooled to 0° C. TFAA (2.51 mL, 17.80 mmol) was added drop wise to the reaction mixture. The reaction mixture was allowed to warm to room temperature and stirred for 30 min. The reaction mixture was diluted with ice cold water (50 mL) and extracted with ethyl acetate (2×20 mL). The organic layers were combined, dried over anhydrous sodium sulphate and concentrated under reduced pressure. The crude material was purified by flash chromatography (24 g silica gel cartridge; A=Hex, B=EtOAc; 30 min grad.; 0% B to 40% B; flow rate=30 mL/min). The pure fractions were combined, concentrated and dried in vacuo to afford the title compound (850 mg, 1.97 mmol, 55% yield) as pale brown gummy oil. MS (ESI) 431 (M+H).

Step H. Intermediate 49H. Preparation of (E)-N-(3-bromophenyl)-3-fluoro-N-((4-(N'-hydroxycarbamimidoyl)bicyclo[2.2.2]octan-1-yl)methyl)bicyclo[1.1.1]pentane-1-carboxamide

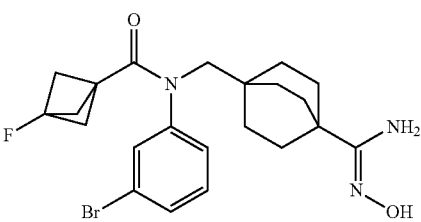 [SMILES: N/C(=N\O)C12CCC(CN(C(=O)C34CC(F)(C3)C4)c3cccc(Br)c3)(CC1)CC2]

To a stirred solution of Intermediate 49G (0.47 g, 1.090 mmol) in ethanol (10 mL) was added hydroxylamine (0.336 mL, 5.45 mmol) at room temperature. The reaction mixture was heated to 90° C. for 3 h. The reaction mixture was concentrated under reduced pressure to afford crude product. Ice water was added to this residue and the aqueous layer was extracted with EtOAc (2×50 mL) and the combined organic layers were dried over MgSO$_4$. The solvent was removed under reduced pressure to afford the title compound (400 mg, 0.844 mmol, 77% yield). MS (ESI) 464 (M+H).

Step I. Intermediate 491. Preparation of N-(3-bromophenyl)-N-((4-(5-(1,1-difluoroethyl)-1,2,4-oxadiazol-3-yl)bicyclo[2.2.2]octan-1-yl)methyl)-3-fluorobicyclo[1.1.1]pentane-1-carboxamide

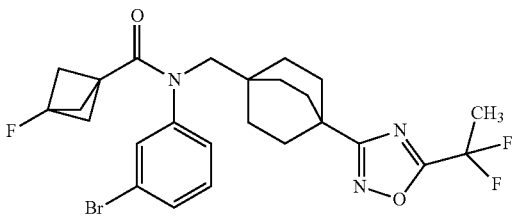 [SMILES: CC(F)(F)c1nc(C23CCC(CN(C(=O)C45CC(F)(C4)C5)c4cccc(Br)c4)(CC2)CC3)no1]

To a stirred solution of Intermediate 49H (300 mg, 0.646 mmol) in DMF (10 mL) at room temperature was added 2,2-difluoropropanoic acid (71.1 mg, 0.646 mmol), TEA (0.360 mL, 2.58 mmol) followed by BOP (314 mg, 0.711 mmol). After stirring for 3 h at room temperature, the reaction mixture was heated overnight at 110° C. The reaction mixture was concentrated under reduced pressure, diluted with water (20 mL) and extracted with ethyl acetate (2×20 mL). The combined organic layers were dried over anhydrous sodium sulfate, filtered and concentrated under reduced pressure. The crude product was purified by flash column chromatography (4 g silica cartridge, 0-40% EtOAc/pet ether) to afford the title compound (250 mg, 0.464 mmol, 72% yield) as brown solid. $^1$H NMR (400 MHz, DMSO-$d_6$) δ 7.74-7.68 (m, 1H), 7.61 (dt, J=7.3, 1.7 Hz, 1H), 7.49-7.36 (m, 2H), 3.58 (br. s., 1H), 3.51 (br. s., 1H), 2.23-2.05 (m, 3H), 1.88 (br. s., 6H), 1.82-1.69 (m, 6H), 1.53-1.33 (m, 6H). MS (ESI) 538 (M+H).

Step J. Example 49. Preparation of N-((4-(5-(1,1-difluoroethyl)-1,2,4-oxadiazol-3-yl) bicyclo[2.2.2]octan-1-yl)methyl)-3-fluoro-N-(3-(3-hydroxy-3-methylbut-1-yn-1-yl)phenyl)bicyclo[1.1.1]pentane-1-carboxamide The title compound was prepared according to the method described for the synthesis of Example 48 by substituting Intermediate 491 where appropriate. (13 mg, 0.024 mmol, 51.2% yield). $^1$H NMR (400 MHz, DMSO-$d_6$) δ 7.50-7.35 (m, 4H), 5.52 (s, 1H), 3.70-3.61 (m, 1H), 3.46 (br s, 1H), 2.14 (t, J=19.7 Hz, 3H), 1.97-1.67 (m, 12H), 1.45-1.33 (m, 6H). FXR $EC_{50}$ (nM)=39. MS (ESI) 452 (M+H).

Biological Evaluation

The exemplified compounds of the present invention were tested in the transient human FXR/Gal4-luciferase reporter assay, and assay results were reported in Table 1 and Examples 1 to 3 together with other analytical data.

A Gal4-hFXR fusion construct reporter system was used as the primary assay to characterize compound activity. A construct including 5 copies of the Gal4 promoter response element upstream of a firefly luciferase reporter cDNA was stably expressed in HEK293 cells. This reporter cell line was maintained in Dulbecco's Modified Eagle's medium (DMEM; Gibco) supplemented with 1% penicillin-streptomycin (P/S) solution, 500 µg/ml Zeocin and 10% charcoal/dextran-treated fetal bovine serum (cs-FBS) at 37° C. in a humidified 5% $CO_2$ atmosphere. Another plasmid was constructed in which the human cytomegalovirus promoter in the pcDNA3.1 vector directs the expression of the cDNA encoding a fusion protein comprised of the DNA binding domain from the Gal4 transcription factor fused to the ligand binding domain from human FXR.

The day prior to transfection, the reporter cells in culture are detached from the plate with trypsin and plated into a T75 flask at a sufficient density to achieve approximately 90% confluence the next morning. The transfection reagents are prepared by separately diluting 25 µg of the pcDNA3.1-Gal4-FXR plasmid into 1.87 mL of Opti-MEM (Thermo-Fisher), and 40 µL of Lipofectamine 2000 (Thermo-Fisher) into 1.87 mL of Opti-MEM, and then adding the diluted DNA solution into the diluted Lipofectamine 2000 solution and incubating at room temperature for 15-20 minutes. The mixture is further diluted with 10 ml of a solution comprised of DMEM, 10% cs-FBS, and 1% P/S immediately prior to transferring to the cells. The maintenance culture media is aspirated from the cells and the final transfection mixture is added before the cells are incubated overnight at 37° C. in a humidified 5% $CO_2$ atmosphere. This protocol can be scaled up, and the transiently transfected cells can be cryopreserved in an assay-ready format.

For compound testing, 100 nL of the compounds (serial dilutions in DMSO) are dispensed with an Echo acoustic dispenser (Labcyte) into the wells of a Corning/Costar clear bottom 384-well white plate. The transfected cells are harvested, counted, and diluted such that 10-25,000 cells in 25 µL are plated into each well of the 384-well compound assay plate. The compound-treated cells are incubated overnight at 37° C. in a humidified 5% $CO_2$ atmosphere. The next morning 25 µL of Steady-Glo (Promega) are added to each well of the plate, the mixture is incubated for 15 min. with shaking, and luminescence is measured on an Envision (Perkin Elmer) plate reader. Background counts from cells treated with DMSO alone are subtracted from all raw counts, and the corrected values are converted to a percentage of the control response attained with 8 µM GW-4064. These data are fit to a 4-parameter log agonist-response equation to calculate an $EC_{50}$ value.

In Vivo Testing Example: Acute Mouse PK/PD

Male, C57BL6/NTac mice, weighing 25-28 g, are purchased from Taconic Labs (Hudson, NY) and maintained on Teklad Global 18% Protein Rodent Diet (Harlan Laboratories). After 1 week acclimation, mice are sorted into groups based upon body weight. Mice are administered a single oral dose of vehicle or experimental compound. Systemic compound exposure is evaluated in plasma derived from blood collected via the submandibular vein at 1 hour post-dose, and at study termination (6 h). At study termination, the animals are euthanized and rapidly dissected. The medial lobe of the liver is divided, with one half being homogenized and analyzed for compound exposure, and the other half saved in RNAlater (Thermo-Fisher Scientific). The ileum is also dissected and preserved in RNAlater. Tissue samples in RNAlater are homogenized with MP Biomedicals' beads. RNA is extracted using the MagMax-96 Total RNA Isolation kit (Thermo-Fisher Scientific) according to the manufacturer's protocol. RNA Concentration is determined with the Nano-Drop 8000 Spectrophotometer (Thermo Fisher). Reverse transcription is done with Invitrogen's SuperScript® VILO cDNA Synthesis Kit according to the manufacturer's protocol. Real time PCR is done with Applied Biosystems' Taqman PCR master mixture according to the manufacturer's protocol. All primers are purchased from Thermo-Fisher Scientific. Mouse genes analyzed include Nr0b2 (which encodes the small heterodimer partner, SHP), Abcb11 (which encodes the bile salt excretion pump, BSEP), Cyp7a1, & Cyp8b1 in liver, and Fgf15, Fabp6 (which encodes ileal bile acid binding protein, I-BABP), Slc51a (which encodes organic solute transporter alpha subunit, OSTA), and Slc51b (which encodes organic solute transporter beta subunit, OSTB) in the ileum. The statistical significant changes in FGF15 gene expression are expressed as fold increase and $CYP_{7A1}$ expression as a percent reduction relative to vehicle control.

Other features of the invention should become apparent in the course of the above descriptions of exemplary embodiments that are given for illustration of the invention and are not intended to be limiting thereof. The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

What is claimed is:

1. A compound of Formula (I):

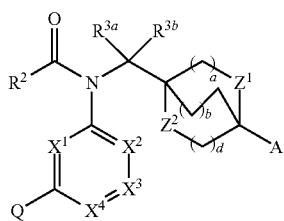

(I)

or a stereoisomer, a tautomer, or a salt or solvate thereof, wherein:
$X^1$ is $CR^{5a}$ or N;
$X^2$ is $CR^{5b}$ or N;
$X^3$ is $CR^{5c}$ or N;
$X^4$ is $CR^{5d}$ or N; provided that zero, 1, or 2 of $X^1$, $X^2$, $X^3$, and $X^4$ are N;
$Z^1$ and $Z^2$ are independently $CH_2$ or O; provided that at least one of $Z^1$ and $Z^2$ is $CH_2$;
a is zero or 1;
b is zero, 1, or 2;
d is zero, 1, or 2; provided that $Z^1$ and $Z^2$ are each $CH_2$ when a, b, and d are each zero;
Q is $C_{2-6}$ alkenyl or $C_{2-6}$ alkynyl, each substituted with zero to 2 $R^1$;
each $R^1$ is independently —C(O)$OR^x$, —C(O)$NR^xR^x$, or $C_{1-4}$ hydroxyalkyl;
each $R^{1a}$ is independently halo, oxo, cyano, hydroxyl, —$NH_2$, $C_{1-6}$ alkyl, $C_{1-6}$ alkoxy, —NH($C_{1-6}$ alkyl), —N($C_{1-6}$ alkyl)2, or —$NR^xC(O)(C_{1-6}$ alkyl), wherein each of said alkyl and alkoxy is substituted with zero to 6 $R^{1b}$;
each $R^{1b}$ is independently halo, hydroxyl, —$NR^wR^w$, oxo, cyano, $C_{1-3}$ alkoxy, $C_{1-3}$ haloalkoxy, —C(O)$OR^x$, —C(O)$NR^wR^w$, or —$NR^xC(O)R^y$;
or when $X^1$ is $CR^{5a}$, Q and $R^{5a}$ can be joined together to form a —$CR^{1a}$=$CR^1CH_2CH_2$— bridge;

$R^2$ is:
(i) $C_{1-6}$ alkyl, $C_{2-6}$ alkenyl, $C_{2-6}$ alkynyl, $C_{1-6}$ alkoxy, or —NR'$R^y$, wherein each of said alkyl, alkenyl, alkynyl, and alkoxy is substituted with zero to 6 $R^{2a}$;
(ii) $C_{3-8}$ carbocyclyl, $C_{6-8}$ spirobicyclyl, 4- to 7-membered heterocyclyl, phenyl, or 5- to 6-membered heteroaryl, wherein each of said carbocyclyl, spirobicyclyl, heterocyclyl, phenyl, and heteroaryl is substituted with zero to 3 $R^{2b}$; or
(iii) —$CH_2(C_{3-6}$ cycloalkyl), —$CH_2$(4- to 6-membered heterocyclyl), —$NR^x(CH_2)_{0-2}(C_{3-6}$ cycloalkyl), —$NR^x(CH_2)_{0-2}(C_{5-8}$ bicycloalkyl), —$NR^x(CH_2)_{0-2}$ ($C_{5-8}$ spirobicyclyl), —$NR^x(CH_2)_{0-2}$(4- to 6-membered heterocyclyl), —$NR^x(CH_2)_{0-2}$(5- to 6-membered heteroaryl), —$NR^x(CH_2)_{0-2}$(phenyl), —O($CH_2)_{0-2}(C_{3-6}$ cycloalkyl), —O($CH_2)_{0-2}(C_{5-8}$ bicycloalkyl), —O($CH_2)_{0-2}(C_{5-8}$ spirobicyclyl), —O($CH_2)_{0-2}$(4- to 6-membered heterocyclyl), —O($CH_2)_{0-2}$(5- to 6-membered heteroaryl), or —O($CH_2)_{0-2}$(phenyl), wherein each of said cycloalkyl, heterocyclyl, bicycloalkyl, spirobicyclyl, aryl, and heteroaryl is substituted with zero to 3 $R^{2b}$;
each $R^{2a}$ is independently halo, cyano, hydroxyl, oxo, $C_{1-3}$ haloalkyl, $C_{1-3}$ alkoxy, $C_{1-3}$ haloalkoxy, —$NR^xR^x$, —C(O)($C_{1-6}$ alkyl), —C(O)($C_{3-6}$ cycloalkyl), —$NR^xC(O)R^y$, —C(O)($C_{1-6}$ alkyl), —C(O)$OR^x$, —C(O)$NR^wR^w$, —S(O)$_2R^y$, —S(O)$_2(C_{1-3}$ fluoroalkyl), —NRS(O)$_2(C_{1-3}$ alkyl), —$NR^xS(O)_2(C_{3-6}$ cycloalkyl), —S(O)$_2$ $NR^zR^z$, or —P(O)$R^yR^y$;
each $R^{2b}$ is independently halo, cyano, hydroxyl, oxo, $C_{1-6}$ alkyl, $C_{1-6}$ alkoxy, —$NR^xR^x$, —$NR^xC(O)O(C_{1-3}$ alkyl), —C(O)($C_{1-3}$ alkyl), or —S(O)$_2(C_{1-3}$ alkyl), wherein each of said alkyl and alkoxy is substituted with zero to 6 $R^{2a}$;
$R^3a$ and $R^{3b}$ are independently hydrogen, $C_{1-3}$ alkyl, $C_{1-3}$ haloalkyl, or $C_{3-6}$ cycloalkyl, or $R^3a$ and $R^{3b}$; taken together with the carbon atom to which they are attached, form a $C_{3-6}$ cycloalkyl;
A is:
(i) cyano;
(ii) phenyl or a 5- to 10-membered heteroaryl containing 1 to 4 heteroatoms independently selected from N, O, and S, wherein each of said phenyl and heteroaryl is substituted with zero to 3 $R^{4a}$; or

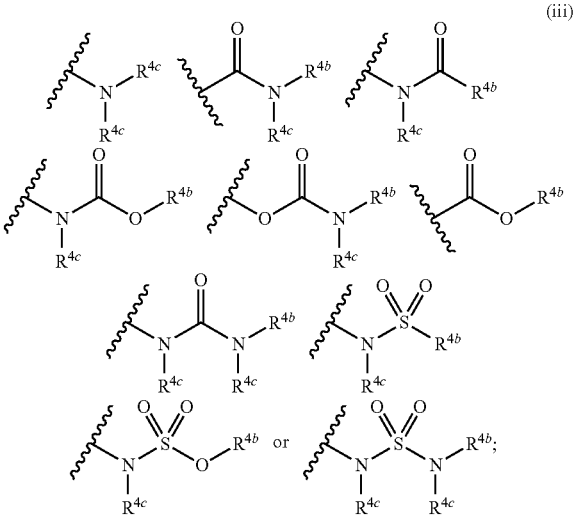

(iii)

each $R^{4a}$ is independently halo, cyano, hydroxyl, —NH$_2$, C$_{1-6}$ alkyl, C$_{2-6}$ alkenyl, C$_{2-6}$ alkynyl, C$_{1-6}$ alkoxy, —(CH$_2$)$_{0-3}$NH(C$_{1-6}$ alkyl), —(CH$_2$)$_{0-2}$N(C$_{1-6}$ alkyl)$_2$, —(CH$_2$)$_{0-3}$(C$_{3-6}$ cycloalkyl), or —(CH$_2$)$_{0-3}$(4- to 6-membered heterocyclyl), wherein each of said alkyl, alkoxy, alkenyl, and alkynyl is substituted with zero to 6 $R^{4d}$ and each of said cycloalkyl and heterocyclyl is substituted with zero to 3 $R^{4e}$;

$R^{4b}$ is C$_{1-6}$ alkyl, —(CH$_2$)$_{0-3}$(C$_{3-6}$ cycloalkyl), or —(CH$_2$)$_{0-3}$(4- to 6-membered heterocyclyl), wherein each of said alkyl is substituted with zero to 6 $R^{4d}$ and each of said cycloalkyl and heterocyclyl is substituted with zero to 3 $R^{4e}$;

each $R^4$, is independently hydrogen, C$_{1-6}$ alkyl, C$_{3-6}$ cycloalkyl, 4- to 6-membered heterocyclyl, phenyl, or 5- to 6-membered heteroaryl;

each $R^{4d}$ is independently halo, hydroxyl, —NR$^x$R$^x$, oxo, cyano, C$_{1-3}$ alkoxy, or C$_{1-3}$ haloalkoxy;

each $R^{4e}$ is independently halo, oxo, cyano, hydroxyl, —NH$_2$, C$_{1-6}$ alkyl, C$_{1-6}$ alkoxy, —NH(C$_{1-6}$ alkyl), or —N(C$_{1-6}$ alkyl)$_2$, wherein each of said alkyl and alkoxy is substituted with zero to 6 $R^{4d}$;

each of $R^{5a}$, $R^{5b}$, $R^{5c}$, and $R^{5d}$ is independently hydrogen, halo, hydroxy, cyano, C$_{1-6}$ alkyl substituted with zero to 6 $R^{5e}$, C$_{1-6}$ alkoxy substituted with zero to 6 $R^{5e}$, —C(O)OR$^x$, —C(O)NR$^w$R$^w$, —S(O)$_2$R$^y$, —S(O)$_2$NR$^z$R$^z$, or phenyl substituted with zero to 3 $R^{5f}$;

each of $R^{5e}$ is independently halo, hydroxyl, —NR$^x$R$^x$, oxo, cyano, C$_{1-3}$ alkoxy, or C$_{1-3}$ haloalkoxy;

each $R^{5f}$ is independently halo, oxo, cyano, hydroxyl, —NH$_2$, C$_{1-6}$ alkyl, C$_{1-6}$ alkoxy, —NH(C$_{1-6}$ alkyl), or —N(C$_{1-6}$ alkyl)$_2$, wherein each of said alkyl and alkoxy is substituted with zero to 6 $R^{5e}$;

each R is independently hydrogen, C$_{1-6}$ alkyl, or alternatively, two R, taken together with the nitrogen atom to which they are attached, form a 4- to 7-membered bicyclic or spirocyclic ring moiety containing zero to 2 additional heteroatoms independently selected from N, O, and S, wherein each ring can be substituted with zero to 6 $R^{2a}$;

each $R^w$ is independently hydrogen, C$_{1-6}$ alkyl, or C$_{3-6}$ cycloalkyl; or alternatively, two $R^w$, taken together with the nitrogen atom to which they are attached, form a 4- to 7-membered ring moiety containing zero to 2 additional heteroatoms independently selected from N, O, and S;

each $R^x$ is independently hydrogen, C$_{1-6}$ alkyl, or C$_{3-6}$ cycloalkyl;

$R^y$ is C$_{1-6}$ alkyl or C$_{3-6}$ cycloalkyl; and each $R^z$ is independently hydrogen, C$_{1-6}$ alkyl, or C$_{3-6}$ cycloalkyl; or alternatively, two $R^z$, taken together with the nitrogen atom to which they are attached, form a 4- to 7-membered ring moiety containing zero to 2 additional heteroatoms independently selected from N, O, and S.

2. The compound according to claim 1 or a stereoisomer, a tautomer, or a salt or solvate thereof, wherein:

Q is —CR$^{1c}$=CR$^{1c}$R$^1$ or —C≡CR$^1$;

$R^1$ is —C(O)OR$^x$, —C(O)NR$^x$R$^x$ or C$_{1-4}$ hydroxyalkyl;

each $R^{1c}$ is independently H or —CH$_3$;

or when X$^1$ is CR$^{5a}$, X$^2$ is CR$^{5b}$, X$^3$ is CR$^{5c}$, X$^4$ is CR$^{5d}$, then Q and R$^{5a}$ can be joined together to form a —CR$^{1a}$=CR$^1$CH$_2$CH$_2$— bridge;

$R^2$ is:
(i) C$_{1-4}$ alkyl, C$_{1-4}$ alkoxy, or —NR R, wherein each of said alkyl and alkoxy is substituted with zero to 4 $R^{2a}$;

(ii) C$_{3-8}$ carbocyclyl, C$_{6-8}$ spirobicyclyl, phenyl, or 4- to 7-membered heterocyclyl, wherein each of said carbocyclyl, spirobicyclyl, and heterocyclyl is substituted with zero to 3 $R^{2b}$; or (iii) —CH$_2$(C$_{3-5}$ cycloalkyl), —CH$_2$(4- to 6-membered heterocyclyl), —NR$^x$(CH$_2$)$_{0-2}$(C$_{3-5}$ cycloalkyl), —NR$^x$(CH$_2$)$_{0-2}$(4- to 6-membered heterocyclyl), —NR$^x$(CH$_2$)$_{0-2}$(phenyl), —O(phenyl), or —S(O)$_2$(C$_{3-6}$ cycloalkyl), wherein each of said cycloalkyl, heterocyclyl, and phenyl is substituted with zero to 3 $R^{2b}$;

each $R^{2a}$ is independently F, Cl, hydroxyl, —NR$^x$R$^x$, oxo, cyano, C$_{1-3}$ alkoxy, C$_{1-3}$ haloalkoxy, or —C(O)OH;

each $R^2$b is independently F, Cl, cyano, hydroxyl, C$_{1-4}$ alkyl, C$_{1-3}$ alkoxy, —NR$^x$R$^x$, —NR$^x$C(O)O(C$_{1-3}$ alkyl), —C(O)(C$_{1-2}$ alkyl), or —S(O)$_2$(C$_{1-2}$ alkyl), wherein each of said alkyl and alkoxy is substituted with zero to 4 $R^{2a}$;

A is:
(i) cyano;
(ii) phenyl or a 5- to 6-membered heteroaryl containing 1 to 4 heteroatoms independently selected from N, O, and S, wherein each of said phenyl and heteroaryl is substituted with zero to 3 $R^{4a}$; or

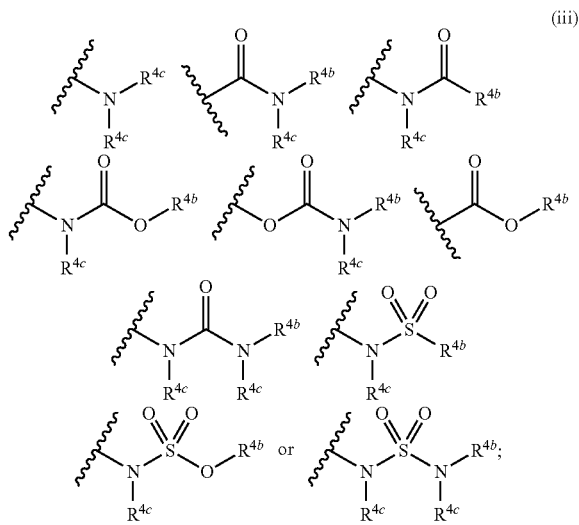

(iii)

each $R^{4a}$ is independently F, Cl, cyano, hydroxyl, —NH$_2$, C$_{1-4}$ alkyl, C$_{1-4}$ alkoxy, —(CH$_2$)$_{0-3}$NH(C$_{1-6}$ alkyl), —(CH$_2$)$_{0-3}$N(C$_{1-6}$ alkyl)$_2$, —(CH$_2$)$_{0-3}$(C$_{3-6}$ cycloalkyl), or —(CH$_2$)$_{0-3}$(4- to 6-membered heterocyclyl), wherein each of said alkyl and alkoxy is substituted with zero to 4 $R^{4d}$ and each of said cycloalkyl and heterocyclyl is substituted with zero to 3 $R^4$e;

$R^{4b}$ is C$_{1-4}$ alkyl, —(CH$_2$)$_{0-3}$(C$_{3-6}$ cycloalkyl), or —(CH$_2$)$_{0-3}$(4- to 6-membered heterocyclyl), wherein each of said alkyl is substituted with zero to 4 $R^{4d}$ and each of said cycloalkyl and heterocyclyl is substituted with zero to 3 $R^{4e}$;

each $R^4$, is independently hydrogen, C$_{1-3}$ alkyl, or C$_{3-6}$ cycloalkyl;

each $R^{4d}$ is independently F, Cl, hydroxyl, —NR$^x$R$^x$, oxo, cyano, C$_{1-3}$ alkoxy, or C$_{1-3}$ fluoroalkoxy;

each $R^{4e}$ is independently F, Cl, oxo, cyano, hydroxyl, —NH$_2$, C$_{1-4}$ alkyl, C$_{1-4}$ alkoxy, or —NH(C$_{1-6}$ alkyl), or —N(C$_{1-6}$ alkyl)$_2$, wherein each of said alkyl and alkoxy is substituted with zero to 4 R$^{4d}$;

each of R$^{5a}$, R$^{5b}$, R$^{5c}$, and R$^{5d}$ is independently hydrogen, F, Cl, hydroxy, cyano, C$_{1-3}$ alkyl substituted with zero to 4 R$^{5e}$, C$_{1-3}$ alkoxy substituted with zero to 4 R$^{5e}$, —C(O)OR$^x$, —C(O)NR$^R$w, —S(O)$_2$R$^y$, —S(O)$_2$NR$^z$R$^z$, or phenyl substituted with zero to 3 R$^{5f}$;

each R$^w$ is independently hydrogen, C$_{1-4}$ alkyl, or C$_{3-6}$ cycloalkyl; or alternatively, two R$^w$, taken together with the nitrogen atom to which they are attached, form a 4- to 7-membered ring moiety containing zero to 2 additional heteroatoms independently selected from N, O, and S;

each R$^x$ is independently H, C$_{1-4}$ alkyl, or C$_{3-6}$ cycloalkyl;

R$^y$ is C$_{1-4}$ alkyl or C$_{3-6}$ cycloalkyl; and each R$^z$ is independently hydrogen, C$_{1-4}$ alkyl, or C$_{3-6}$ cycloalkyl; or alternatively, two R$^z$, taken together with the nitrogen atom to which they are attached, form a 4- to 7-membered ring moiety containing zero to 2 additional heteroatoms independently selected from N, O, and S.

3. The compound according to claim 1 or a stereoisomer, a tautomer, or a salt or solvate thereof, wherein:

X$^1$ is CH;
X$^2$ is CH;
X$^3$ is CH;
X$^4$ is CH;
a is 1;
b is 1;
d is 1;
Q is —CH=CHC(O)OH, —CH=CHC(O)OCH$_3$, —C(CH$_3$)=CHC(O)OCH$_3$, —CH=CHC(O)N(CH$_3$)$_2$, or —C≡CC(CH$_3$)$_2$OH;
R$^2$ is —CH(CH$_3$)$_2$ or a cyclic group selected from cyclobutyl, cyclohexyl, cycloheptyl, bicyclo[1.1.1]pentyl, piperidinyl, and tetrahydropyranyl, each cyclic group substituted with zero to 1 substituents independently selected from F and —CH$_3$;
R$^{3a}$ is hydrogen or —CH$_3$;
R$^{3b}$ is hydrogen;
A is oxadiazolyl, phenyl, indazolyl, or benzothiazolyl, each substituted with zero to 1 R$^{4a}$; and
each R$^{4a}$ is independently —CH$_3$, —CH(CH$_3$)$_2$, —C(CH$_3$)$_3$, —CH(CH$_3$)$_2$, —CF$_2$CH$_3$, —OCH$_3$, —N(CH$_3$)$_2$, —N(CH$_2$CH$_3$)$_2$, or a cyclic group selected from cyclopropyl, azetidinyl, pyrrolidinyl, tetrahydropyranyl, and morpholinyl.

4. The compound according to claim 1 or a stereoisomer, a tautomer, or a salt or solvate thereof, wherein Z$^1$ is CH$_2$; and Z$_2$ is CH$_2$.

5. The compound according to claim 1 or a stereoisomer, a tautomer, or a salt or solvate thereof, wherein one of Z$^i$ and Z$^2$ is CH$_2$, and the other of Z$^1$ and Z$^2$ is O.

6. The compound according to claim 1 or a stereoisomer, a tautomer, or a salt or solvate thereof, wherein A is a phenyl or a 5- to 6-membered heteroaryl containing 1 to 4 heteroatoms independently selected from N, O, and S, wherein each of said phenyl and heteroaryl is substituted with zero to 3 R$^{4a}$.

7. The compound according to claim 1 or a salt thereof, wherein compound has the structure of Formula (II):

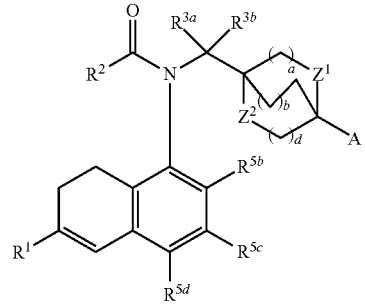

(II)

wherein

R$^1$ is —C(O)OR$^x$, —C(O)NR$^x$R$^x$, or C$_{1-4}$ hydroxyalkyl; and each R$^x$ is independently hydrogen or —CH$_3$.

8. The compound according to claim 1 or a stereoisomer, a tautomer, or a salt or solvate thereof, wherein A is oxadiazolyl or phenyl, each substituted with zero to 1 R$^{4a}$.

9. The compound according to claim 1 or a stereoisomer, a tautomer, or a salt or solvate thereof, wherein said compound is:

methyl (E)-3-(3-(N-((4-(4-(dimethylamino)phenyl) bicyclo[2.2.2]octan-1-yl)methyl) cyclohexanecarboxamido)phenyl)acrylate (1);

(E)-3-(3-(N-((4-(4-(dimethylamino)phenyl)bicyclo[2.2.2]octan-1-yl)methyl) cyclohexanecarboxamido) phenyl)acrylic acid (2);

(E)-methyl 3-(3-(N-((4-(4-morpholinophenyl)bicyclo[2.2.2]octan-1-yl)methyl) cyclohexanecarboxamido) phenyl) acrylate (3);

(E)-methyl 3-(3-(N-((4-(4-(pyrrolidin-1-yl)phenyl)bicyclo[2.2.2]octan-1-yl)methyl) cyclohexanecarboxamido)phenyl)acrylate (4);

(E)-methyl 3-(3-(N-((4-(4-(azetidin-1-yl)phenyl)bicyclo[2.2.2]octan-1-yl)methyl) cyclohexanecarboxamido) phenyl)acrylate (5);

methyl (E)-3-(3-(N-((4-(4-(dimethylamino)phenyl)bicyclo[2.2.2]octan-1-yl)methyl) tetrahydro-2H-pyran-4-carboxamido)phenyl)acrylate (6);

methyl (E)-3-(3-(N-((4-phenylbicyclo[2.2.2]octan-1-yl) methyl) cyclohexanecarboxamido)phenyl)acrylate (7);

(E)-methyl 3-(3-(N-((1-(1-methyl-1H-indazol-5-yl)-2-oxabicyclo[2.2.2]octan-4-yl) methyl)tetrahydro-2H-pyran-4-carboxamido) phenyl)acrylate (8);

(E)-methyl 3-(3-(1-methyl-N-((1-(1-methyl-1H-indazol-5-yl)-2-oxabicyclo[2.2.2]octan-4-yl)methyl)piperidine-4-carboxamido)phenyl)acrylate (9);

methyl (E)-3-(3-(N-((1-(4-methoxyphenyl)-2-oxabicyclo[2.2.2]octan-4-yl)methyl) cyclohexanecarboxamido) phenyl)acrylate (10);

methyl (E)-3-(3-(N-((4-(4-morpholinophenyl)bicyclo[2.2.2]octan-1-yl)methyl) cyclohexanecarboxamido) phenyl) but-2-enoate (14);

methyl (E)-3-(3-(N-((4-(4-methoxyphenyl)bicyclo[2.2.2]octan-1-yl)methyl) cyclohexanecarboxamido)phenyl) acrylate (15);

methyl (E)-3-(3-(N-((4-(4-methoxyphenyl)bicyclo[2.2.2]octan-1-yl)methyl) cyclohexanecarboxamido)phenyl) but-2-enoate (16);

methyl (E)-3-(3-(N-((4-(3-methyl-1,2,4-oxadiazol-5-yl) bicyclo[2.2.2]octan-1-yl)methyl) cyclohexanecarboxamido)phenyl)but-2-enoate (19);

methyl (E)-3-(3-(N-((4-(3-methyl-1,2,4-oxadiazol-5-yl) bicyclo[2.2.2]octan-1-yl)methyl) cyclohexanecarboxamido)phenyl)acrylate (20);

methyl (E)-3-(3-(N-((4-(3-methyl-1,2,4-oxadiazol-5-yl) bicyclo[2.2.2]octan-1-yl)methyl) cyclopropanecarboxamido)phenyl)acrylate (21);

methyl (E)-3-(3-(N-((4-(3-methyl-1,2,4-oxadiazol-5-yl) bicyclo[2.2.2] octan-1-yl)methyl) isobutyramido)phenyl)acrylate (22);

methyl (E)-3-(3-(N-((4-(3-methyl-1,2,4-oxadiazol-5-yl) bicyclo[2.2.2]octan-1-yl)methyl) tetrahydro-2H-pyran-4-carboxamido)phenyl)acrylate (23);

methyl (E)-3-(3-(N-((4-(3-methyl-1,2,4-oxadiazol-5-yl) bicyclo[2.2.2]octan-1-yl)methyl) cycloheptanecarboxamido)phenyl)acrylate (24);

methyl (E)-3-(3-(3-fluoro-N-((4-(3-methyl-1,2,4-oxadiazol-5-yl)bicyclo[2.2.2]octan-1-yl) methyl)bicyclo [1.1.1]pentane-1-carboxamido)phenyl)acrylate (25);

methyl (E)-3-(3-(3,3-difluoro-N-((4-(3-methyl-1,2,4-oxadiazol-5-yl)bicyclo[2.2.2] octan-1-yl)methyl)cyclobutane-1-carboxamido)phenyl)acrylate (26);

(E)-N-(3-(3-(dimethylamino)-3-oxoprop-1-en-1-yl)phenyl)-N-((4-(3-methyl-1,2,4-oxadiazol-5-yl)bicyclo [2.2.2]octan-1-yl)methyl)cyclohexanecarboxamide (27);

methyl (E)-3-(3-(N-((4-(4-cyclopropylphenyl)bicyclo [2.2.2]octan-1-yl)methyl) cyclopropanecarboxamido) phenyl)acrylate (28);

methyl (E)-3-(3-(N-((4-(4-cyclopropylphenyl)bicyclo [2.2.2]octan-1-yl)methyl) cyclohexanecarboxamido) phenyl)acrylate (29);

methyl (E)-3-(3-(N-((4-(benzo[d]thiazol-2-yl)bicyclo [2.2.2]octan-1-yl)methyl) cyclopropanecarboxamido) phenyl)acrylate (33);

methyl (E)-3-(3-(N-((4-(benzo[d]thiazol-2-yl)bicyclo [2.2.2]octan-1-yl)methyl) cyclohexanecarboxamido) phenyl)acrylate (34);

methyl (E)-3-(3-(N-((4-(4-cyclopropylphenyl)bicyclo [2.2.2]octan-1-yl)methyl) cyclopropanecarboxamido) phenyl)but-2-enoate (36);

methyl (E)-3-(3-(N-((4-(4-cyclopropylphenyl)bicyclo [2.2.2]octan-1-yl)methyl) cyclohexanecarboxamido) phenyl)but-2-enoate (37);

methyl (E)-3-(3-(N-((4-(4-isopropylphenyl)bicyclo [2.2.2]octan-1-yl)methyl) cyclohexanecarboxamido) phenyl) acrylate (38);

methyl (E)-3-(3-(N-((4-(4-isopropylphenyl)bicyclo [2.2.2]octan-1-yl)methyl) cyclopropanecarboxamido) phenyl)acrylate (39);

methyl (E)-3-(3-(N-((4-(3-cyclopropyl-1,2,4-oxadiazol-5-yl)bicyclo[2.2.2]octan-1-yl) methyl)cyclohexane carboxamido)phenyl)acrylate (41);

methyl (E)-3-(3-(N-((4-(3-morpholino-1,2,4-oxadiazol-5-yl)bicyclo[2.2.2]octan-1-yl) methyl)cyclohexanecarboxamido)phenyl)acrylate (42);

methyl (E)-3-(3-(N-((4-(3-(tetrahydro-2H-pyran-4-yl)-1,2,4-oxadiazol-5-yl) bicyclo[2.2.2]octan-1-yl)methyl) cyclohexanecarboxamido)phenyl)acrylate (43);

methyl (E)-3-(3-(N-((4-(5-methyl-1,2,4-oxadiazol-3-yl) bicyclo[2.2.2]octan-1-yl)methyl) cyclohexanecarboxamido)phenyl)acrylate (44);

methyl (E)-3-(3-(N-(1-(4-(3-methyl-1,2,4-oxadiazol-5-yl)bicyclo[2.2.2]octan-1-yl) ethyl)cyclohexanecarboxamido)phenyl)acrylate (46-47);

N-((4-(5-(tert-butyl)-1,3,4-oxadiazol-2-yl)bicyclo[2.2.2] octan-1-yl) methyl)-3-fluoro-N-(3-(3-hydroxy-3-methylbut-1-yn-1-yl)phenyl)bicyclo[1.1.1]pentane-1-carboxamide (48); or N-((4-(5-(1,1-difluoroethyl)-1,2,4-oxadiazol-3-yl) bicyclo[2.2.2]octan-1-yl)methyl)-3-fluoro-N-(3-(3-hydroxy-3-methylbut-1-yn-1-yl) phenyl)bicyclo[1.1.1] pentane-1-carboxamide (49).

10. The compound according to claim 1 or a stereoisomer, a tautomer, or a salt or solvate thereof, wherein said compound is:

methyl 5-(N-((4-(4-morpholinophenyl)bicyclo[2.2.2]octan-1-yl)methyl) cyclohexanecarboxamido)-3,4-dihydronaphthalene-2-carboxylate (11);

methyl 5-(N-((4-(4-(dimethylamino)phenyl)bicyclo [2.2.2]octan-1-yl)methyl) cyclohexanecarboxamido)-3,4-dihydronaphthalene-2-carboxylate (12);

methyl 5-(N-((4-(4-(diethylamino)phenyl)bicyclo[2.2.2] octan-1-yl)methyl) cyclohexanecarboxamido)-3,4-dihydronaphthalene-2-carboxylate (13);

5-(N-((4-(4-methoxyphenyl) bicyclo[2.2.2]octan-1-yl) methyl) cyclohexanecarboxamido)-3,4-dihydronaphthalene-2-carboxylic acid (17);

methyl 5-(N-((4-(4-methoxyphenyl)bicyclo[2.2.2]octan-1-yl) methyl)cyclohexanecarboxamido)-3,4-dihydronaphthalene-2-carboxylate (18);

methyl 5-(N-((4-(4-cyclopropylphenyl)bicyclo[2.2.2]octan-1-yl)methyl) cyclohexanecarboxamido)-3,4-dihydronaphthalene-2-carboxylate (30);

methyl 5-(N-((4-(4-cyclopropylphenyl)bicyclo[2.2.2]octan-1-yl)methyl) cyclopropanecarboxamido)-3,4-dihydronaphthalene-2-carboxylate (31);

methyl 5-(N-((4-(4-cyclopropylphenyl) bicyclo[2.2.2]octan-1-yl)methyl) isobutyramido)-3,4-dihydronaphthalene-2-carboxylate (32);

methyl 5-(N-((4-(3-methyl-1,2,4-oxadiazol-5-yl)bicyclo [2.2.2]octan-1-yl)methyl) cyclohexanecarboxamido)-3,4-dihydronaphthalene-2-carboxylate (40); or methyl 5-(N-((1-(1-methyl-1H-indazol-5-yl)-2-oxabicyclo[2.2.2]octan-4-yl)methyl) cyclohexanecarboxamido)-3,4-dihydronaphthalene-2-carboxylate (45).

11. A pharmaceutical composition comprising a pharmaceutically acceptable carrier and a compound according to claim 1, or a stereoisomer, a tautomer, or a pharmaceutically acceptable salt or solvate thereof.

12. A method of treating a disease or disorder, comprising administering to a mammalian patent a compound according to claim 1 or a pharmaceutically acceptable salt thereof, wherein the disease or disorder is pathological fibrosis, metabolic disorder, or cholestatic disorder.

13. The method according to claim 12, wherein the pathological fibrosis is liver fibrosis, renal fibrosis, biliary fibrosis, or pancreatic fibrosis.

14. The method according to claim 12, wherein the metabolic disorder or cholestatic disorder is nonalcoholic steatohepatitis (NASH), non-alcoholic fatty liver disease (NAFLD), chronic kidney disease, diabetic kidney disease, primary sclerosing cholangitis (PSC), or primary biliary cirrhosis (PBC).

15. A method of treating a disease or disorder, comprising administering to a mammalian patent a compound according to claim 1 or a pharmaceutically acceptable salt thereof, wherein the disease or disorder is idiopathic pulmonary fibrosis (IPF).

* * * * *